United States Patent
Garcia et al.

(10) Patent No.: US 9,820,755 B2
(45) Date of Patent: Nov. 21, 2017

(54) STERNAL CLOSURE CERCLAGE, PLATE IMPLANT AND INSTRUMENTATION

(71) Applicant: Zimmer Biomet CMF and Thoracic, LLC, Jacksonville, FL (US)

(72) Inventors: Saddy Garcia, St. Augustine, FL (US); Rachel Hale, Jacksonville, FL (US); Bryan Wilcox, St. Augustine, FL (US); Benjamin Witten, Jacksonville, FL (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 0 days.

(21) Appl. No.: 15/204,515

(22) Filed: Jul. 7, 2016

(65) Prior Publication Data
US 2016/0317161 A1 Nov. 3, 2016

Related U.S. Application Data

(63) Continuation-in-part of application No. 15/174,041, filed on Jun. 6, 2016, which is a continuation of
(Continued)

(51) Int. Cl.
*A61B 17/16* (2006.01)
*A61B 17/88* (2006.01)
(Continued)

(52) U.S. Cl.
CPC ...... *A61B 17/1611* (2013.01); *A61B 17/3403* (2013.01); *A61B 17/8076* (2013.01);
(Continued)

(58) Field of Classification Search
CPC ............ A61B 17/1611; A61B 17/3403; A61B 17/823; A61B 17/1604; A61B 17/1606;
(Continued)

(56) References Cited

U.S. PATENT DOCUMENTS

| | | | | | |
|---|---|---|---|---|---|
| 571,040 | A | * | 11/1896 | De Vilbiss | A61B 17/1611 606/83 |
| 1,037,864 | A | * | 9/1912 | Carlson et al. | A61B 17/0469 112/169 |

(Continued)

FOREIGN PATENT DOCUMENTS

| CN | 106413608 A | 2/2017 |
|---|---|---|
| DE | 3538645 A1 | 5/1987 |

(Continued)

OTHER PUBLICATIONS

"International Application Serial No. PCT/US2015/019976, International Preliminary Report on Patentability dated Sep. 22, 2016", 12 pgs.

(Continued)

*Primary Examiner* — Christian Sevilla
(74) *Attorney, Agent, or Firm* — Schwegman Lundberg & Woessner, P.A.

(57) ABSTRACT

A system including a bone punch tool and a needle guide. The bone punch tool can include a support arm having a support arm proximal portion and a support arm distal portion, a pivot arm having a pivot arm proximal portion and a pivot arm distal portion, and an arcuate punch configured to punch through bone. The pivot arm distal portion can be pivotably coupled to the support arm distal portion, such that the pivot arm proximal portion is configured to be moved away from the support arm proximal portion to extend the arcuate punch into a punch position to punch an arcuate hole through bone. The needle guide can be configured to guide a needle through the arcuate hole.

16 Claims, 100 Drawing Sheets

Related U.S. Application Data application No. 14/500,010, filed on Sep. 29, 2014, now Pat. No. 9,358,054, which is a continuation of application No. PCT/US2014/028903, filed on Mar. 14, 2014, application No. 15/204,515, which is a continuation-in-part of application No. 15/174,783, filed on Jun. 6, 2016, which is a continuation of application No. 14/500,010, which is a continuation of application No. PCT/US2014/028903.

(60) Provisional application No. 61/794,648, filed on Mar. 15, 2013, provisional application No. 61/794,518, filed on Mar. 15, 2013, provisional application No. 61/794,290, filed on Mar. 15, 2013.

(51) Int. Cl.

| | | |
|---|---|---|
| *A61B 17/82* | (2006.01) | |
| *A61B 17/34* | (2006.01) | |
| *A61B 17/80* | (2006.01) | |
| *A61B 17/86* | (2006.01) | |

(52) U.S. Cl.
CPC ............ *A61B 17/82* (2013.01); *A61B 17/823* (2013.01); *A61B 17/86* (2013.01); *A61B 17/8861* (2013.01); *A61B 17/8869* (2013.01)

(58) Field of Classification Search
CPC ............ A61B 17/1608; A61B 17/8869; A61B 17/8076; A61B 17/82
See application file for complete search history.

(56) References Cited

U.S. PATENT DOCUMENTS

| | | | |
|---|---|---|---|
| 1,962,964 | A | 6/1934 | Morrison |
| 2,226,393 | A | 12/1940 | Seeger et al. |
| 2,443,335 | A | 6/1948 | Louis |
| 3,045,306 | A | 7/1962 | Taylor |
| 4,371,192 | A | 2/1983 | Alix |
| 2,151,555 | A | 7/1985 | Ikeda et al. |
| 5,070,805 | A | 12/1991 | Plante |
| 5,190,545 | A | 3/1993 | Corsi et al. |
| 5,335,400 | A | 8/1994 | Sales |
| 5,356,412 | A | 10/1994 | Golds et al. |
| 5,383,905 | A | 1/1995 | Golds et al. |
| 5,415,658 | A | 5/1995 | Kilpela et al. |
| 5,423,821 | A | 6/1995 | Pasque |
| 6,015,428 | A | 1/2000 | Pagedas |
| 6,017,347 | A | 1/2000 | Huebner et al. |
| 6,030,410 | A | 2/2000 | Zurbrugg |
| 6,066,160 | A | 5/2000 | Colvin et al. |
| 6,120,505 | A | 9/2000 | Huebner |
| 6,302,889 | B1 | 10/2001 | Keller |
| 6,682,533 | B1 | 1/2004 | Dinsdale et al. |
| 6,974,452 | B1 | 12/2005 | Gille et al. |
| 7,052,499 | B2 | 5/2006 | Steger et al. |
| 7,458,981 | B2 | 12/2008 | Fielding et al. |
| 7,803,176 | B2 | 9/2010 | Teague et al. |
| 8,172,887 | B2 | 5/2012 | Gabele |
| 8,652,137 | B2 * | 2/2014 | Blain ................ A61B 17/1608 606/167 |
| 8,992,533 | B2 * | 3/2015 | Blain ................ A61B 17/1608 606/79 |
| 9,060,787 | B2 | 6/2015 | Blain et al. |
| 9,295,507 | B2 | 3/2016 | Albertson et al. |
| 9,358,054 | B2 | 6/2016 | Garcia et al. |
| 2006/0111721 | A1 | 5/2006 | Puricelli |
| 2006/0195104 | A1 | 8/2006 | Schlafli et al. |
| 2007/0260251 | A1 * | 11/2007 | Weier ................ A61B 17/823 606/74 |
| 2008/0140128 | A1 | 6/2008 | Smisson et al. |
| 2010/0094294 | A1 | 4/2010 | Gillard et al. |
| 2010/0179600 | A1 | 7/2010 | Steger et al. |
| 2011/0028979 | A1 | 2/2011 | Schwab |
| 2012/0059377 | A1 | 3/2012 | Belliard |
| 2012/0130373 | A1 | 5/2012 | Larroque-Lahitette |
| 2012/0157998 | A1 | 6/2012 | Belliard |
| 2012/0215224 | A1 | 8/2012 | Songer |
| 2012/0290017 | A1 | 11/2012 | Haidukewych |
| 2012/0303065 | A1 | 11/2012 | Larroque-lahitette et al. |
| 2013/0178854 | A1 * | 7/2013 | Sholev ................ A61B 17/0469 606/79 |
| 2013/0261625 | A1 | 10/2013 | Koch et al. |
| 2015/0038969 | A1 | 2/2015 | Garcia et al. |
| 2015/0045794 | A1 | 2/2015 | Garcia et al. |
| 2015/0342657 | A1 | 12/2015 | Voisard et al. |
| 2016/0296262 | A1 | 10/2016 | Garcia et al. |
| 2017/0086894 | A1 | 3/2017 | Garcia et al. |

FOREIGN PATENT DOCUMENTS

| | | | |
|---|---|---|---|
| DE | 4021246 A1 | 1/1992 | |
| EP | 876798 A2 | 11/1998 | |
| JP | 2017507758 A | 3/2017 | |
| WO | WO-9522294 A1 | 8/1995 | |
| WO | WO-03037196 A1 | 5/2003 | |
| WO | WO-2007056399 A1 | 5/2007 | |
| WO | WO-2009100339 A1 | 8/2009 | |
| WO | WO-20110035008 A1 | 2/2011 | |
| WO | WO-2013003719 A1 | 1/2013 | |
| WO | WO-2014144479 A1 | 9/2014 | |
| WO | WO-PCT/US2014/028903 A1 | 9/2014 | |
| WO | WO-2015142588 A2 | 9/2015 | |
| WO | WO-2015142588 A3 | 9/2015 | |

OTHER PUBLICATIONS

"U.S. Appl. No. 14/466,485, Restriction Requirement dated May 23, 2017", 7 pgs.
"U.S. Appl. No. 15/174,041, Notice of Allowance dated Jun. 14, 2017", 7 pgs.
"U.S. Appl. No. 15/174,041, Preliminary Amendment filed Dec. 20, 2016", 6 pgs.
"European Application Serial No. 15734485.4, Response filed Jun. 2, 2017 to Communication pursuant to Rules 161(1) and 162 EPC dated Nov. 22, 2016", 16 pgs.
"U.S. Appl. No. 14/500,010, Final Office Action dated Oct. 26, 2015", 6 pgs.
"U.S. Appl. No. 14/500,010, Non Final Office Action dated Jun. 9, 2015", 7 pgs.
"U.S. Appl. No. 14/500,010, Notice of Allowance dated Feb. 5, 2016", 6 pgs.
"U.S. Appl. No. 14/500,010, Response filed Jan. 26, 2016 to Final Office Action dated Oct. 26, 2015", 9 pgs.
"U.S. Appl. No. 14/500,010, Response filed May 29, 2015 to Restriction Requirement dated Mar. 5, 2015", 11 pgs.
"U.S. Appl. No. 14/500,010, Response filed Oct. 9, 2015 to Non Final Office Action dated Jun. 9, 2015", 13 pgs.
"U.S. Appl. No. 14/500,010, Restriction Requirement dated Mar. 5, 2015", 8 pgs.
"English translation of EP 876798", (Jun. 3, 2015), 6 pgs.
"European Application Serial No. 14716195.4, Response filed May 16, 2016 to Communication pursuant to Rules 161(1) and 162 EPC dated Nov. 5, 2015", 10 pgs.
"International Application Serial No. PCT/US2012/044920, International Search Report dated Sep. 25, 2012", 3 pgs.
"International Application Serial No. PCT/US2012/044920, Written Opinion dated Sep. 25, 2012", 8 pgs.
"International Application Serial No. PCT/US2014/028903, International Preliminary Report on Patentability dated Sep. 24, 2015", 7 pgs.
"International Application Serial No. PCT/US2014/028903, International Search Report dated Jun. 30, 2014", 3 pgs.
"International Application Serial No. PCT/US2014/028903, Written Opinion dated Jun. 30, 2014".
"International Application Serial No. PCT/US2015/019976, International Search Report dated Nov. 17, 2015", 7 pgs.

(56) References Cited

OTHER PUBLICATIONS

"International Application Serial No. PCT/US2015/019976, Invitation to Pay Additional Fees and Partial Search Report dated Sep. 7, 2015", 6 pgs.
"International Application Serial No. PCT/US2015/019976, Written Opinion dated Nov. 17, 2015", 10 pgs.
"Locking Mechanism to Secure the Ends of an Implantable Braid", Patentability Search Report, (dated Feb. 5, 2011).

* cited by examiner

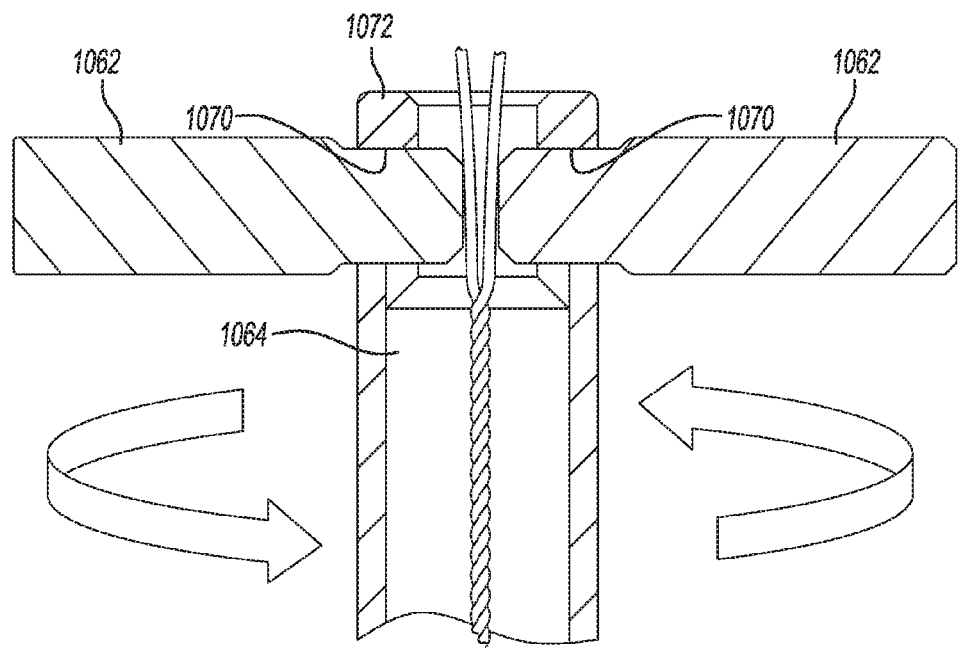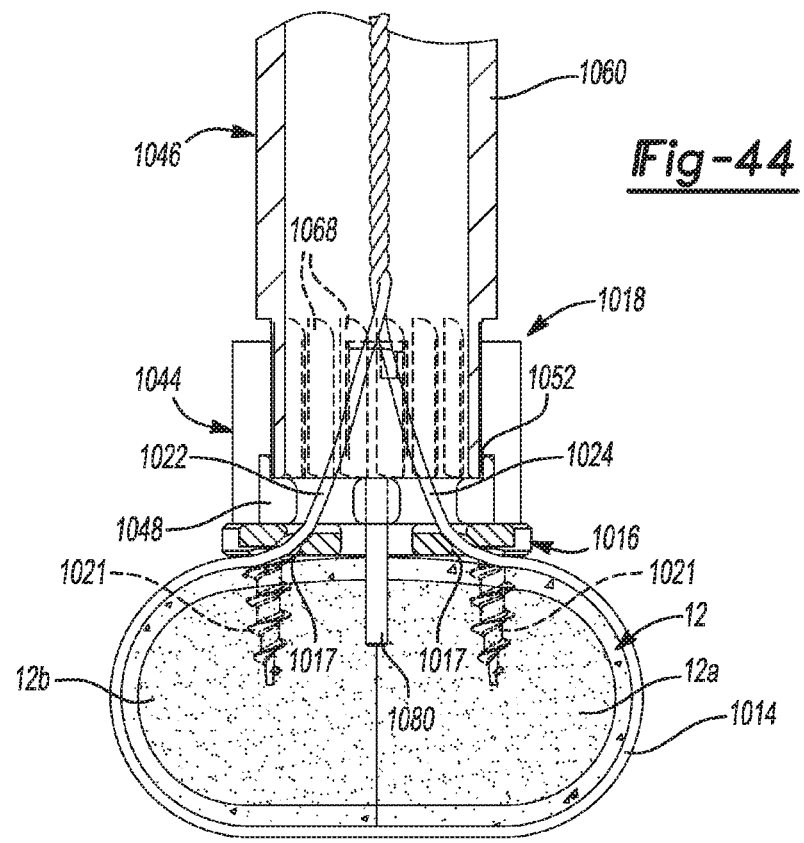
Fig-44

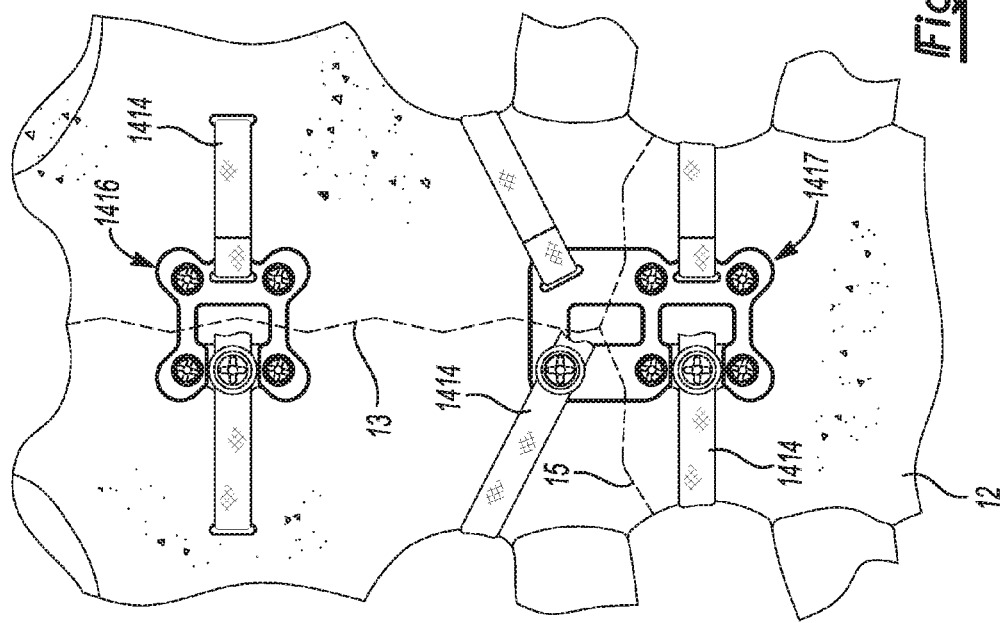
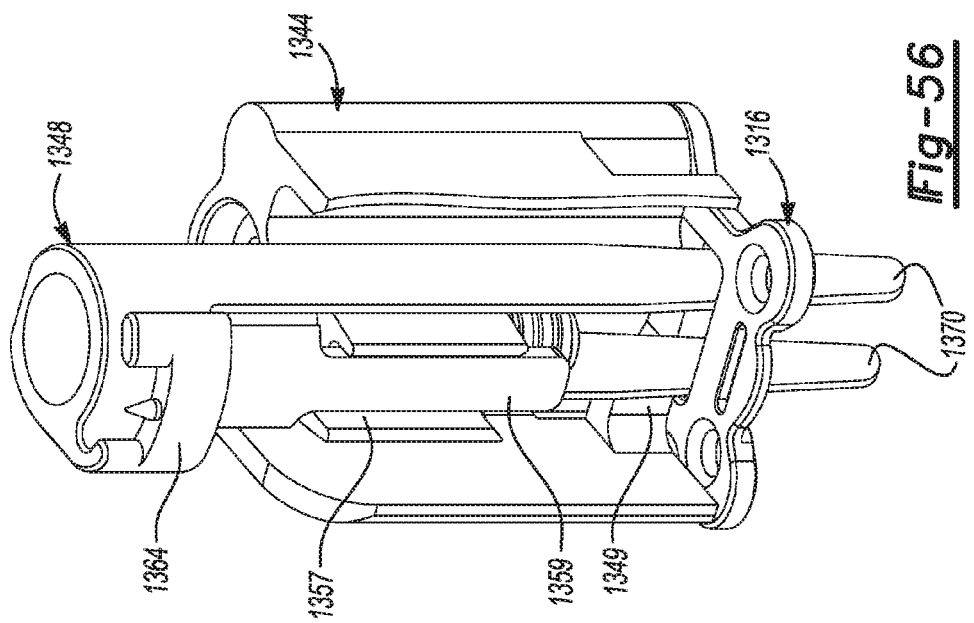

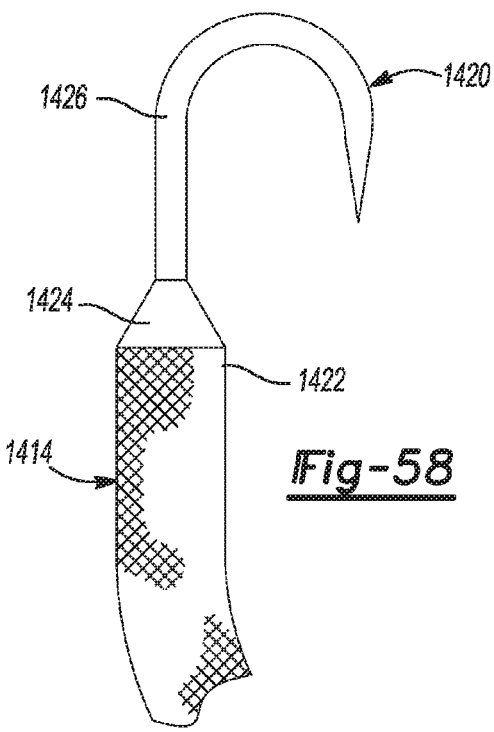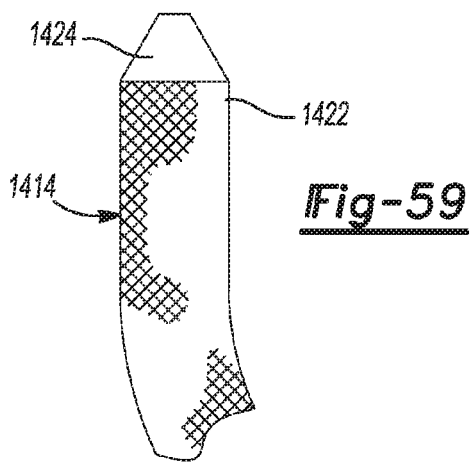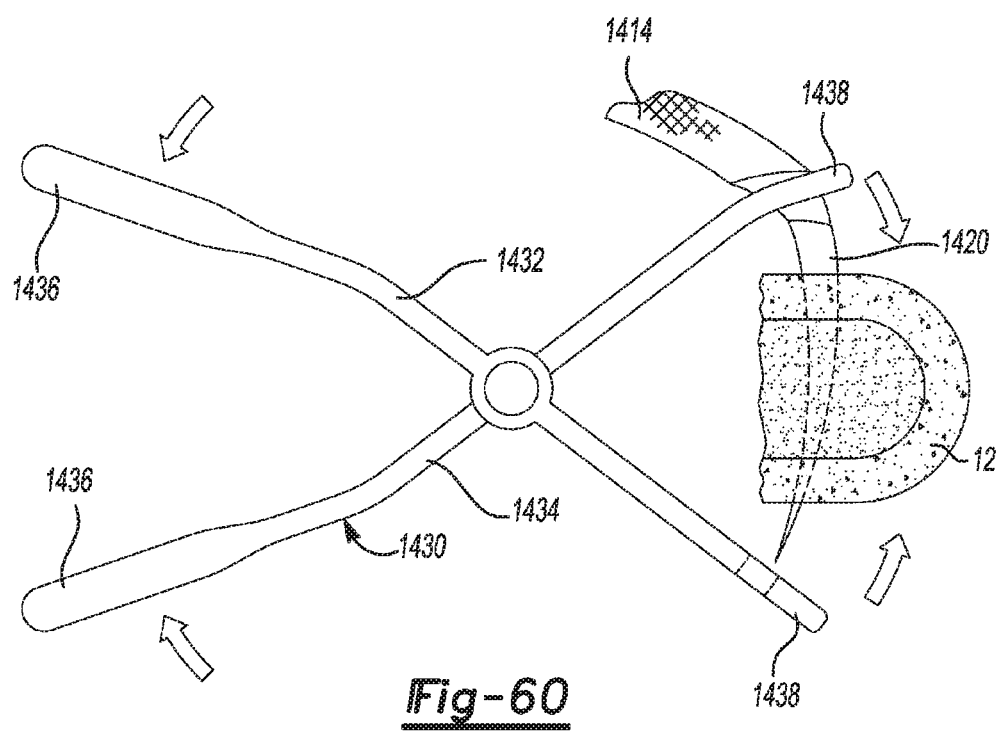

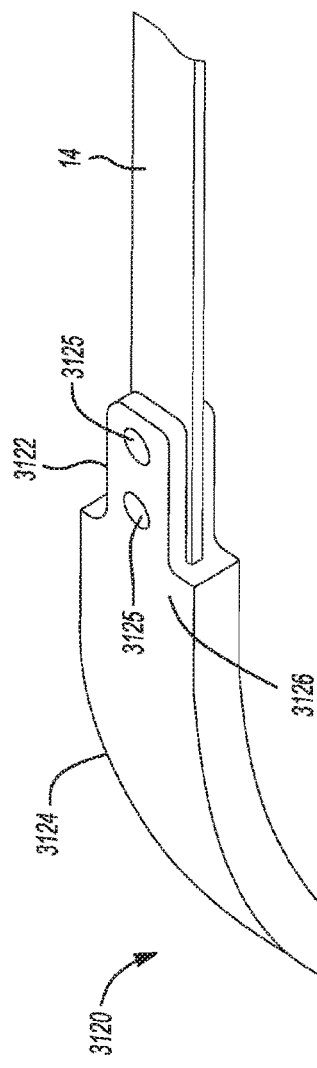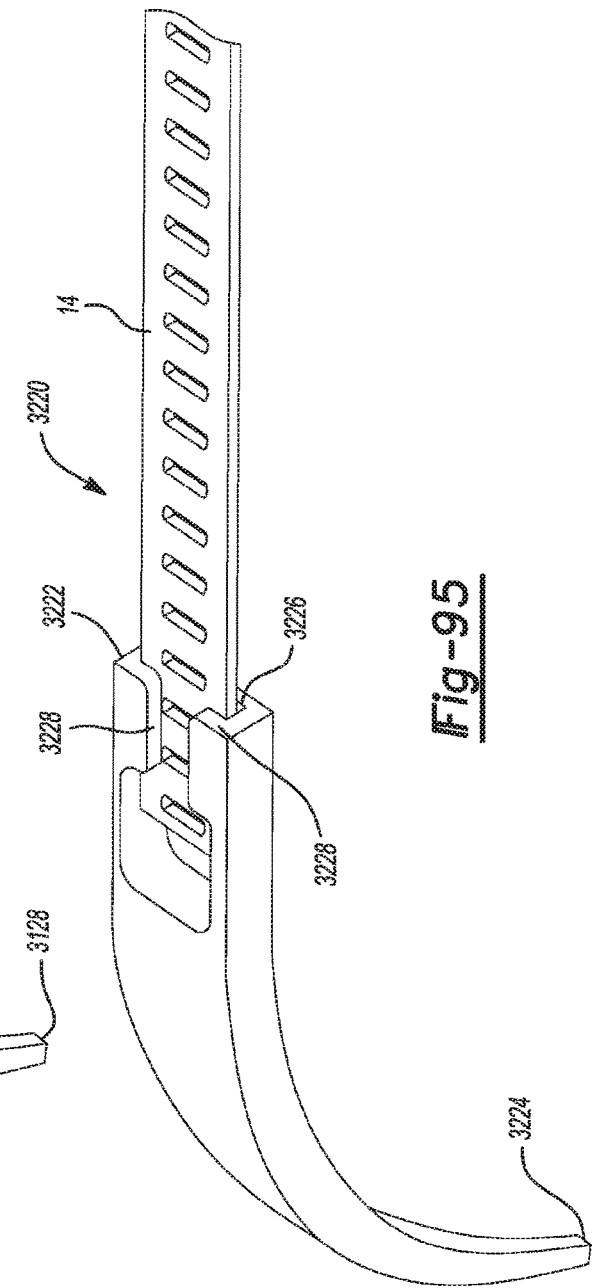

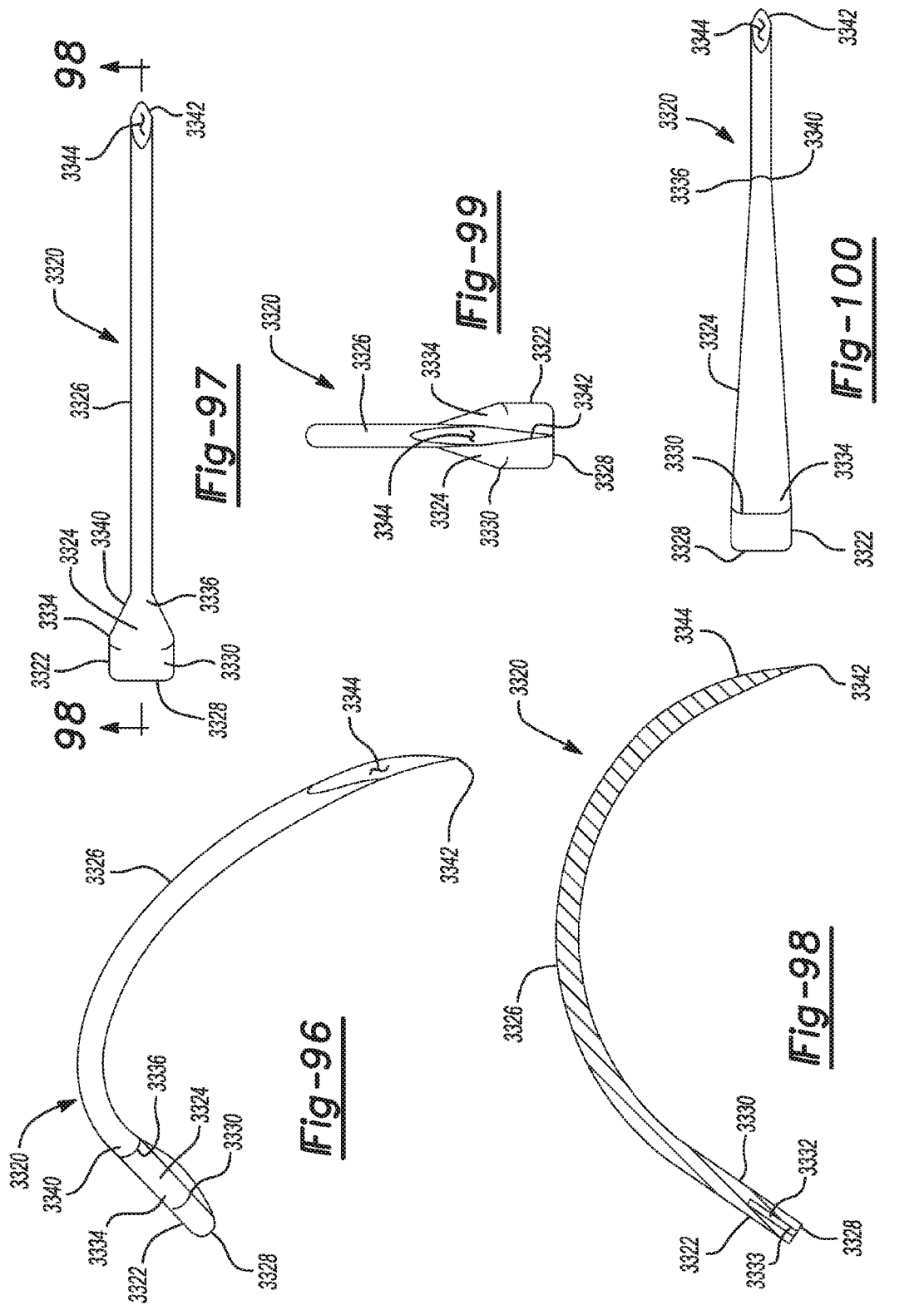

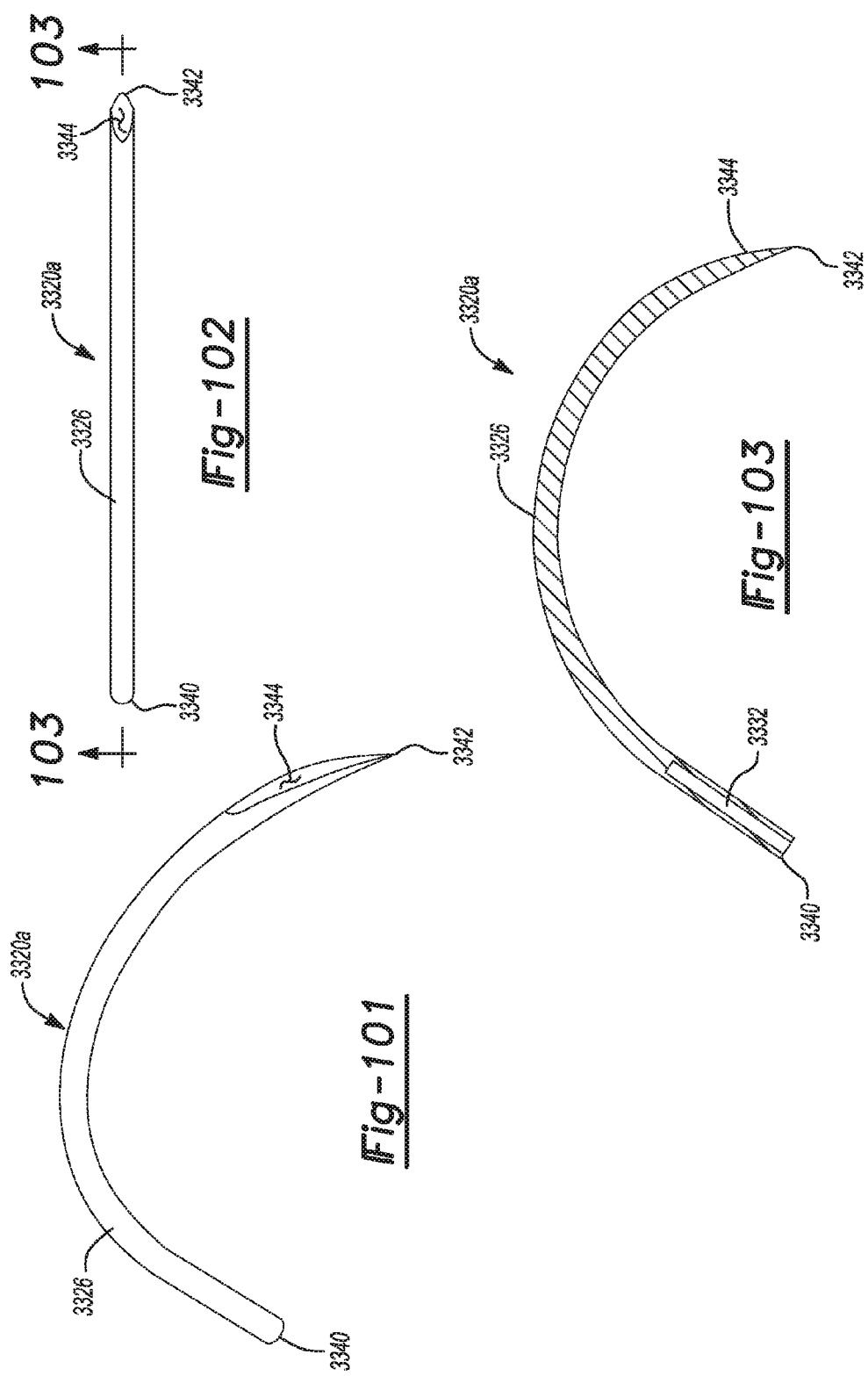

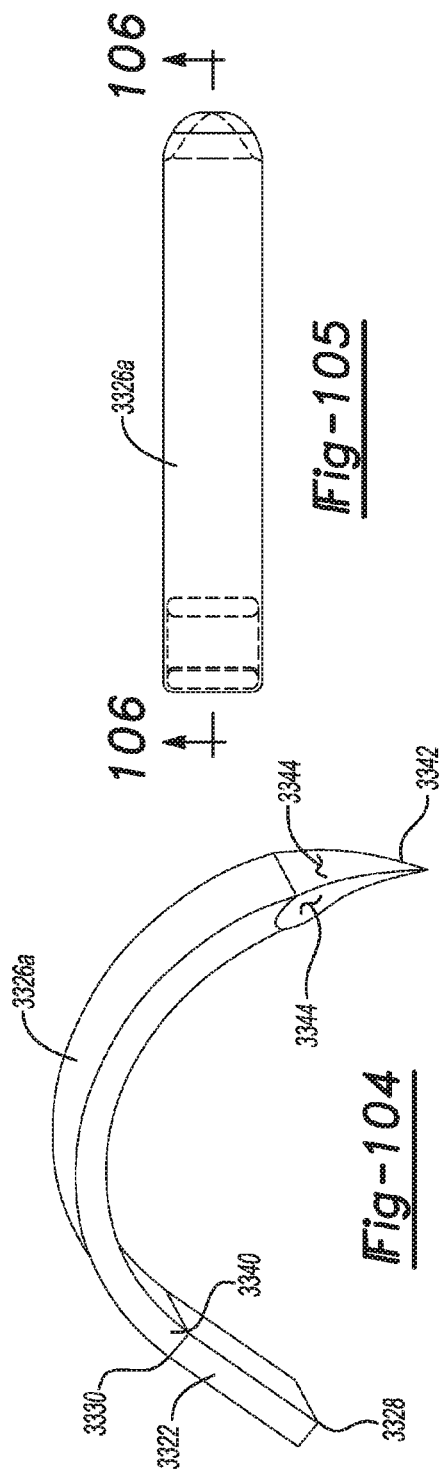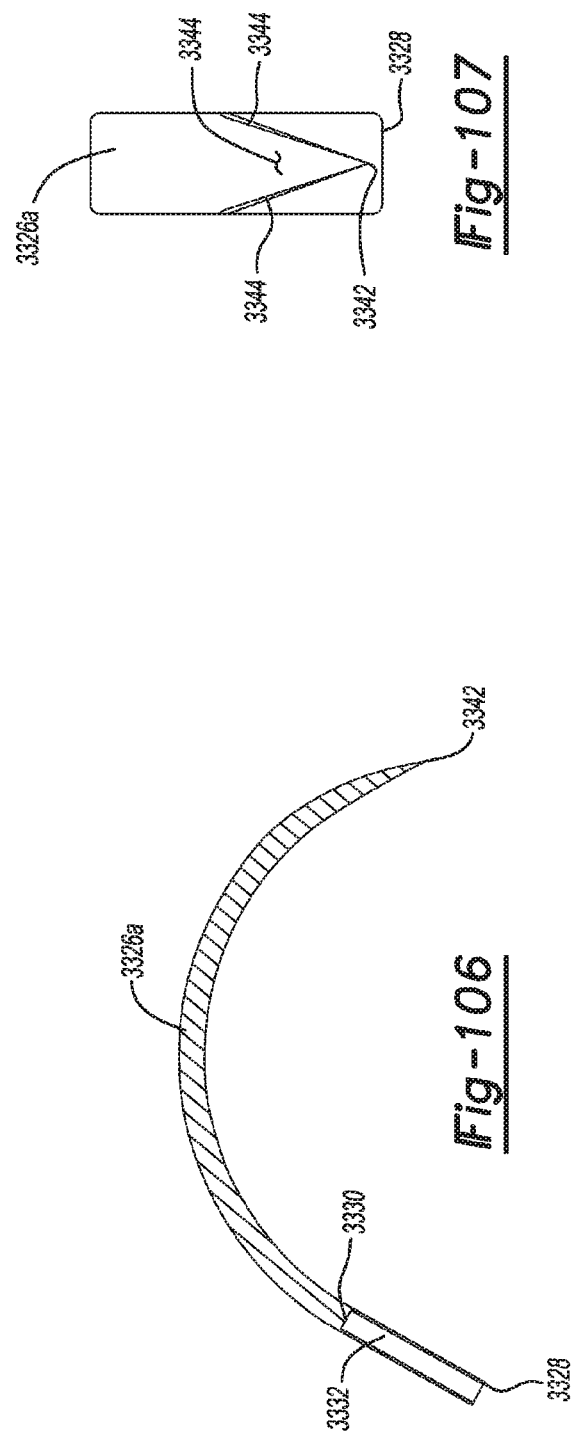

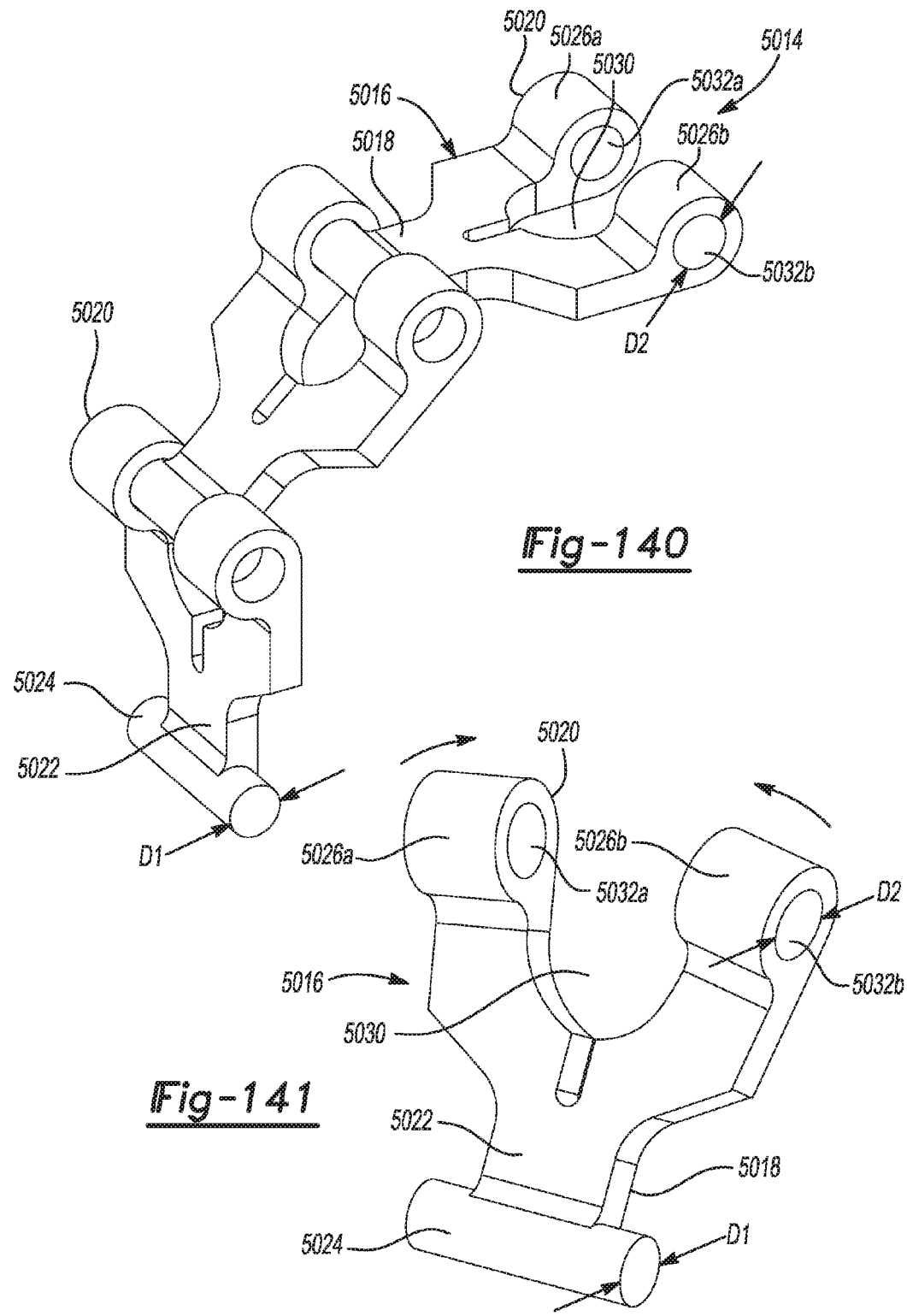

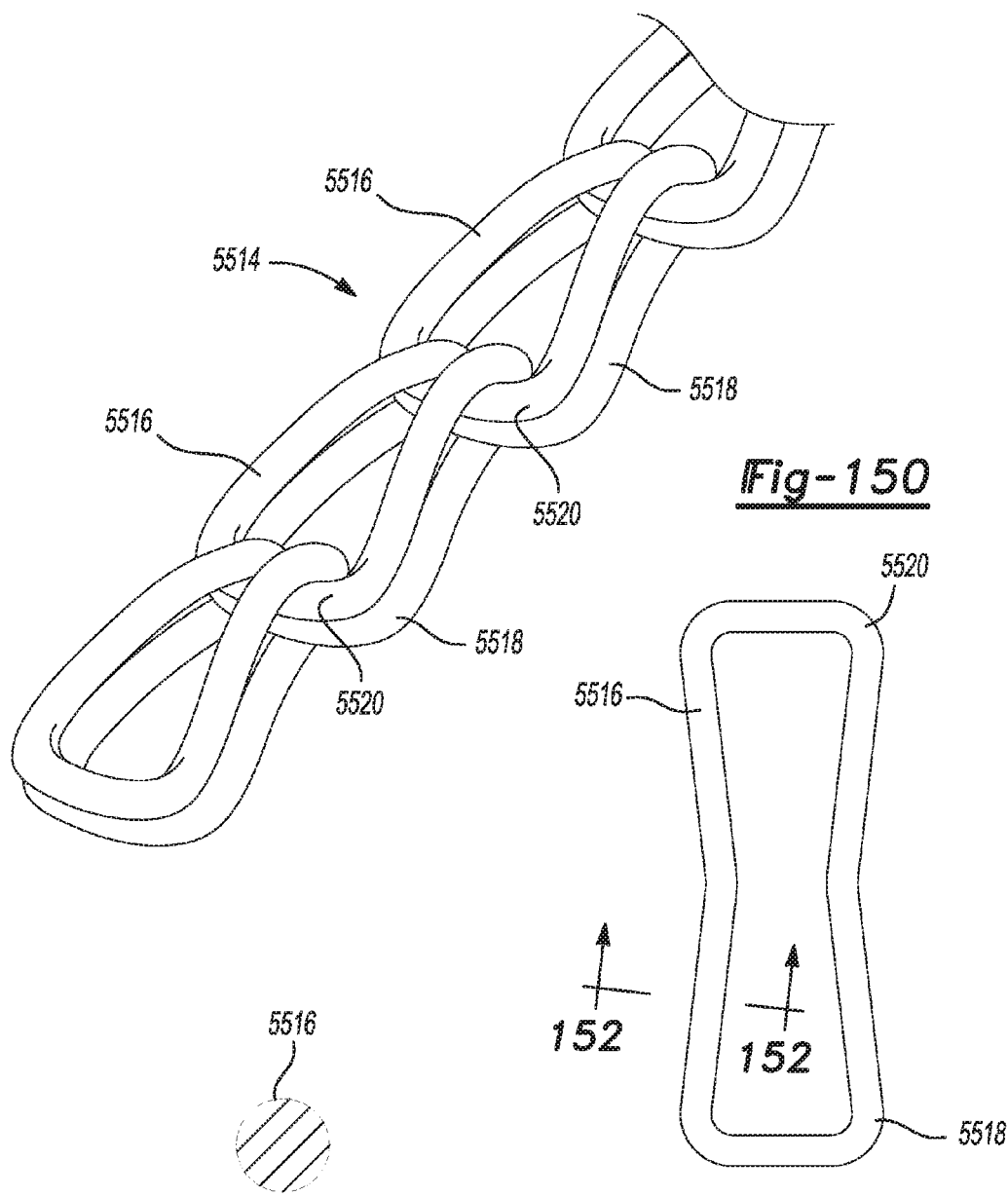

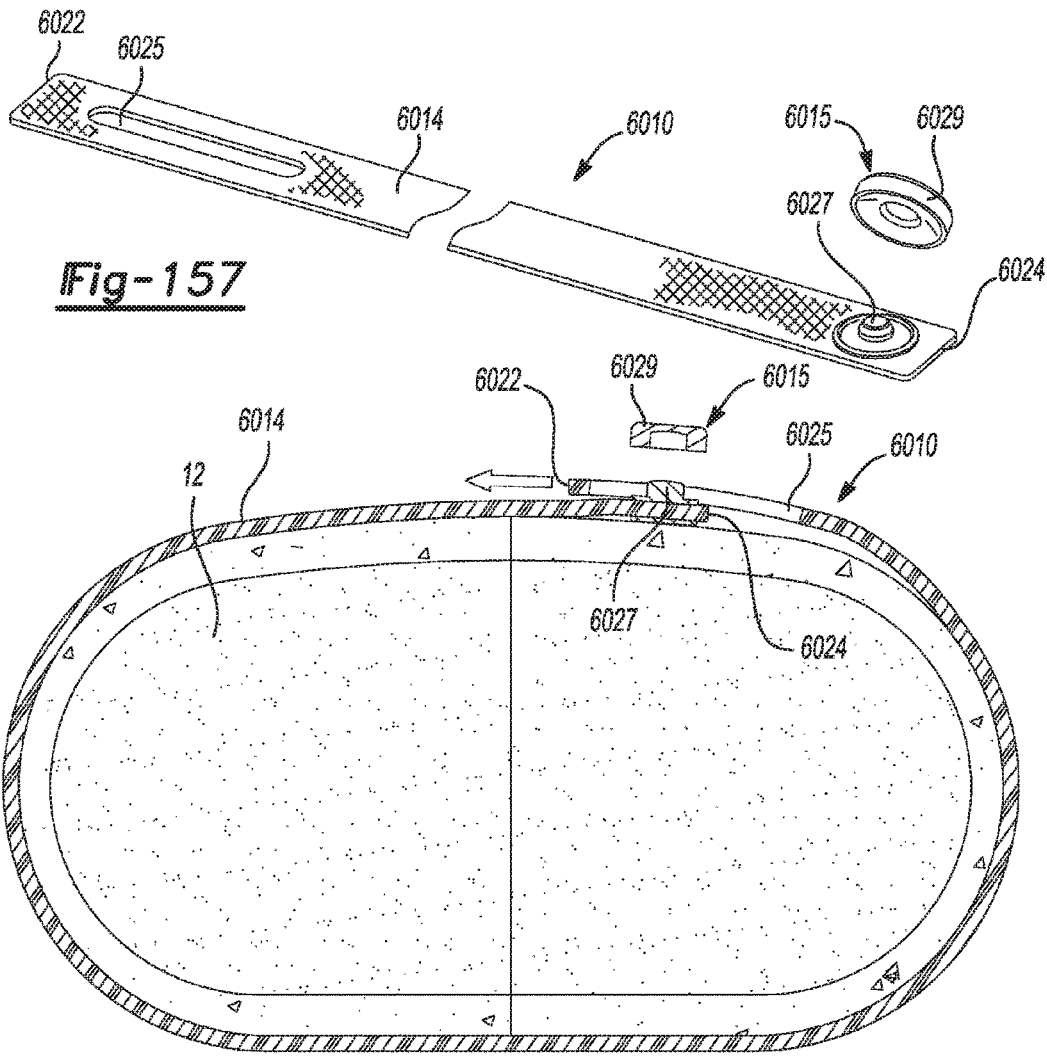
Fig-157
Fig-158
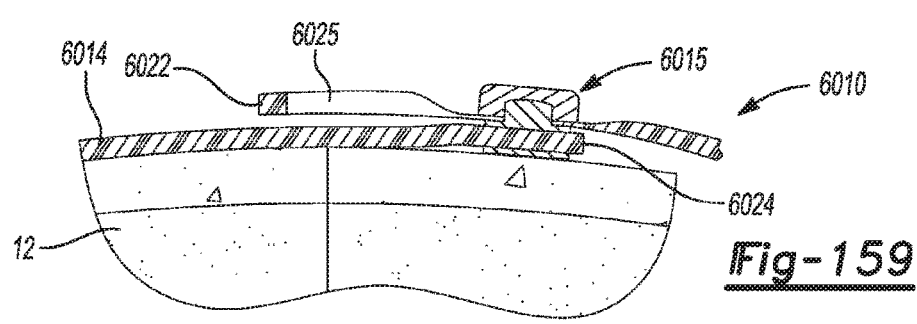
Fig-159

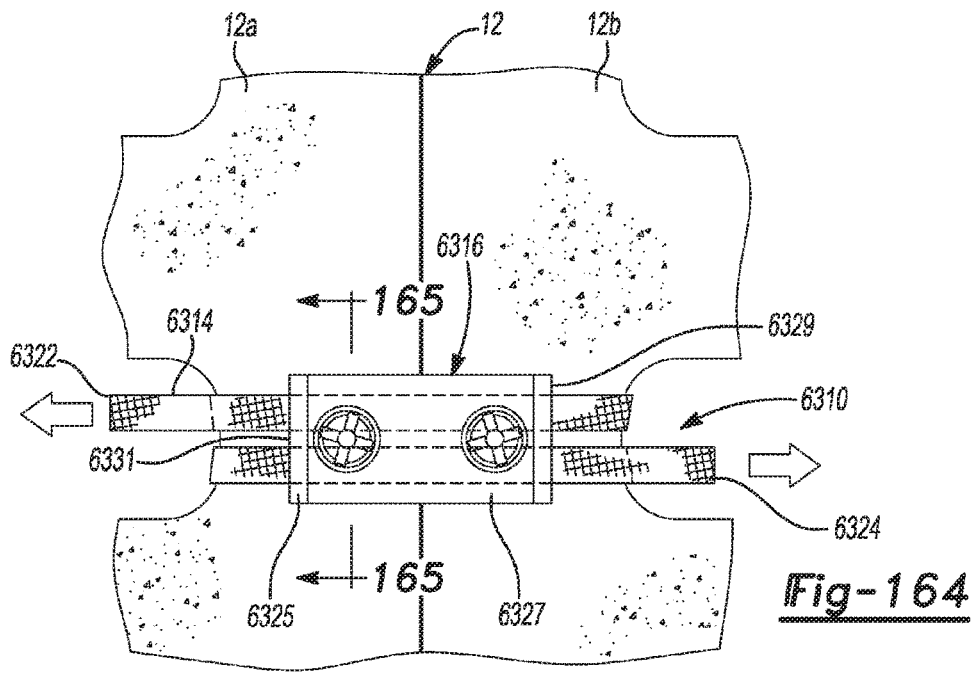
Fig-164
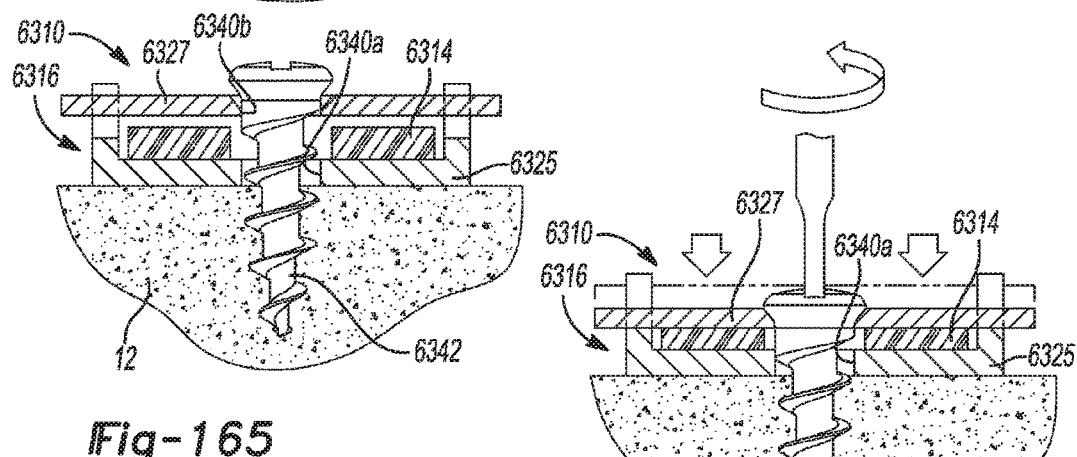
Fig-165
Fig-166
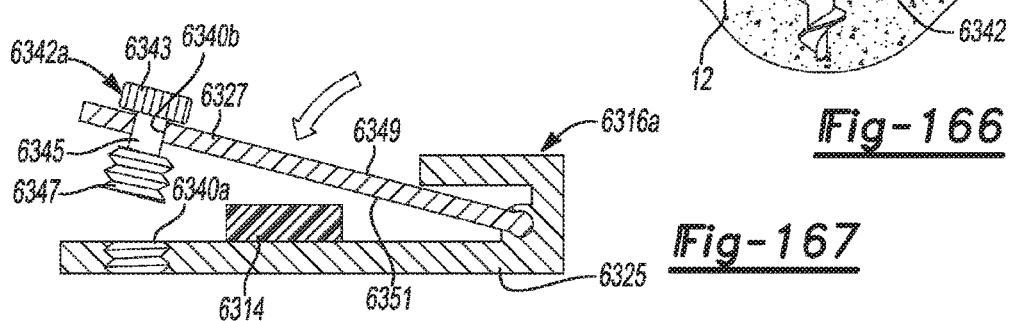
Fig-167

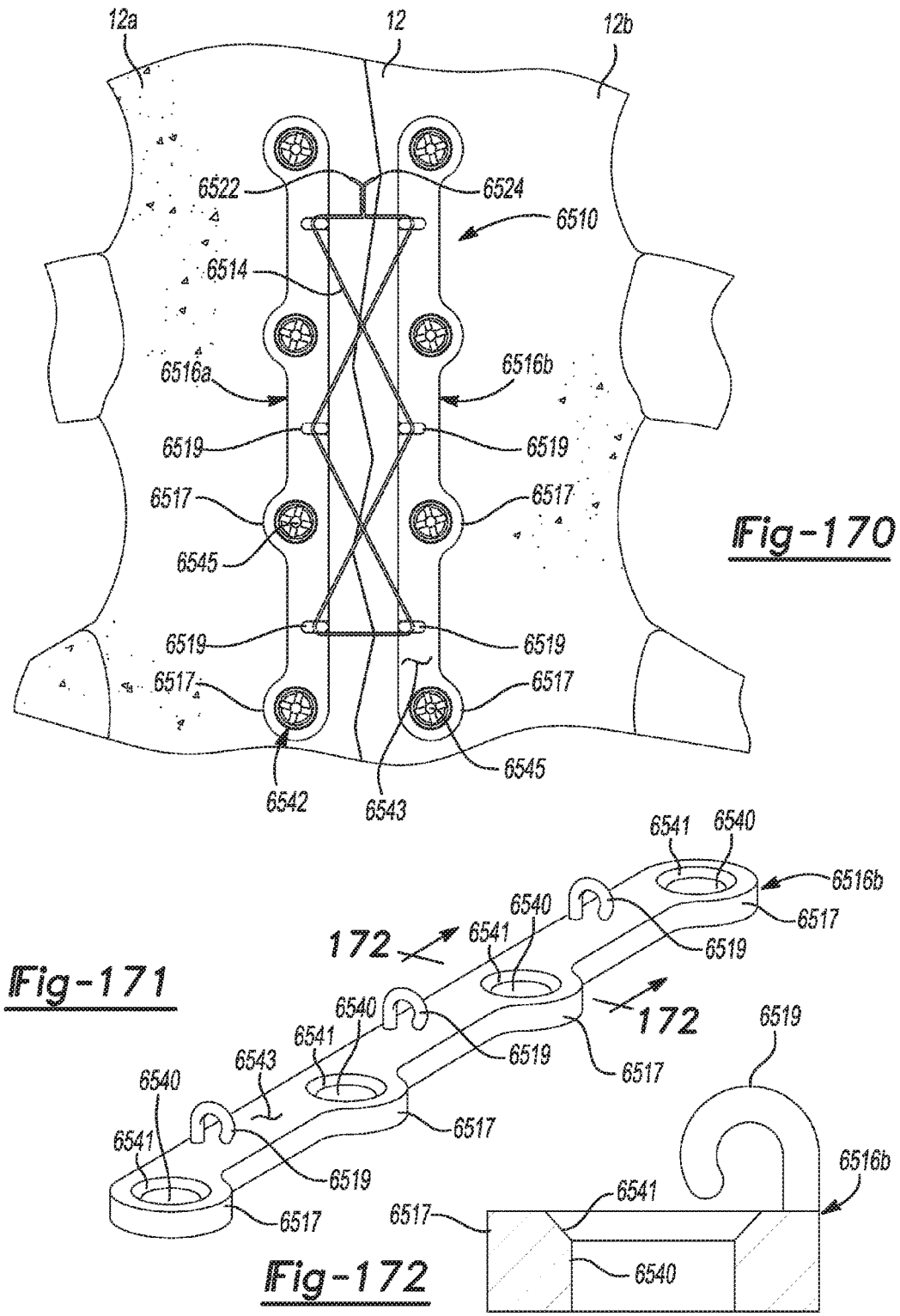

STERNAL CLOSURE CERCLAGE, PLATE IMPLANT AND INSTRUMENTATION

CROSS-REFERENCE TO RELATED APPLICATIONS

This application is a Continuation-in-Part of U.S. application Ser. No. 15/174,041, filed Jun. 6, 2016, which application is a continuation of U.S. application Ser. No. 14/500,010, filed Sep. 29, 2014, now issued on Jun. 7, 2016 as U.S. Pat. No. 9,358,054, which application is a continuation of International Application No. PCT/US2014/028903, filed Mar. 14, 2014, which application claims the benefit of priority to U.S. Provisional Application No. 61/794,648 filed on Mar. 15, 2013, U.S. Provisional Application No. 61/794,518 filed on Mar. 15, 2013 and U.S. Provisional Application No. 61/794,290 filed on Mar. 15, 2013.

This application is a Continuation-in-Part of U.S. application Ser. No. 15/174,783, filed Jun. 6, 2016, which application is a continuation of U.S. application Ser. No. 14/500,010, filed Sep. 29, 2014, now issued on Jun. 7, 2016 as U.S. Pat. No. 9,358,054, which application is a continuation of International Application No. PCT/US2014/028903, filed Mar. 14, 2014, which application claims the benefit of priority to U.S. Provisional Application No. 61/794,648 filed on Mar. 15, 2013, U.S. Provisional Application No. 61/794,518 filed on Mar. 15, 2013 and U.S. Provisional Application No. 61/794,290 filed on Mar. 15, 2013.

The entire disclosure of each of the above applications is incorporated herein by reference.

BACKGROUND

Surgeries are often performed on humans and animals to treat disease or injury. Such surgeries can result in the surgeon having to repair a separated, cut or fractured bone. In the case of an injury, the surgeon may need to immobilize and fix two or more bone portions together to allow the bone to heal over time. Treating certain diseases, such as heart disease, for example, often requires the surgeon to cut a patient's sternum to gain access to and perform a procedure on the patient's heart. Once the heart procedure is complete, the cut sternum may be repaired by immobilizing and joining the separate portions of the sternum together to allow the sternum to heal over time. It is often desirable to apply a compressive force urging the bone portions together to facilitate healing of the bone.

OVERVIEW

To better illustrate the instrument disclosed herein, a non-limiting list of examples is provided here:

In Example 1, a bone punch apparatus can include a support arm having a support arm proximal portion and a support arm distal portion, a pivot arm having a pivot arm proximal portion and a pivot arm distal portion, the pivot arm distal portion pivotably coupled to the support arm distal portion, and an arcuate punch that can be configured to punch through bone, the arcuate punch coupled to the pivot arm distal portion, and optionally configured such that the pivot arm proximal portion moves away from the support arm proximal portion so as to extend the arcuate punch into a punch position.

In Example 2, the bone punch apparatus of Example 1, is optionally configured such that the pivot arm proximal portion is configured to be moved toward the support arm proximal portion to retract the arcuate punch into a retracted position.

In Example 3, the bone punch apparatus of Example 1, is optionally configured such that the pivot arm pivots about a pivot point positioned at the support arm distal portion at a center of curvature of the arcuate punch.

In Example 4, the bone punch apparatus of Example 1, can optionally include a protrusion extending from the support arm distal portion and configured to receive a bone piercing tip of the arcuate punch when in the punch position.

In Example 5, the bone punch apparatus of Example 4, can optionally include a housing coupled to the support arm distal portion, the housing and the protrusion together defining a receptacle configured to receive a bone portion.

In Example 6, the bone punch apparatus of Example 5, is optionally configured such that the receptacle is a u-shaped receptacle configured to receive a portion of a sternum.

In Example 7, the bone punch apparatus of Example 1, is optionally configured such that the arcuate punch is configured to form an arcuate hole through a bone portion.

In Example 8, the bone punch apparatus of Example 1, can optionally include a locking member configured to urge the pivot arm proximal portion toward the support arm proximal portion.

In Example 9, a bone punch apparatus can include a support arm having a support arm proximal portion, a support arm distal portion, and a support arm alignment guide, a pivot arm having a pivot arm proximal portion and a pivot arm distal portion, the pivot arm distal portion pivotably coupled to the support arm distal portion, and an arcuate punch configured to punch through bone, the arcuate punch coupled to the pivot arm distal portion, is optionally configured such that the support arm alignment guide is configured to indicate an orientation of the arcuate punch.

In Example 10, the bone punch apparatus of Example 9, is optionally configured such that the pivot arm proximal portion is configured to be moved away from the support arm proximal portion to extend the arcuate punch into a punch position, and the pivot arm proximal portion is configured to be moved toward the support arm proximal portion to retract the arcuate punch into a retracted position.

In Example 11, the bone punch apparatus of Example 9, is optionally configured such that the support arm alignment guide includes a window.

In Example 12, the bone punch apparatus of Example 11, is optionally configured such that a width of the window corresponds to a width of the arcuate punch.

In Example 13, the bone punch apparatus of Example 9, is optionally configured such that the support arm alignment guide is configured to align with a completed punch hole.

In Example 14, the bone punch apparatus of Example 9, is optionally configured such that the pivot arm includes a pivot arm alignment guide configured to indicate an orientation of the arcuate punch.

In Example 15, a system can include a bone punch tool configured to form an arcuate hole through a bone, the bone punch tool can include a support arm having a support arm proximal portion and a support arm distal portion, a pivot arm having a pivot arm proximal portion and a pivot arm distal portion, the pivot arm distal portion pivotably coupled to the support arm distal portion, and an arcuate punch configured to punch through the bone, the arcuate punch coupled to the pivot arm distal portion, is optionally configured such that the pivot arm proximal portion is configured to be moved away from the support arm proximal portion to extend the arcuate punch into a punch position, and a needle guide configured to guide a needle through the arcuate hole.

In Example 16, the system of Example 15, is optionally configured such that the arcuate punch is dimensioned to form the arcuate hole with geometry corresponding to an arcuate geometry of the needle.

In Example 17, the system of Example 16, is optionally configured such that the needle guide includes a handle, an arcuate portion coupled to the handle, the arcuate portion configured to be inserted into the arcuate hole, and a grasping portion at an end of the arcuate portion, the grasping portion configured to grasp a tip of the needle.

In Example 18, the system of Example 17, is optionally configured such that the grasping portion includes a slot formed in the arcuate portion.

In Example 17, the system of Example 18, is optionally configured such that the grasping portion includes an aperture and at least one slot intersecting the aperture, such that the end of the arcuate portion is configured to expand with receipt of the needle within the aperture.

In Example 20, the system of Example 17, is optionally configured such that the arcuate portion is configured to be removed from the arcuate hole while grasping the needle, such that the needle guide is configured to guide the needle through the arcuate hole.

In Example 21, the apparatus or system of any one or any combination of Examples 1-20 can optionally be configured such that multiple or all elements or options recited are available to use or select from.

These and other examples and features of the present devices, systems, and methods will be set forth in part in the following Detailed Description. This overview is intended to provide a summary of subject matter of the present patent application. It is not intended to provide an exclusive or exhaustive description of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

FIG. 44 is a cross-sectional view of the tensioning device and closure device of FIG. 40 attached to a sternum.

FIG. 56 is a perspective view of an exemplary configuration of the closure device and tensioning device of FIG. 53.

FIG. 57 is a perspective view of multiple closure devices attached to a sternum.

FIG. 58 is a partial plan view of a band and needle according to the principles of the present disclosure.

FIG. 59 is a partial plan view of the band of FIG. 58.

FIG. 60 is a partially cross-sectioned view of a needle passer passing the band and needle of FIG. 58 through a sternum.

FIG. 94 is a perspective view of a needle operatively connected to a band of a closure device according to the principles of the present disclosure.

FIG. 95 is a perspective view of another configuration of a needle operatively connected to a band of a closure device according to the principles of the present disclosure.

FIG. 96 is a perspective view of another configuration of a needle of a closure device according to the principles of the present disclosure.

FIG. 97 is a top view of the needle of FIG. 96.

FIG. 98 is a cross-sectional view of the needle of FIG. 96, taken along the line 98-98 of FIG. 97.

FIG. 99 is an end view of the needle of FIG. 96.

FIG. 100 is a bottom view of the needle of FIG. 96.

FIG. 101 is a perspective view of another configuration of a needle of a closure device according to the principles of the present disclosure.

FIG. 102 is a top view of the needle of FIG. 101.

FIG. 103 is a cross-sectional view of the needle of FIG. 101, taken along the line 103-103 of FIG. 102.

FIG. 104 is a perspective view of another configuration of a needle of a closure device according to the principles of the present disclosure.

FIG. 105 is a top view of the needle of FIG. 104.

FIG. 106 is a cross-sectional view of the needle of FIG. 104, taken along the line 106-106 of FIG. 105.

FIG. 107 is an end view of the needle of FIG. 104.

FIG. 118 is a partial cross-sectional view of the closure device of FIG. 117.

FIG. 119 is a perspective view of an anterior side of a sternum and ribs of a human body having another configuration of a closure device attached thereto according to the principles of the present disclosure.

FIG. 120 is a perspective view of a tensioning device and a link of another configuration of a closure device according to the principles of the present disclosure.

FIG. 121 is a cross-sectional view of the tensioning device and link taken through the line 120-120 of FIG. 120.

FIG. 122 is a top view of an anterior side of a sternum and ribs of a human body having another configuration of a closure device attached thereto according to the principles of the present disclosure.

FIG. 123 is a top view of a link member of the closure device of FIG. 122.

FIG. 124 is a perspective view of an anterior side of a sternum and ribs of a human body having another configuration of a closure device attached thereto according to the principles of the present disclosure.

FIG. 125 is a partial cross-sectional view of the closure device taken through the line 125-125 of FIG. 124.

FIG. 126 is a partial cross-sectional view of another configuration of a closure device according to the principles of the present disclosure.

FIG. 127 is a top view of a receiver of the closure device of FIG. 126.

FIG. 128 is a top view of another configuration of a receiver of the closure device of FIG. 126.

FIG. 129 is a perspective view of another configuration of a closure device according to the principles of the present disclosure.

Figure 130:
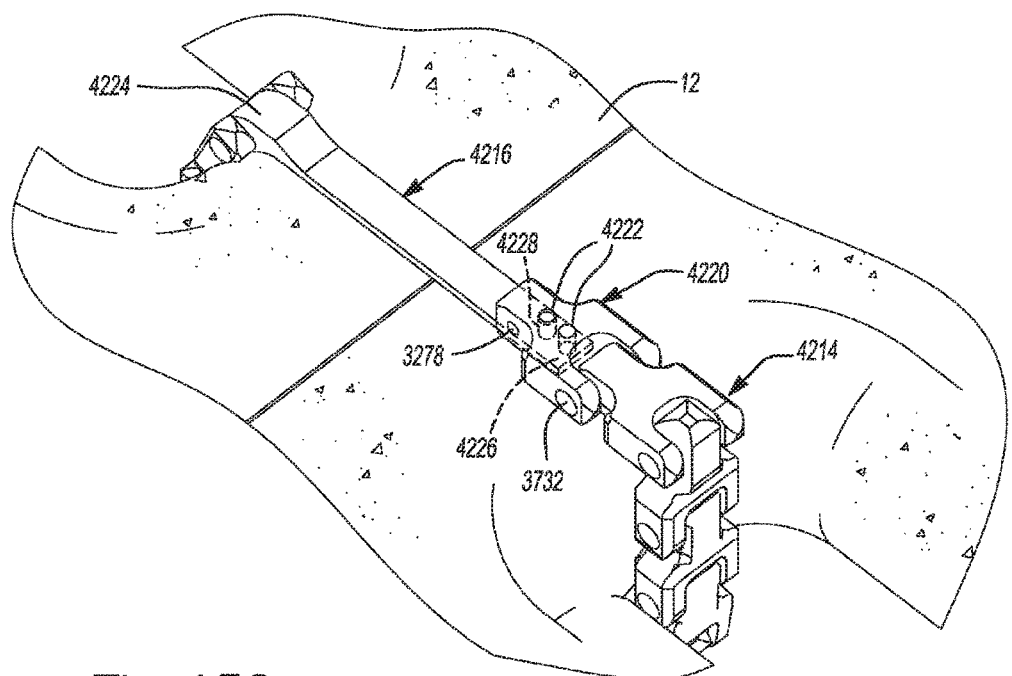

FIG. 130 is a perspective view of an anterior side of a sternum and ribs of a human body having another configuration of a closure device attached thereto according to the principles of the present disclosure.

Figure 130A:
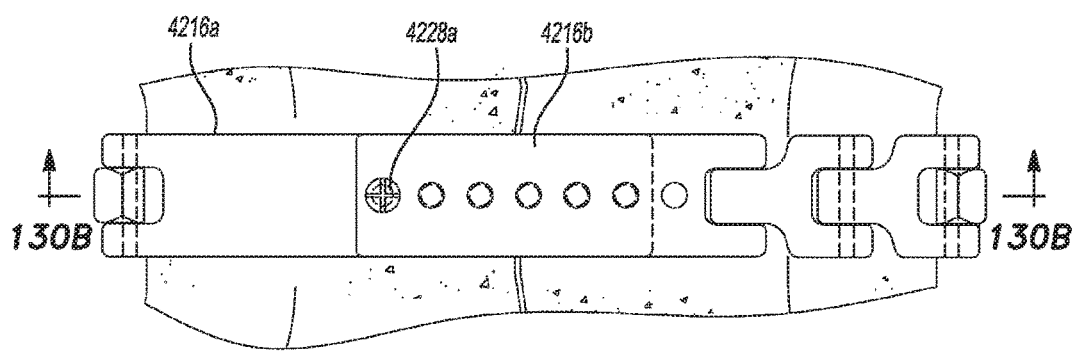

FIG. 130A is a top view of an anterior side of a sternum and ribs of a human body having another configuration of a closure device attached thereto according to the principles of the present disclosure.

Figure 130B:
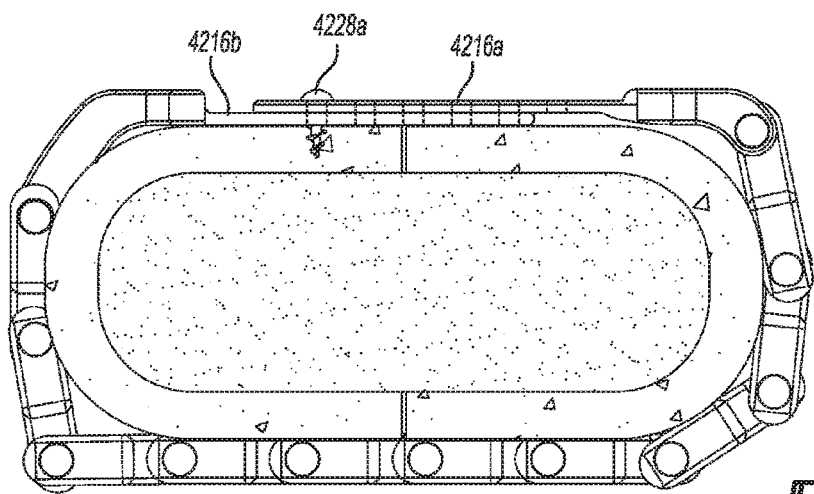

FIG. 130B is a cross-sectional view of the closure device taken through the line 130b-130b of FIG. 130a.

Figure 131:
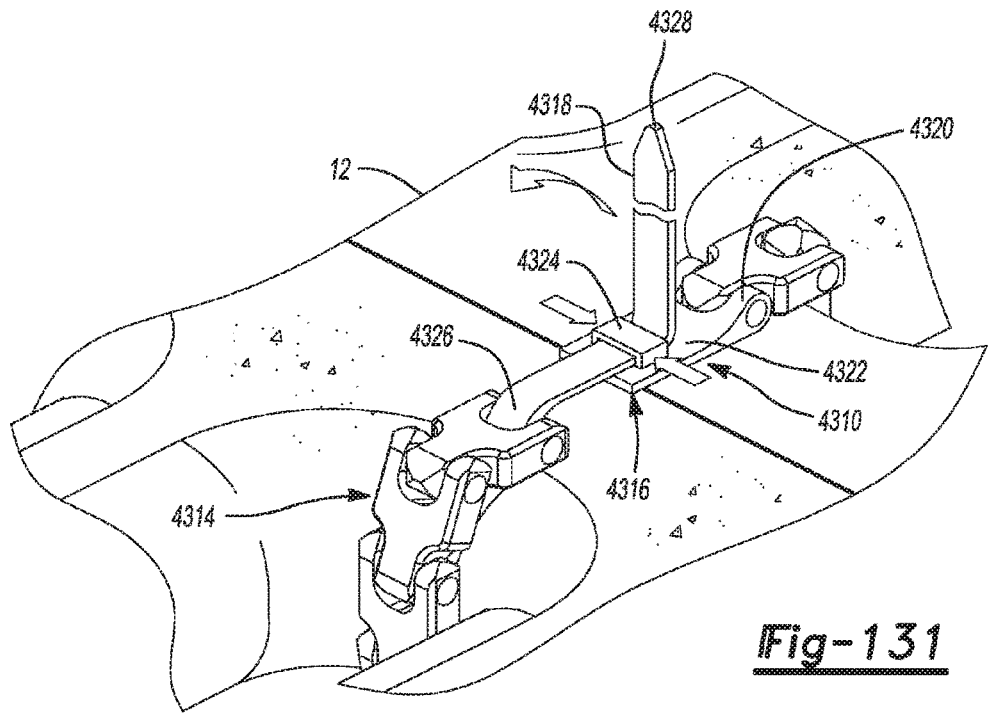

FIG. 131 is a perspective view of an anterior side of a sternum and ribs of a human body having another configuration of a closure device attached thereto according to the principles of the present disclosure.

Figure 132:
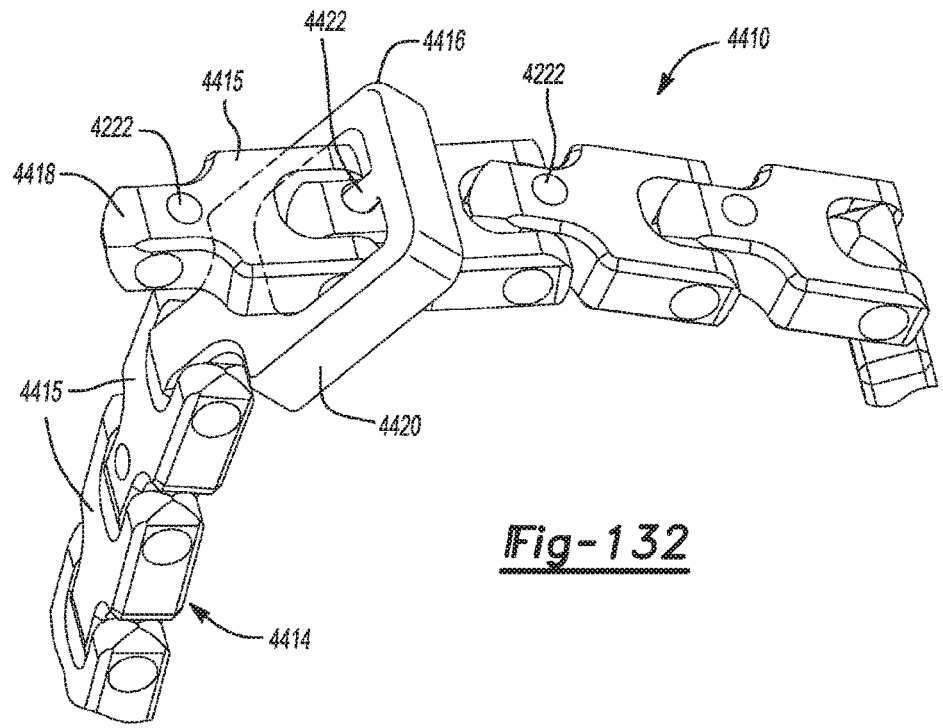

FIG. 132 is a perspective view of a portion of another configuration of a closure device according to the principles of the present disclosure.

Figure 133:
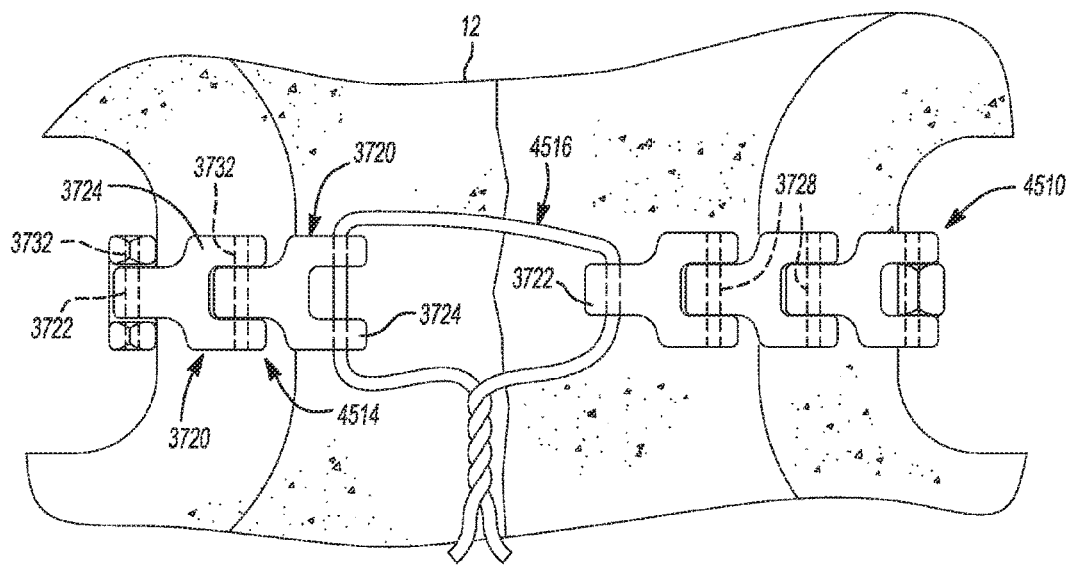

FIG. 133 is a top view of an anterior side of a sternum and ribs of a human body having another configuration of a closure device attached thereto according to the principles of the present disclosure.

Figure 134:
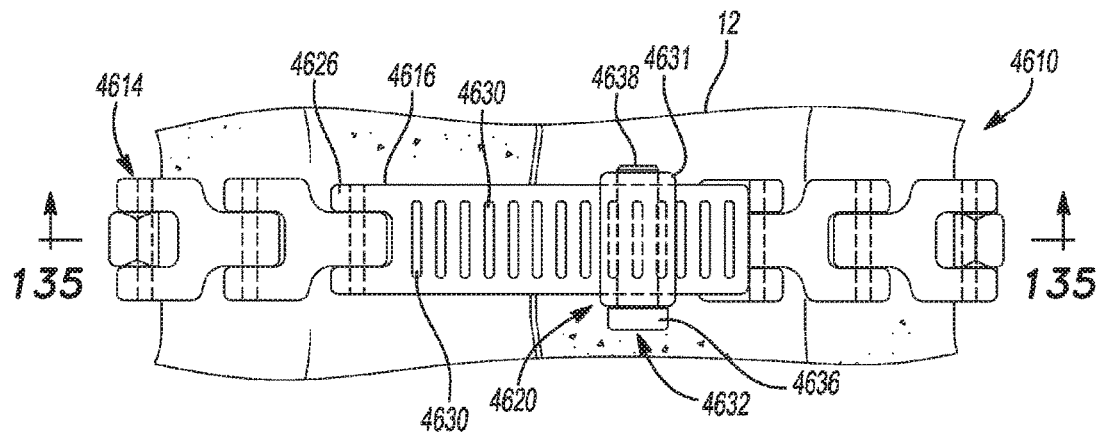

FIG. 134 is a top view of an anterior side of a sternum and ribs of a human body having another configuration of a closure device attached thereto according to the principles of the present disclosure.

Figure 135:
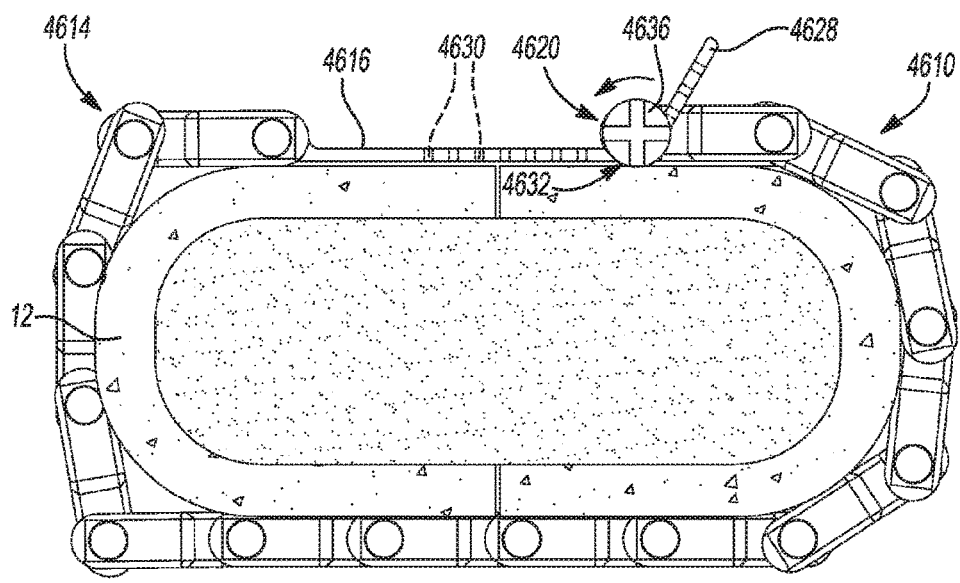

FIG. 135 is a cross-sectional view of the closure device taken through the line 135-135 of FIG. 134.

Figure 136:
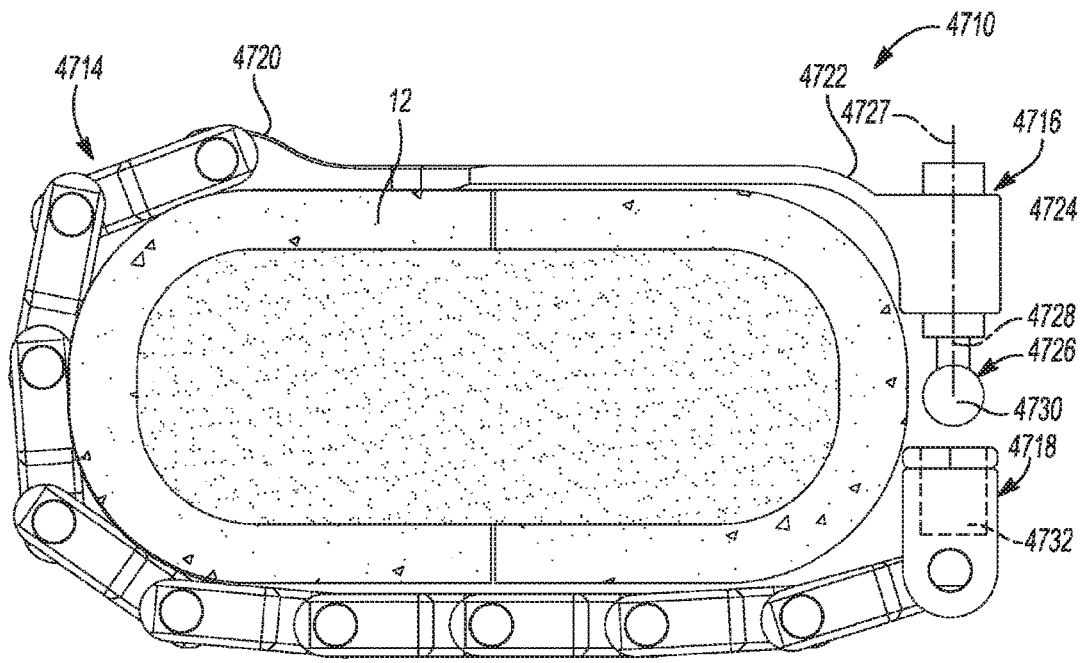

FIG. 136 is a cross-sectional view of a sternum and ribs of a human body having another configuration of a closure device attached thereto according to the principles of the present disclosure.

Figure 137:
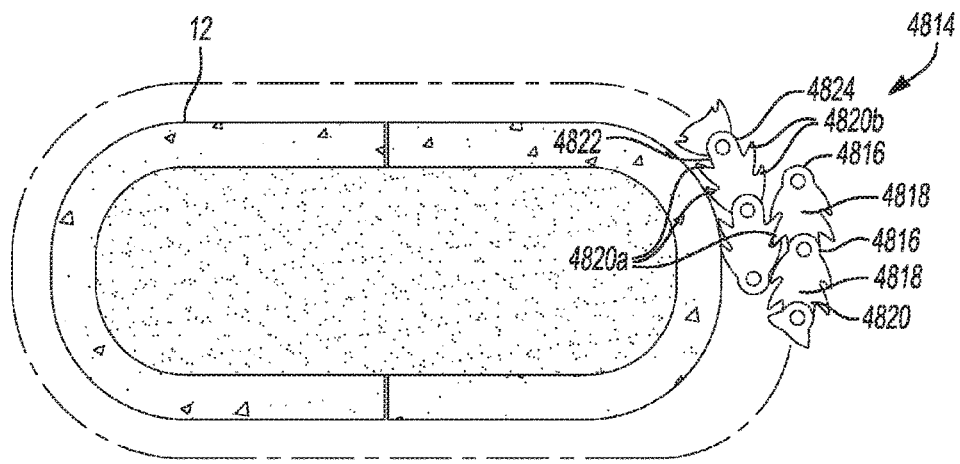

FIG. 137 is a cross-sectional view of a sternum and ribs of a human body having another configuration of a closure device attached thereto according to the principles of the present disclosure.

Figure 138:
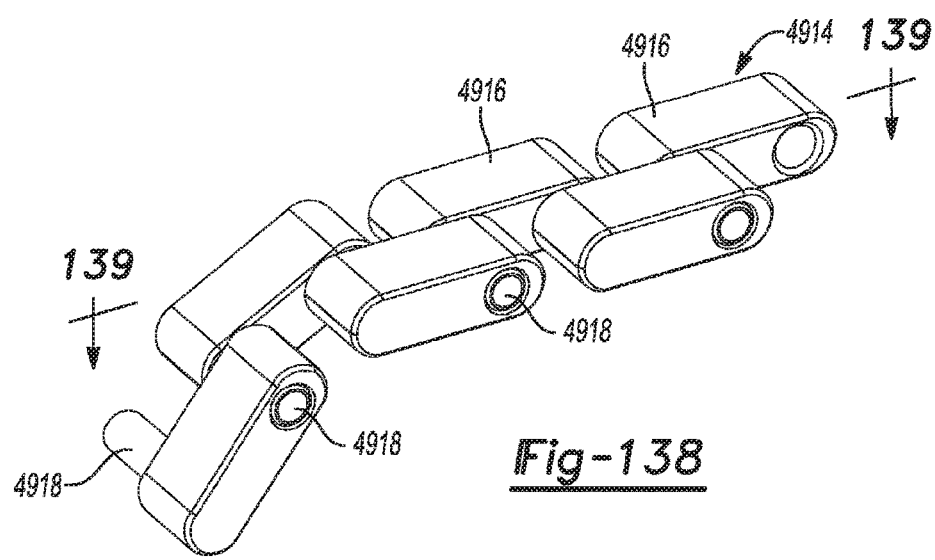

FIG. 138 is a perspective view of another configuration of a band of a closure device.

Figure 139:
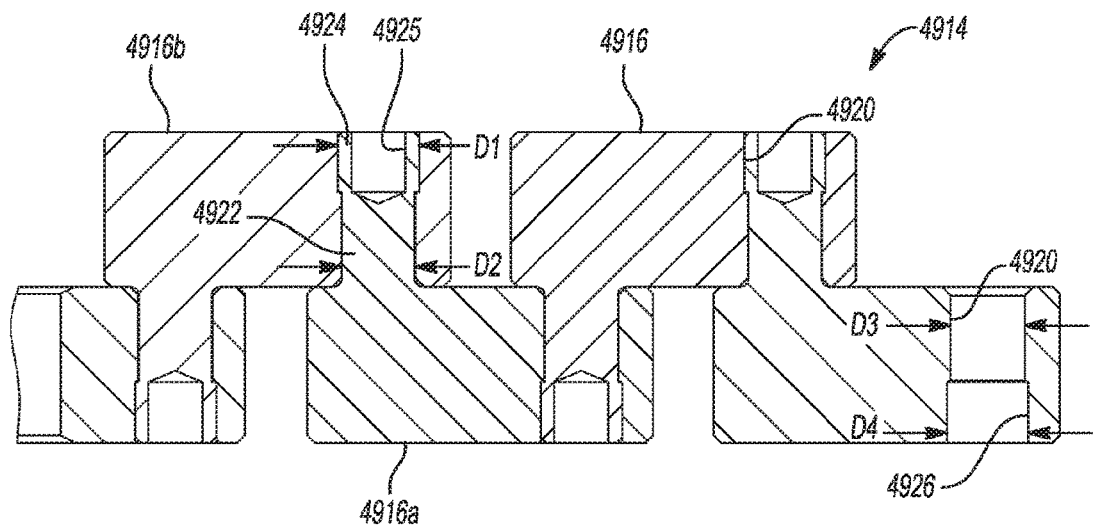

FIG. 139 is a cross-sectional view of the band taken through the line 139-139 of FIG. 138.

FIG. 140 is a perspective view of another configuration of a band of a closure device.

FIG. 141 is a perspective view of a link of the band of FIG. 140 in another configuration.

Figure 142:
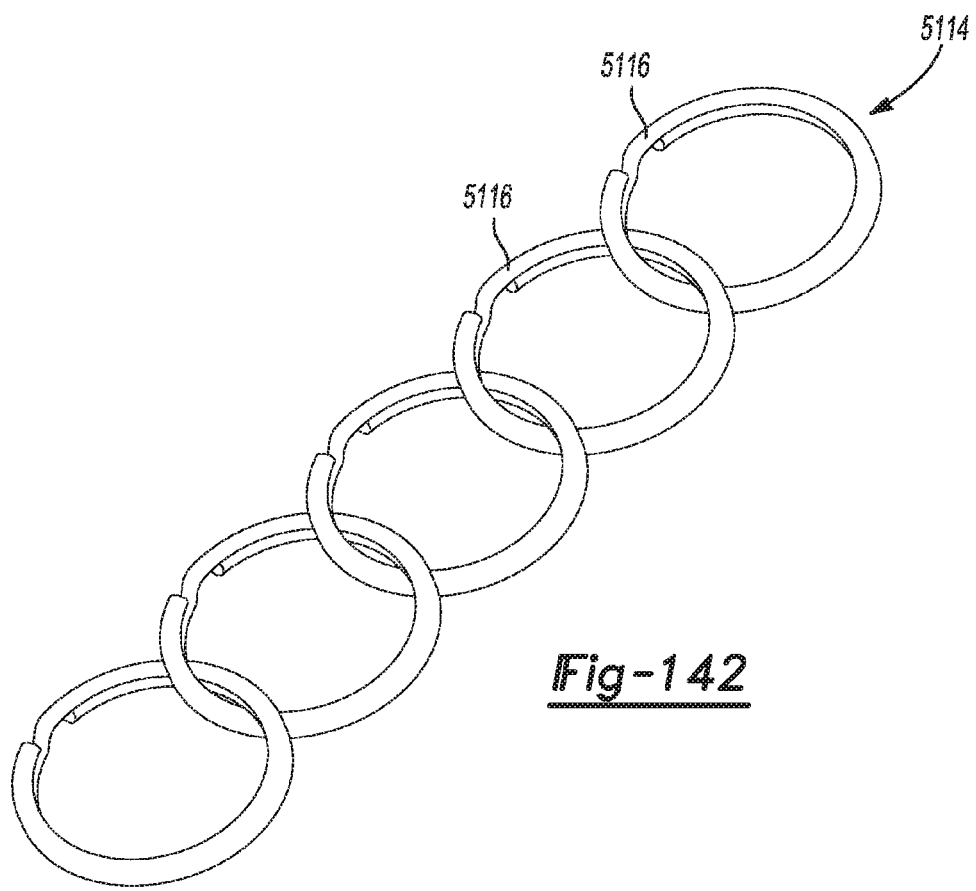

FIG. 142 is a perspective view of another configuration of a band and a link of a closure device.

Figure 143:
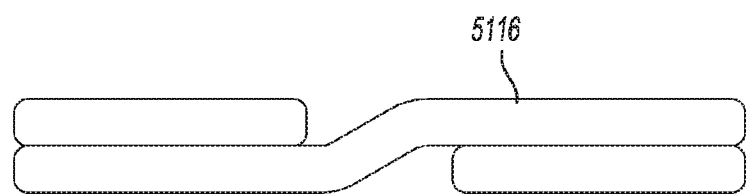

FIG. 143 is a bottom view of the link of FIG. 142.

Figure 144:
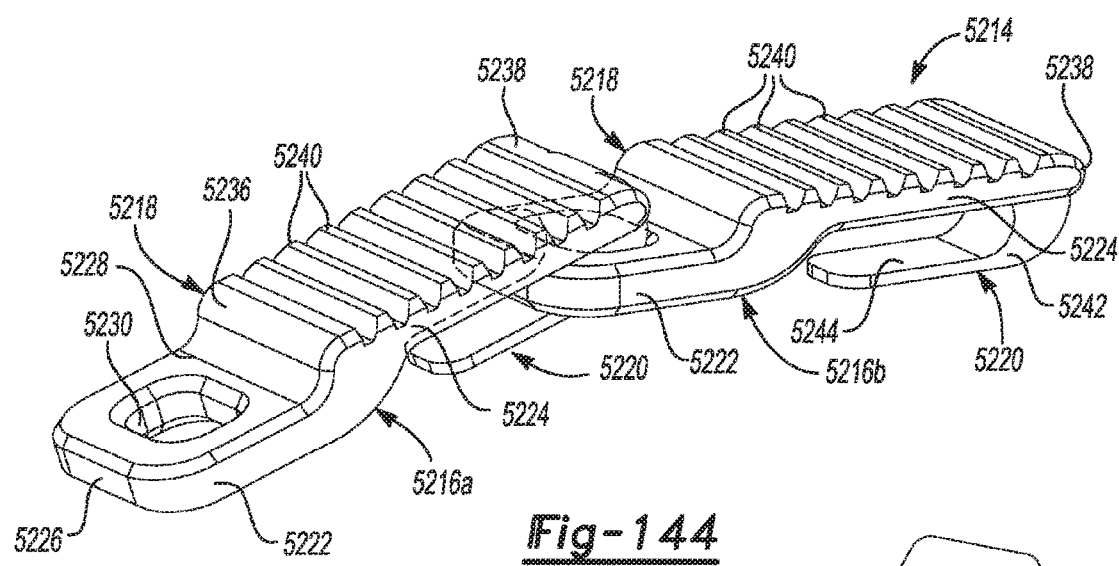

FIG. 144 is a perspective view of another configuration of a band and a link of a closure device according to the principles of the present disclosure.

Figure 144A:
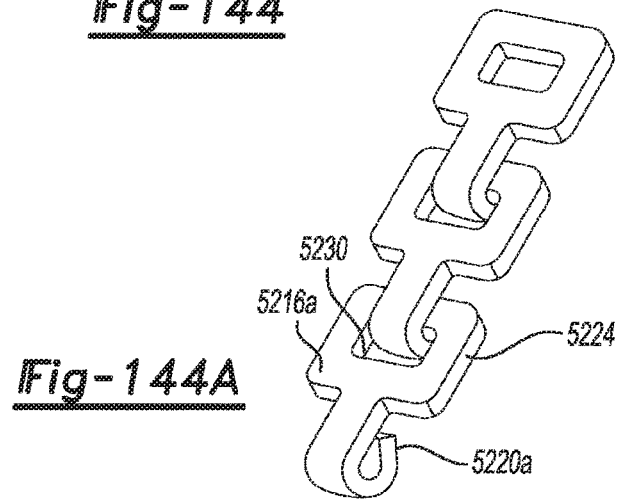

FIG. 144A is a perspective view of another configuration of a band and a link of a closure device according to the principles of the present disclosure.

Figure 144B:
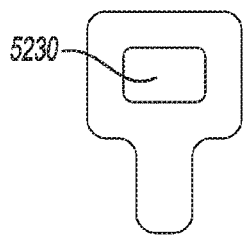

FIG. 144B is a top view of the link of FIG. 144A.

Figure 144C:
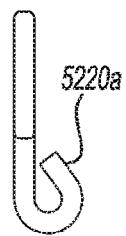

FIG. 144C is a side view of the link of FIG. 144A.

Figure 145:
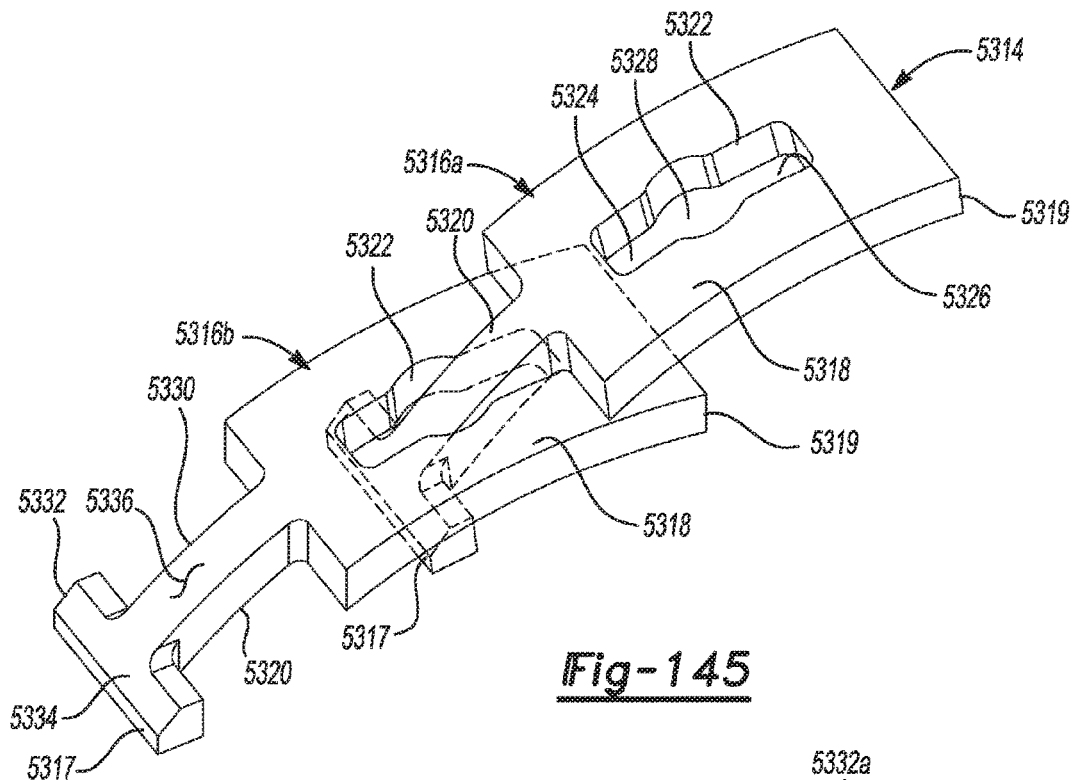

FIG. 145 is a perspective view of another configuration of a band and a link of a closure device according to the principles of the present disclosure.

Figure 146:
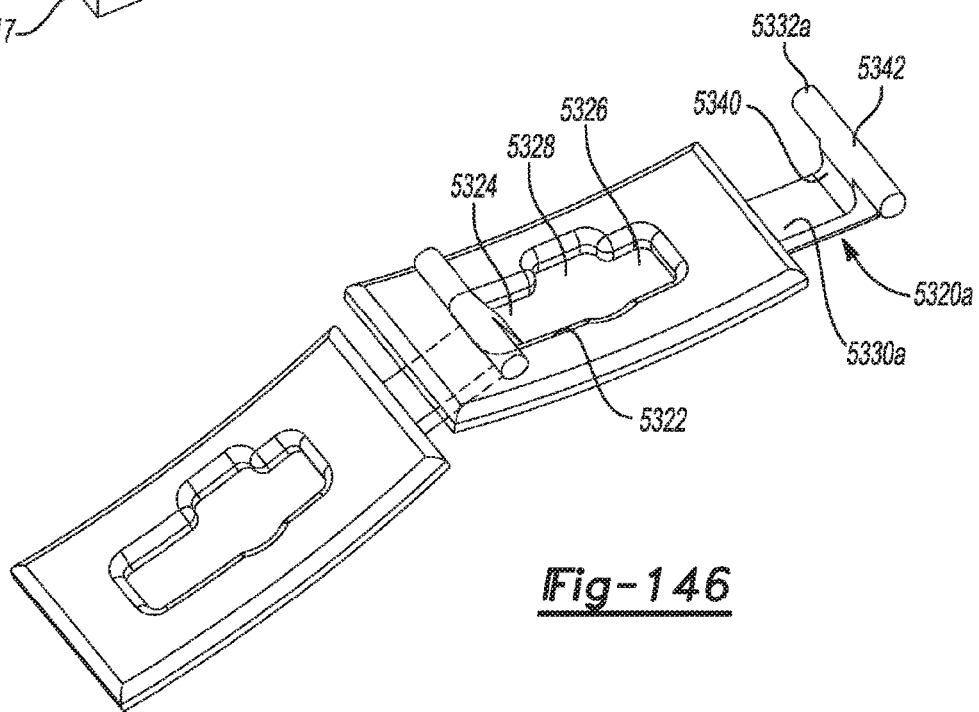

FIG. 146 is a perspective view of another configuration of a band and a link of a closure device according to the principles of the present disclosure.

Figure 147:
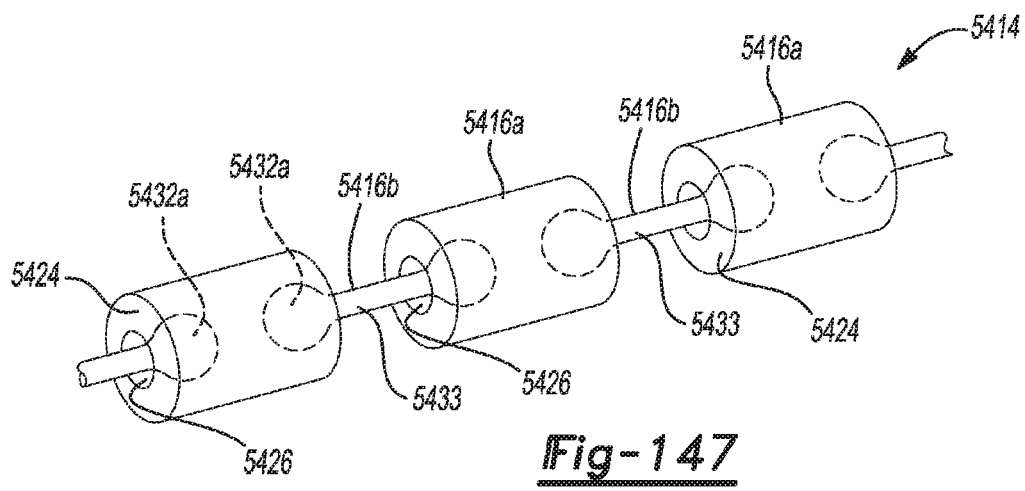

FIG. 147 is a perspective view of another configuration of a band and a link of a closure device according to the principles of the present disclosure.

Figure 148:
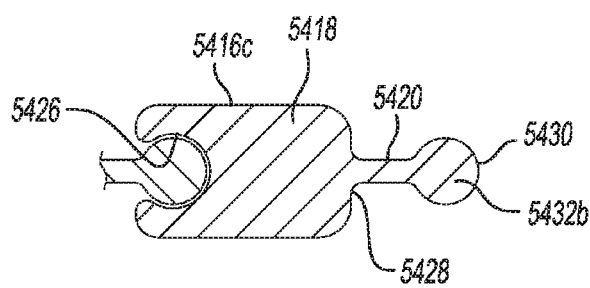

FIG. 148 is a cross-sectional view of a first configuration of the link of FIG. 147.

Figure 149:
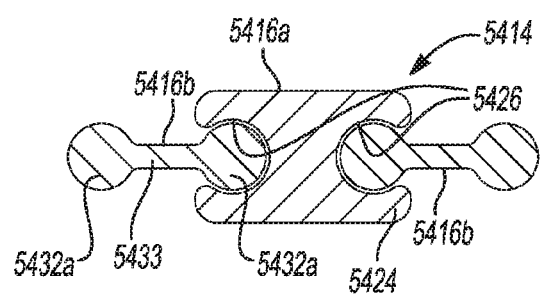

FIG. 149 is a cross-sectional view of a second configuration of the link of FIG. 147.

FIG. 150 is a perspective view of another configuration of a band and a link of a closure device according to the principles of the present disclosure.

FIG. 151 is a top view of the link of FIG. 150 in a disassembled configuration.

FIG. 152 is a cross-sectional view of the link taken through the line 152-152 of FIG. 151.

Figure 153:
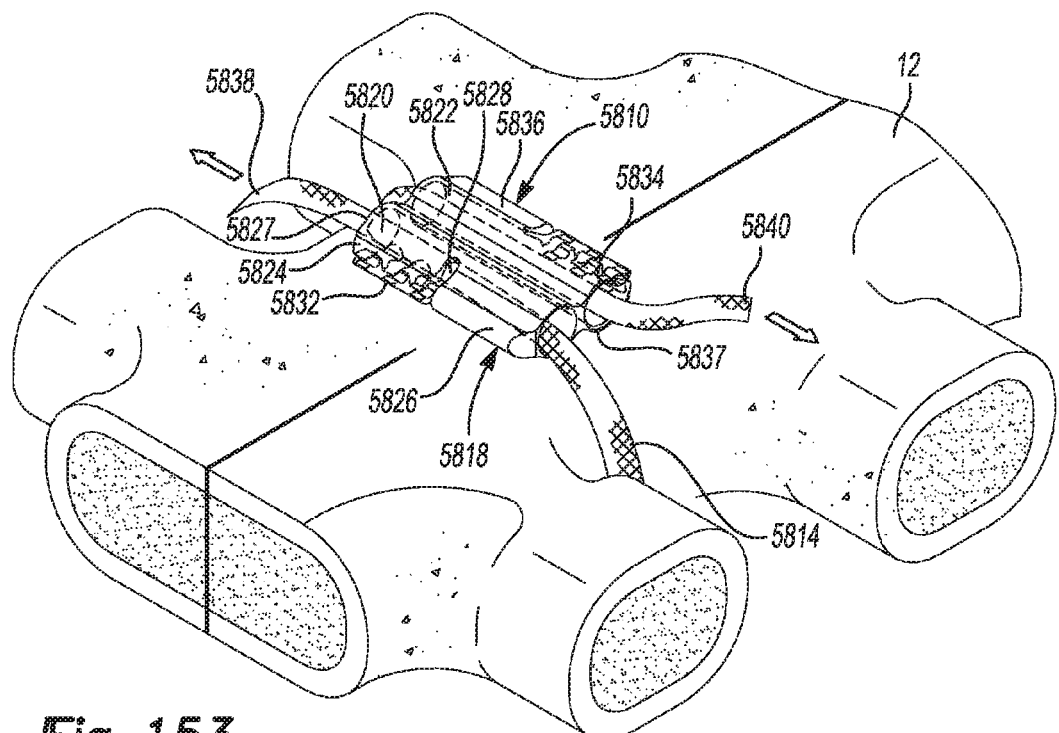

FIG. 153 is a perspective view of an anterior side of a sternum and ribs of a human body having another configuration of a closure device attached thereto in an unsecured configuration according to the principles of the present disclosure.

Figure 154:
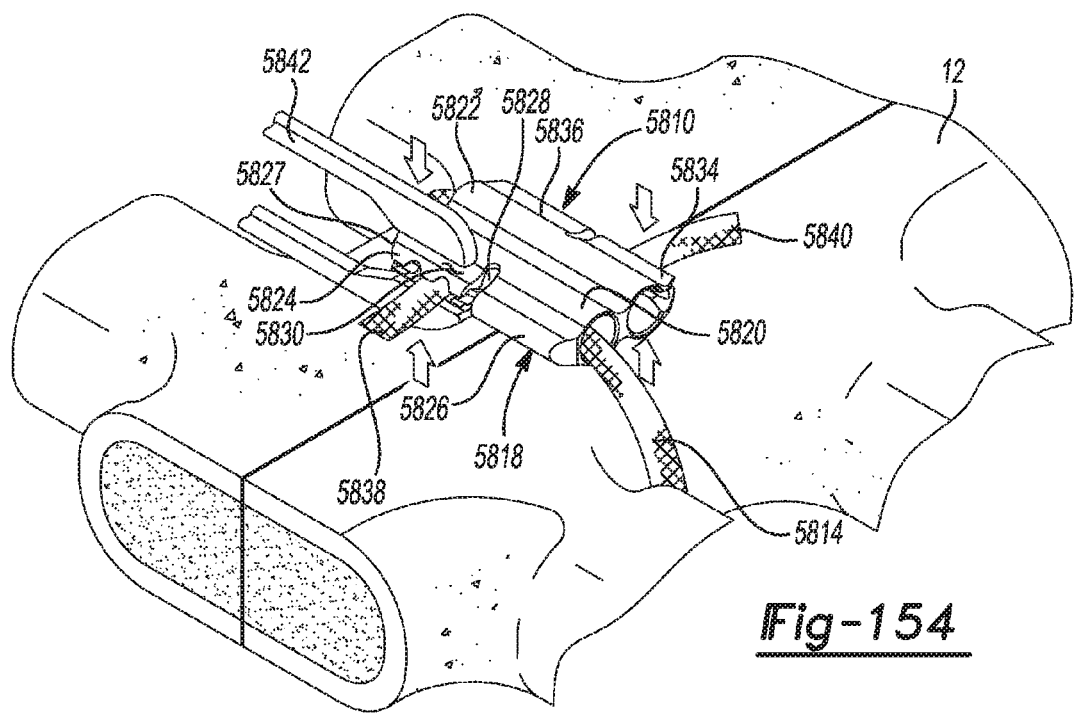

FIG. 154 is a perspective view of the closure device of FIG. 153, depicting a tool for securing the closure device.

Figure 155:
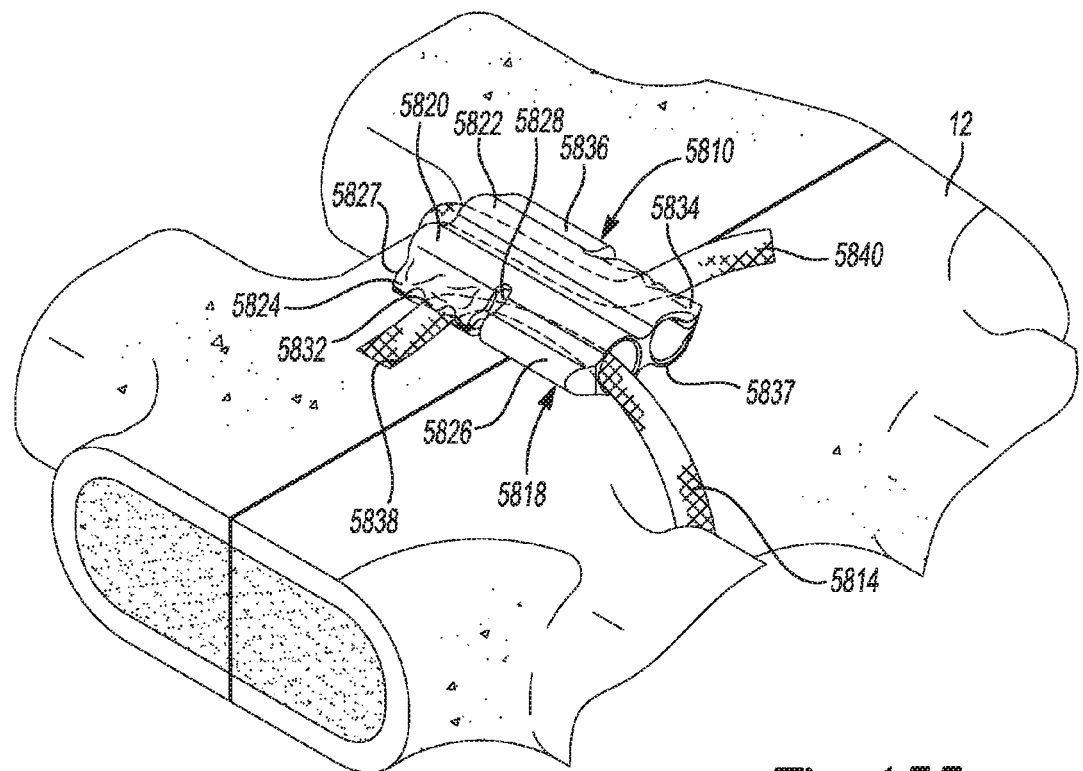

FIG. 155 is a perspective view of the closure device of FIG. 153, depicting the closure device in a secured configuration.

Figure 156:
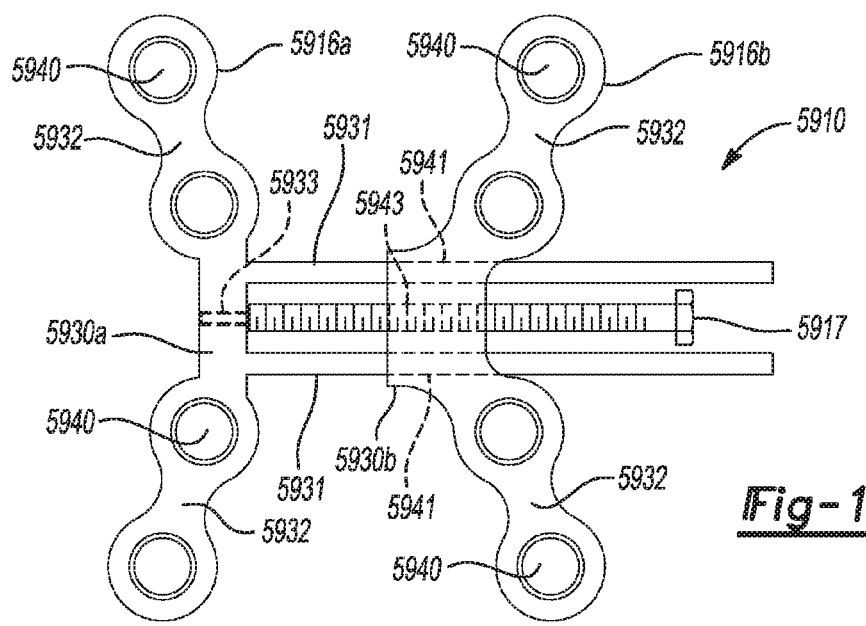

FIG. 156 is a top view of another configuration of a closure device according to the principles of the present disclosure.

FIG. 157 is a perspective view of another configuration of a closure device according to the principles of the present disclosure.

FIG. 158 is a cross-sectional view of the closure device of FIG. 157 operatively attached to a sternum.

FIG. 159 is a cross-sectional view of a portion of the closure device of FIG. 157.

Figure 160:
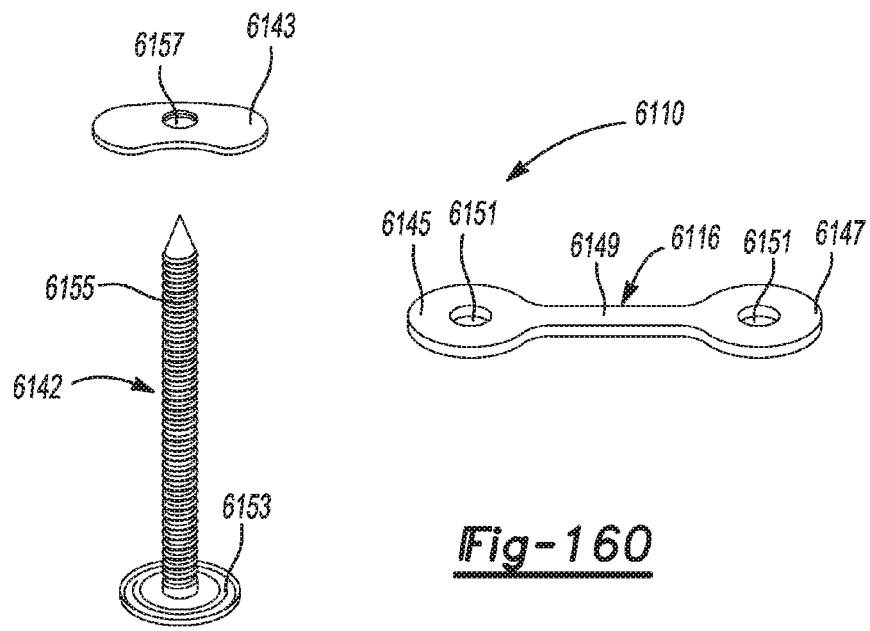

FIG. 160 is a perspective view of another configuration of a closure device according to the principles of the present disclosure.

Figure 161:
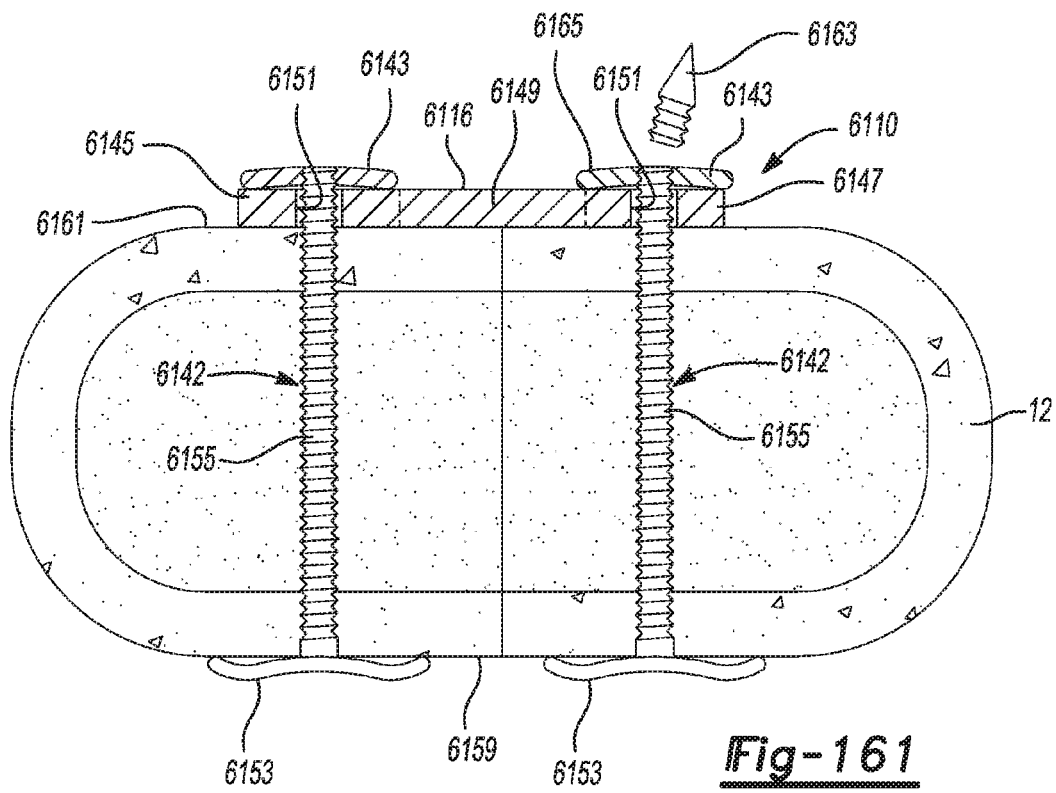

FIG. 161 is a cross-sectional view of the closure device of FIG. 160 operatively attached to a sternum.

Figure 162:
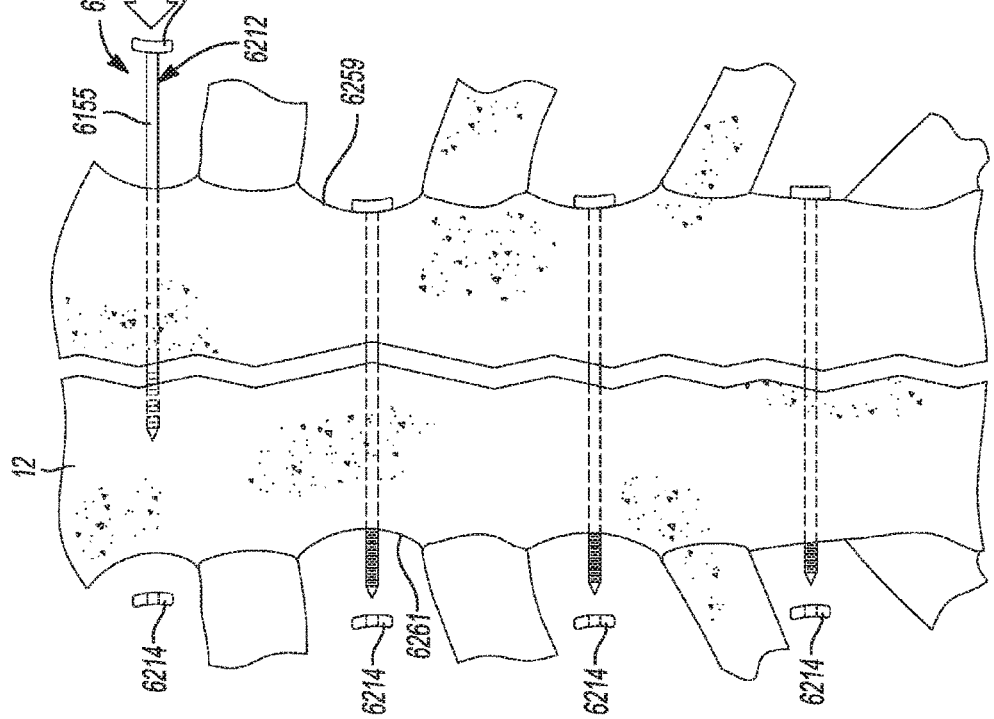

FIG. 162 is a top view of an anterior side of a sternum and ribs of a human body having another configuration of a closure device attached thereto in an unsecured configuration according to the principles of the present disclosure.

Figure 163:
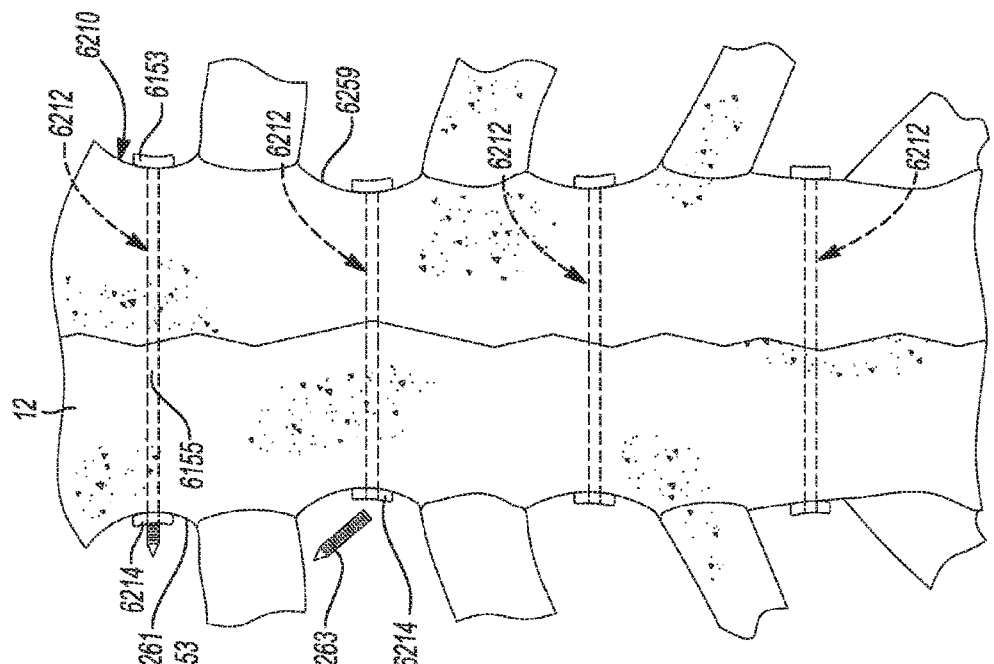

FIG. 163 is a top view of the closure device of FIG. 162, depicting the closure device in a secured configuration.

FIG. 164 is a top view of an anterior side of a sternum and ribs of a human body having another configuration of a closure device attached thereto according to the principles of the present disclosure.

FIG. 165 is a cross-sectional view of the closure device of FIG. 164 taken through the line 165-165, depicting a fastener in a first configuration.

FIG. 166 is a cross-sectional view of the closure device of FIG. 164 taken through the line 165-165, depicting a fastener in a second configuration.

FIG. 167 is a partial cross-sectional view of the closure device of FIG. 164, depicting an alternative configuration for securing a cover.

Figure 168:
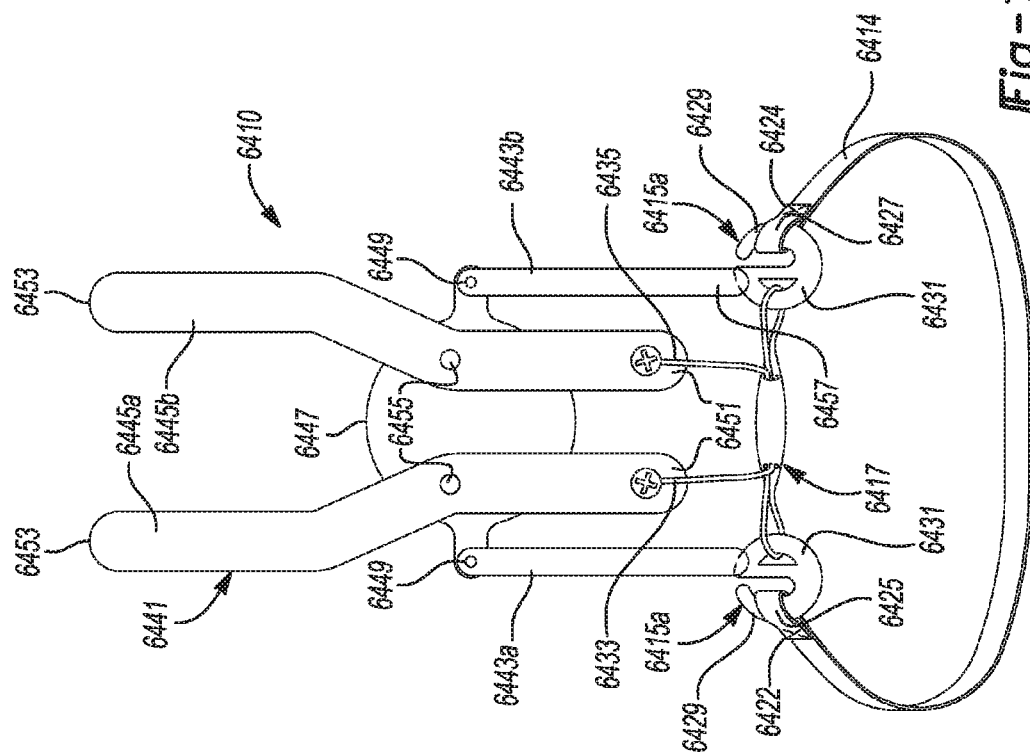

FIG. 168 is a perspective view of another configuration of a closure device according to the principles of the present disclosure, depicting a tool for configuring the closure device.

Figure 169:
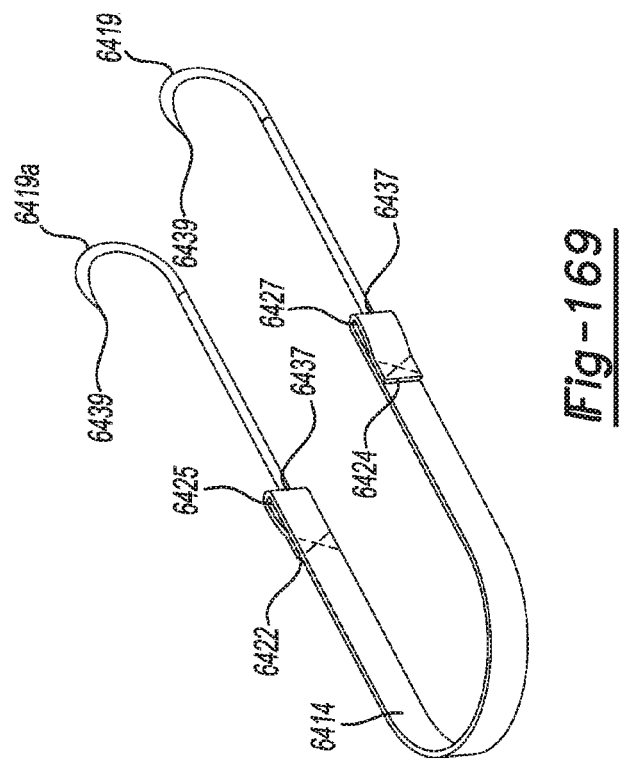

FIG. 169 is a perspective view of the closure device of FIG. 168, depicting a hook portion associated with the closure device.

FIG. 170 is a top view of an anterior side of a sternum and ribs of a human body having another configuration of a closure device attached thereto according to the principles of the present disclosure.

FIG. 171 is a perspective view of a portion of the closure device of FIG. 170.

FIG. 172 is a cross-sectional view of the closure device of FIG. 170 taken through the line 172-172 of FIG. 171.

Figure 173:
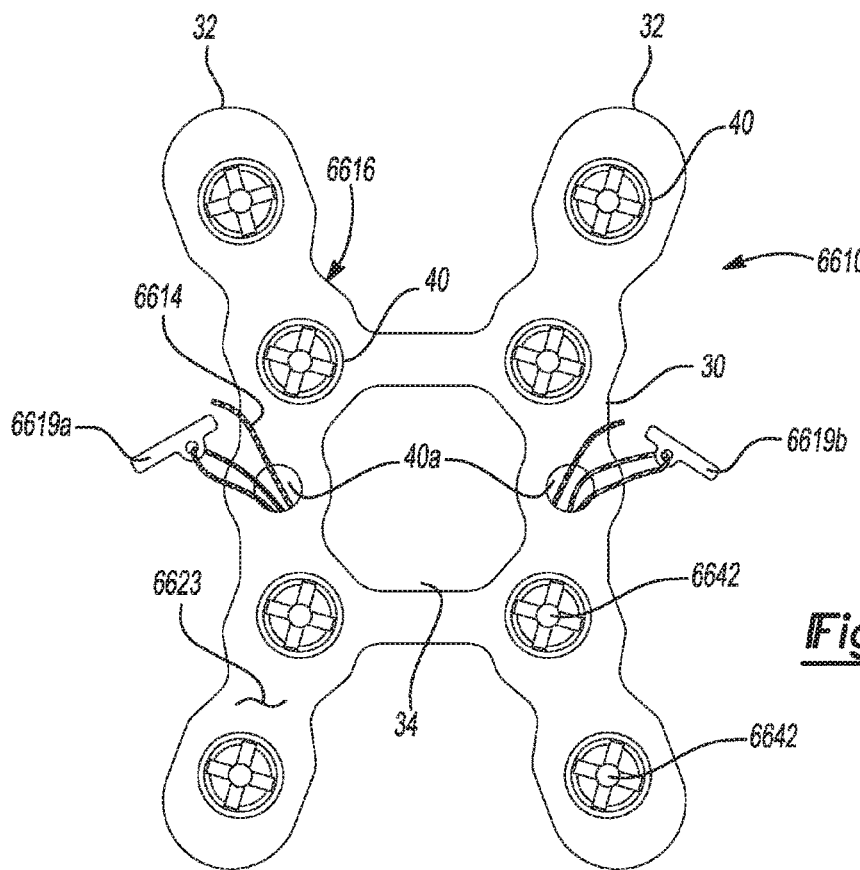

FIG. 173 is a top of another configuration of a closure device according to the principles of the present disclosure.

Figure 174:
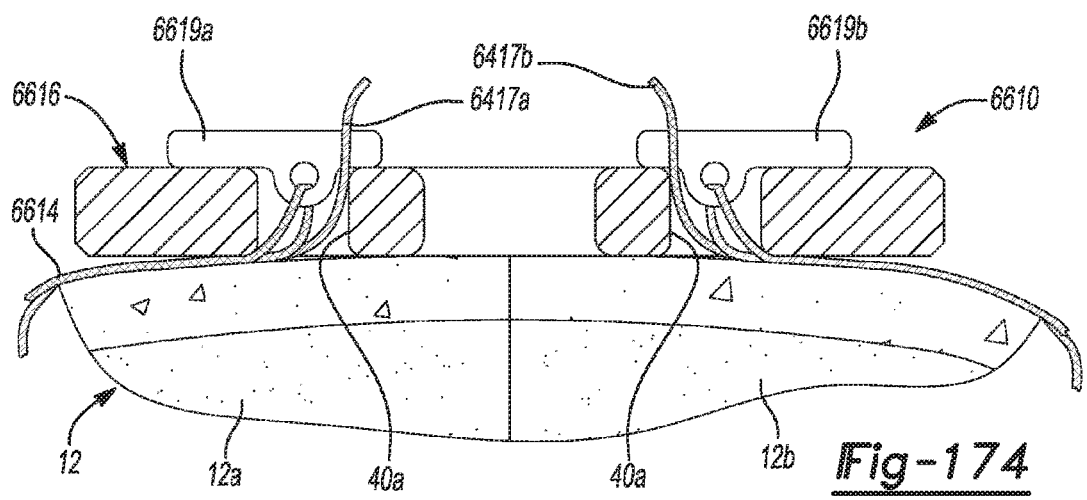

FIG. 174 is a cross-sectional view of the closure device of FIG. 173, depicting the closure device attached to a sternum of a human body.

Figure 175:
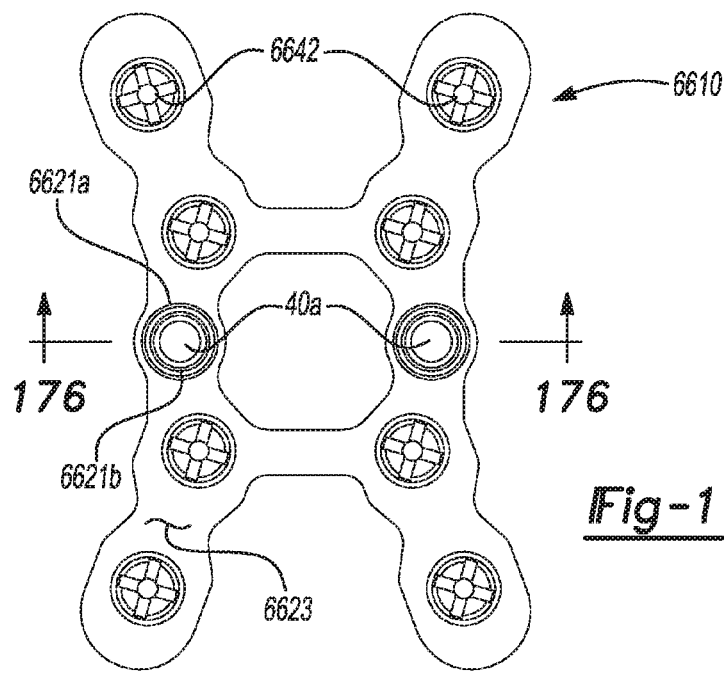

FIG. 175 is a top view of another configuration of a closure device according to the principles of the present disclosure.

Figure 176:
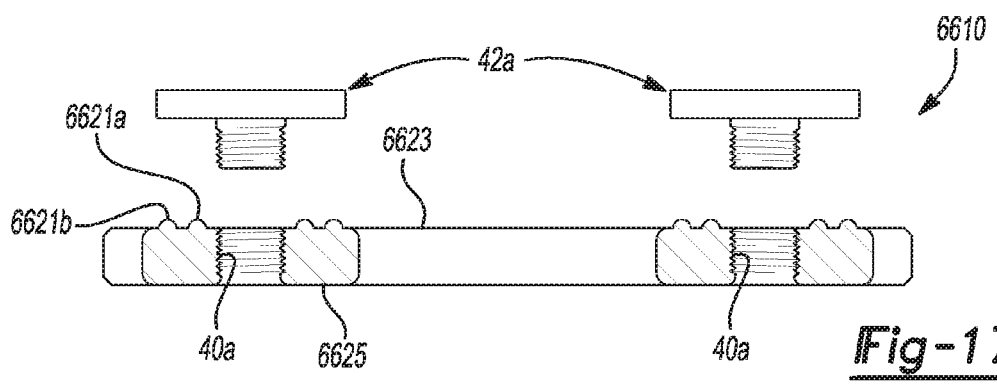

FIG. 176 is a cross-sectional view of the closure device of FIG. 175, depicting a fastener in an unsecured configuration.

Figure 177:
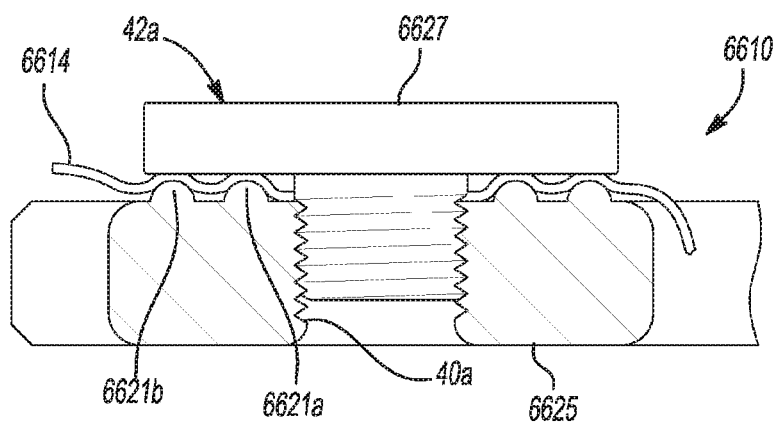

FIG. 177 is a cross-sectional view of the closure device of FIG. 175, depicting a fastener in a secured configuration.

Figure 178:
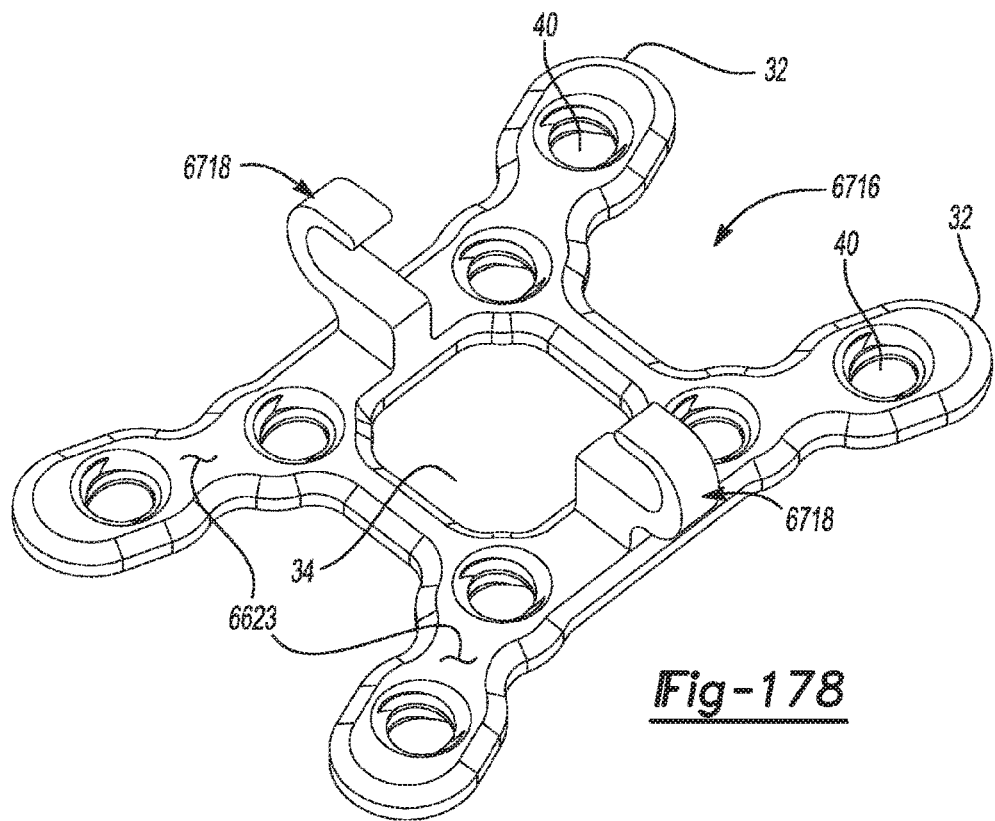
Figure 179:
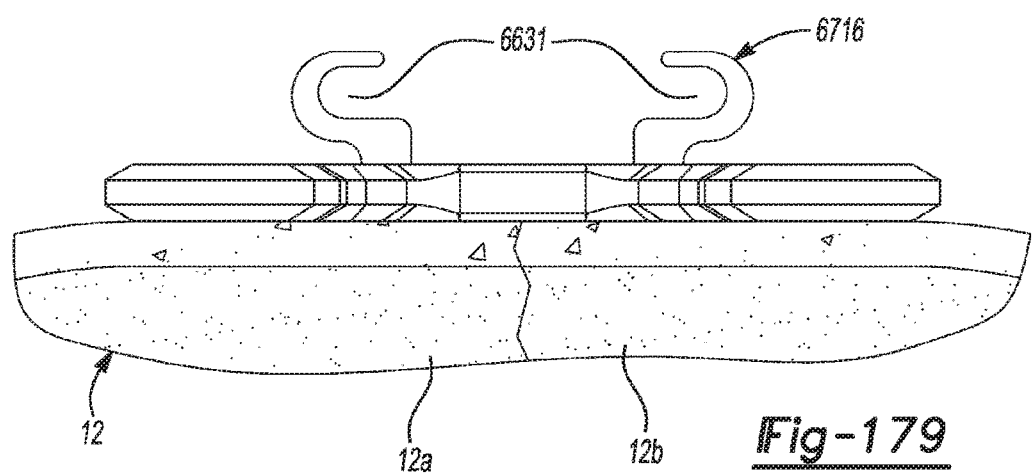

FIG. 178 is a perspective view of another configuration of a closure device according to the principles of the present disclosure; and FIG. 179 is a cross-sectional view of the closure device of FIG. 178, depicting the closure device attached to a sternum of a human body.

Figure 180:
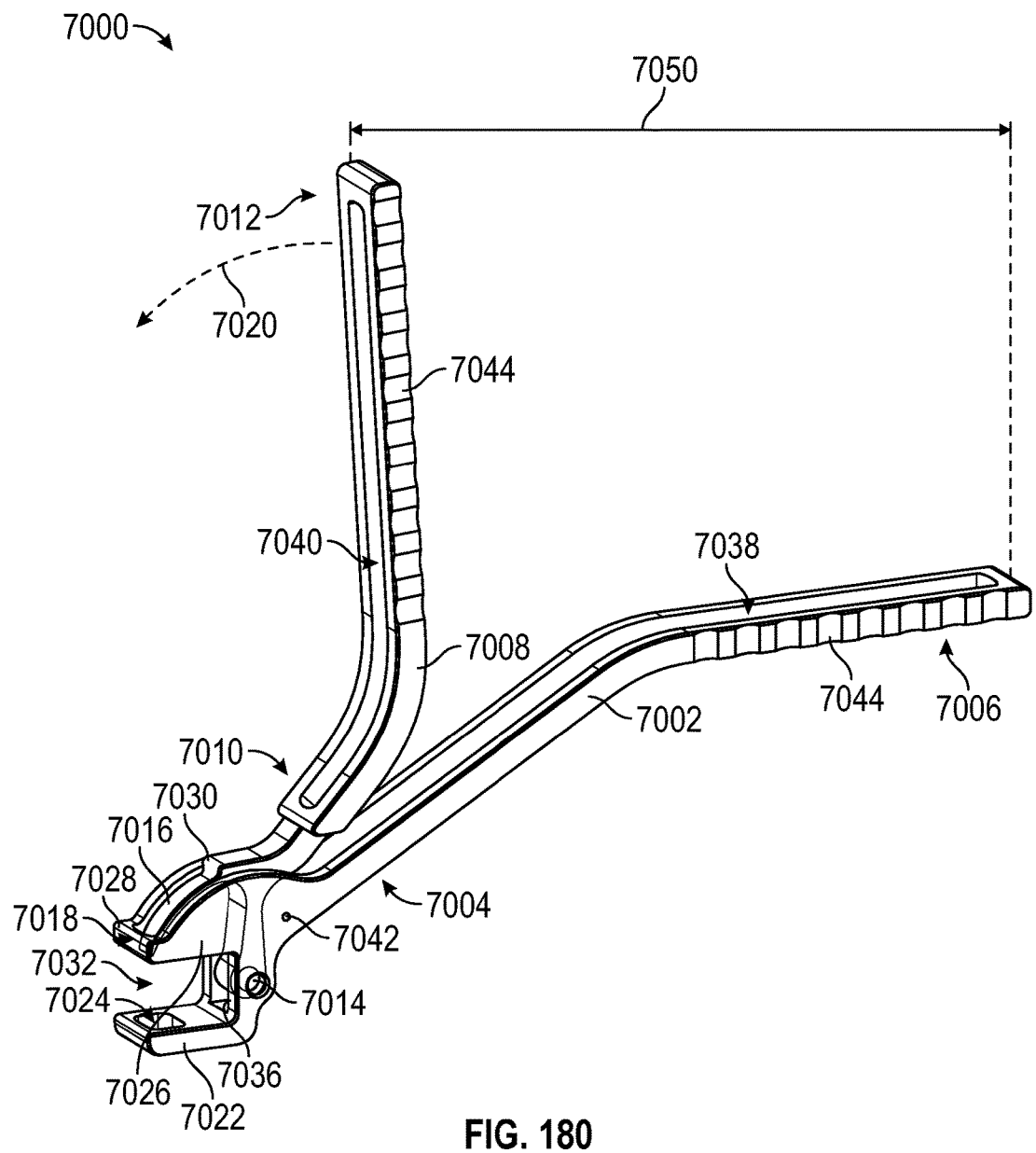

FIG. 180 is a perspective view of a bone punch tool in a retracted position, in accordance with at least one example of the present disclosure.

Figure 181:
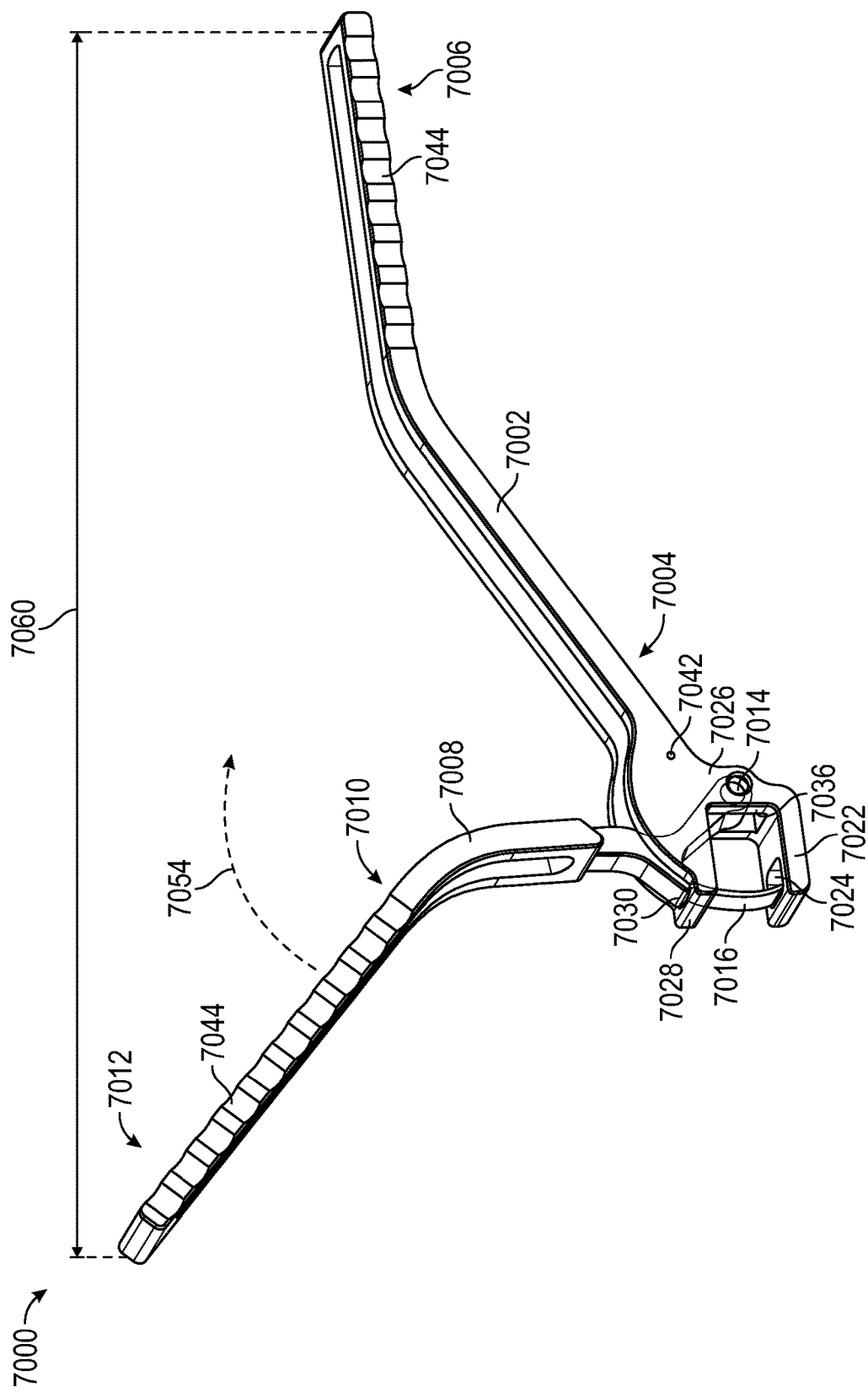

FIG. 181 is a perspective view of the bone punch tool of FIG. 180 in punch position, in accordance with at least one example of the present disclosure.

Figure 182A:
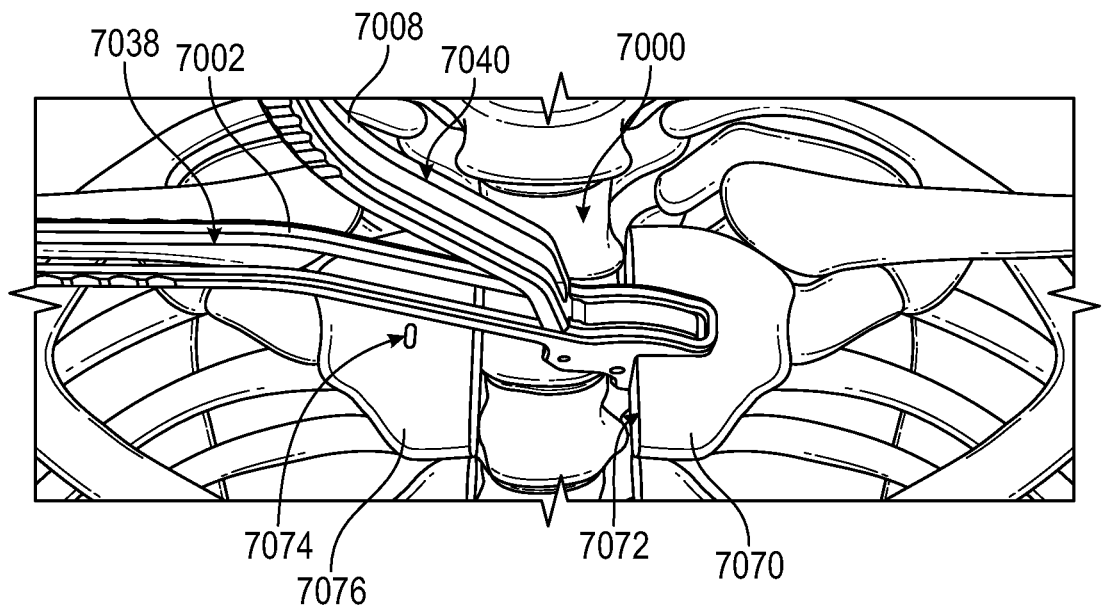
Figure 182B:
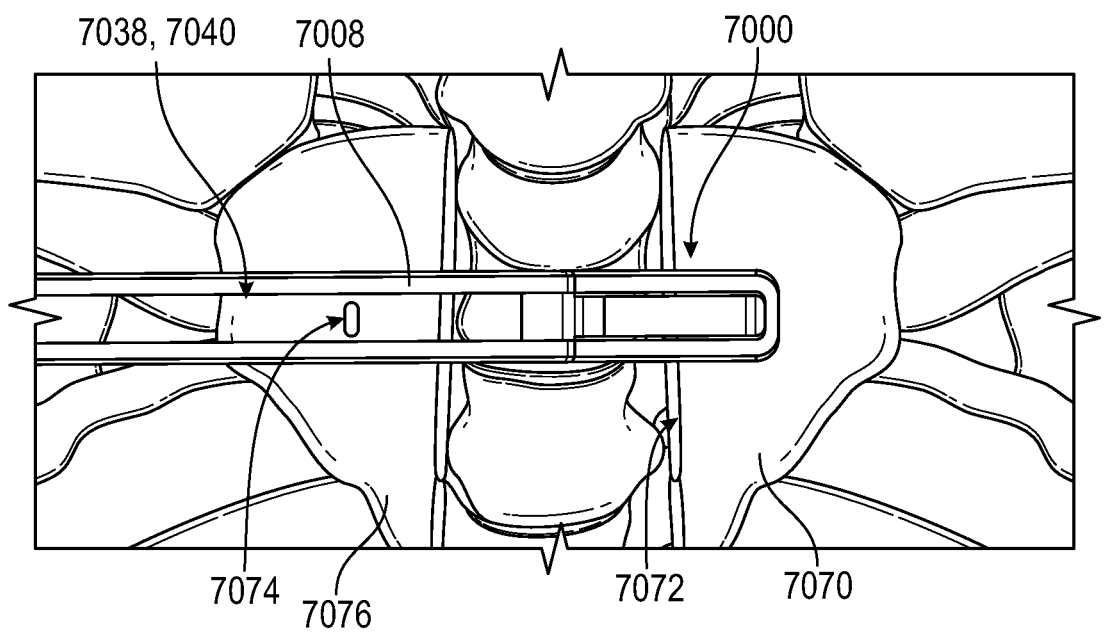

FIGS. 182A and 182B are a perspective view and a top view, respectively, of the bone punch tool of FIGS. 180 and 181 engaging a manubrium in the retracted position, in accordance with at least one example of the present disclosure.

Figure 183A:
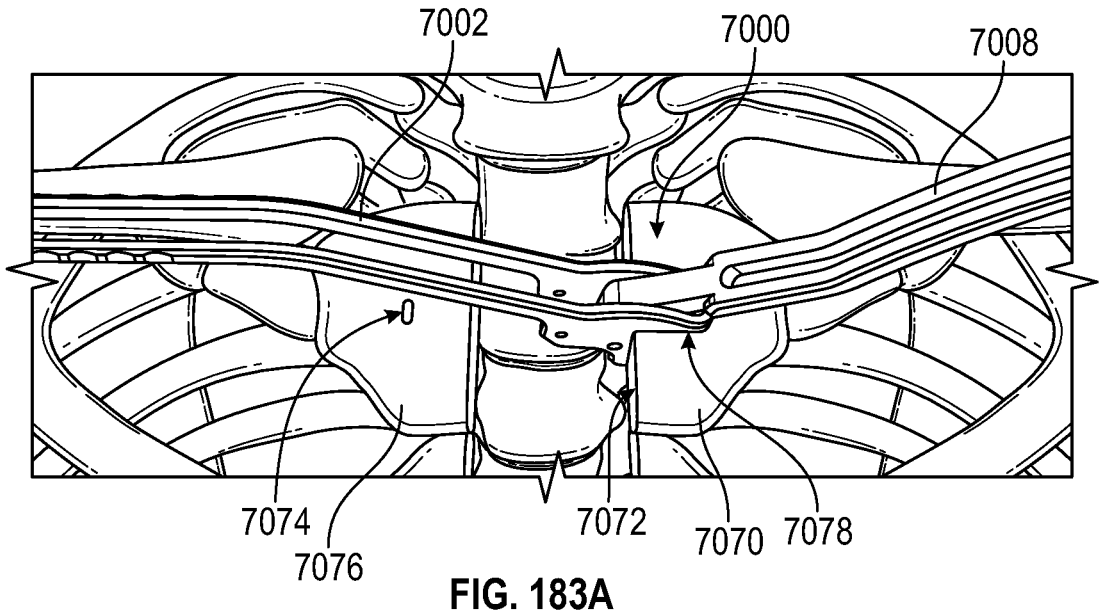
Figure 183B:
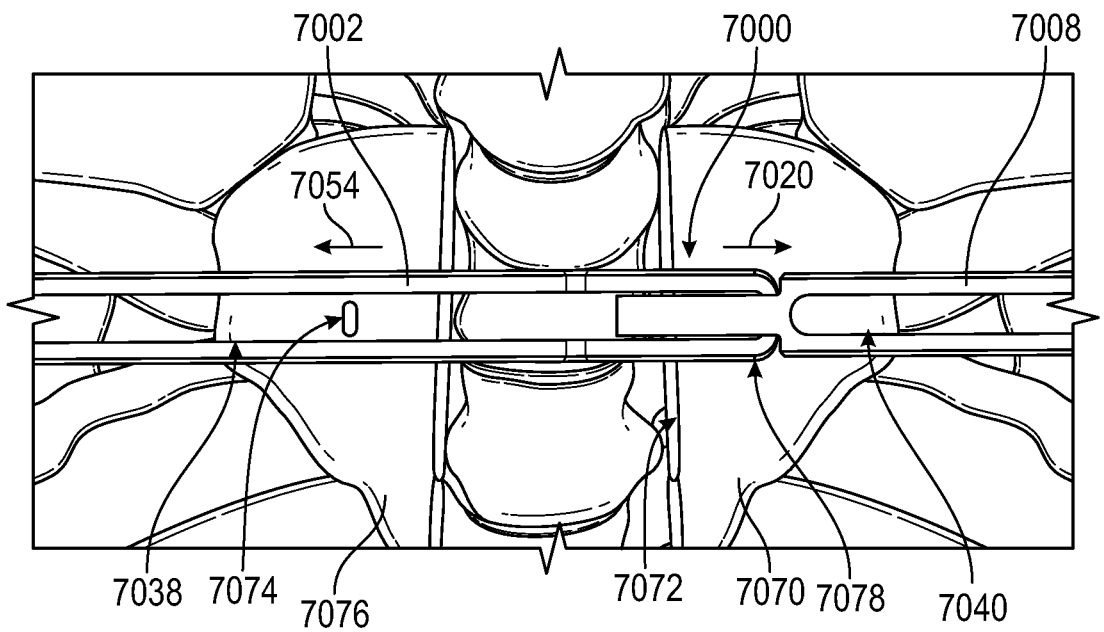

FIGS. 183A and 183B are a perspective view and a top view, respectively, of the bone punch tool of FIGS. 180-

182B engaging the manubrium in the punch position, in accordance with at least one example of the present disclosure.

Figure 184:
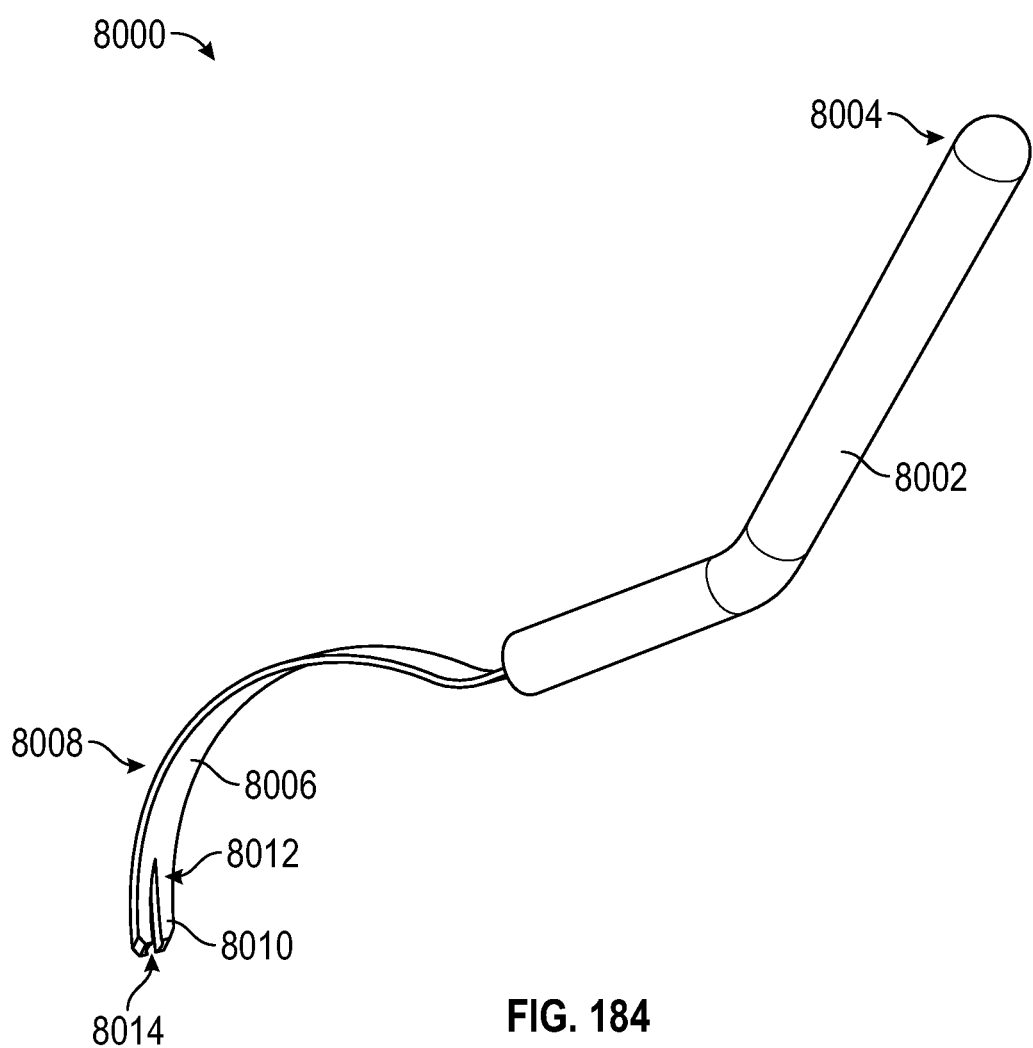

FIG. 184 is a perspective view of a needle guide, in accordance with at least one example of the present disclosure.

Figure 185A:
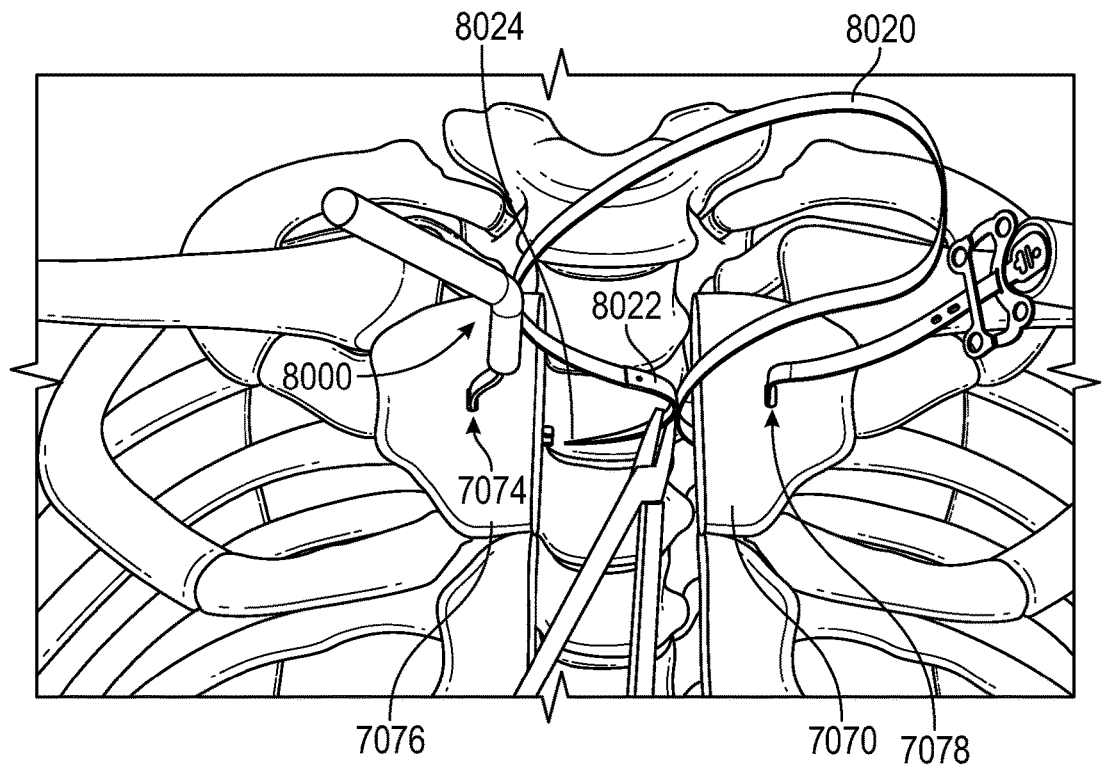
Figure 185B:
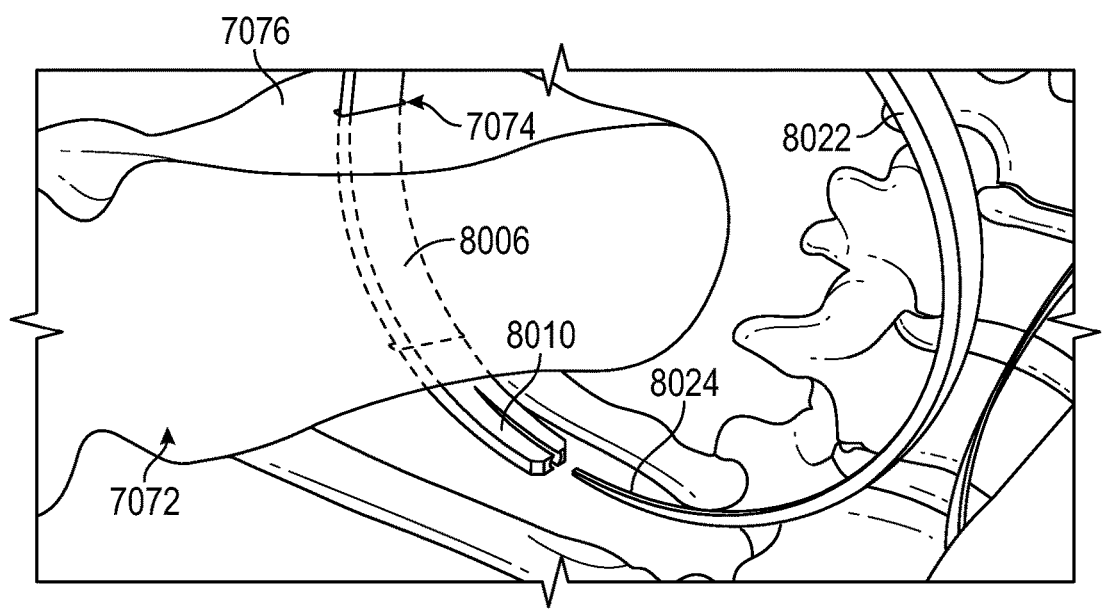

FIGS. 185A and 185B are perspective views of the needle guide of FIG. 184 inserted through an arcuate hole in a bone, in accordance with at least one example of the present disclosure.

Figure 186A:
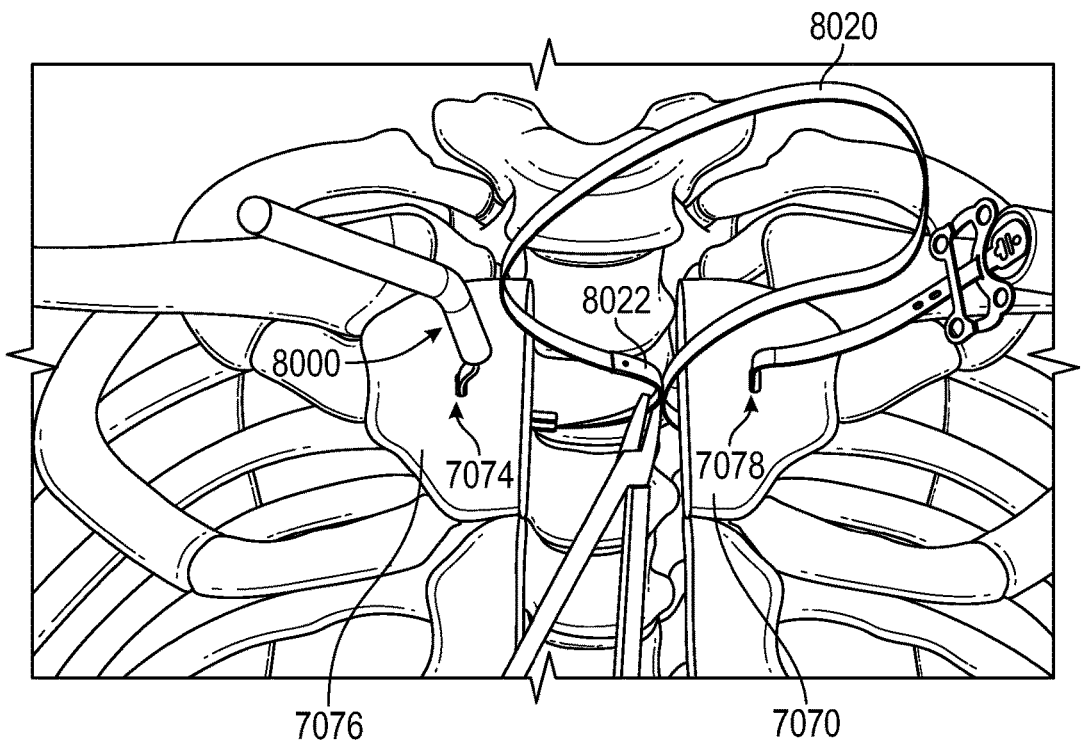
Figure 186B:
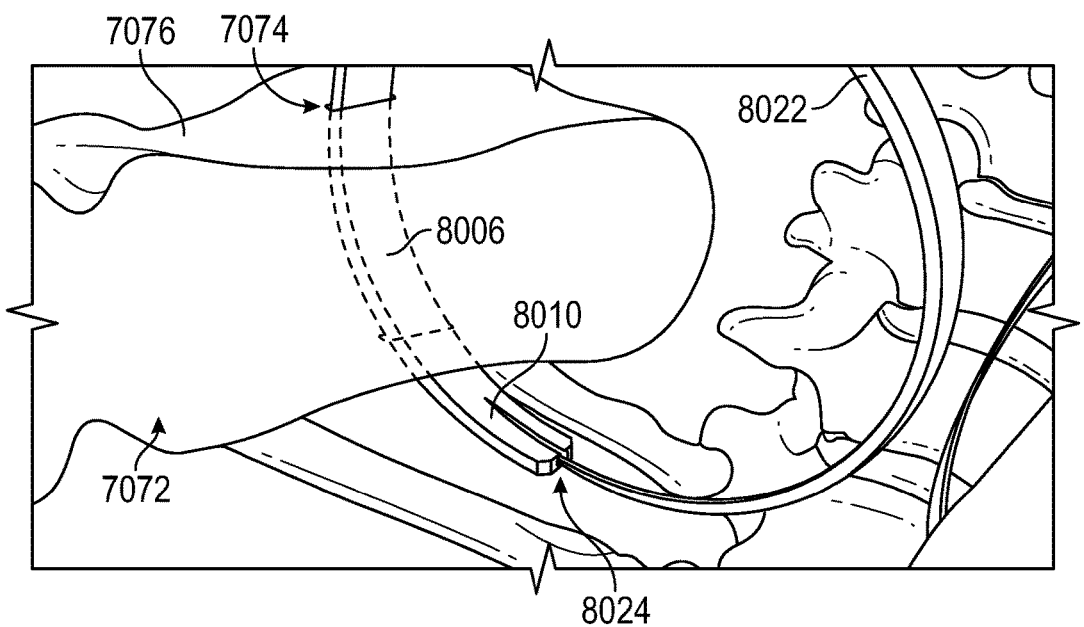

FIGS. 186A and 186B are perspective views of the needle guide of FIGS. 184-185B engaging a needle, in accordance with at least one example of the present disclosure.

Figure 187A:
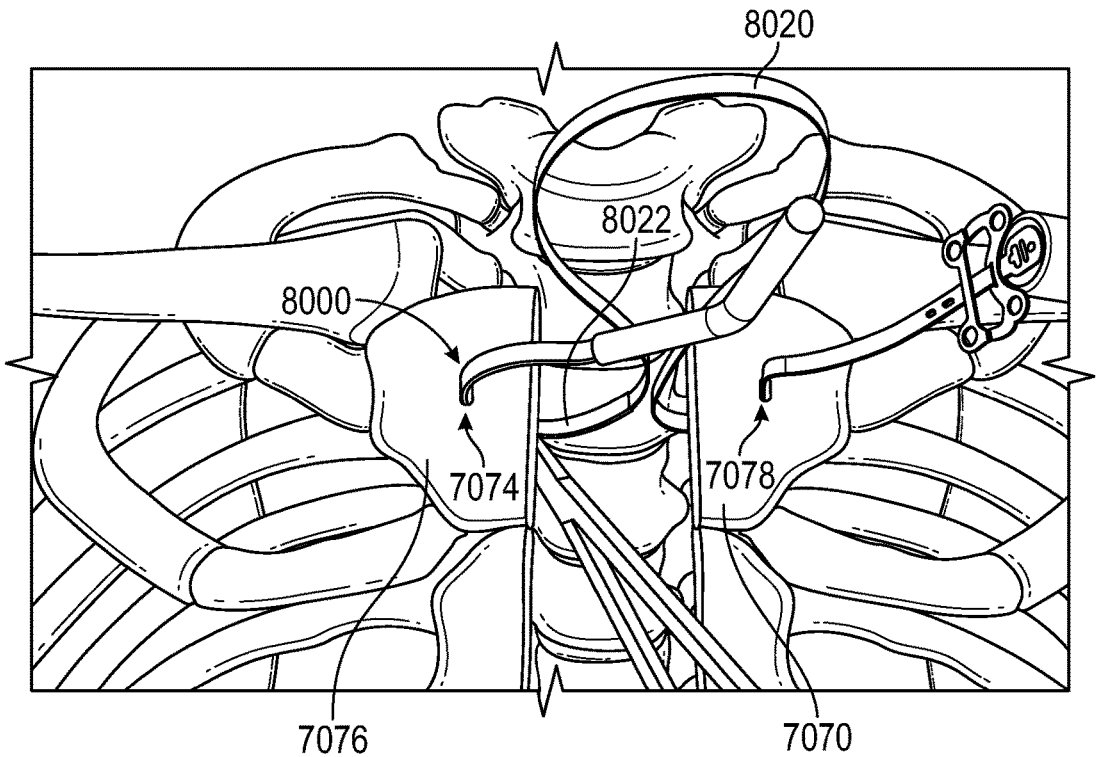
Figure 187B:
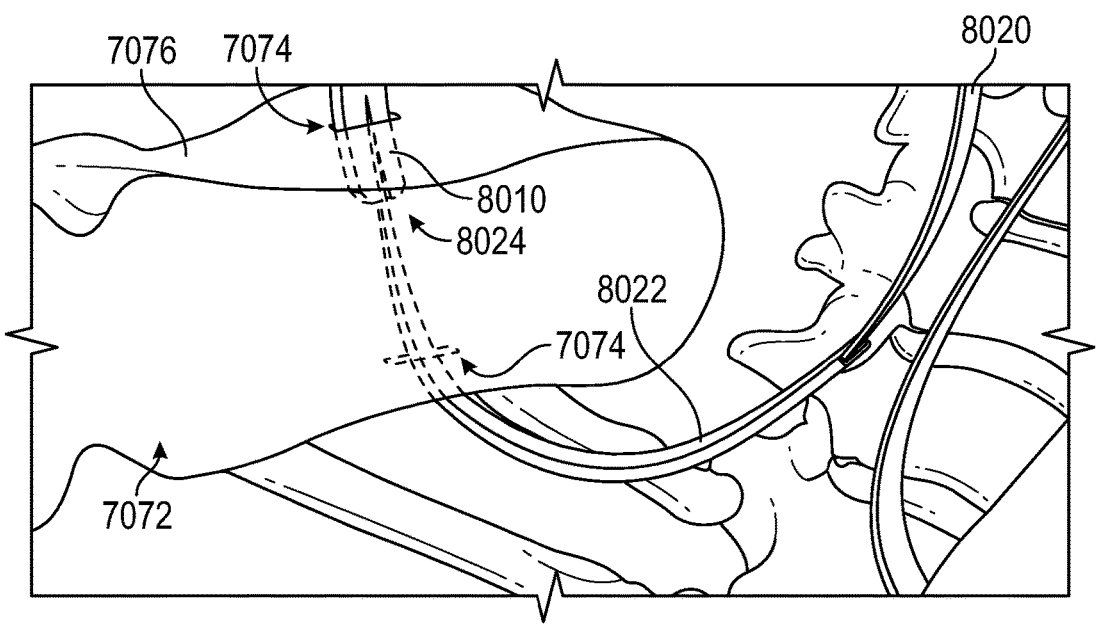

FIGS. 187A and 187B are perspective views of the needle guide of FIGS. 184-186B guiding the needle through the arcuate hole, in accordance with at least one example of the present disclosure.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these 17 elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 1:
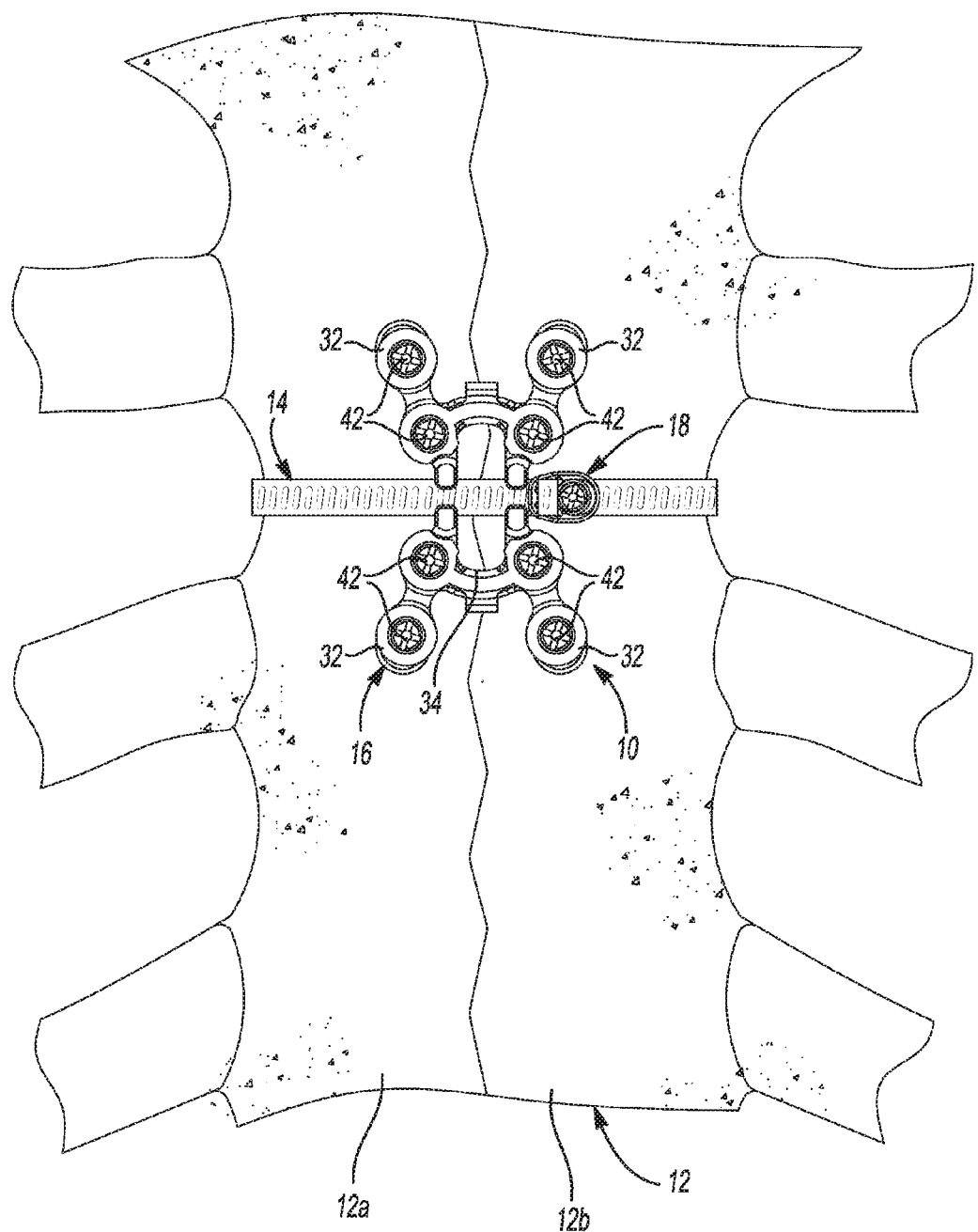
FIG. 1 is a partial perspective view of an anterior side of a sternum and ribs of a human body having a closure device attached thereto according to the principles of the present disclosure, in accordance with at least one example of the present disclosure.

With reference to FIG. 1, a closure system according to the principles of the present disclosure is generally identified with reference numeral 10. The system 10 is depicted operatively associated with a sternum 12 of a human body. The sternum 12, as shown, has previously undergone a medical procedure known as median sternotomy. As a result of this procedure, the sternum 12 has been severed, thus permitting a physician access to tissues and/or organs located in the patient's thoracic cavity. However, the sternum 12 has since been reapproximated such that the previously severed portions 12a, 12b are now bound together by the system 10.

Figure 2:
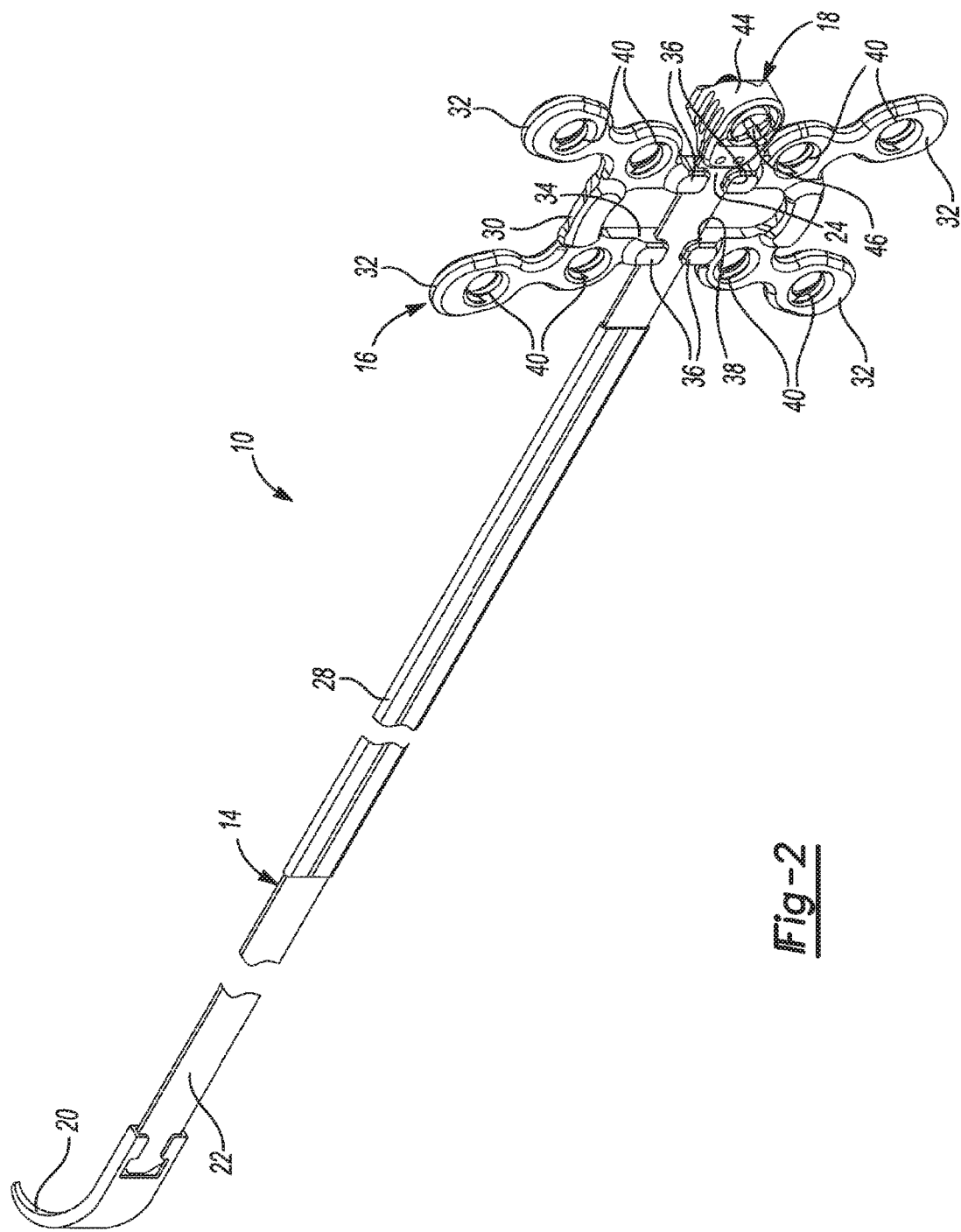
FIG. 2 is a perspective view of the closure device.
Figure 3:
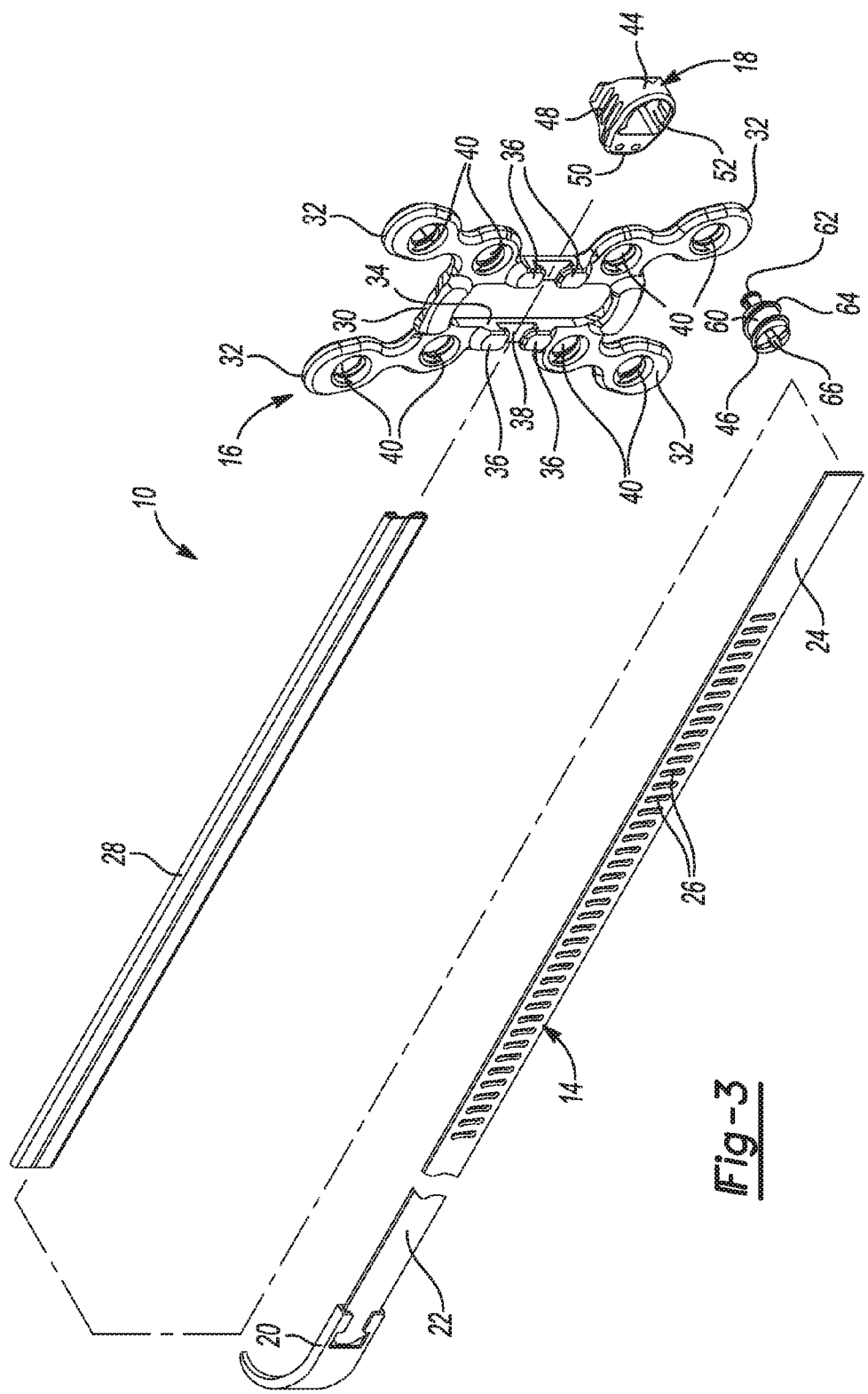
FIG. 3 is an exploded perspective view of the closure device.
Figure 4:
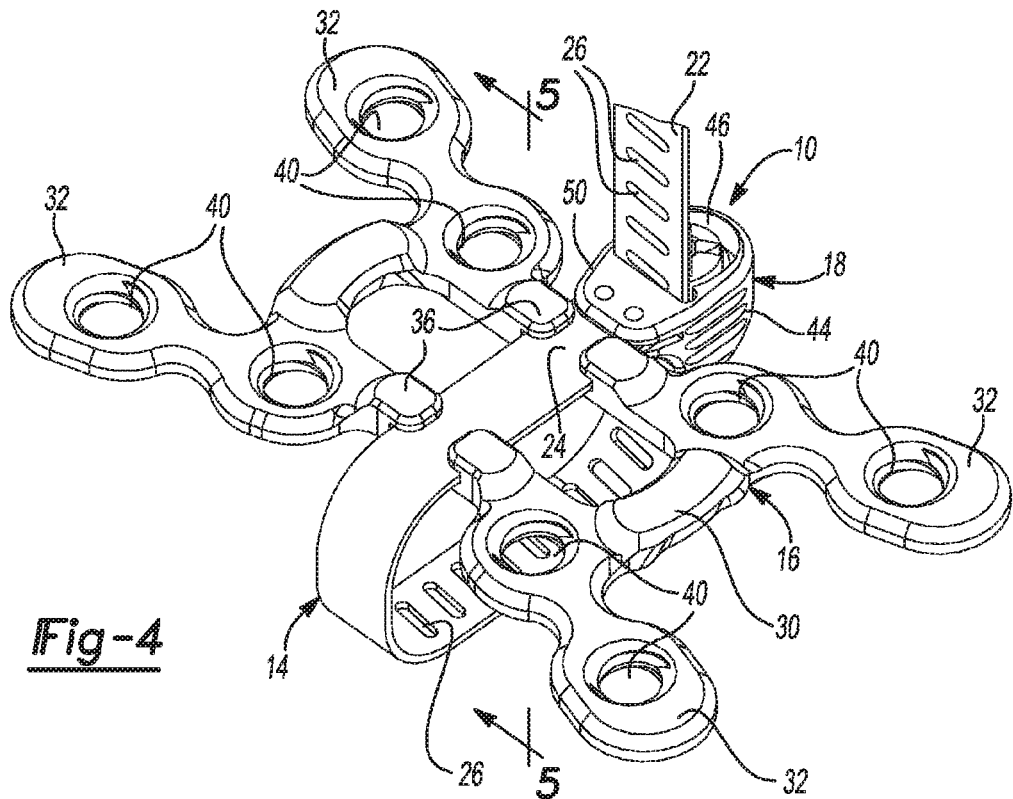
FIG. 4 is a perspective view depicting a tensioning device of the closure device adjustably engaging a band of the closure device.

With continued reference to FIGS. 1-10, the system 10 may include a cerclage or band 14, a bracket 16, and a tensioning device 18. As shown in FIG. 2, a needle 20 may be temporarily attached to a first end 22 of the band 14. The needle 20 may be attached to the first end 22 may fasteners 18 and/or a press or snap fit, for example. A second end 24 of the band 14 may be fixed to the tensioning device 18. The band 14 may be a flat, elongated and flexible member formed from a metallic material and/or a polymeric material, for example. In some embodiments, the band 14 could include a braided material. The band 14 may include a plurality of parallel slots 26 formed therein. In some embodiments, a sleeve 28 (FIGS. 2 and 3) may receive a portion of the band 14. In some embodiments, the sleeve 28 may be molded over the band 14 or otherwise integrally formed therewith.

The bracket 16 may be a plate formed from a metallic and/or polymeric material and may include a body portion 30 and a plurality of legs 32 extending outward from the body portion 30. The bracket 16 may be relatively flexible to enable the bracket 16 to conform to the contours of the sternum 12 when the bracket 16 is fastened thereto (as shown in FIG. 1). The body portion 30 may include an opening 34 extending therethrough. The opening 34 may allow the bracket 16 to be readily cut using band cutters, for example, or other standard operating room tools in case the sternum 12 needs to reopened after installation of the system 10. The body portion 30 may also include a plurality of tabs 36 that cooperate to define a channel 38 through which the band 14 is slidably received. Each of the plurality of legs 32 may include one or more apertures 40 extending therethrough. Self-tapping threaded fasteners 42 may extend through the apertures 40 and may threadably engage the sternum 12 to fix the bracket 16 to the sternum 12 (as shown in FIG. 1).

Figure 5:
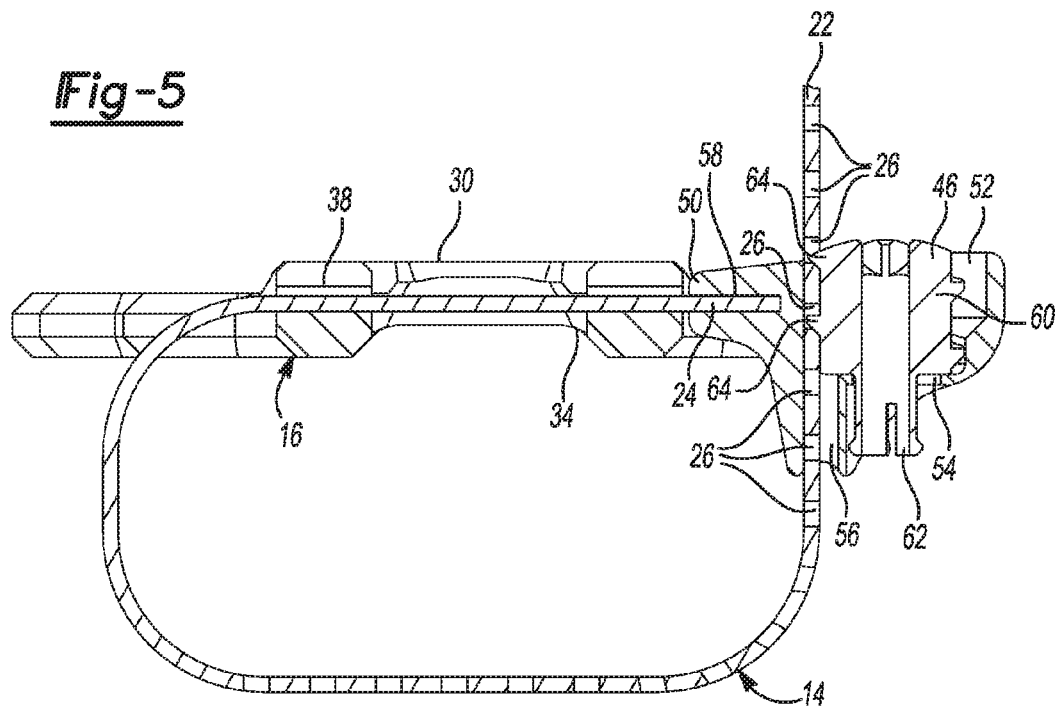
FIG. 5 is a cross-sectional view of the closure device taken along line 5-5 of FIG. 4.

The tensioning device 18 may include a receiver 44 and a tensioning screw 46. The receiver 44 may include a body portion 48 and a tab 50. As shown in FIG. 5, the body portion 48 may include a recess 52, a first opening 54 and a second opening 56. The first and second openings 54, 56 may be generally adjacent each other and are in communication with the recess 52. The tab 50 may extend outward from the body portion 48 and may fixedly engage the second end 24 of the band 14. The second end 24 may be received within a slot 58 (FIG. 5) in the tab 50 and may be fixed therein by pins, welding, crimping, and/or one or more fasteners, for example, or any other suitable means.

As shown in FIG. 5, the tensioning screw 46 may include a head portion 60 and a stem 62. The head portion 60 may include threads 64 and 19 one or more slots 66 that can receive the tip of a screwdriver. The head portion 60 may be received in the recess 52 of the receiver 44 so that the stem 62 extends through the first opening 54 of the receiver 44. As shown in FIG. 5, the second end 22 of the band 14 may be inserted through the second opening 56 and the recess 52 of the receiver 44. The threads 64 of the tensioning screw 46 may engage the slots 26 in the band 14 such that when the tensioning screw 46 is rotated relative to the receiver 44, the band 14 is moved up or down (relative to the frame of reference of FIG. 5) relative to the receiver 44 based on the direction that the tensioning screw 46 is rotated.

With continued reference to FIGS. 1-10, a method will be described for attaching the system 10 to the sternum 12 and tensioning the band 14 to reapproximate the sternum 12. With the needle 20 attached to the first end 22 of the band 14 (as shown in FIG. 2), the first end 22 of the band 14 may be looped around the posterior side of the sternum 12 so that the band 14 substantially circumscribes the sternum 12. Once the band 14 is looped around the sternum 12, the needle 20 may be removed from the band 14, and the first end 22 of the band 14 may be inserted up through the receiver 44 (as shown in FIG. 5). As shown in FIG. 1, the bracket 16 may be positioned so that the fracture separating the two portions 12a, 12b of the sternum 12 is visible in the opening 34 in the bracket 16 (i.e., so that the two of the legs 32 of the bracket 14 are aligned with one portion 12a, 12b of the sternum 12 and the other two legs 32 are aligned with the other portion 12a, 12b of the sternum 12).

Figure 6:
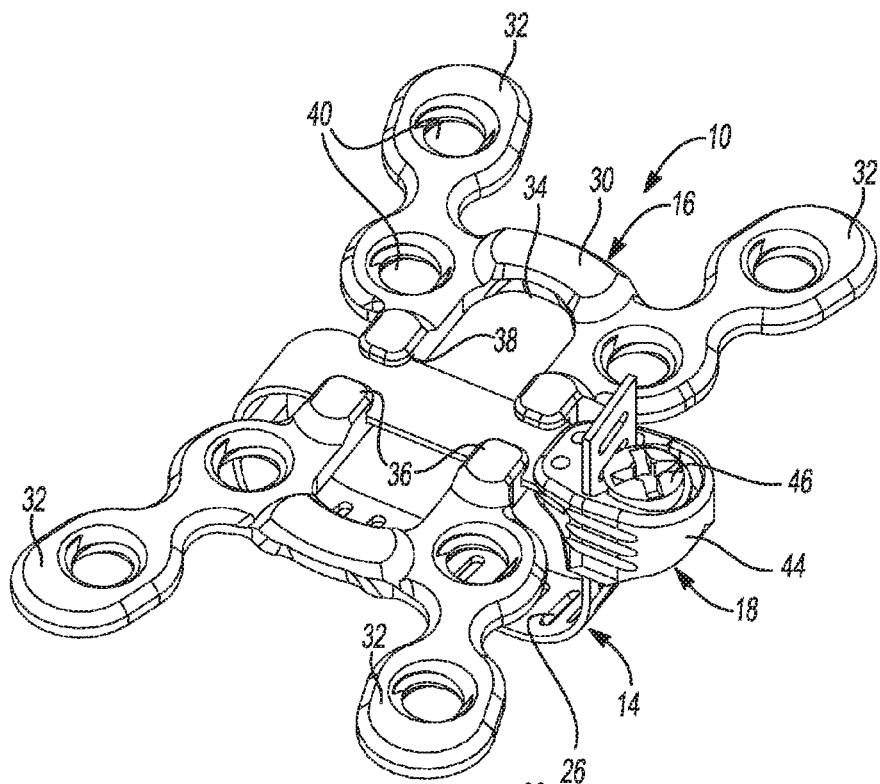
FIG. 6 is a perspective view of the closure device after an end of the band has been trimmed according to the principles of the present disclosure.
Figure 7:
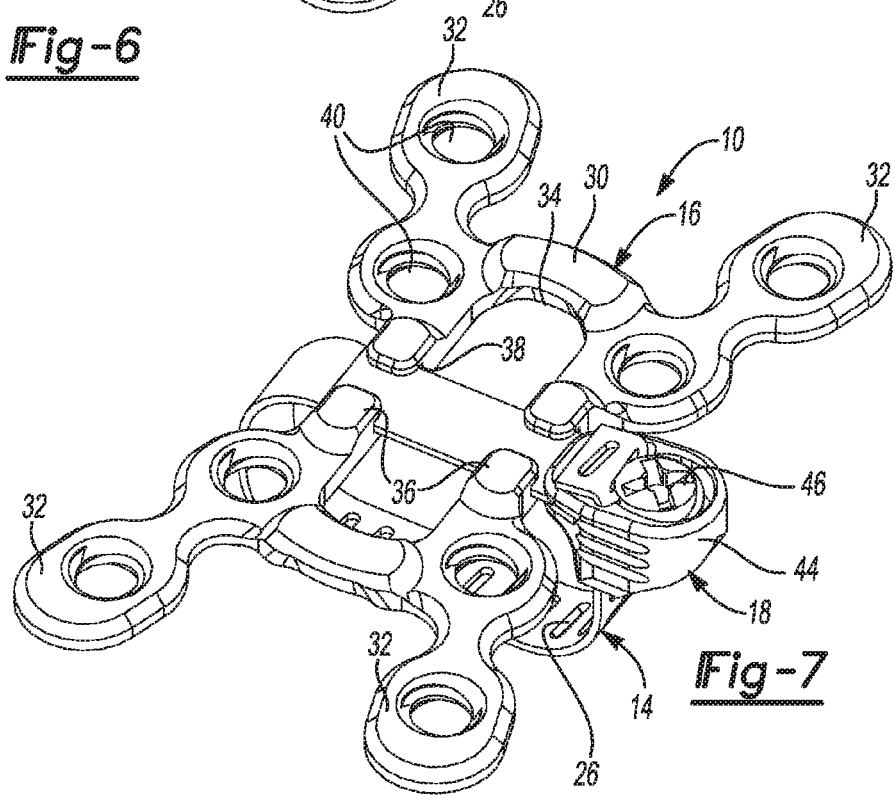
FIG. 7 is a perspective view of the closure device after the end of the band has been bent according to the principles of the present disclosure.

The tensioning device 18 may be used to tighten the band 14 around the sternum 12 to bind the portions 12a, 12b of the sternum 12 together. As described above, the tensioning screw 46 may be rotated relative to the receiver 44 to move the band 14 up (relative to the frame of reference of FIG. 5) to tighten the band 14 around the sternum 12 to a desired amount. Once the band 14 has been tightened to the desired amount, the first end 22 of the band 14 may be trimmed (as shown in FIG. 6) and subsequently folded over onto the tab 50 of the receiver 44 (as shown in FIG. 7).

Figure 8:
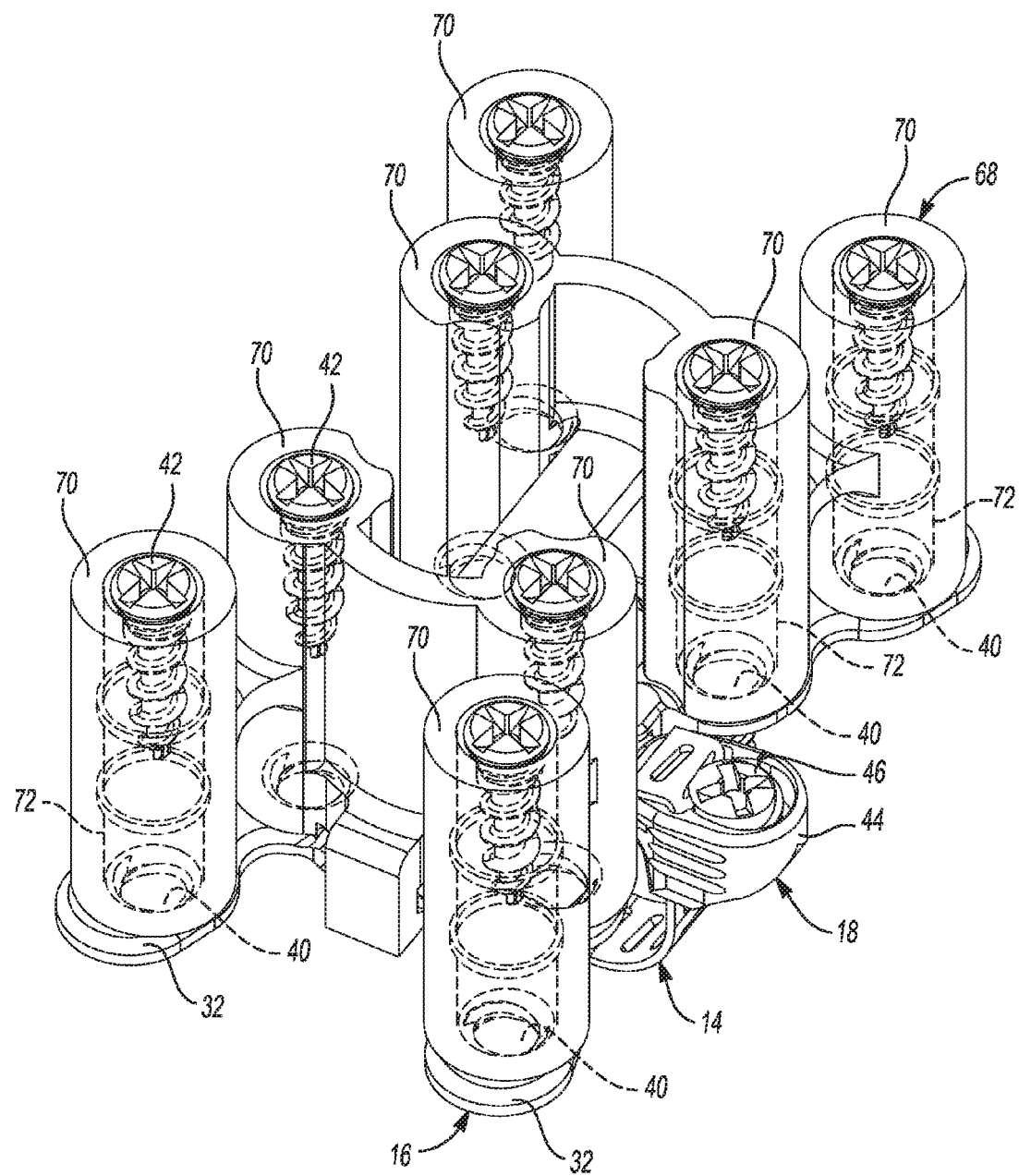
FIG. 8 is a perspective view of the closure device and a fixture aligning a plurality of fasteners relative to the closure device.
Figure 9:
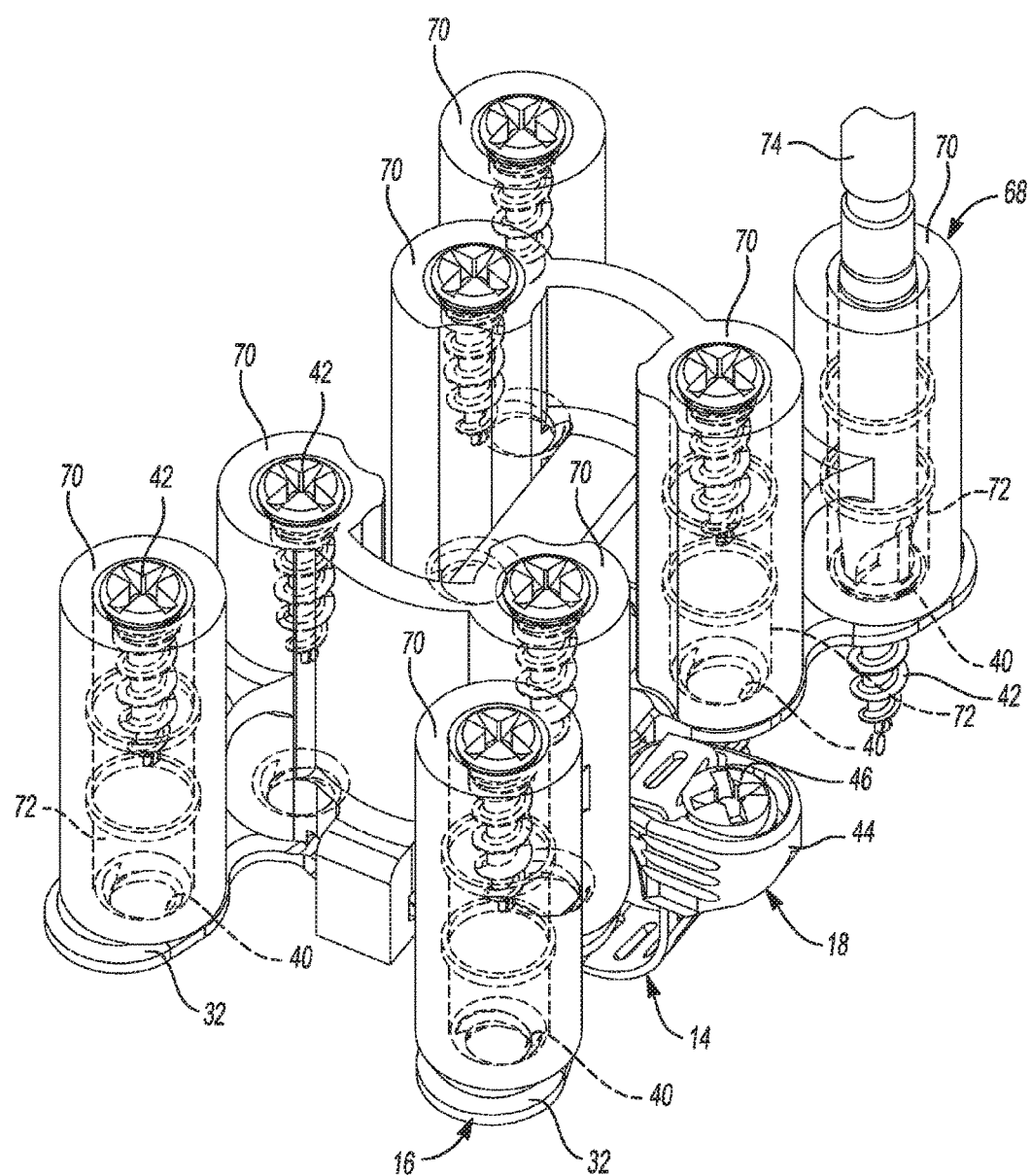
FIG. 9 is a perspective view of the closure device and fixture of FIG. 8 depicting a screwdriver driving one of the fasteners.
Figure 10:
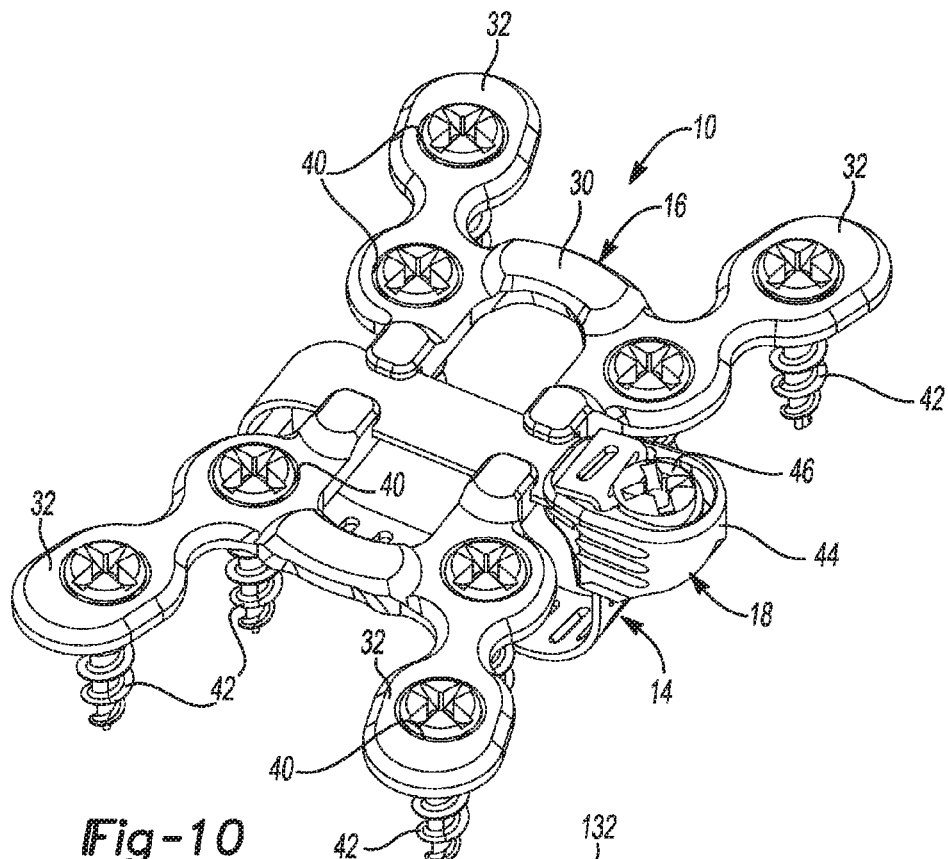
FIG. 10 is a perspective view of the closure device with all of the fasteners driven through a bracket of the closure device.

With the band 14 sufficiently tightened around the sternum 12, the bracket 16 may be fixed to the sternum 12 with the fasteners 42. That is, the fasteners 42 may be inserted through the apertures 40 in the bracket 16 and 20 driven into the sternum 12 using a screwdriver (e.g., a manual screwdriver or an electric screwdriver). As shown in FIGS. 8 and 9, a fixture 68 may be employed to hold the fasteners 42 as they are driven through the apertures 40 and into the sternum 12. The fixture 68 may include a plurality of tubes 70 having apertures 72 sized to receive the fasteners 42. The tubes 70 may have the same spacing and relative orientation as that of the apertures 40 so that the fixture 68 can be aligned relative to the bracket 16 such that the apertures 72 are aligned with the apertures 40 (as shown in FIG. 8). With the fixture 68 in this position, a screwdriver 74 (FIG. 9) can drive the fasteners through the apertures 72, 40 and into the sternum 12.

While the system 10 is described above as including the bracket 16, it will be appreciated that the band 14 and tensioning device 18 could be used without the bracket 16 to reapproximate the sternum 12.

Figure 11:
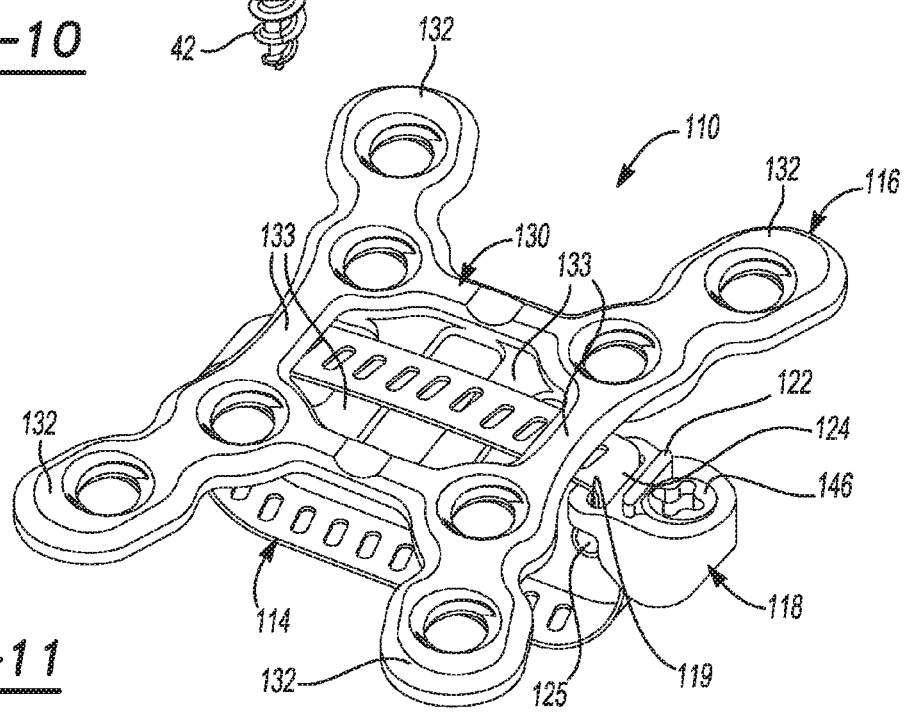
FIG. 11 is a perspective view of another closure device having a tensioning device according to the principles of the present disclosure.

With reference to FIG. 11, another closure system 110 is provided. The system 110 may include a band 114, a bracket 116, and a tensioning device 118. The structures and functions of the band 114, bracket 116 and tensioning device 118 may be similar or identical to that of the band 14, bracket 16 and tensioning device 18 described above, apart from any exceptions described below and/or shown in the figures. Therefore, similar features may not be described again in detail.

The band 114 may include a first end 122 and a second end 124. The band 114 may extend through a slot 119 formed in the tensioning device 118. The second end 124 may include an enlarged portion or loop 125 that prevents the second end 124 from sliding through the slot 119. In this manner, interference between the loop 125 and the slot 119 fixes the second end 124 relative to the tensioning device 118 when the first end 122 is pulled taught by tensioning screw 146 of the tensioning device 118. Like the bracket 16, the bracket 116 may include a body 130 and a plurality of legs 132. Instead of tabs 36, the body 130 may include a plurality of ribs 133 that define a channel 138 through which the band 114 is received.

Figure 12:
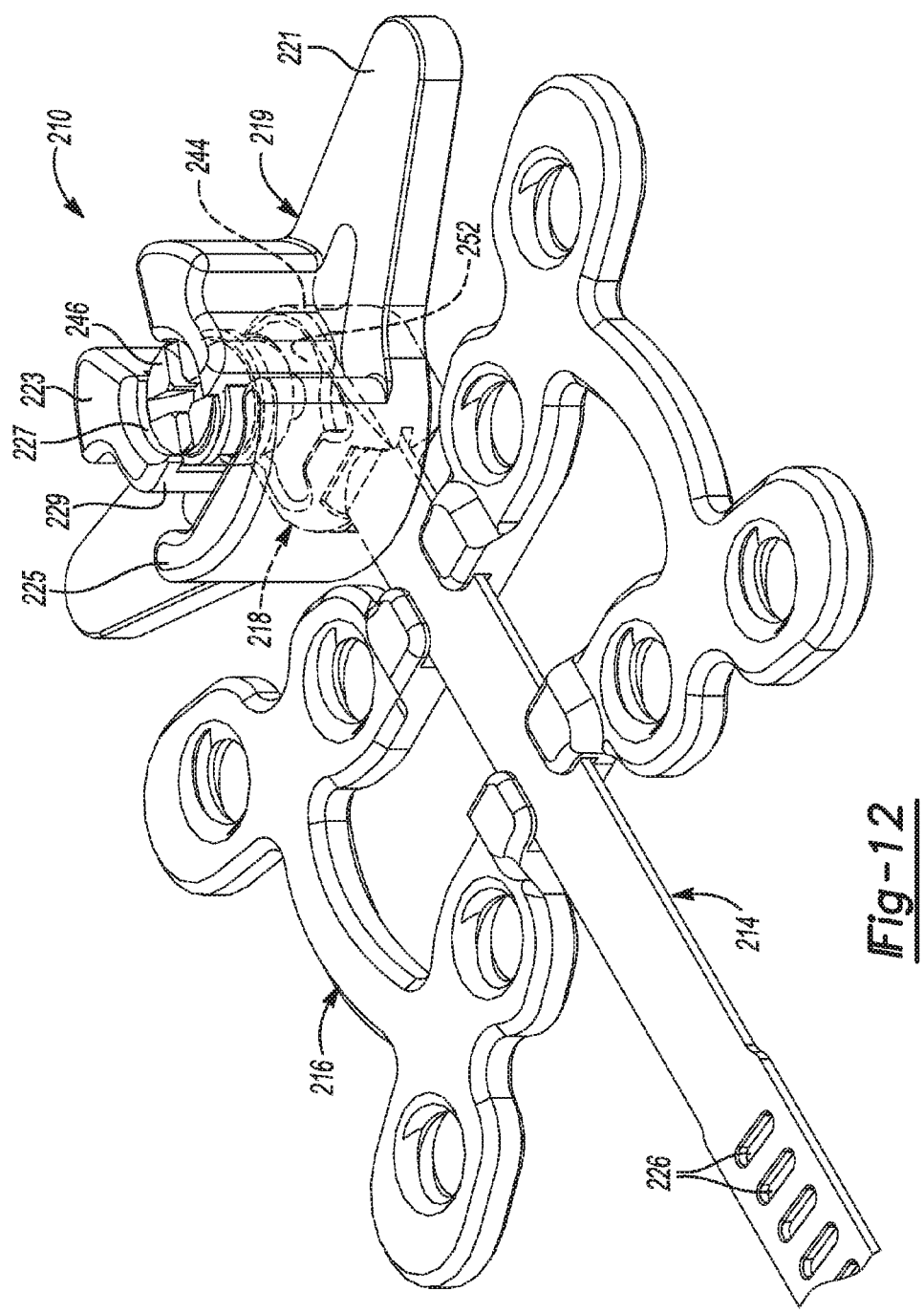
FIG. 12 is a perspective view of yet another closure device having a tensioning device according to the principles of the present disclosure.
Figure 13:
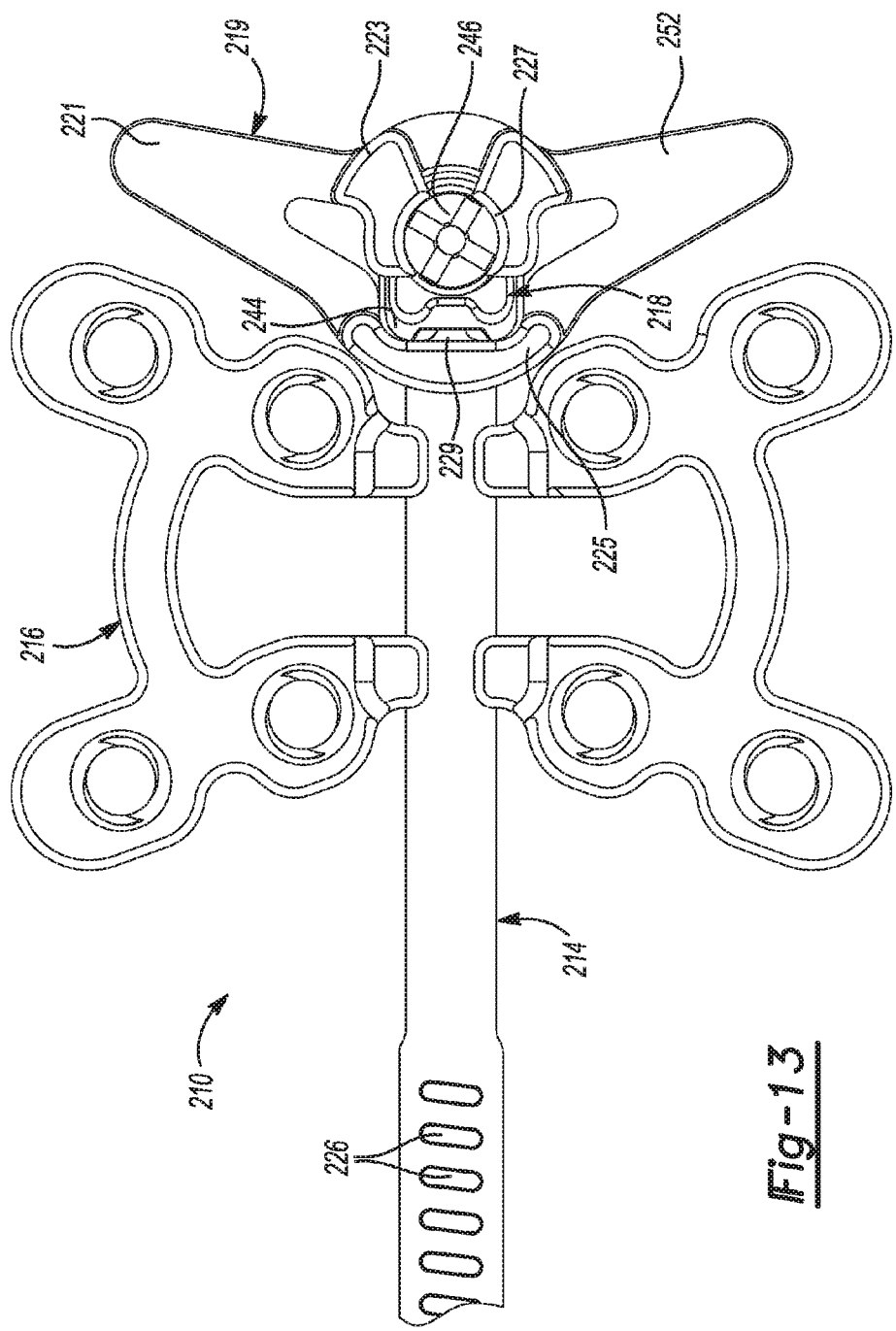
FIG. 13 is a plan view of the closure device of FIG. 12.

With reference to FIGS. 12 and 13, another closure system 210 is provided. The system 210 may include a band 214, a bracket 216, a tensioning device 218 and a detachable fixture device 219. The structures and functions of 21 the band 214, bracket 216 and tensioning device 218 may be similar or identical to that of the band 14, bracket 16 and tensioning device 18 described above, apart from any exceptions described below and/or shown in the figures. Therefore, similar features may not be described again in detail.

As described above, the tensioning device 218 may include a receiver 244 and a tensioning screw 246 that may be similar or identical to the receiver 44 and tensioning screw 46 described above. The fixture device 219 may include a base portion 221, a barrel portion 223 and a tongue portion 225. The barrel and tongue portions 223, 225 may extend upward from the base portion 221. The barrel portion 223 may define an aperture 227 that may threadably receive the tensioning screw 246 of the tensioning device 218. The tongue portion 225 may be spaced apart from the barrel portion 223 such that a passageway 229 is define therebetween.

When tensioning the band 214 around the sternum 12, the fixture device 219 may be placed over the receiver 244 so that the passageway 229 can receive the free end of the band 214 extending upward from the receiver 244 and so that the aperture 227 is generally aligned with a recess 252 of the receiver 244.

With the fixture device 219 in this position, a surgeon may threadably advance the tensioning screw 246 through the aperture 227 in the fixture device 219 and into the recess 252 of the tensioning device 218 to engage slots 226 in the band 214 to pull the free end of the band 214 through the tensioning device 218 in the manner described above. The fixture device 219 can be removed from the tensioning device 218 once the tensioning screw 246 is securely engaged with the receiver 244 or once the band 214 has been tensioned to a desired degree. The barrel and tongue portions 223, 225 of the fixture device 219 provide additional surface area that the surgeon can grip when inserting the tensioning screw 246 into the receiver 244 and tensioning the band 214. The barrel portion 223 may hold the tensioning screw 246 in a position aligned with the recess 252 in the receiver 244 so that the surgeon can easily threadably advance the tensioning screw 246 into the receiver 244.

With reference to FIGS. 14-17, another closure system 310 is provided. The system 310 may include a band 314, a bracket 316, a locking device 317, and a detachable tensioning device 318. The structures and 22 functions of the band 314 and bracket 316 may be similar or identical to that of the band 14 and bracket 16 described above, apart from any exceptions described below and/or shown in the figures. Therefore, similar features may not be described again in detail.

The locking device 317 may include a receiver 344, a locking cam 345, and a tab 346. The receiver 344 may include a recess 348 that receives a head 347 of the locking cam 345. The recess 348 may be in communication with a threaded aperture 352 that threadably engages a threaded shaft 349 (FIG. 15) of the locking cam 345. The receiver 344 may include a first slot 350 in communication with the recess 348 through which a first end 322 of the band 314 may extend. The receiver 344 may also include a second slot 351 that receives a second end 324 of the band 314. The second end 324 of the band 314 may be fixed in the second slot 351 by pins, welding, crimping, and/or one or more fasteners, for example, or any other suitable means.

Figure 15:
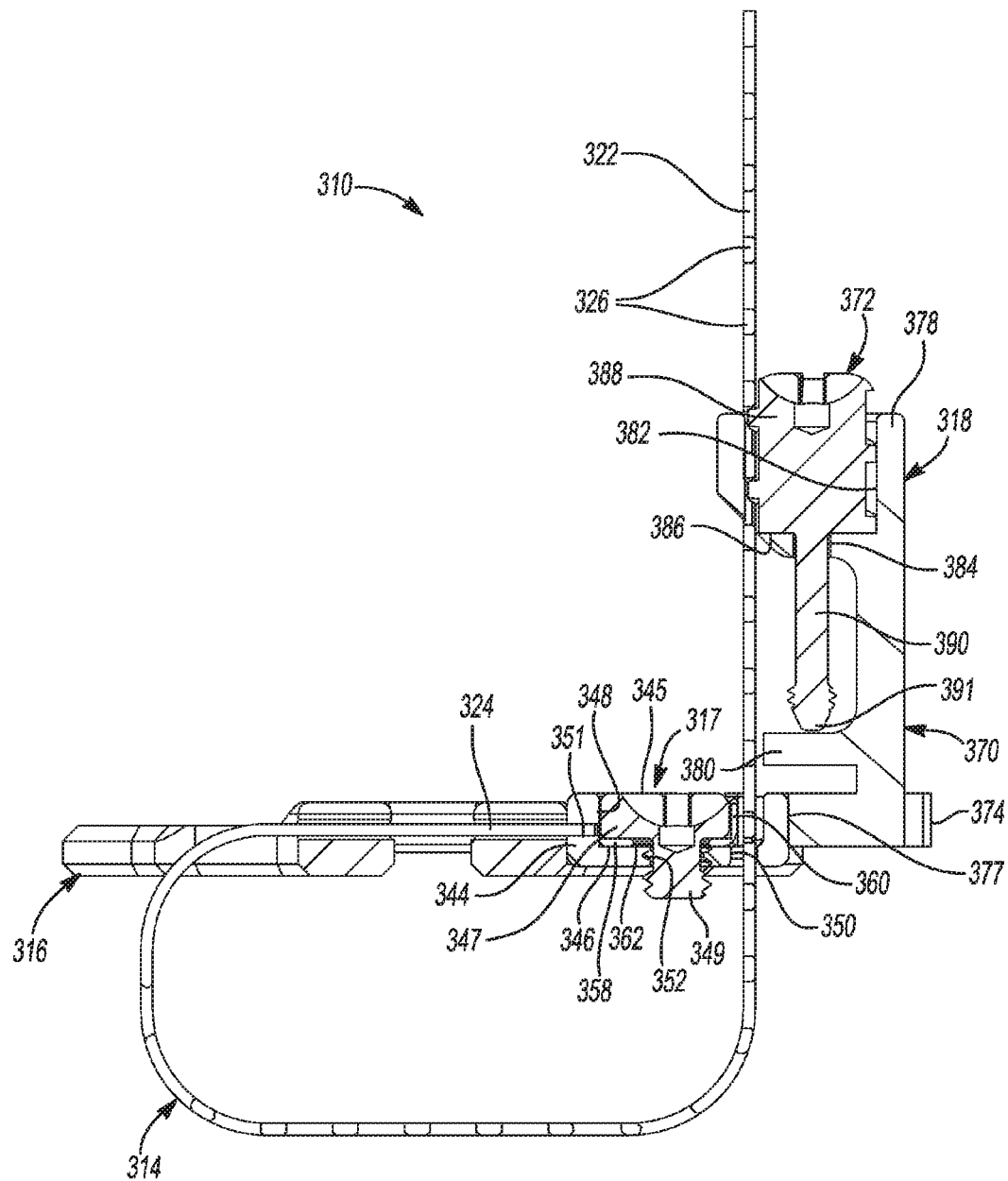
FIG. 15 is a cross-sectional view of the closure device of FIG. 12.
Figure 16:
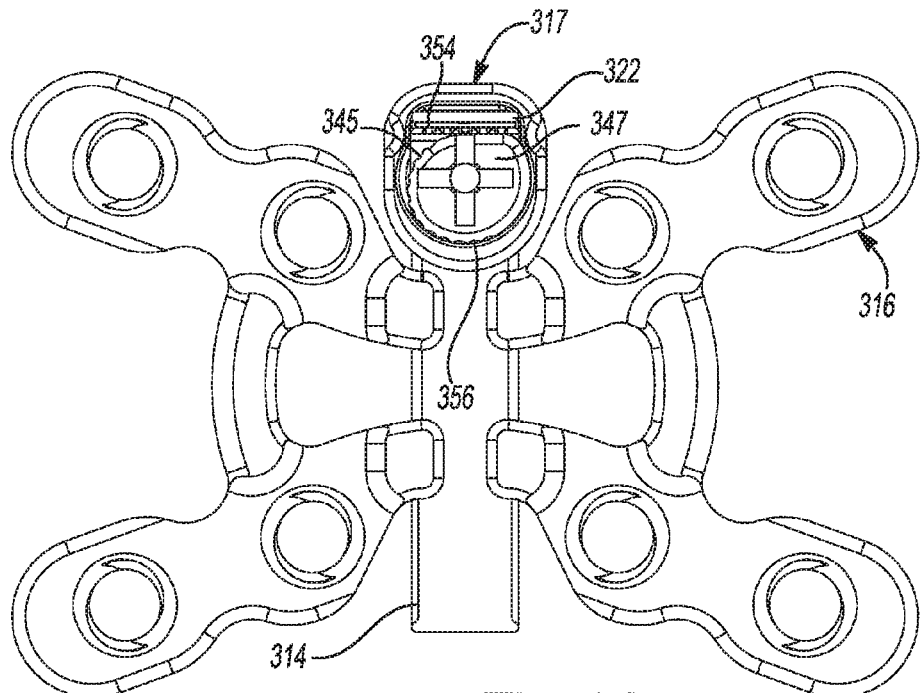
FIG. 16 is a plan view of the closure device of FIG. 14 with a locking cam of the tensioning device in an unlocked position.

A periphery of the head 347 of the locking cam 345 may include a flat portion 354 and a round portion 356. The tab 346 may be a generally L-shaped member having a first leg 358 and a second leg 360 (FIG. 15). The first leg 358 may be disposed between the head 347 and the axial end of the recess 348 and may include an aperture 362 through which the shaft 349 of the locking cam 345 extends. The second leg 360 may extend upward from the first leg 358 adjacent the periphery of the head 347.

Figure 17:
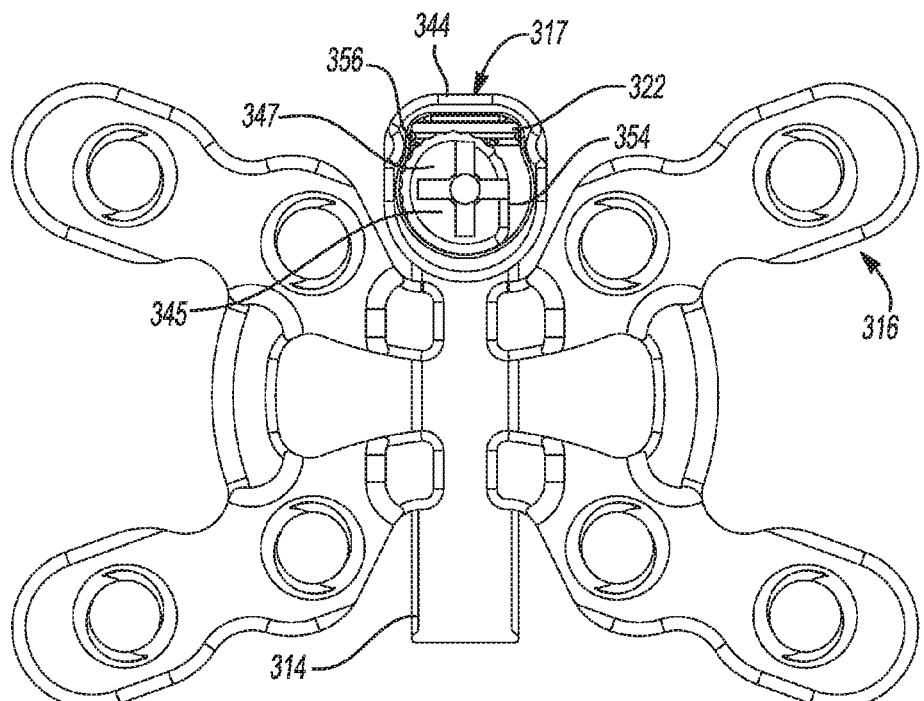
FIG. 17 is a plan view of the closure device of FIG. 14 with a locking cam of the tensioning device in a locked position.

The locking cam 345 may be movable between an unlocked position (FIGS. 14-16) and a locked position (FIG. 17). In the unlocked position, the flat portion 354 of the locking cam 345 may be facing the portion of the band 314 extending through the first slot 350 of the receiver 344 and may allow the band 314 to freely move through the first slot 350. In the locked position, the round portion 356 of the locking cam 345 may force the second leg 360 of the tab 346 against the portion of the band 314 extending through the first slot 350, thereby clamping the band 314 in place relative to the receiver 344. Once the band 314 has been tensioned by the tensioning device 318 (as described below) to a desired amount, a surgeon may use a screwdriver to engage slots in the head 347 of the locking cam 345 to threadably move the locking cam 345 from the unlocked position to the locked position.

In some embodiments, the locking device 317 may not include the tab 346, and in such embodiments, the round portion 356 may press directly against the band 314 to clamp the band 314 in place. In some embodiments, the periphery of the head 347 may include a thread or one or more annular ribs that engages one or more of the slots 326 of the band 314 when the locking cam 345 is in the locked position to fix the band 314 relative to the receiver 344.

Figure 14:
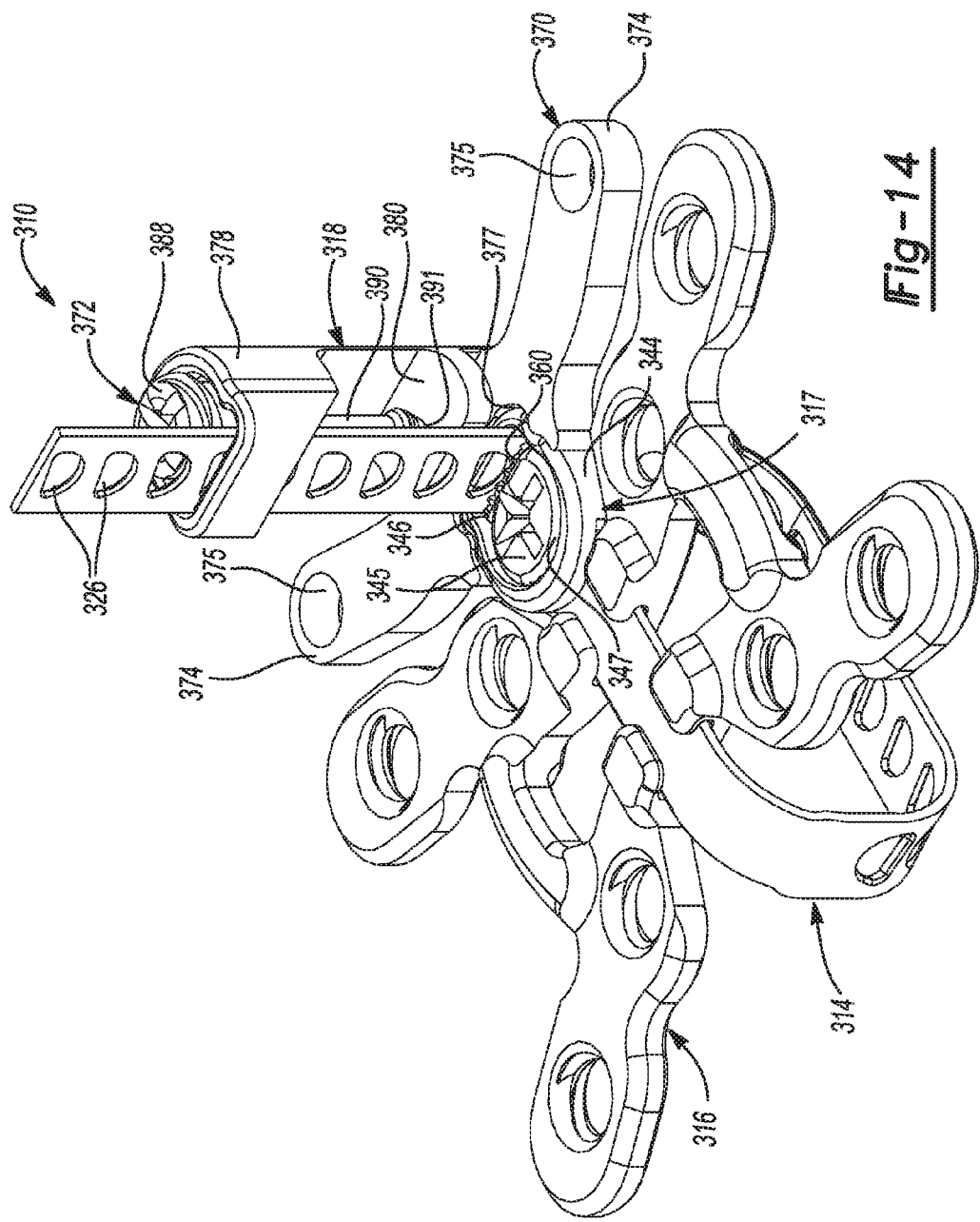
FIG. 14 is a perspective view of yet another closure device having a tensioning device according to the principles of the present disclosure.

The tensioning device 318 may include a base 370 and a tensioning screw 372. The base 370 may include a pair of legs 374 and an upright portion 376 that extends upward from the legs 374. In some embodiments, the legs 374 may include apertures 375 for temporarily fastening the base 370 to the sternum 12. The receiver 344 of the locking device 317 may nest within a recess 377 formed in the legs 374 (as shown in FIG. 14). The upright portion 376 may include a receiver 378 and a reaction platform 380. As shown in FIG. 15, the receiver 378 may include a recess 382, an aperture 384 in communication with the recess 382, and a slot 386 in communication with the recess 382.

The tensioning screw 372 may include a threaded head 388 and a shaft 390 extending from the head 388. The head 388 may be received in the recess and non-threadably rotatable therein. The shaft 390 may extend through the aperture 384 in the receiver 378. A distal end 391 of the shaft 390 may contact the reaction platform 380.

To tension the band 314 around the sternum 12, the first end 322 of the band 314 may first be inserted through the slot 386 in the receiver 378 so that the threads on the head 388 can engage the slots 326 in the band 314. Then, with the locking cam 345 in the unlocked position, the surgeon may use a screwdriver to turn the tensioning screw 372 relative to the receiver 378, thereby pulling the band 314 upward (relative to the view shown in FIG. 15) through the receiver 378. Once the band 314 is sufficiently taught around the sternum 12, the surgeon may turn the locking cam 345 to the locked position to fix the band 314 relative to the receiver 344 of the locking device 317. Thereafter, the tensioning device 318 can be removed, and the first end 322 of the band 314 can be trimmed, as desired.

Figure 18:
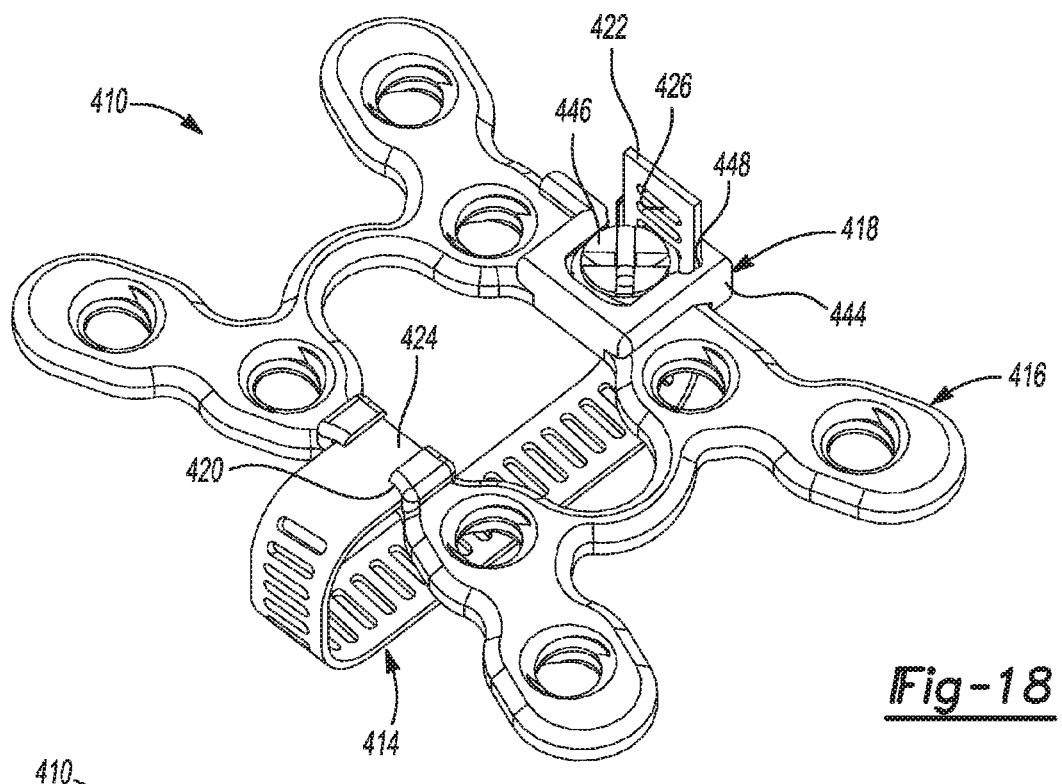
FIG. 18 is a perspective view of yet another closure device having a tensioning device according to the principles of the present disclosure.
Figure 19:
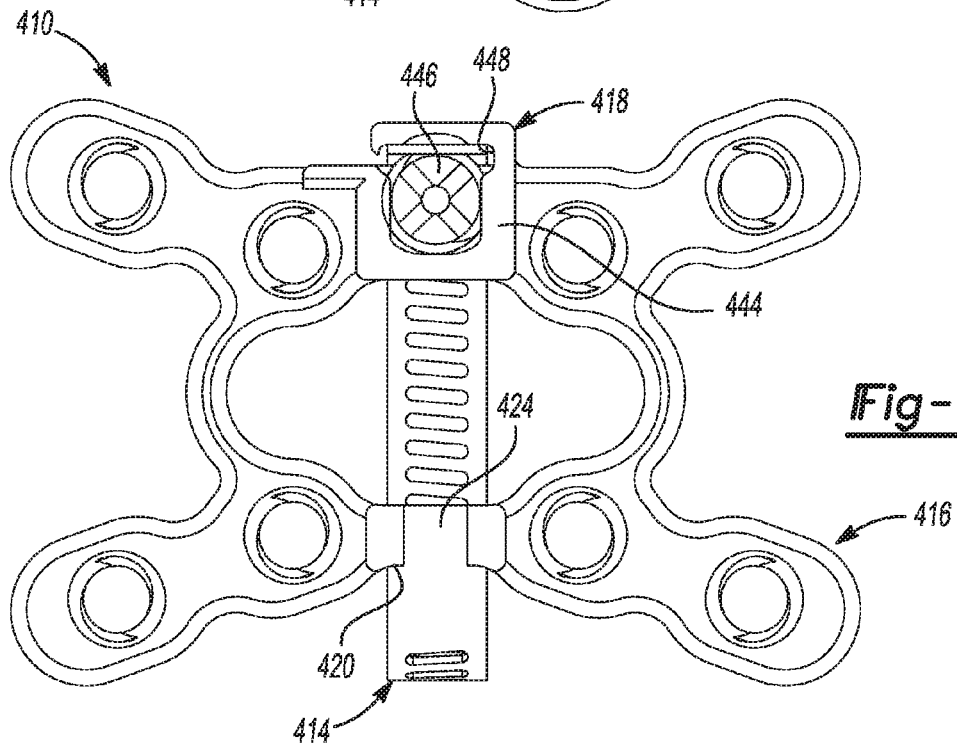
FIG. 19 is a plan view of the closure device of FIG. 18.
Figure 20:
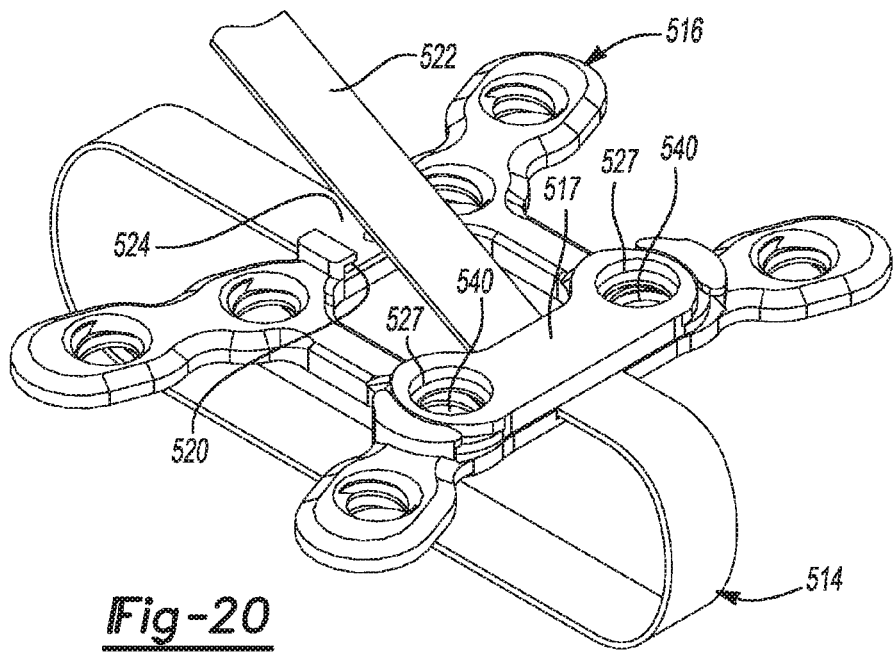
FIG. 20 is a perspective view of yet another closure device according to the principles of the present disclosure.

With reference to FIGS. 18 and 19, another closure system 410 is provided. The system 410 may be similar to the system 10 described above, apart from any differences described below and/or shown in the figures. Therefore, similar features will not be described again in detail. The system 410 may include a band 414, a bracket 416, and a tensioning device 418. The structure and function of the band 414, bracket 416 and tensioning device 418 may be similar or identical to that of the band 14, bracket 16 and tensioning device 18 described above, apart from the differences described above.

One end 424 of the band 414 may be received in a channel 420 formed in the bracket 416 and fixed therein by one or more pins (not shown), fasteners (not shown), crimping and/or any other suitable means. The other end 422 of the band 414 may be received through the tensioning device 418.

The tensioning device 418 may include a receiver 444 and a tensioning screw 446. The receiver 444 may be fixedly attached to or integrally formed with the bracket 416 and may rotatably receive the tensioning screw 446 therein. A slot 448 may be formed in the receiver 444 through which the end 424 of the band 414 may be received. A radial periphery of the tensioning screw 446 may engage slots 426 in the band 414 so that when the tensioning screw 446 is rotated (e.g., with a screwdriver), the band 414 is advanced through the slot 448. In this manner, the band 414 can be tensioned around the patient's bone and/or other tissue in the manner described above. Once the band 414 has been tensioned to a desired amount, the end 422 of the band 414 may be trimmed and/or folded over.

Figure 21:
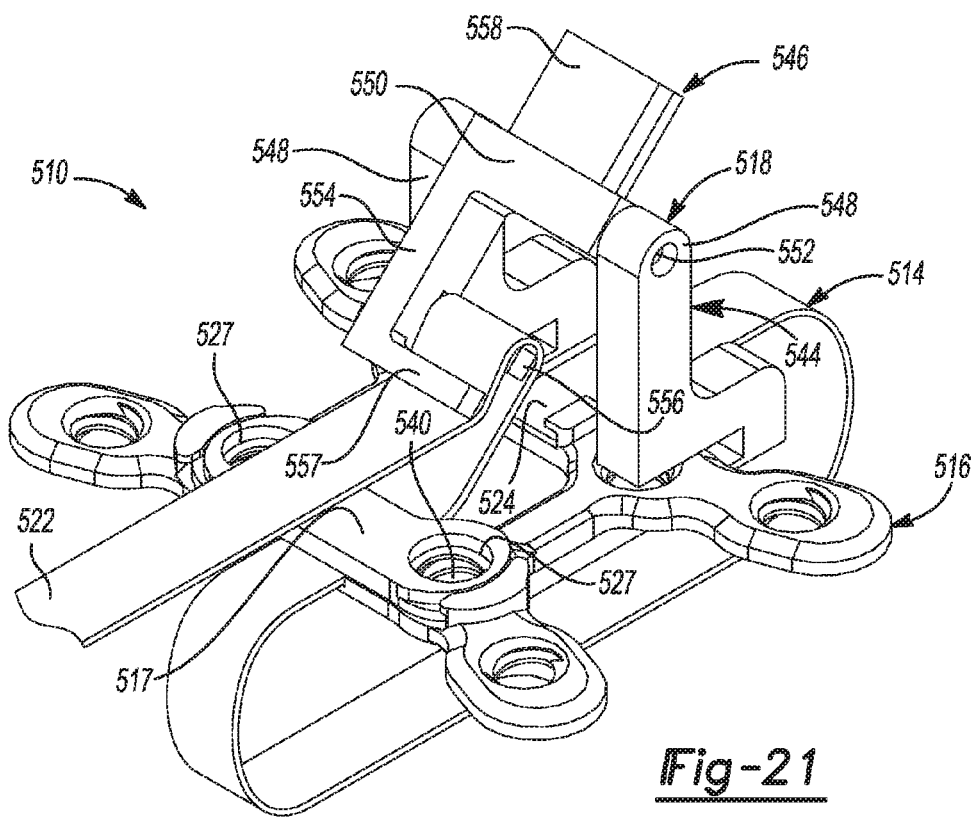
FIG. 21 is a perspective view of the closure device of FIG. 20 and a tensioning device according to the principles of the present disclosure.
Figure 22:
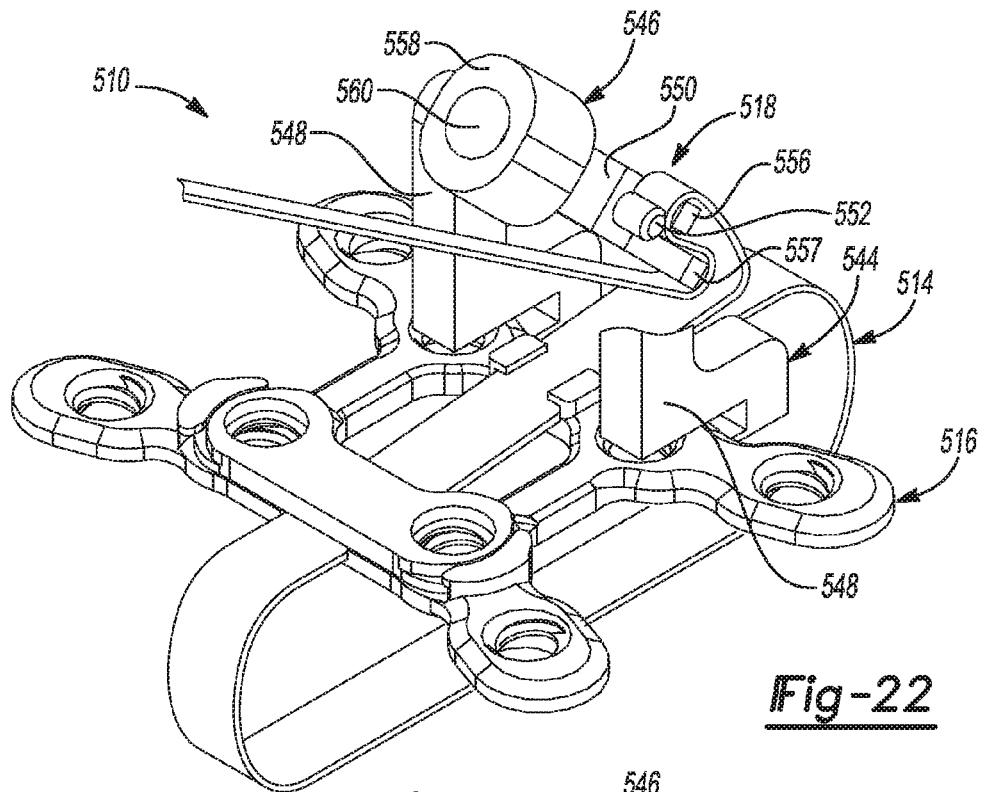
FIG. 22 is another perspective view of the closure device and tensioning device of FIG. 20.
Figure 23:
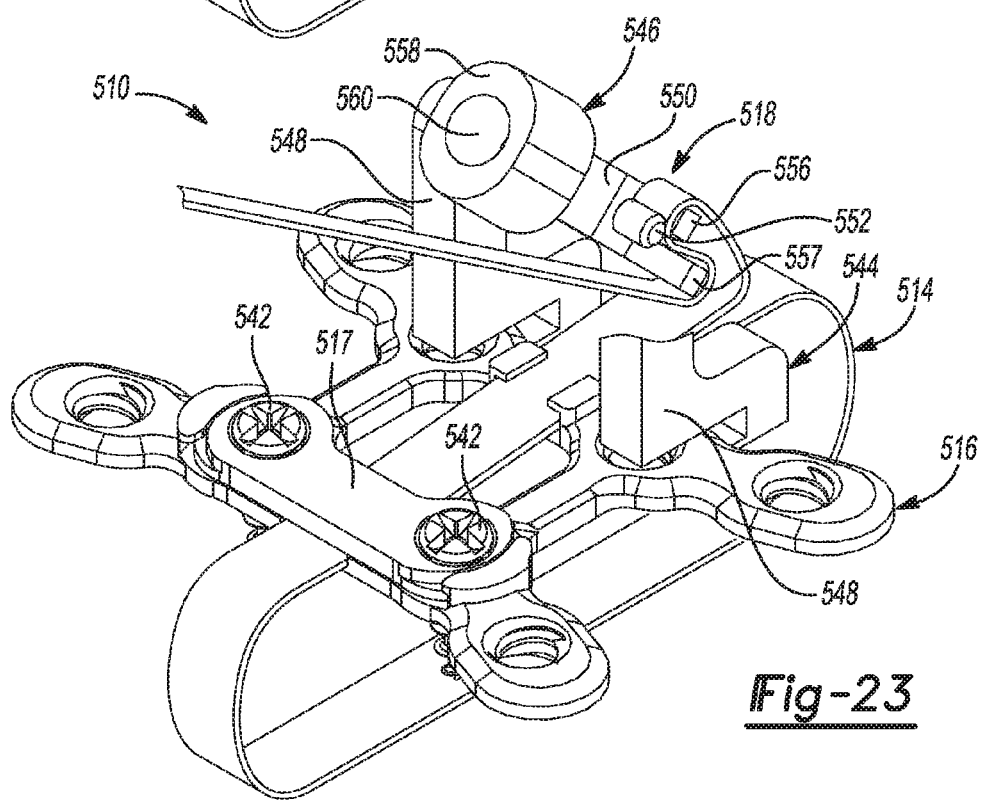
FIG. 23 is yet another perspective view of the closure device and tensioning device of FIG. 20.

With reference to FIGS. 20-25, another closure system 510 is provided. The system 510 may include a band 514, a bracket 516, a clamp 517 and a tensioning device 518 (FIGS. 21-23). The band 514 and bracket 516 can be similar to the bands and brackets described above. Therefore, similar features will not be described again in detail.

One end 524 of the band 514 may be received in a channel 520 formed in the bracket 516 and fixed therein by one or more pins (not shown), fasteners (not shown), crimping and/or any other suitable means. The other end 522 of the band 514 may be received through the clamp 517 and the tensioning device 518.

Figure 24:
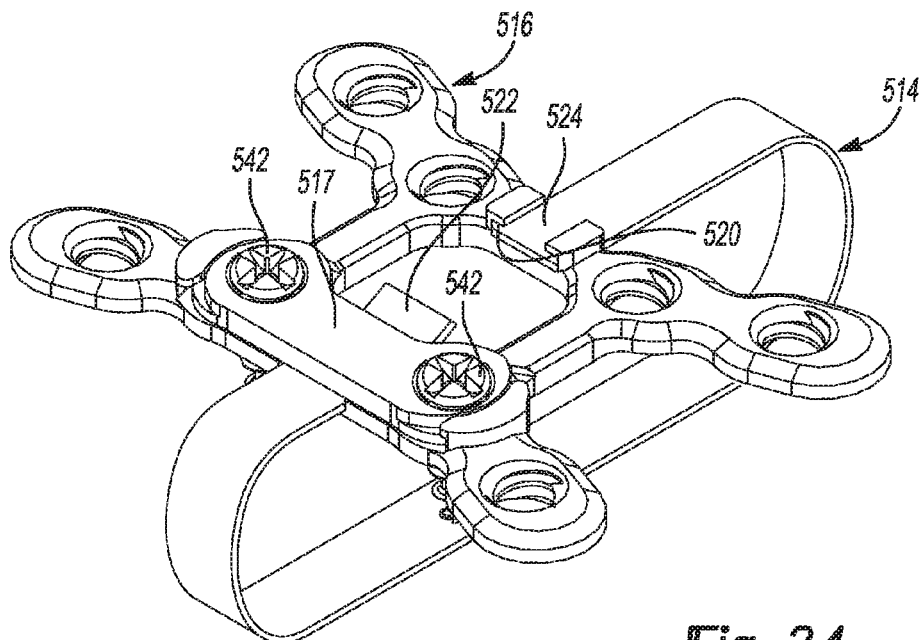
FIG. 24 is a perspective view of the closure device of FIG. 20 with the tensioning device removed.
Figure 25:
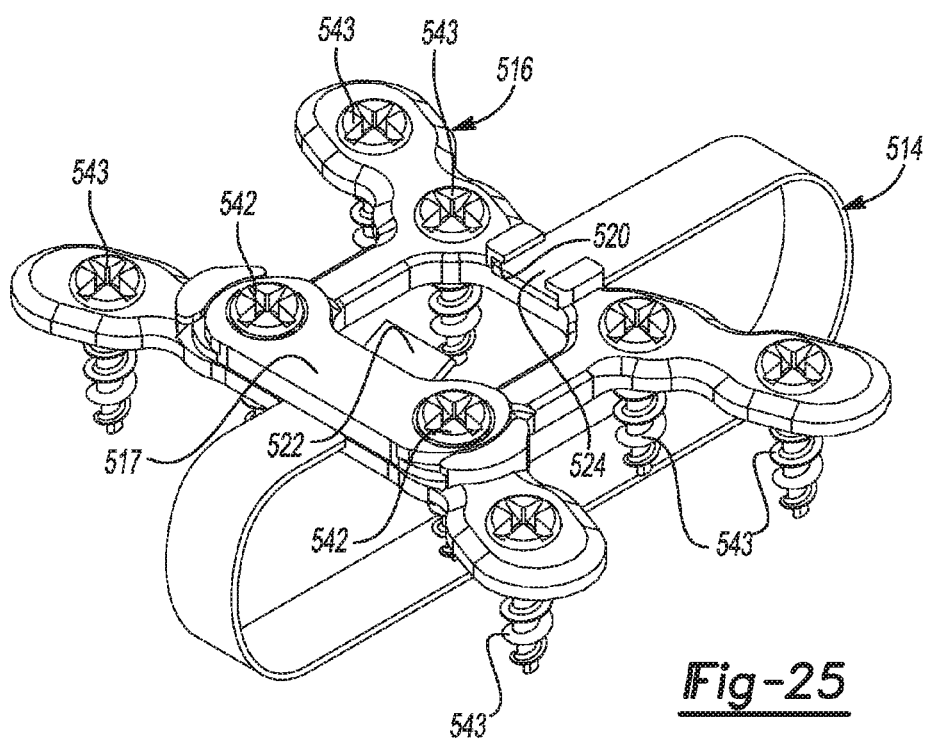
FIG. 25 is another perspective view of the closure device of FIG. 20.

The clamp 517 may be a generally flat member including a pair of apertures 527 formed therein. The apertures 527 may be aligned with a pair of apertures 540 formed in the bracket 516 so that a pair of fasteners 542 may be driven through the apertures 527, 540, as shown in FIGS. 23-25. As shown in FIGS. 20-25, the band 514 may be disposed between the clamp 517 and the bracket 516 so that when the fasteners 542 are tightened within the apertures 527, 540, the band 514 may be fixedly clamped between the clamp 517 and the bracket 516.

Prior to fixedly clamping the band 514 between the clamp 517 and the bracket 516, the band 514 may be tensioned around the patient's bone and/or tissue using the tensioning device 518. The tensioning device 518 may include a base 544 and a tensioning lever 546. The base 544 may include a pair of generally L-shaped legs 548 that rotatably support the tensioning lever 546 therebetween. The tensioning lever 546 may include a main body 550 having a pair of pegs 552 extending therefrom. The pegs 552 may rotatably engage the legs 548 of the base 544. The tensioning lever 546 may be rotatable relative to the base 544 about an axis defined by the pegs 552 between a first position (FIG. 21) and a second position (FIGS. 22 and 23). A first arm 554 (FIG. 21) may extend from the main body 550 in a first direction and may include first and second tabs 556, 557 that engage the band 514. A second arm 558 may extend from the main body 550 in a second direction opposite the first direction and may include an aperture 560 formed therein.

To tension the band 514 around the patient's bone and/or tissue using the tensioning device 518, the end 522 of the band 514 may be looped around the first tab 556 and under the second tab 557 with the tensioning lever 546 in the first position, as shown in FIG. 21. The band 514 may be manually pulled taught to remove the slack in the band 514 around the bone and/or tissue and so that the band 514 is fixed relative to the first and second tabs 556, 557. Then, the tensioning lever 546 may be rotated relative to the base 544 to the second position, as shown in FIGS. 22 and 23. Moving the tensioning lever 546 to the second position may further tighten the band 514 around the bone and/or tissue. The tensioning lever 546 can be rotated to the second position by gripping the first and/or second arms 554, 558 manually or with a tool such as pliers or vice 26 grips, for example. The tensioning lever 546 could also be rotated to the second position by inserting a screwdriver or other tool into the aperture 560 in the second arm 558 and forcing the tensioning lever 546 to the second position using the screwdriver. With the tensioning lever 546 in the second position, the fasteners 542 can be tightened to clamp the band 514 between the clamp 517 and the bracket 516, thereby fixing the band 514 in the tensioned condition, as shown in FIGS. 24 and 25.

After tensioning and clamping the band 514, the tensioning lever 546 can be moved back to the first position so that the band 514 can be removed from the tensioning lever 546 and the tensioning device 518 can be removed from the bracket 516. The end 522 of the band 514 can then be trimmed to a desired length. As shown in FIG. 25, additional fasteners 543 can be used to fasten the bracket 516 to the bone and/or tissue.

Figure 26:
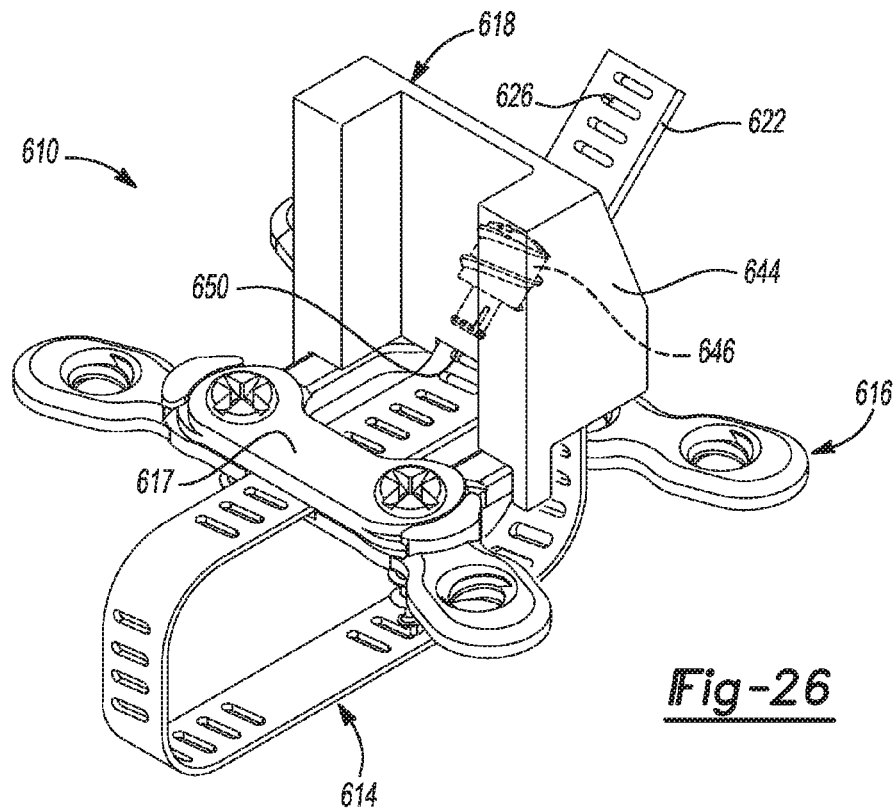
FIG. 26 is a perspective view of yet another closure device having a tensioning device according to the principles of the present disclosure.
Figure 27:
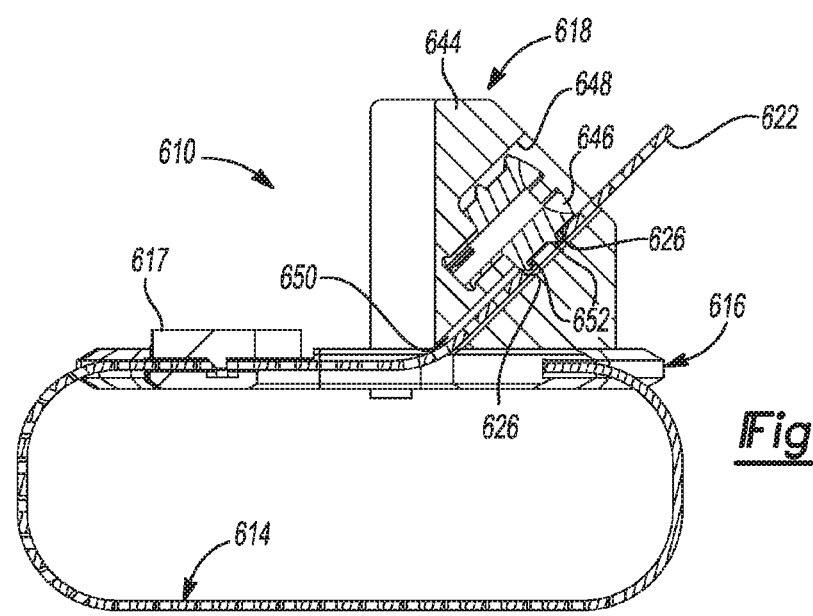
FIG. 27 is a cross-sectional view of the closure device and tensioning device of FIG. 26.

With reference to FIGS. 26 and 27, another closure system 610 is provided. The system 610 may include a band 614, a bracket 616, a clamp 617 and a tensioning device 618. The structure and function of the band 614, bracket 616 and clamp 617 can be similar or identical to that of the band 514, bracket 516 and clamp 517 described above. Therefore, similar features will not be described again in detail. While the band 514 described above may not necessarily include slots or apertures, the band 614 may include slots 626 or apertures, as shown in FIGS. 26 and 27.

The tensioning device 618 may include a base 644 and a tensioning screw 646. The base 644 may include a recess 648 and a channel 650 in communication with the recess 648. The tensioning screw 646 may be similar or identical to the tensioning screw 46, for example, and may be rotatably received in the recess 648. The base 644 may be placed over or on the bracket 616 so that an end 622 of the band 614 may be received through the channel 650 and into the recess 648 as shown in FIG. 27. Threads 652 of the tensioning screw 646 may engage the slots 626 in the band so that the band 614 is advanced through the channel 650 as the tensioning screw is rotated relative to the base 644. The tensioning screw 646 may be rotated until the band 614 has been tensioned, as desired, around the patient's bone and/or tissue. Once tensioned, fasteners 642 may tighten the clamp 617 against the bracket 616 to fix 27 the band in the tensioned condition. Thereafter, the end 622 of the band 614 can be trimmed so that the tensioning device 618 can be removed from the bracket 616.

Figure 28:
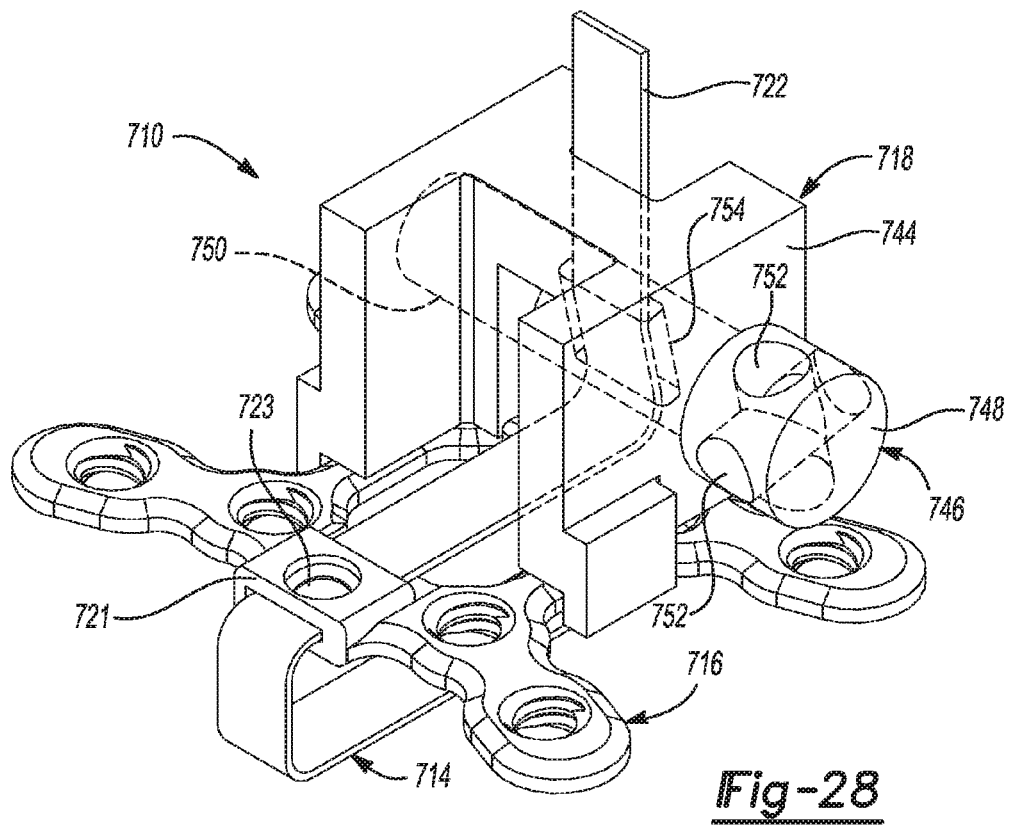
FIG. 28 is a perspective view of yet another closure device having a tensioning device according to the principles of the present disclosure.
Figure 29:
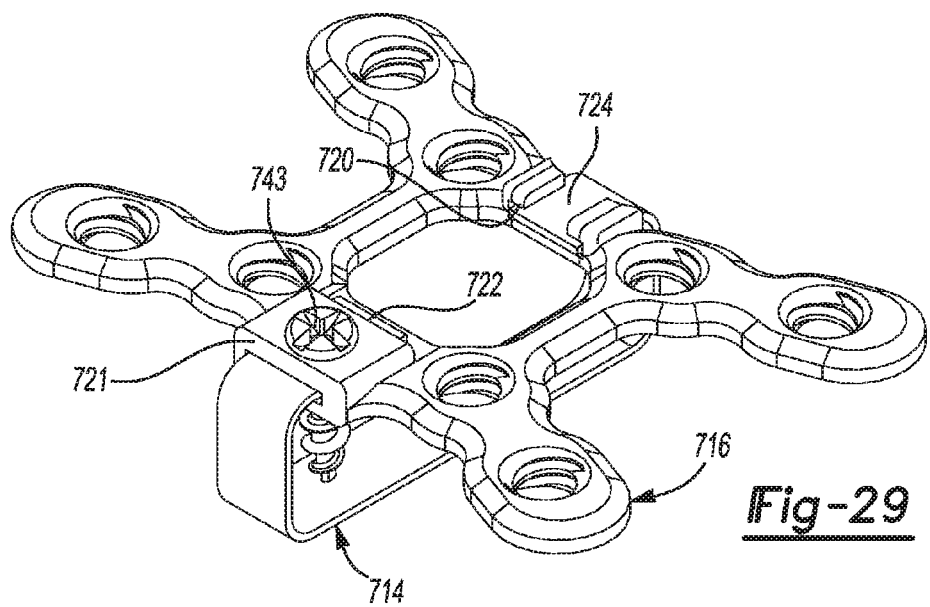
FIG. 29 is a perspective view of the closure device of FIG. 28 with the tensioning device removed.
Figure 30:
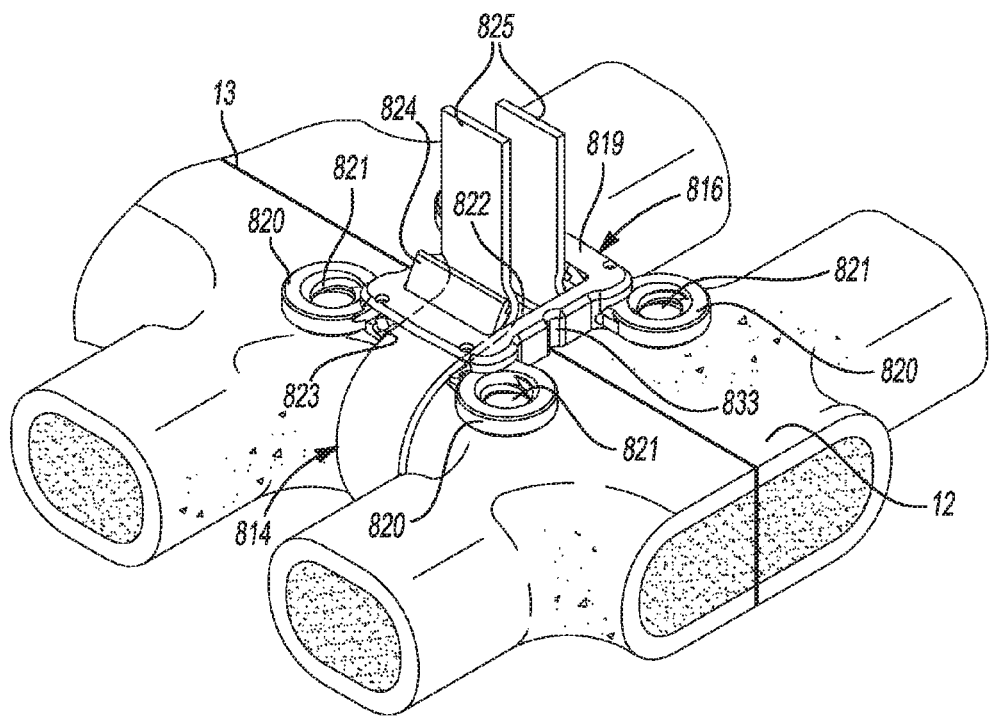
FIG. 30 is a perspective view of yet another closure device according to the principles of the present disclosure.
Figure 31:
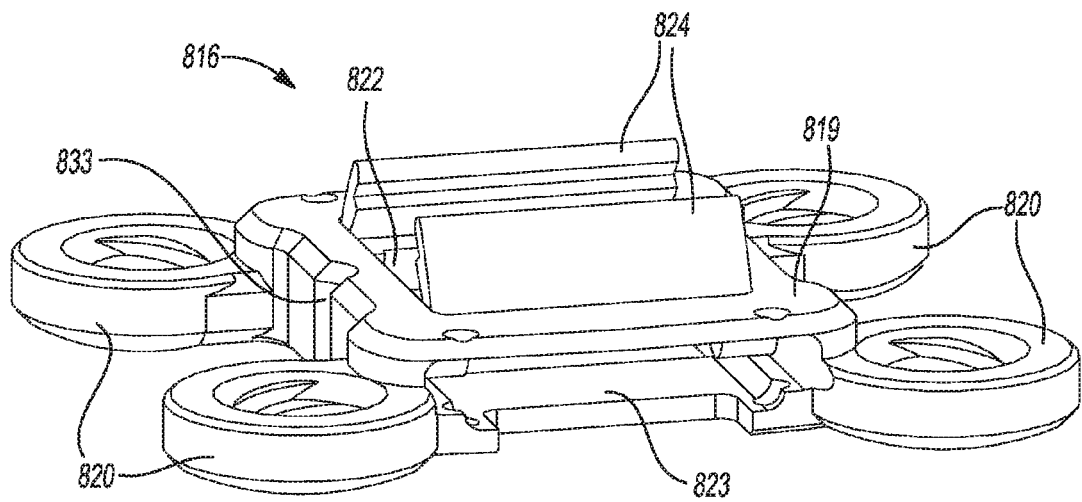
FIG. 31 is a perspective view of a bracket of the closure device of FIG. 30.

With reference to FIGS. 28 and 29, another closure system 710 is provided. The system 710 may include a band 714, a bracket 716 and a tensioning device 718. The structure and function of the band 714 and bracket 716 can be similar or identical to that of the band 514 and bracket 516 described above. Therefore, similar features will not be described again in detail.

The bracket 716 may include a channel 720 in which an end 724 of the band 714 is fixedly received and a sleeve 721 in which another end 722 of the band 714 is received. The sleeve 721 may include an aperture 723 extending therethrough. As shown in FIG. 29, a fastener 743 may be driven through the aperture 723 and through the band 714 to fix the end 722 relative to the bracket 716 once the band 714 has been tensioned using the tensioning device 718.

The tensioning device 718 may include a base 744 and a tensioning pin 746. The base 744 may be a generally H-shaped member and may fit over or on the bracket 716, as shown in FIG. 28. The base 744 may rotatably support the tensioning pin 746. The tensioning pin 746 may include a head 748 and a shaft 750. The head 748 may include one or more apertures 752 adapted to receive a shaft of a screwdriver or a wrench (not shown), for example, or any other elongated object that can be inserted through one of the apertures 752 and used as a lever for rotating the tensioning pin 746. The shaft 750 of the tensioning pin 746 may include a slot 754 that extends radially therethrough.

As shown in FIG. 28, the end 722 of the band 714 may be received though the slot 754. Once the band 714 is received through the slot 754, the tensioning pin 746 may be rotated, thereby wrapping the band 714 around the shaft 750 and applying a tensioning force on the band 714. The tensioning pin 746 can be rotated until the band 714 is sufficiently tensioned around the patient's bone and/or tissue. After the band 714 is sufficiently tensioned, the fastener 743 may be driven through the aperture 723 and through the band 714 to fix the band 714 relative to the bracket 716 in the tensioned condition, as shown in FIG. 29. Thereafter, the end 722 of the band 714 can be trimmed and the tensioning device 718 can be removed from the bracket 716, as shown in FIG. 29.

With reference to FIGS. 30-36, another closure system 810 is provided. The system 810 may include a band 814, a bracket 816 and a tensioning device 818 (FIGS. 32-35). The bracket 816 may include a body 819 and a plurality of feet 820 extending therefrom. A mounting aperture 821 may extend through each foot 820 and may receive a fastener 813 (FIG. 36) to secure the bracket 816 to the sternum 12. The body 819 may include a central opening 822 and a pair of passages 823 in communication with the opening 822. A pair of cleats 824 may be disposed within the opening 822 and may be pivotable relative to the body 819 between an unlocked position (FIGS. 30, 31, 34 and 35) allowing ends 825 of the band 814 to freely slide through the passages 823 and opening 822 and a locked position (FIG. 36) fixing the ends 825 of the band 814 relative to the passages 823 and opening 822. The cleats 824 may be configured so that the ends 815 of the band 814 can be pulled up through the central opening 822, but the cleats 824 will move into the locked position as soon as the ends 815 begin to move back through the central opening in the opposite direction. That is, the cleats 824 will allow the band 814 to be tensioned, but will move into the locked position to prevent the band 814 from loosening, unless they are manually held in the unlocked position.

Figure 32:
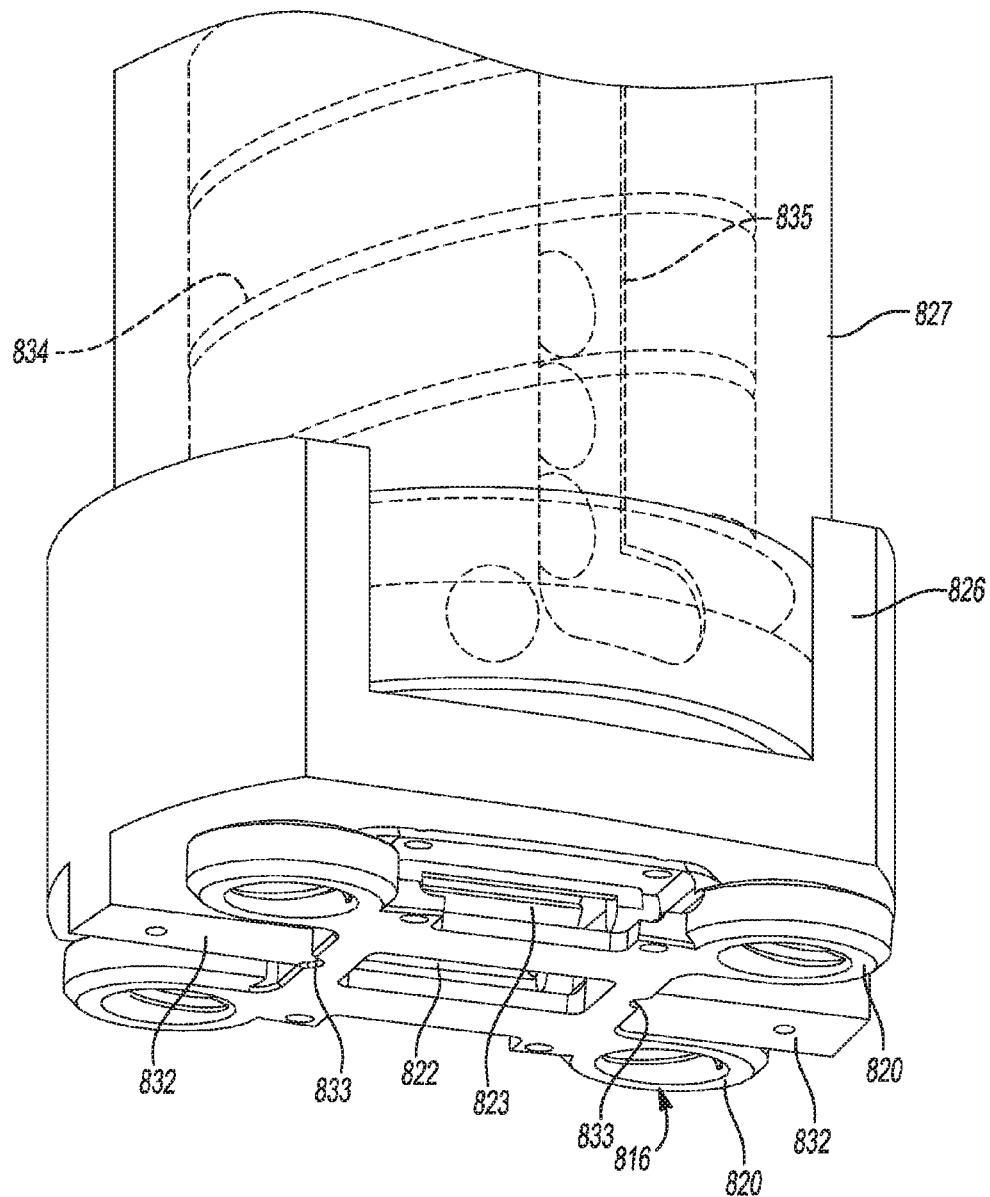
FIG. 32 is a partial perspective view of the closure device of FIG. 30 and a tensioning device according to the principles of the present disclosure.
Figure 33:
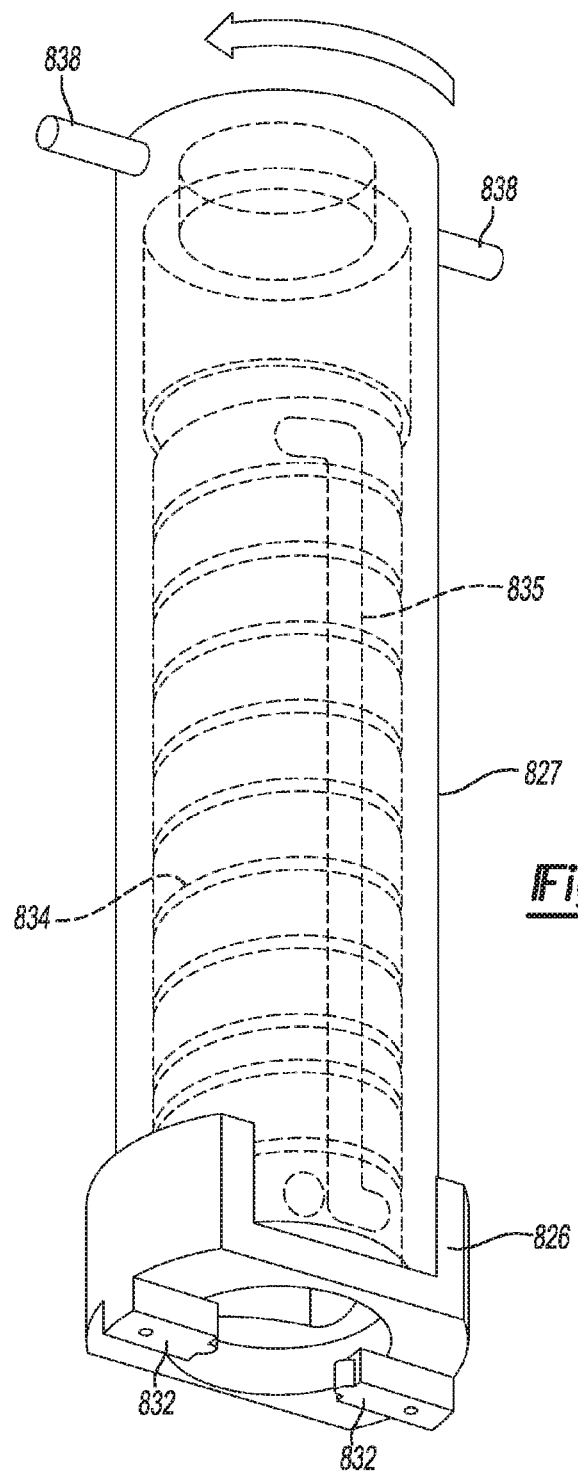
FIG. 33 is a perspective view of the tensioning device of FIG. 32.
Figure 34:
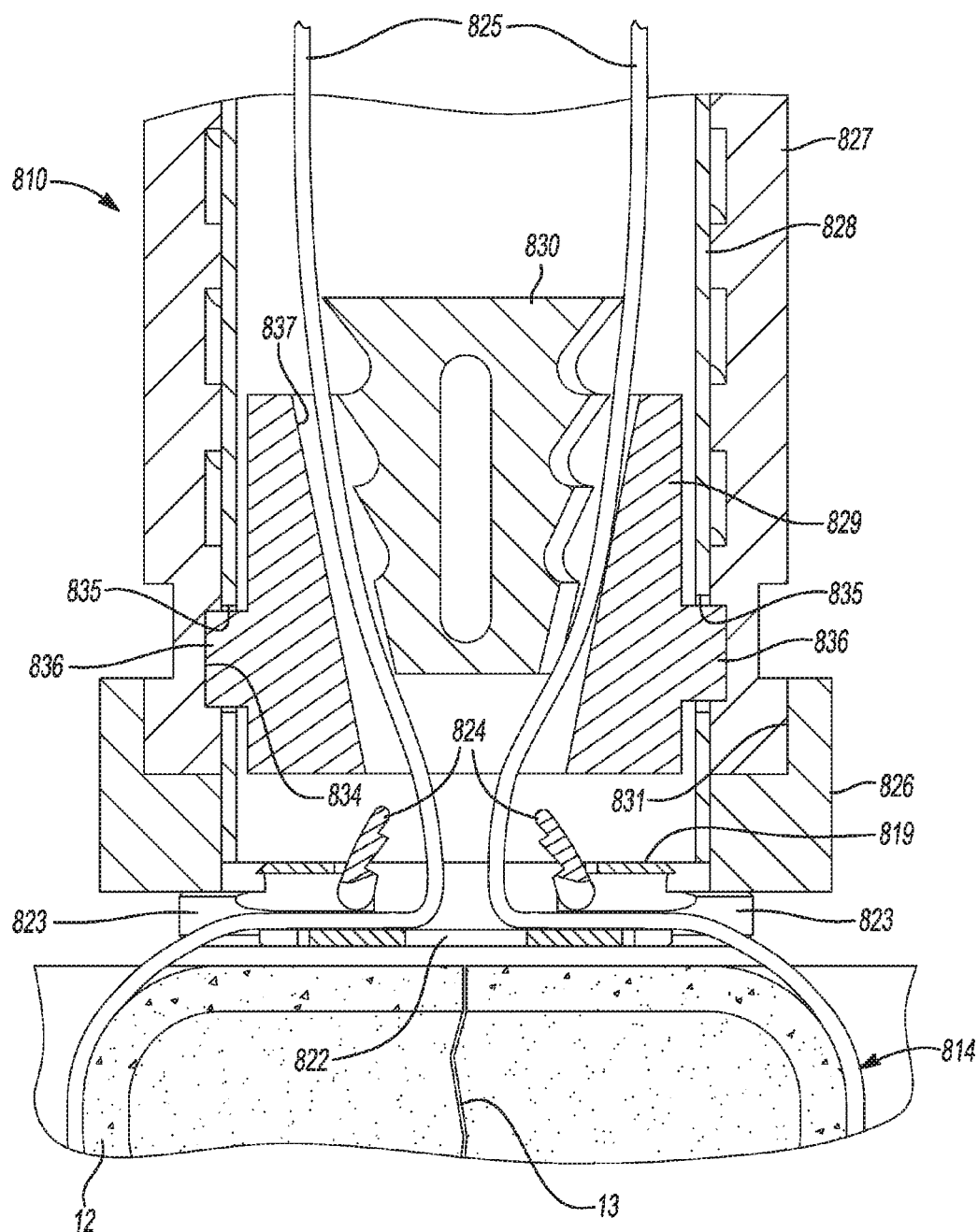
FIG. 34 is a partial cross-sectional view of the tensioning device and the closure device of FIG. 32 attached to a sternum.
Figure 35:
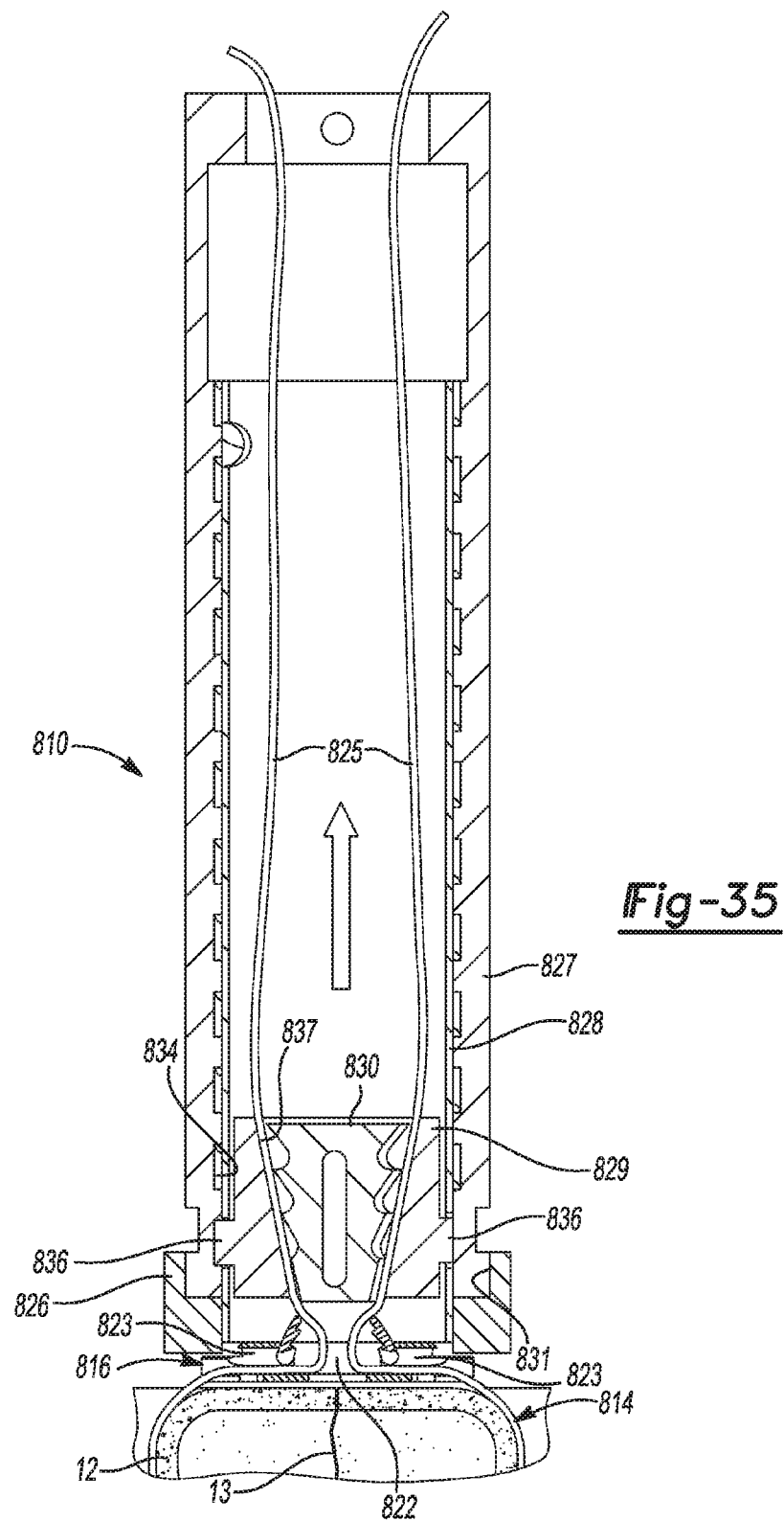
FIG. 35 is a cross-sectional view of the tensioning device and the closure device of FIG. 32 attached to the sternum.
Figure 36:
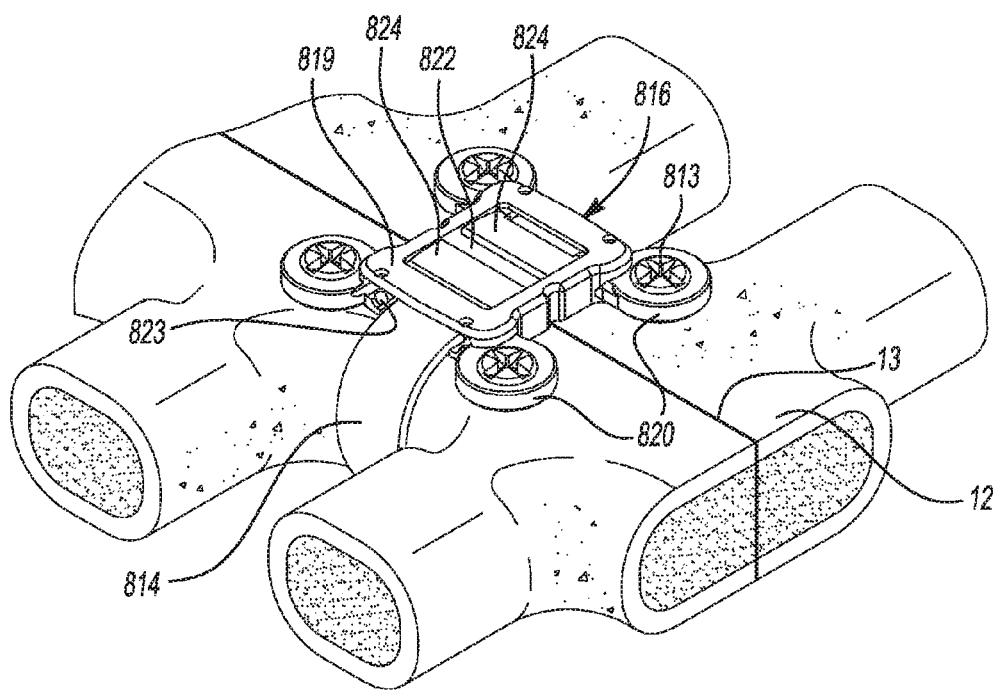
FIG. 36 is a perspective view of the closure device attached to the sternum.

Referring now to FIGS. 32-35, the tensioning device 818 may include a base 826, an outer tube 827, an inner tube 828, a first gripping member 829 and a second gripping member 830. The base 826 may define a recess 831 within which the outer tube 827 and inner tube 828 may be received. The base 826 may include feet 832 that matingly engage notches 833 in the bracket 816, as shown in FIG. 32.

The outer tube 827 may include a spiral groove 834 formed in its inner diametrical surface. The inner tube 828 may be received within the outer tube 827 and may include a pair of axially extending grooves 835 formed through the inner and outer diametrical surfaces of the inner tube 828. The first gripping member 829 may be disposed within the inner tube 828 and may include a pair of pegs 836 and a tapered central aperture 837. Each of the pegs 836 may extend through a corresponding one of the axially extending grooves 835 in the inner tube 828 and slidably engage the spiral groove 834 in the outer tube 827. In this manner, relative rotation between the outer and inner tubes 827, 828 causes axial 29 movement of the first gripping member 829 within the inner tube 828. That is, the pegs 836 move axially along the axially extending grooves 835 as the outer tube 827 rotates relative to the inner tube 828. One or more handles 838 (FIG. 33) may extend outward from the outer tube 827 which may be gripped by a surgeon to facilitate rotation of the outer tube 827 relative to the inner tube 828.

The second gripping member 830 may be disposed within the tapered central aperture 837 of the first gripping member 829. The second gripping member 830 may be axially movable relative to the first gripping member 829 between an unlocked position (FIG. 34) and a locked position (FIG. 35) in which ends 815 of the band 814 are gripped between the first and second gripping members. When the second gripping member 830 is in the locked position, upward axial movement of the first gripping member 829 (i.e., during rotation of the outer tube 827 relative to the inner tube 828) causes the first and second gripping members 829, 830 to pull the ends 815 of the band 814 upward relative to the bracket 816, thereby tensioning the band 814 around the sternum 12.

Figure 37:
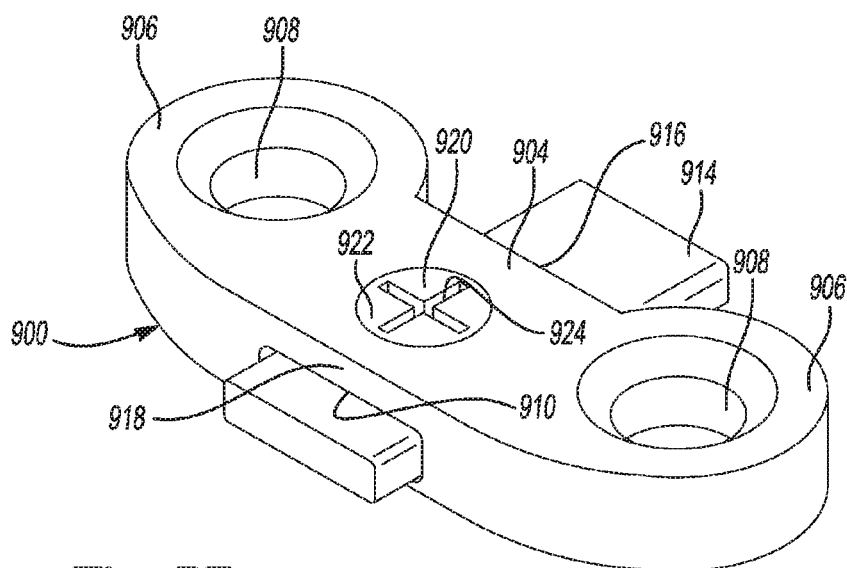
FIG. 37 is a perspective view of a clamping device and band according to the principles of the present disclosure.
Figure 38:
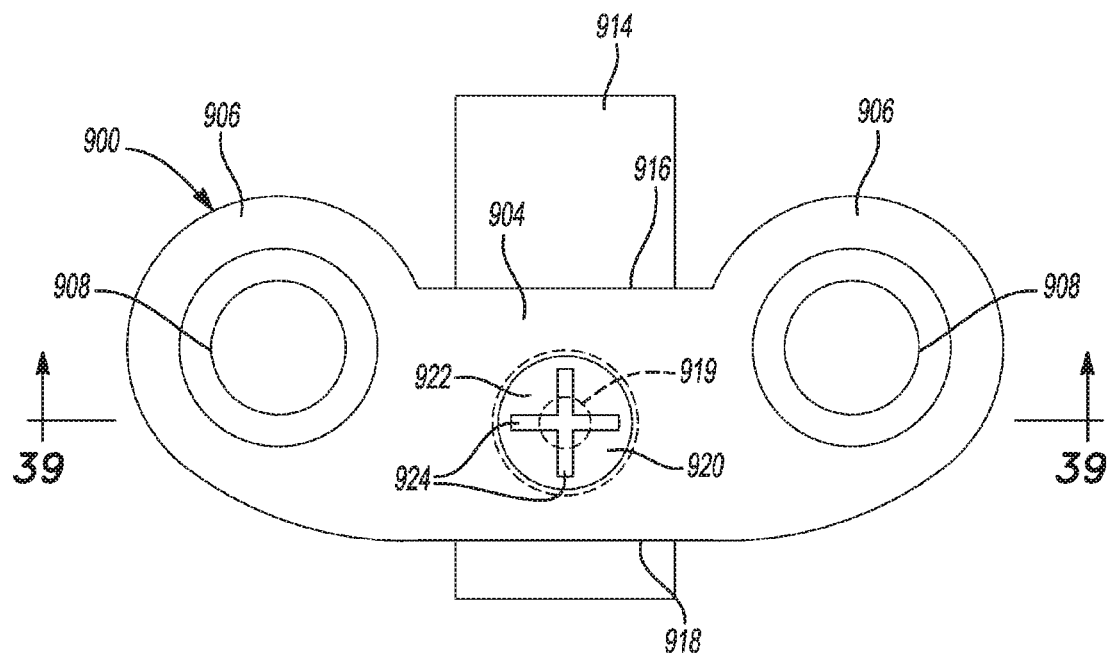
FIG. 38 is a plan view of the clamping device and band of FIG. 37.
Figure 39:
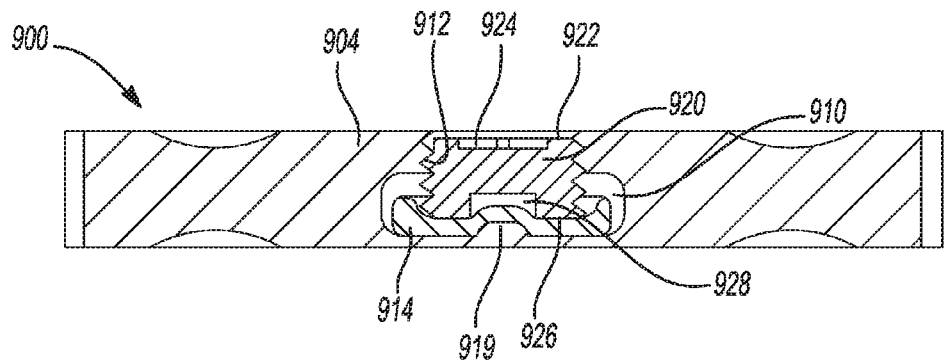
FIG. 39 is a cross-sectional view of the clamping device and band of FIG. 37.
Figure 41:
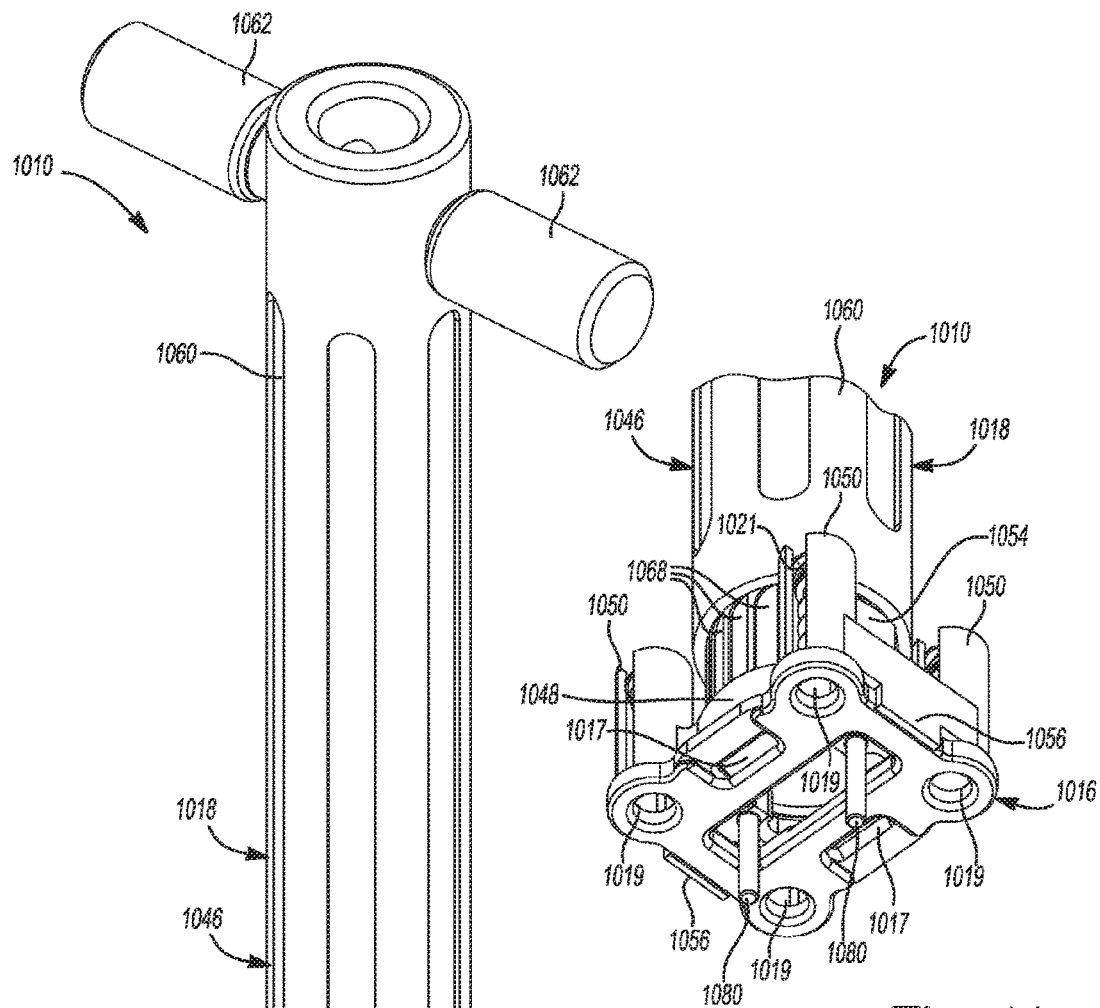
FIG. 41 is a partial perspective view of the closure device and tensioning device of FIG. 40.
Figure 40:
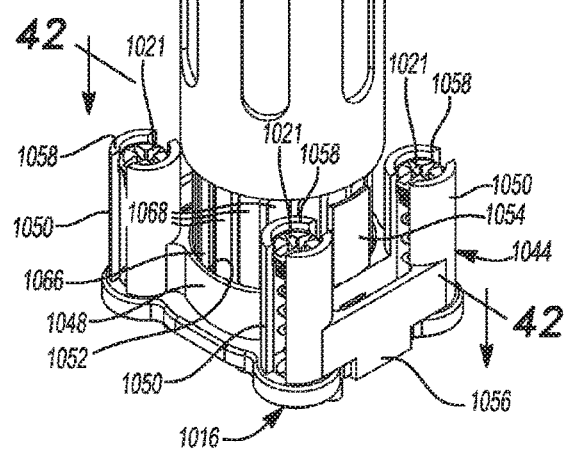
FIG. 40 is a perspective view of yet another closure device having a tensioning device according to the principles of the present disclosure.
Figure 42:
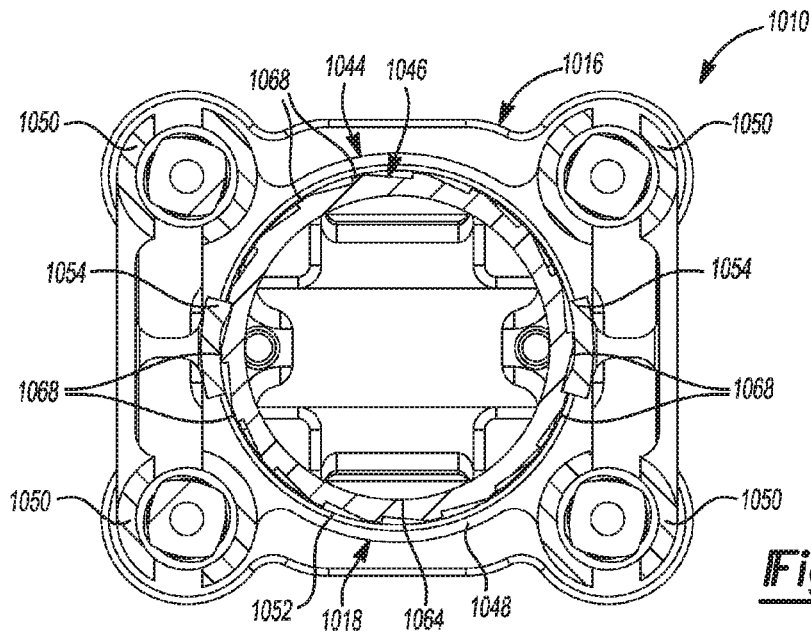
FIG. 42 is a cross-sectional view of the closure device and tensioning device of FIG. 40.
Figure 43:
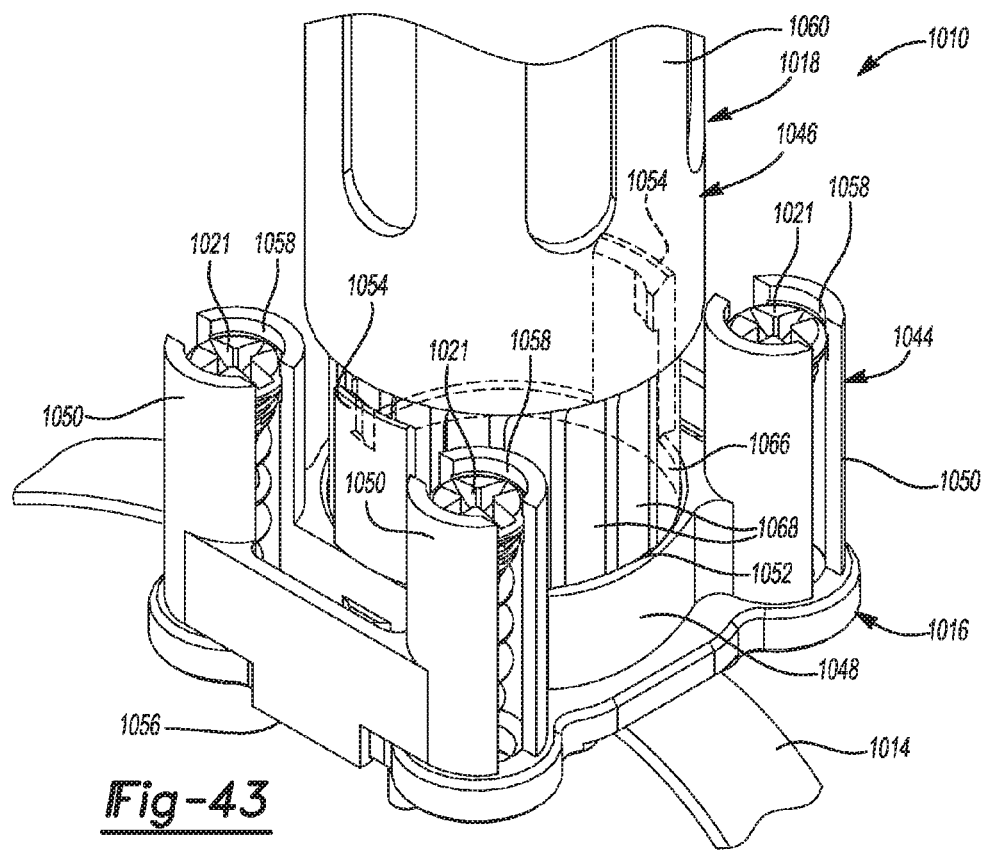
FIG. 43 is a partial perspective view of the closure device and tensioning device of FIG. 40.

With reference to FIGS. 37-39, a clamping device 900 is provided that can fixedly retain a band 914 and can be fixed to the patient's bone and/or any of the brackets described above, for example. The band 914 can be similar or identical to any of the bands described above. It will be appreciated that a pair of clamping devices 900 can be used to fixedly retain first and second respective ends of the band 914.

The clamping device 900 may include a central portion 904 and laterally outer portions 906. Each of the outer portions 906 may include a mounting aperture 908 extending therethrough. Fasteners (not shown) may extend through the mounting apertures 908 to fix the clamping device 900 directly to a patient's bone or to a bracket (e.g., any of the brackets described herein).

The central portion 904 may include a channel 910 that extends through first and second sides 916, 918 of the central portion 904. The channel 910 may receive the band 914. A threaded aperture 912 (FIG. 39) may extend partially through the central portion 904 and may communicate with the channel 910. A boss 919 (FIG. 39) may be formed in the channel 910. The boss 919 may be substantially concentric with the threaded aperture 912 or centered on a longitudinal axis of the threaded aperture 912.

A screw 920 may threadably engage the threaded aperture 912. The screw 920 may include a first end 922 having one or more slots 924 (or a hexagonal socket) for engaging a screwdriver and a second end 926 having a depression 928 formed therein. The depression 928 may be sized and positioned so that the boss 919 may be at least partially received therein.

To fix the band 914 within the channel 910, the screw 920 may be threadably advanced through the threaded aperture 912 and into the channel 910 with the band 914 disposed between the boss 919 and the second end 926 of the screw 920. The screw 920 may be tightened down on the band 914 to compress the band 914 between the screw 920 and the boss 919. Compressing the band 914 between the screw 920 and the boss 919 may deform the band 914 around the boss 919 and into the depression 928, thereby fixedly retaining the band 914 in the channel 910.

With reference to FIGS. 40-45, another closure system 1010 is provided. The system 1010 may include a band 1014 (FIGS. 43-45), a bracket 1016 and a tensioning device 1018. The band 1014 can be similar or identical to any of the bands described herein. The bracket 1016 may include openings 1017 (FIGS. 44 and 45) that receive respective ends 1022, 1024 of the band 1014. The bracket 1016 may also include a plurality of mounting apertures 1019 that receive fasteners 1021 for securing the bracket 1016 to the patient's bone 12 and/or tissue.

The tensioning device 1018 may include a base 1044 and a tensioning tube 1046. The base 1044 may be mounted over and/or on the bracket 1016 and may include a main body 1048 and a plurality of fastener guides 1050. The main body 1048 may include a central aperture 1052 extending therethrough. The main body 1048 may include one or more resiliently flexible ratchet tabs 1054 disposed at a periphery of the central aperture 1052 and extending from the main body 1048 in an axial direction (i.e., in a direction substantially parallel to a longitudinal axis of the central aperture 1052.

The fastener guides 1050 may be cylindrical or partially cylindrical members having apertures 1058 extending therethrough that are aligned with mounting apertures 1019 of the bracket 1016. The fasteners 1021 may be received in the fastener guides 1050 and temporarily held in alignment 31 with the mounting apertures 1019 before and/or while the surgeon drives the fasteners 1021 through the mounting apertures 1019 and into the bone 12. A pair of mounting tabs 1056 may extend downward from corresponding pairs of fastener guides 1050 so that the bracket 1016 may be received therebetween to restrict or prevent the base 1044 from sliding relative to the bracket 1016. In some embodiments, the tabs 1056 may clip the base 1044 to the bracket 1016.

The tensioning tube 1046 may include a main body 1060 and a pair of clamping members 1062. The main body 1060 may be a generally cylindrical member having an aperture 1064 extending therethrough and along a longitudinal axis of the main body 1060. A first end 1066 of the main body 1060 may include a plurality of teeth 1068 and may be rotatably received in the aperture 1052 of the main body 1048 of the base 1044. The teeth 1068 and the ratchet tabs 1054 of the base 1044 may cooperate to form a ratcheting mechanism that allows the tensioning tube 1046 to rotate relative to the base 1044 in a clockwise direction (relative to the view shown in FIG. 42), but restricts or prevents rotation of the tensioning tube 1046 relative to the base 1044 in a counterclockwise direction (relative to the view shown in FIG. 42).

The clamping members 1062 may be threadably engaged with apertures 1070 (FIG. 44) that extend through a second end 1072 of the main body 1060. The apertures 1070 are axially aligned with each other and may extend substantially perpendicular to the aperture 1064 in the main body 1060. As shown in FIG. 44, the clamping members 1062 may be threaded into the apertures 1070 toward each other and may clamp ends 1022, 1024 of the band 1014 therebetween.

To secure the band 1014 and bracket 1016 to the patient's bone 12, the ends 1022, 1024 of the band 1014 may be passed through the openings 1017 in the bracket 1016 after the band 1014 is looped around the bone portions 12a, 12b. In some embodiments, one or more guide pins 1080 extending from the base 1044 may be inserted in the seam between the bone portions 12a, 12b to facilitate alignment of the bracket 1016 relative to the bone portions 12a, 12b.

After passing the ends 1022, 1024 of the band 1014 through the openings 1017, the ends 1022, 1024 may be inserted up through the aperture 1052 of the base 1044 and the aperture 1064 of the tensioning tube 1046. The 32 clamping members 1062 may clamp the ends 1022, 1024 therebetween, as described above. With the ends 1022, 1024 clamped with in the tensioning tube 1046, the tensioning tube 1046 can be rotated in a clockwise direction (relative to the view shown in FIG. 42) to twist the ends 1022, 1024 of the band 1014 (as shown in FIG. 44). Continued twisting of the band 1014 may tighten the band 1014 around the bone portions 12a, 12b and drawn the bone portions 12a, 12b together.

Figure 45:
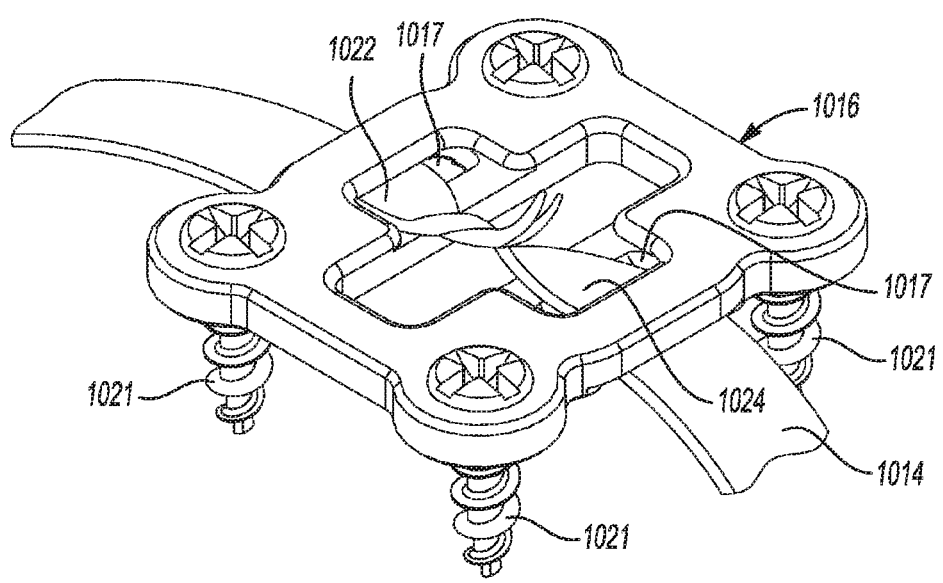
FIG. 45 is a perspective view of the closure device of FIG. 40.
Figure 46:
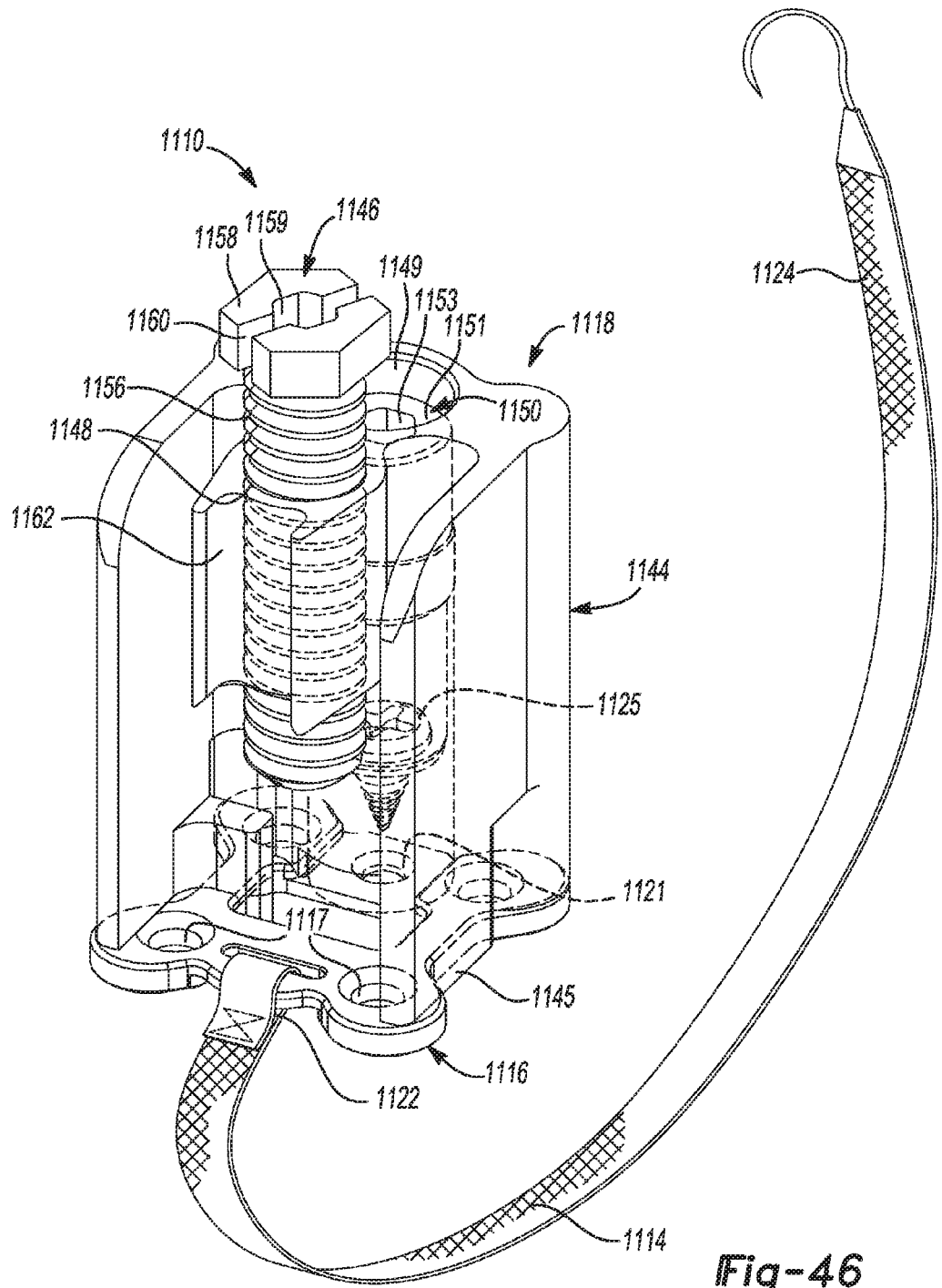
FIG. 46 is a perspective view of yet another closure device having a tensioning device according to the principles of the present disclosure.

With the band 1014 tensioned to a desired amount, the fasteners 1021 can be driven through the apertures 1019 in the bracket 1016 and into the bone portions 12a, 12b, thereby fixing the bracket 1016 to the bone portions 12a, 12b and securing the bone portions 12a, 12b relative to each other. Thereafter, the clamping members 1062 can be threaded back away from each other to release the ends 1022, 1024 of the band 1014, and the tensioning device 1018 can be removed from the bracket 1016. Thereafter, the ends 1022, 1024 can be trimmed and tied to each other, as shown in FIG. 45.

Figure 50:
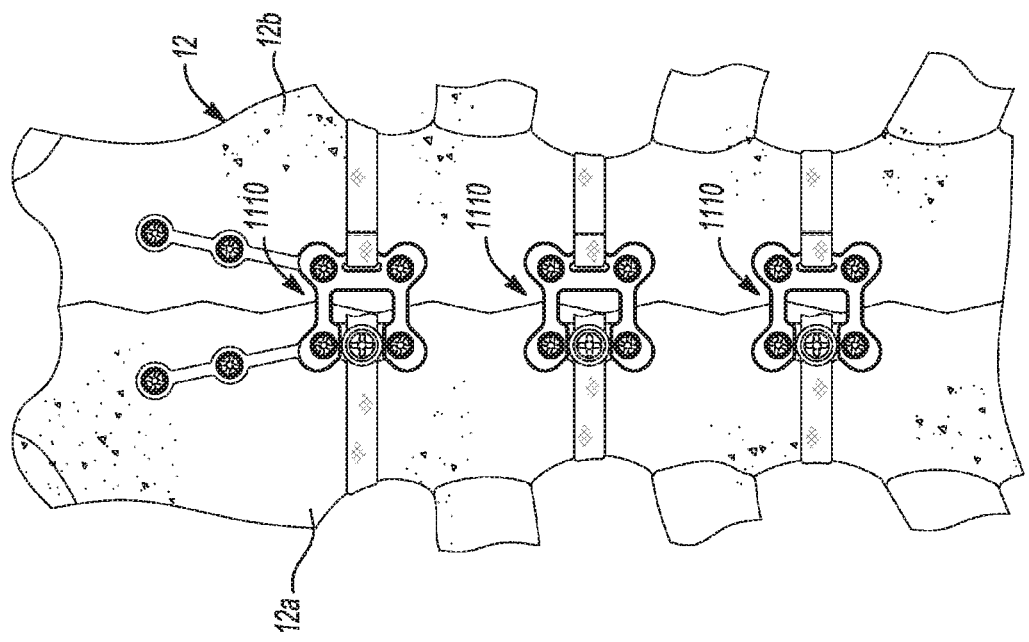
FIG. 50 is a perspective view of multiple closure devices attached to a sternum.
Figure 49:
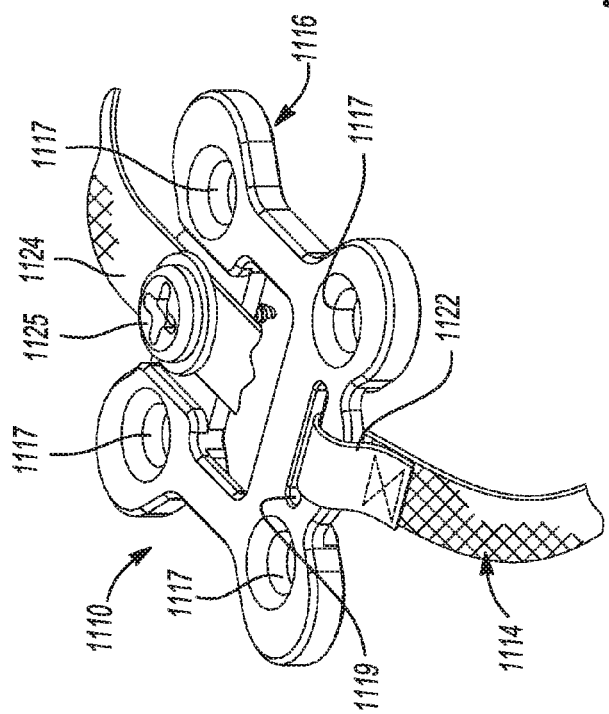
FIG. 49 is a perspective view of the closure device of FIG. 46.

With reference to FIGS. 46-50, another closure system 1110 is provided. The system 1110 may include a band 1114, a bracket 1116 and a tensioning device 1118. The band 1114 can be similar or identical to any of the bands described herein. The bracket 1116 may a plurality of mounting apertures 1117, a loop 1119, and a fastening aperture 1121. As shown in FIG. 50, fasteners 1123 may be driven through the mounting apertures 1117 to secure the bracket 1116 to the patient's bone 12. A first end 1122 of the band 1114 may be stitched or otherwise attached to the loop 1119. A second end 1124 of the band 1114 may be attached to the bracket 1116 by a fastener 1125 that extends through the fastening aperture 1121 (FIG. 49), as will be subsequently described.

The tensioning device 1118 may include a base 1144 and a tensioning bolt 1146. The base 1144 may be mounted over and/or on the bracket 1116 and may include tabs 1145 that clip onto the bracket 1116. The base 1144 may include a central portion 1147 having a first and second apertures 1148, 1149 extending therethrough. The tensioning bolt 1146 may threadably engage the first aperture 1148. The central portion 1147 may also include a generally U-shaped recess 1162 adjacent the first aperture 148 that may guide the band 1114 33 toward the tensioning bolt 1146 before and during the process of tensioning the band 1114 around the patient's sternum 12. In some embodiments, the Li-shaped recess 1162 may include a plurality of spikes (not shown) that may engage the band 1114 to pre-lock the band 1114 before, during and/or after tensioning of the band 1114.

The second aperture 1149 in the base 1144 may be substantially axially aligned with the fastening aperture 1121 in the bracket 1116. The second aperture 1149 may receive the fastener 1125 and a driver-bit 1150. The driver-bit 1150 may include a body 1151 and a tip 1152. The body 1151 may include a socket 1153 adapted to receive a wrench or driver shaft (not shown). A friction ring 1154 (FIG. 48) may engage the body 1151 (or the friction ring 1154 may be integrally formed with the body 1151) and may slidably engage the second aperture 1149. In this manner, the driver-bit 1150 may be held in place within the second aperture 1149 by a friction fit between the second aperture 1149 and the friction ring 1154. The tip 1152 of the driver-bit 1150 may engage a head of the fastener 1125 and may transmit torque to the fastener 1125 to drive the fastener through the band 1114 and the fastening aperture 1121. In some embodiments, the fastener 1125 may also engage the second aperture 1149 by a friction fit. In some embodiments, the fastener 1125 may engage the tip 1152 of the driver-bit 1150 by a friction fit.

Figure 47:
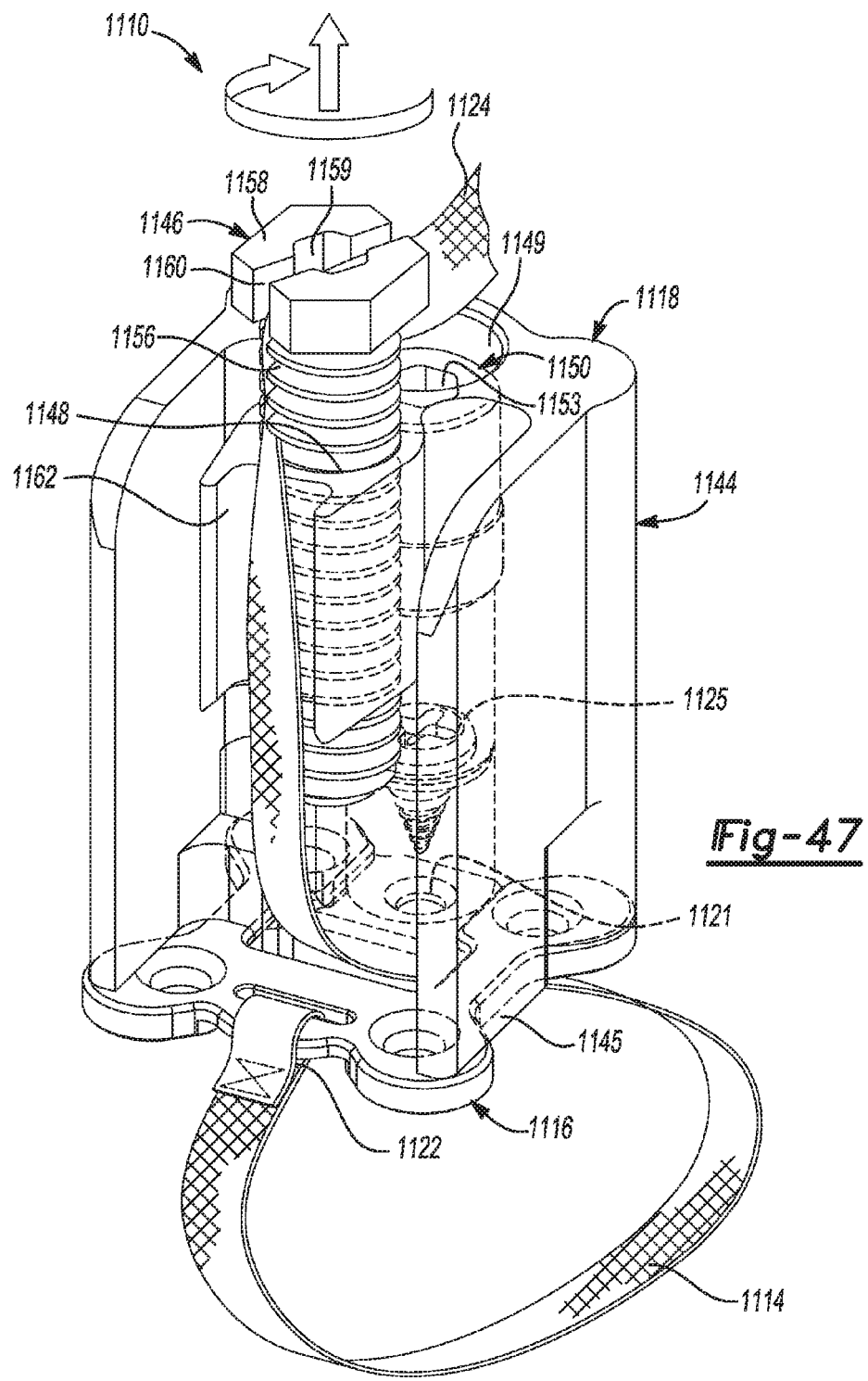
FIG. 47 is another perspective view of the closure device and tensioning device of FIG. 46.
Figure 48:
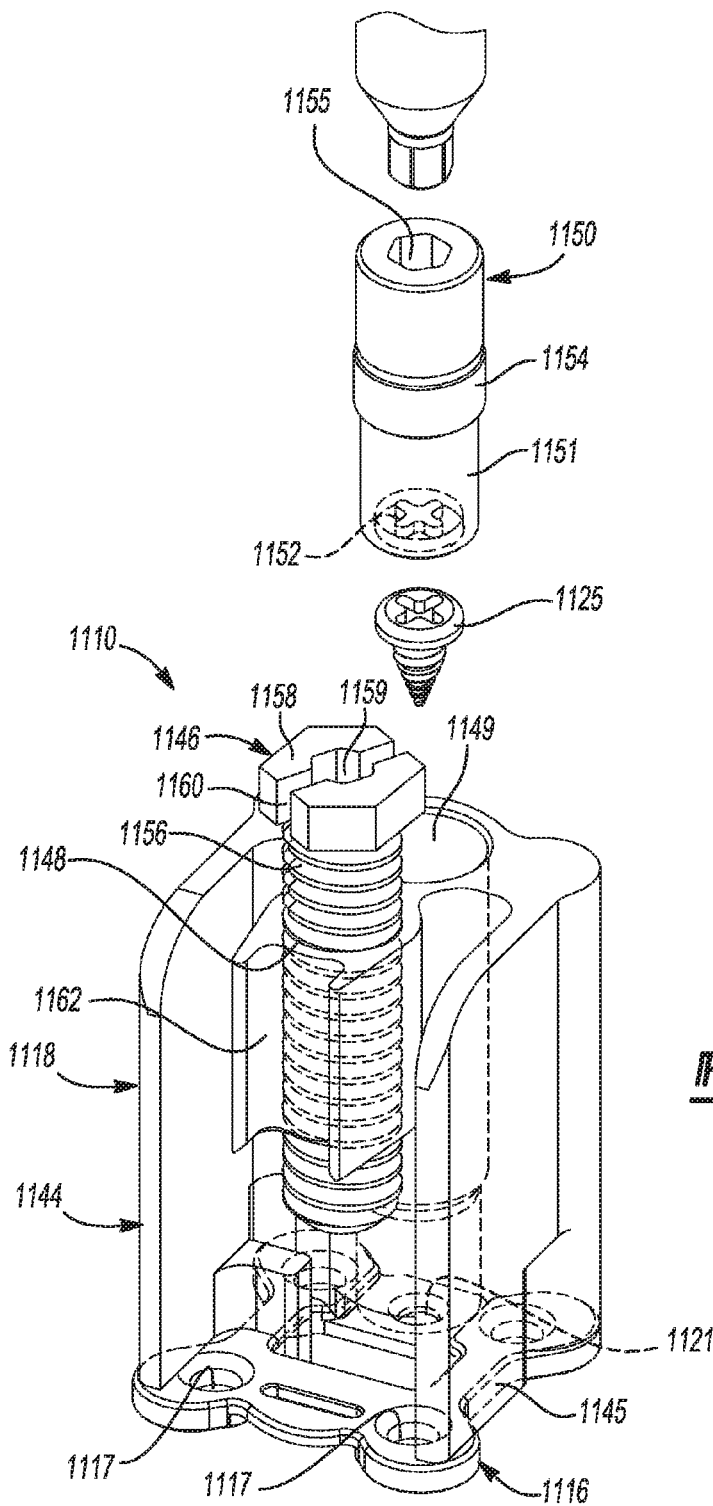
FIG. 48 is a partially exploded perspective view of the closure device and tensioning device of FIG. 46.

The tensioning bolt 1146 may include a threaded shaft 1156 and a head 1158. The head 1158 may include one or more slots or a socket 1159 to receive a wrench or screwdriver, for example. A slot 1160 may extend through the shaft 1156 and the head 1158 and may receive the second end 1124 of the band 1114 therein, as shown in FIG. 47. With the second end 1124 received in the slot 1160, the tensioning bolt 1146 may be threadably rotated in the first aperture 1148, which may wrap the band 1114 around the tensioning bolt 1146 and tension the band 1114 around the patient's sternum 12.

After the band 1114 is sufficiently tightened around the sternum 12 using the tensioning bolt 1146, the fastener 1125 may be driven through the band 1114 and the fastening aperture 1121 to fix the second end 1124 relative to the bracket 1116. The fastener 1125 may threadably engage the fastening aperture 1121 and/or the patient's bone.

Figure 51:
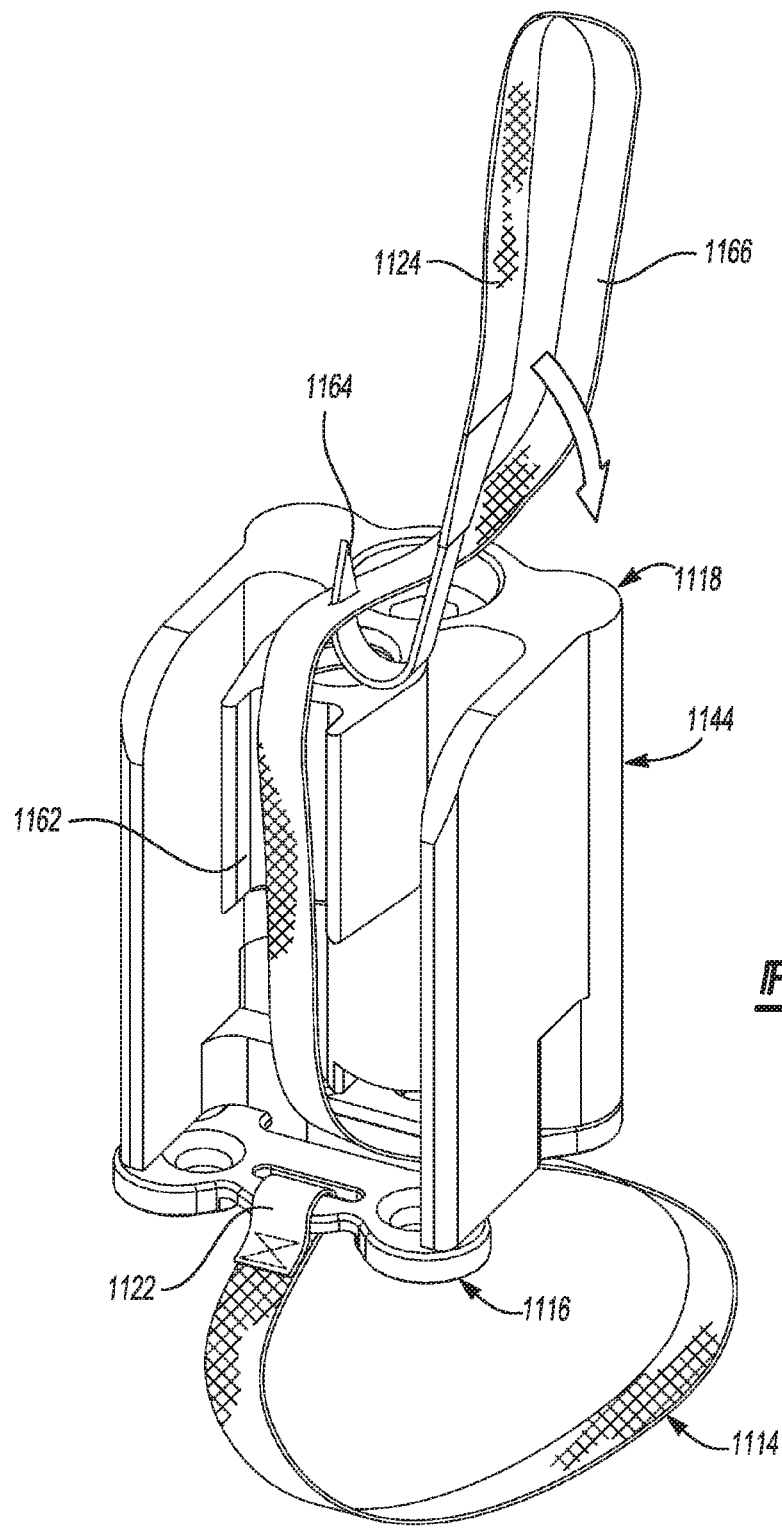
FIG. 51 is another perspective view of the closure device and tensioning device of FIG. 46.

As shown in FIG. 51, tensioning device 1118 may be used to tighten the band 1114 without the tensioning bolt 1146. For example, a hooked needle 1164 attached to the second end 1124 of the band 1114 can be passed through a portion of the band 1114 between the first and second ends 1122, 1124 to form a loop 1166 that can be grasped by the surgeon and pulled to tighten the band 1114 around the patient's bone prior to driving the fastener 1125 through the band 1114 and fastening aperture 1121, as described above.

Figure 52:
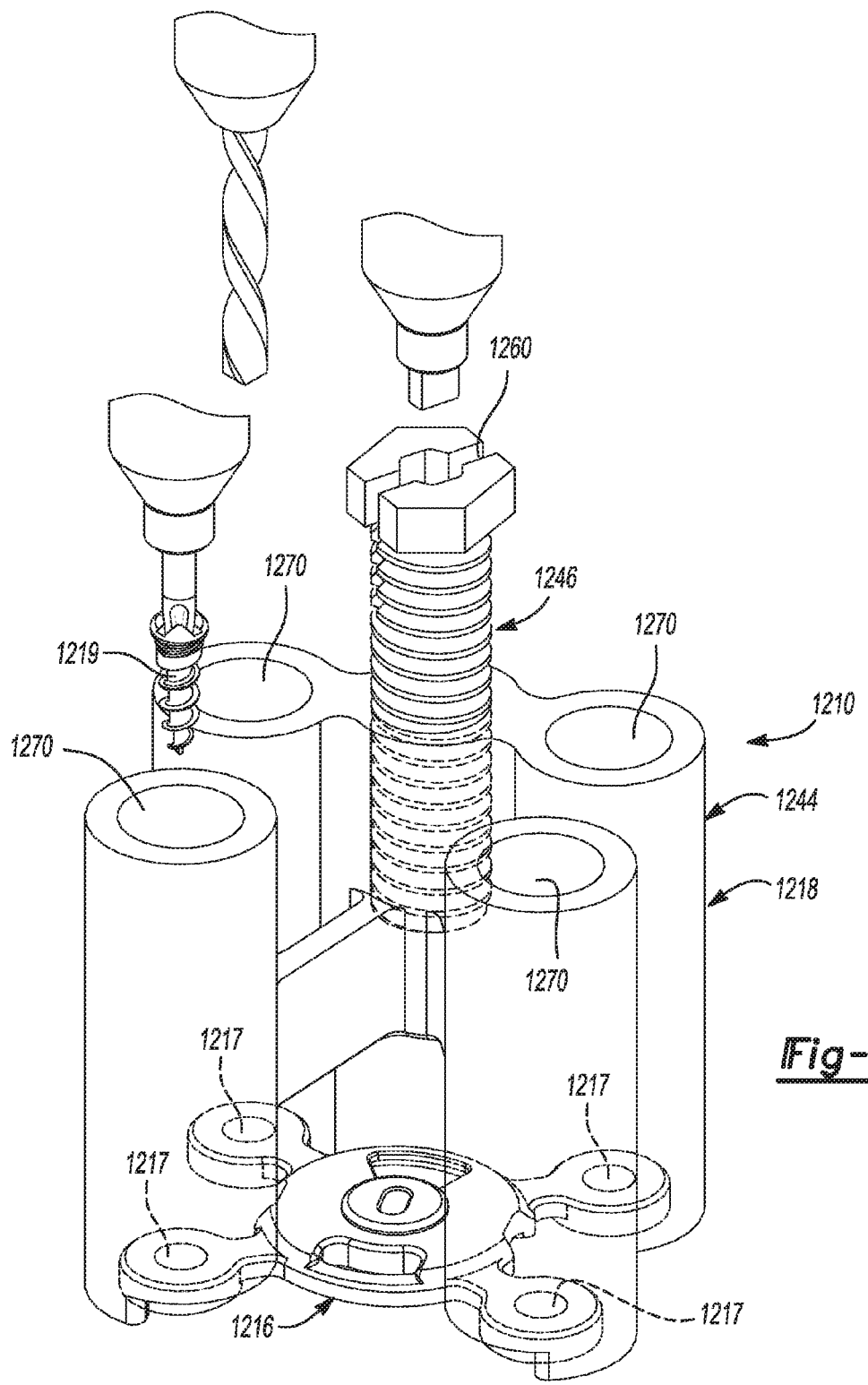
FIG. 52 is a perspective view of yet another closure device having a tensioning device according to the principles of the present disclosure.

With reference to FIG. 52, another closure system 1210 is provided. The system 1210 may include a bracket 1216 and a tensioning device 1218. The tensioning device 1218 may be generally similar to the tensioning device 1118 described above, apart from any exceptions described below and/or shown in the figures. The tensioning device 1218 may include a base 1244 and a tensioning bolt 1246. As with the tensioning device 1118, the tensioning bolt 1246 may threadably engage the base 1244 and may include a slot 1260 to engage the band 1114. With the band 1114 received in the slot 1260, rotation of the tensioning bolt 1246 relative to the base 1244 may tension the band 1114 around the patient's sternum 12, as described above.

The base 1246 may also include a plurality of guide apertures 1270 extending therethrough. The guide apertures 1270 may be configured and arranged relative to each other so that they each may be aligned with a corresponding mounting aperture 1217 of the bracket 1216. The surgeon may use the guide apertures 1270 as guides for drilling holes in the patient's sternum 12 and/or driving screws 1219 through the mounting apertures 1217 into the patient's sternum 12, for example.

With reference to FIGS. 53-56, another closure system 1310 is provided. The system 1310 may include a band 1314, a bracket 1316 and a tensioning device 1318. The tensioning device 1318 may include a base 1344, a tensioning bolt 1346, and a collar 1348. The structure and function of the base 1344 may be generally similar to that of the base 1144 described above, apart from any exceptions described below and/or shown in the figures. Therefore, similar features will not be described again in detail.

Figure 54:
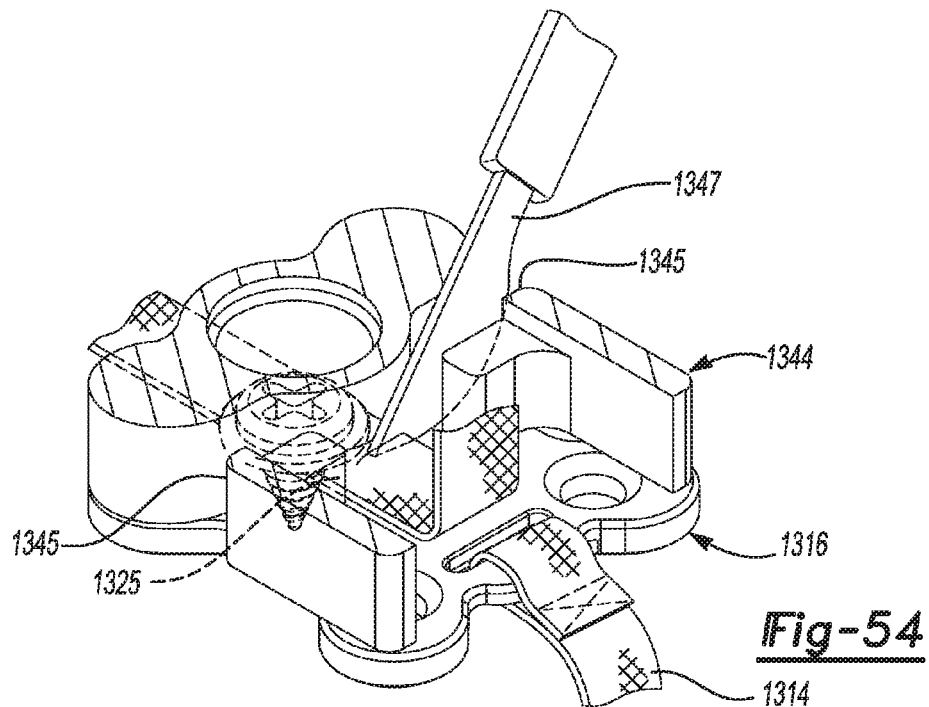
FIG. 54 is a partial perspective view of the closure device of FIG. 53.
Figure 55:
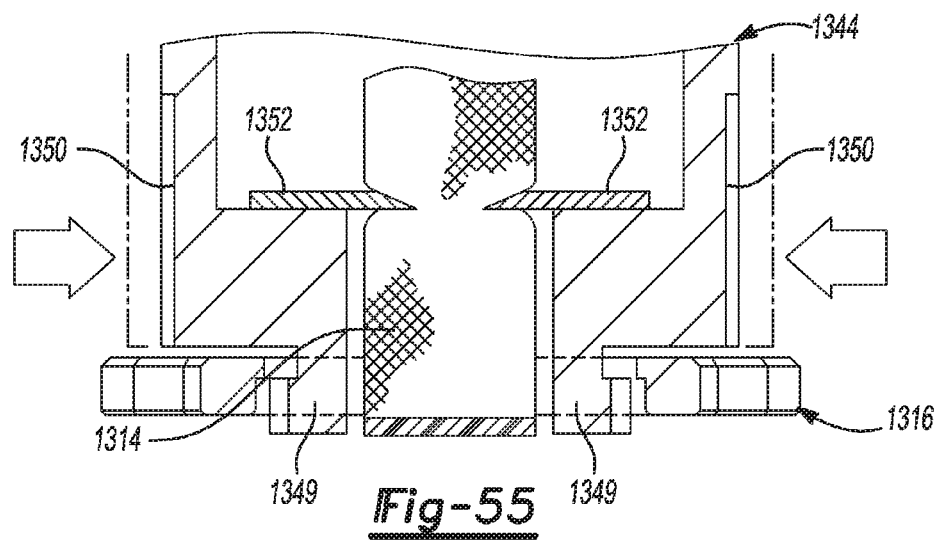
FIG. 55 is a partial cross-sectional view of the closure device and tensioning device of FIG. 53.

As shown in FIG. 54, in some embodiments, the base 1344 may include one or more slots 1345 through which the surgeon may insert a 35 scalpel 1347 or other blade for cutting the band 1314 once the band 1314 is fully tensioned and secured relative to the bracket 1316 by fastener 1325. As shown in FIG. 55, in some embodiments, the base 1344 may include a pair of tabs 1349 that may releasably engage the bracket 1316 to secure the base 1344 relative to the bracket 1316 during tensioning of the band 1314. To release the tabs 1349 from the bracket 1316, the surgeon may squeeze opposing sides 1350 of the base 1344 toward each other and then left the base 1344 upward away from the bracket 1316. In some embodiments, the tabs 1349 may include inwardly extending blades 1352 that may cooperate to cut the band 1314 when the surgeon squeezes the tabs 1349 together to release the base 1344 from the bracket 1316.

Figure 53:
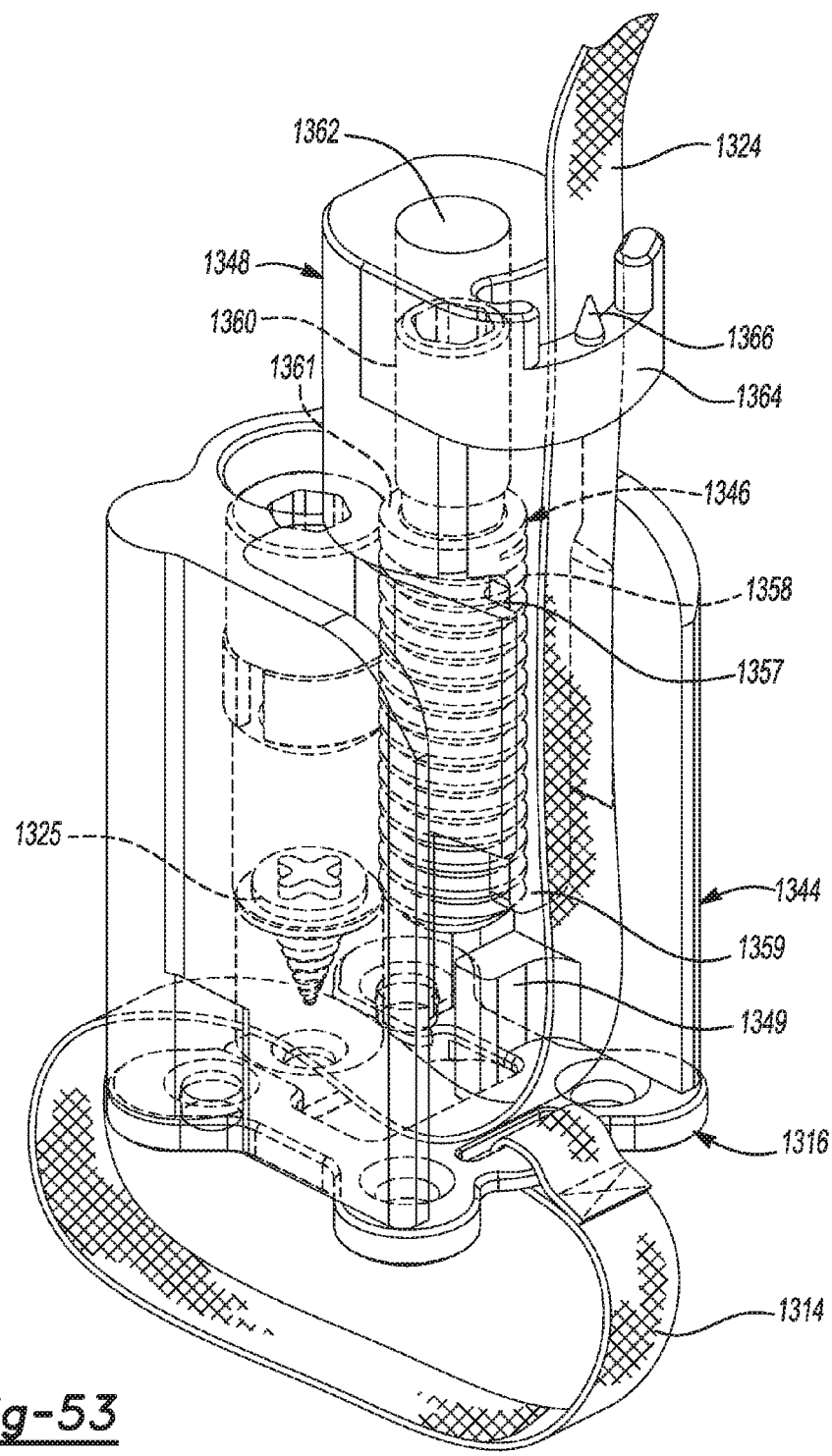
FIG. 53 is a perspective view of yet another closure device having a tensioning device according to the principles of the present disclosure.

Referring now to FIG. 53, the tensioning bolt 1346 may include a threaded portion 1358, an unthreaded portion 1360 and a shoulder 1361. The threaded portion 1358 may threadably engage an aperture in the base 1344 (similar to the tensioning bolt 1146 and aperture 1148 of the base 1144 described above). The unthreaded portion 1360 may rotatably engage an aperture 1362 in the collar 1348 so that the tensioning bolt 1346 can rotate relative to the collar 1348. The collar 1348 may include a tab 1359 that is slidably received in a U-shaped recess 1357 of the base 1344 to restrict relative rotation between the collar 1348 and the base 1344.

The collar 1348 may include a cantilevered arm 1364 having a spike 1366 thereon. The surgeon may press a free end 1324 of the band 1314 onto the spike 1366 to secure the free end 1324 relative to the collar 1348. As the tensioning bolt 1346 is threadably rotated relative to the base 1344 (e.g., with a wrench or screwdriver) in a direction that causes movement of the tensioning bolt 1346 axially upward away from the bracket 1316, the shoulder 1361 of the tensioning bolt 1346 pushes the collar 1348 axially upward with the tensioning bolt 1346, thereby tensioning the band 1314 around the patient's sternum 12.

As shown in FIG. 56, in some embodiments, the collar 1348 may include a pair of fins 1370 that extend downward through the bracket 1316 and engage the sternotomy in the patient's sternum 12 to position the bracket 1316 relative to the sternotomy. The fins 1370 may be retracted out of the 36 sternotomy as the collar 1348 moves axially upward with the tensioning bolt 1346 during tensioning of the band 1314.

With reference to FIGS. 57-60, a closure system 1410 is provided that may include a plurality of bands 1414 and a first bracket 1416 and a second bracket 1417. In the particular example illustrated in FIG. 57, the sternum 12 includes a first vertically extending sternotomy 13 and a second horizontally extending sternotomy 15. The first and second brackets 1416, 1417 and the bands 1414 may cooperate to apply a vertical and horizontal compressive forces on the sternum 12 to close the first sternotomy 13 and the second sternotomy 15.

As shown in FIG. 57, the band 1414 engaging the first bracket 1416 may extending through the sternum 12 (rather than around the sternum 12). This can be done by attaching any suitable needle such as needle 1420 to end 1422 of the band 1414. The needle 1420 may include a break-away base 1424 that allows a hooked tip 1426 of the needle 1420 to be snapped off of the band 1414 by the surgeon after the needle 1420 is pass through or around the sternum 12. In some embodiments, the hooked tip 1426 may be cut off of the base 1424 by the surgeon using wire cutters, for example.

In some embodiments, the surgeon may use needle passer 1430 to pass the needle 1420 through the sternum 12, as shown in FIG. 60. The needle passer 1430 may include first and second elongated members 1432, 1434 that are pivotally coupled to each other. The first and second elongated members 1432, 1434 may include handle portions 1436 at one end that a surgeon may grip to pivot the elongated members 1432, 1434 relative to each other. In this manner, distal ends 1438 of the elongated members 1432, 1434 may be used to pass the needle 1420 through the sternum 1420 without the surgeon having to grip the needle 1420 directly with his or her fingers.

Figure 61:
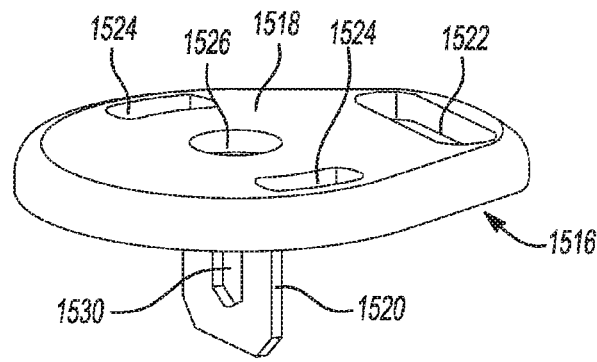
FIG. 61 is a perspective view of yet another closure device according to the principles of the present disclosure.

With reference to FIG. 61, another bracket 1516 is provided that may include a body 1518 and a fin 1520 extending from the body 1518. The body 1518 may include a first slot 1522, a pair of second slots 1524 and an aperture 1526. The first slot 1522 may engage a first end of a band (not shown). For example, the first end of the band may be looped through the first slot 1522 and stitched or otherwise secured to the bracket 1516. The second slots 1524 37 may be configured to receive fasteners (not shown) that may extend therethrough to secure the bracket 1516 to the patient's sternum 12. The aperture 1526 may engage another fastener (not shown) that secures the other end of the band to the bracket 1516 after being tensioned around the sternum 12. The fin 1520 may be inserted into the sternotomy prior to tensioning the band and fastening the bracket 1516 to the sternum 12 in order to position the bracket 1516 relative to the sternotomy in a desired manner. In some embodiments, the fin 1520 may include an aperture 1530 formed therein to allow bone and/or tissue to grow through the fin 1520.

Figure 62:
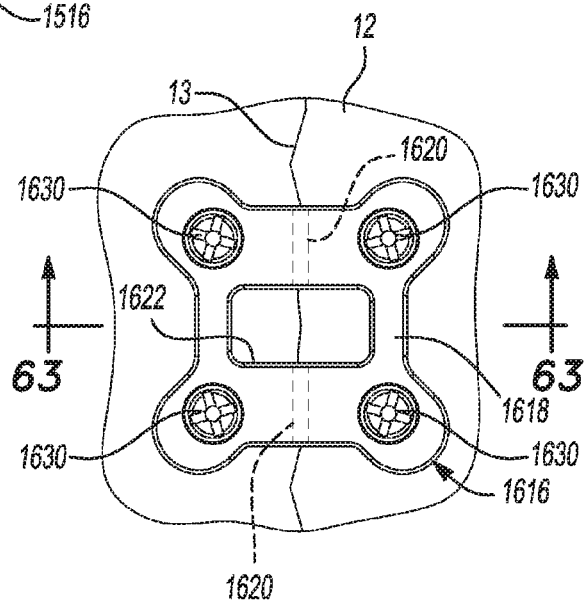
FIG. 62 is a plan view of yet another closure device attached to a sternum according to the principles of the present disclosure.
Figure 63:
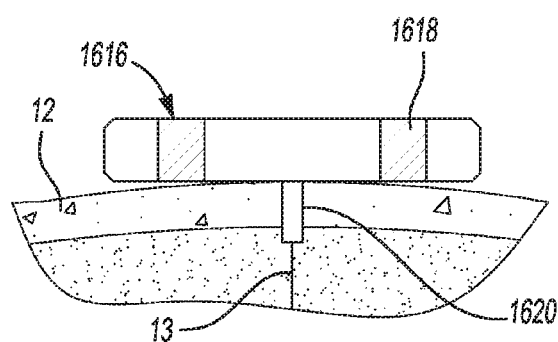
FIG. 63 is a cross-sectional view of yet another closure device attached to a sternum according to the principles of the present disclosure.

With reference to FIGS. 62 and 63, another bracket 1616 is provided that may include a body 1618 and a pair of fins 1620 on either side of an aperture 1622 in the body 1618. As with the bracket 1516, the fins 1620 of the bracket 1616 may be inserted into the sternotomy 13 to align the bracket 1616 relative to the sternotomy 13. Thereafter, a plurality of fasteners 1630 may be driven through corresponding apertures in the body 1618 to secure the bracket 1616 relative to the sternum 12.

Figure 64:
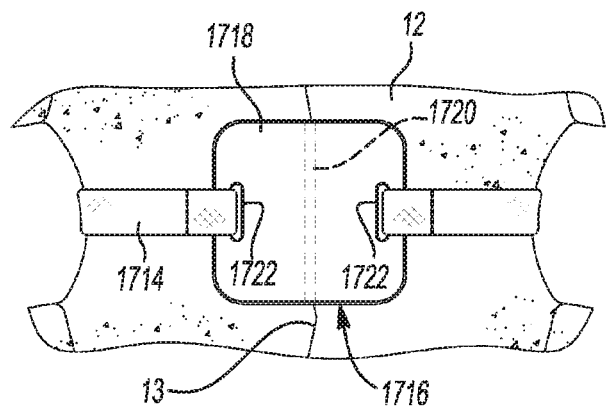
FIG. 64 is a plan view of yet another closure device attached to a sternum according to the principles of the present disclosure.

With reference to FIG. 64, another bracket 1716 is provided that may be generally similar to the brackets 1516, 1616. The bracket 1716 may include a body 1718 and a fin 1720. The body 1718 may include slots 1722 that engage corresponding ends of a band 1714 that has been tensioned around the sternum 12. As described above, the fin 1720 may be inserted into the sternotomy 13 to align the bracket 1716 relative to the sternotomy 13.

Figure 65:
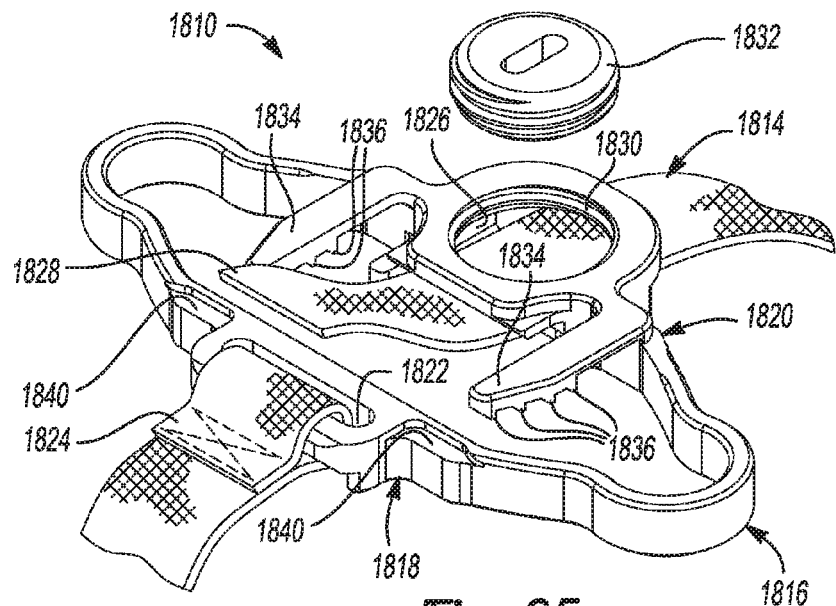
FIG. 65 is a perspective view of yet another closure device having a tensioning device according to the principles of the present disclosure.
Figure 66:
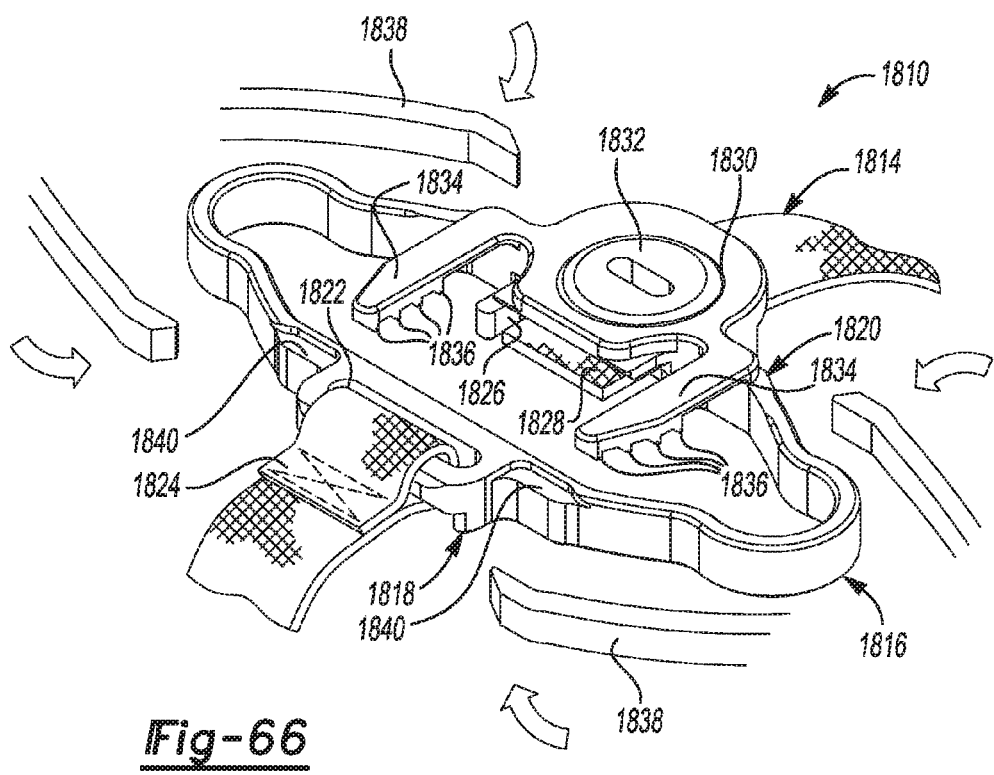
FIG. 66 is another perspective view of the closure device and tensioning device of FIG. 65.
Figure 67:
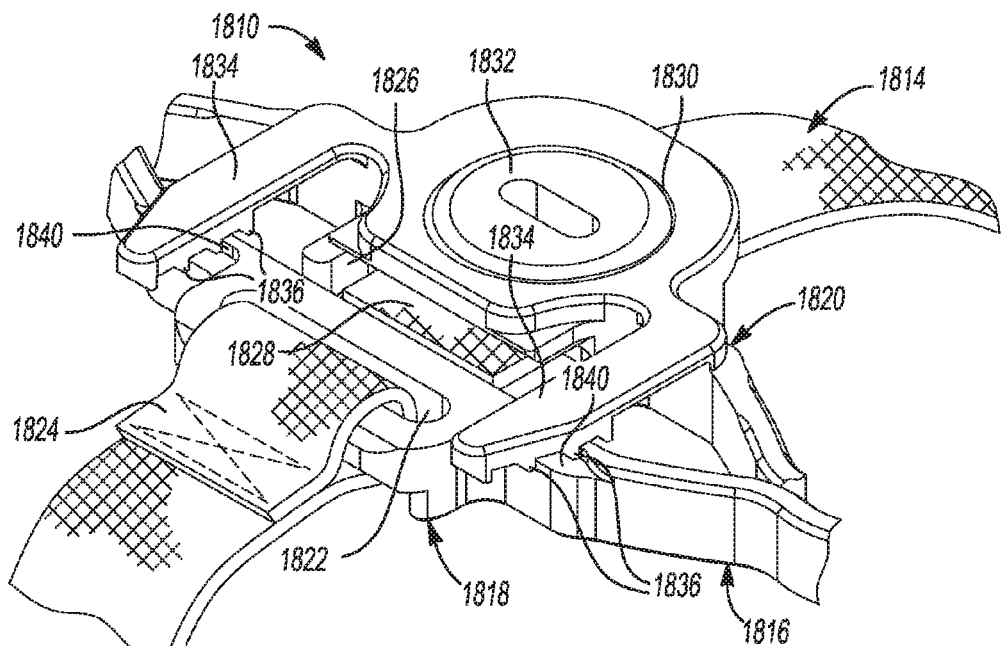
FIG. 67 is a perspective view of the closure device and tensioning device of FIG. 65 in a tensioned condition.

With reference to FIGS. 65-67, another closure system 1810 is provide that may include a band 1814 and a bracket 1816. The bracket 1816 may include first and second sides 1818, 1820 that are resiliently compressible toward each other. The first side 1818 may include a first slot 1822 that engages a first end 1824 of the band 1814. For example, the first end 1824 may be stitched around the first slot 1822.

The second side 1820 may include a second slot 1826 that slidably receives a second end 1828 of the band 1814. A threaded aperture 1830 in the second side 1820 may extend into the second slot 1826. A screw 1832 may threadably engage the threaded aperture 1830 and may clamp the second end 1828 of the band 1814 in the slot 1826 to secure the second end 1828 38 relative to the second side 1820. The second side 1820 may also include a pair of arms 1834 extending therefrom. The arms 1834 may include a plurality of ratchet teeth 1836.

To tension the band 1814 around the patient's sternum 12, the band 1814 may be looped around the sternum 12 with the first end 1824 secured to the first side 1818 of the bracket 1816. Then, the second end 1828 of the band 1814 may be inserted through the second slot 1826 in the second side 1820 of the bracket 1816 and pulled taught around the sternum 12. Then, the surgeon may secure the second end 1828 of the band 1814 to the bracket 1816 by clamping the second end 1828 in place using the screw 1832, as described above. Then, the surgeon may squeeze the first and second sides 1818, 1820 of the bracket 1816 toward each other using pliers 1838, for example. The ratchet teeth 1836 on the second side 1820 may engage ratchet walls 1840 of the first side 1818 to secure the first and second sides 1818, 1820 relative to each other. At any time after clamping the second end 1828 of the band 1814 in the second slot 1826, any access length of the second end 1828 may be trimmed, as desired.

Figure 68:
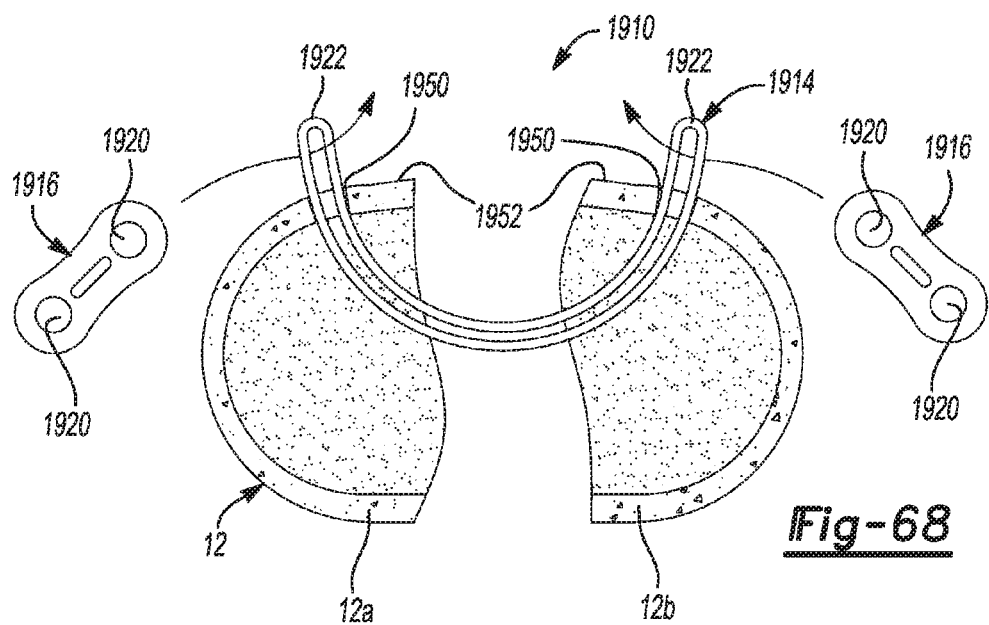
FIG. 68 is a cross-sectional view depicting a step of a method of closing a sternum using another closure device according to the principles of the present disclosure.
Figure 69:
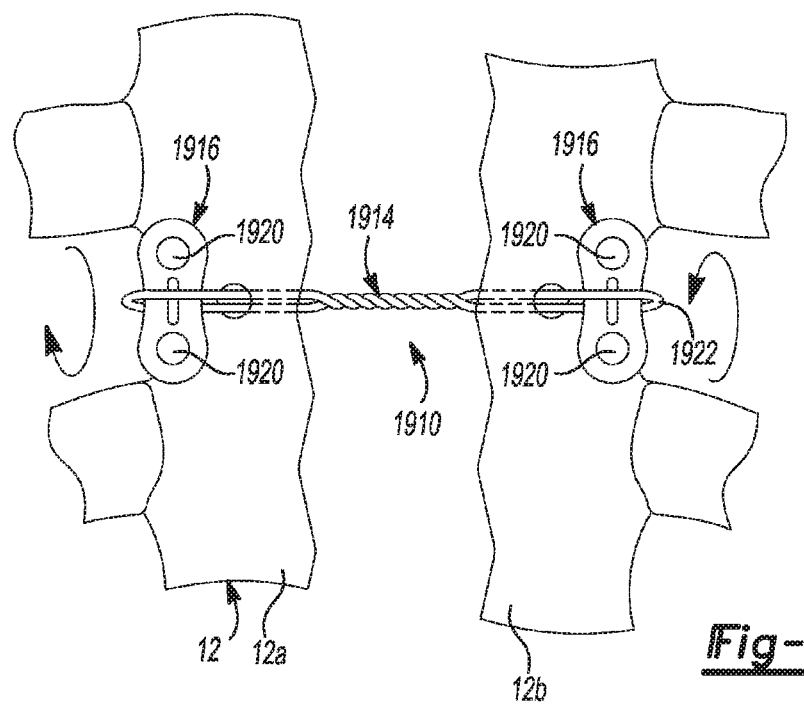
FIG. 69 is a plan view depicting another step of the method of closing the sternum using the closure device of FIG. 68.
Figure 70:
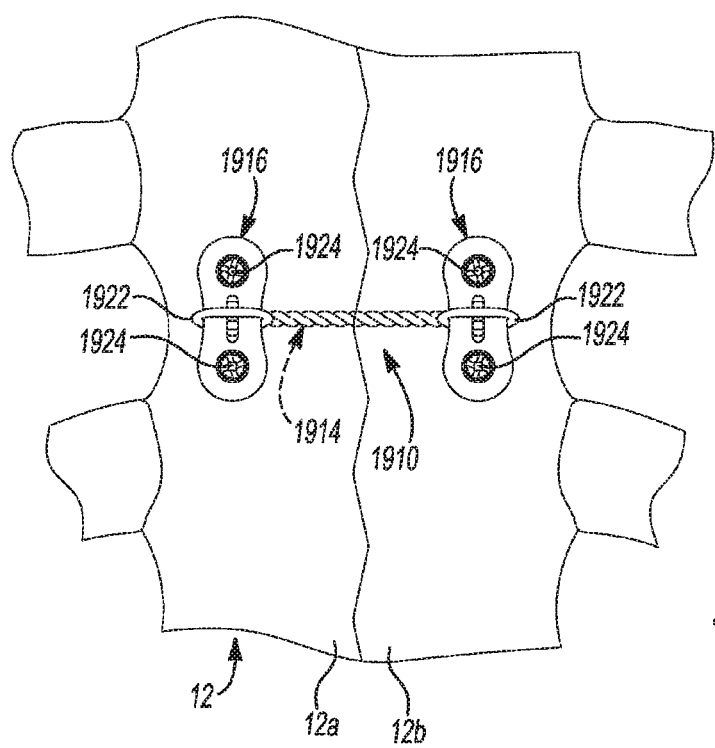
FIG. 70 is a plan view depicting another step of the method of closing the sternum using the closure device of FIG. 68.

With reference to FIGS. 68-70, another closure system 1910 and method of closing the sternum 12 are provided. The closure system 1910 may include a band 1914 and a pair of brackets 1916. The band 1914 may be a closed loop (i.e., a continuous loop). The brackets 1916 may be plates having a pair of apertures 1920 extending therethrough. As will be subsequently described, the brackets 1916 may engage corresponding ends 1922 of the closed-loop band 1914 and may be secured to the sternum 12 by fasteners 1924 that are driven through the apertures 1920.

To close the sternum 12 using the closure system 1910, the surgeon may first drill a holes 1950 in each of the portions 12a, 12b of the sternum 12. Then, the band 1914 may be passed into one of the holes 1950 in the sternum 12 and out of the other hole 1950 so that both ends 1922 of the band 1914 are exposed outside of the sternum 12, as shown in FIG. 68. Thereafter, the brackets 1916 may be inserted through the loops formed between the ends 1922 of the band 1914 and the anterior surface 1952 of the sternum 12. Then, the surgeon may grip the brackets 1916 and twist the brackets 1916 in opposite directions (or hold one bracket 1916 stationary while twisting the other bracket 39 1916), thereby twisting the band 1914. Continued twisting of the band 1914 in this manner draws the portions 12a, 12b of the sternum 12 together. As shown in FIG. 70, when the sternum portions 12a, 12b are sufficiently drawn together, the surgeon may drive the fasteners 1924 through the apertures 1920 of the brackets 1916 to secure the brackets 1916 to the sternum 12.

Figure 71:
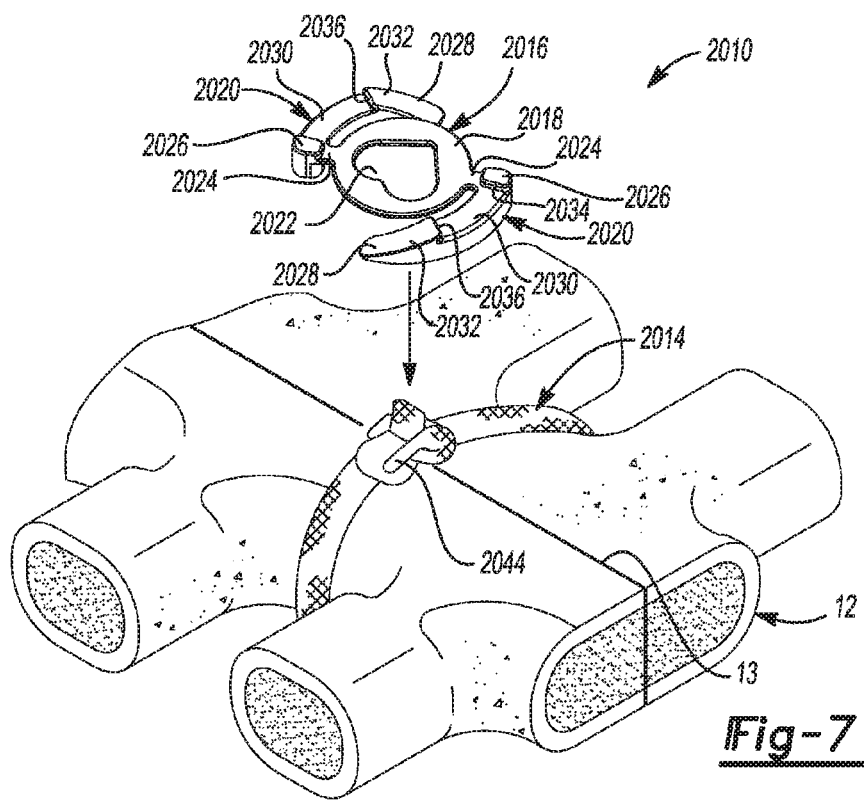
FIG. 71 is a partially exploded perspective view of yet another closure device according to the principles of the present disclosure.
Figure 72:
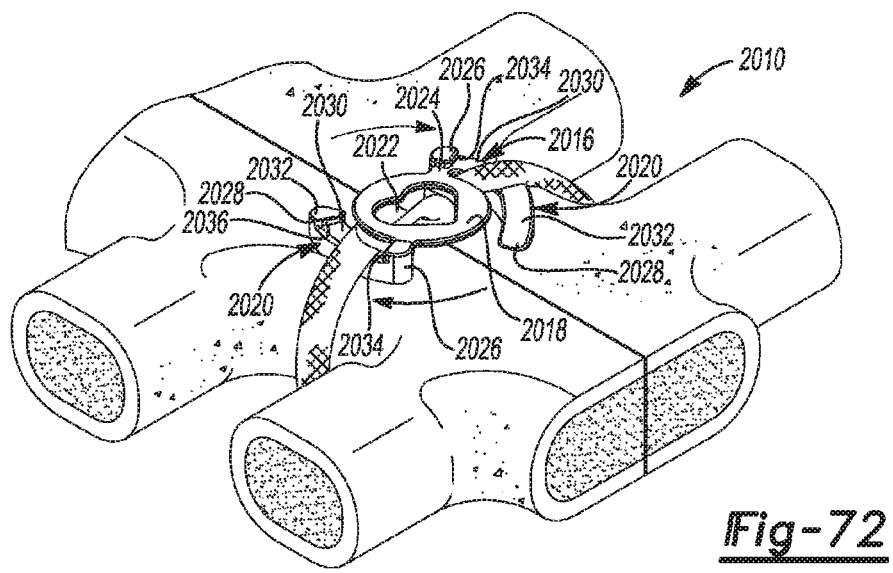
FIG. 72 is a perspective view of the closure device of FIG. 71 attached to a sternum.

With reference to FIGS. 71 and 72, another closure system 2010 and method of closing the sternum 12 are provided. The closure system 2010 may include a band 2014 and a bracket 2016. The bracket 2016 may include a plate 2018 and a pair of curved arms 2020 extending partially around the periphery of the plate 2018 in opposite directions. The plate 2018 may be a generally circular disk and may include a central aperture 2022 extending therethrough. While the aperture 2022 shown in FIGS. 71 and 72 is generally heart-shaped, in other embodiments, the aperture 2022 could be circular or any other shape.

The arms 2020 may each include a stem 2024 extending radially outward from the periphery of the plate 2018. Each arm 2020 may include first and second ends 2026, 2028 and a body 2030 extending between the first and second ends 2026, 2028. The stem 2024 may connect the first end 2026 with the plate 2018. The second end 2028 may include a ramped surface 2032. A first shoulder 2034 may be disposed between the body 2030 and the first end 2026, and a second shoulder 2036 may be disposed between the body 2030 and the second end 2028.

To close the sternum 12 using the closure system 2010, the surgeon may first wrap the band 2014 around the sternum 12 and tie the ends of the band 2014 in a knot 2040, as shown in FIG. 71. Then, the bracket 2016 may be placed over the knot 2040 (e.g., so that the knot 2040 and/or the sternotomy 13 are visible through the aperture 2022). Then, the bracket 2016 may be rotated relative to the band 2014 about an axis extending through the posterior and anterior sides of the sternum 12 so that the ramped surfaces 2032 slide between the sternum 12 and the band 2014. The surgeon may continue to rotate the brackets 2016 until the ends of the band 2014 are received on the body 2030 of the arms 2020 between the first and second shoulders 2034, 2036. Sliding the arms 2020 between the sternum 12 and the band 2014 in this manner 40 may remove any remaining slack in the band 2014, thereby providing the final tensioning of the band 2014 around the sternum 12.

Figure 73:
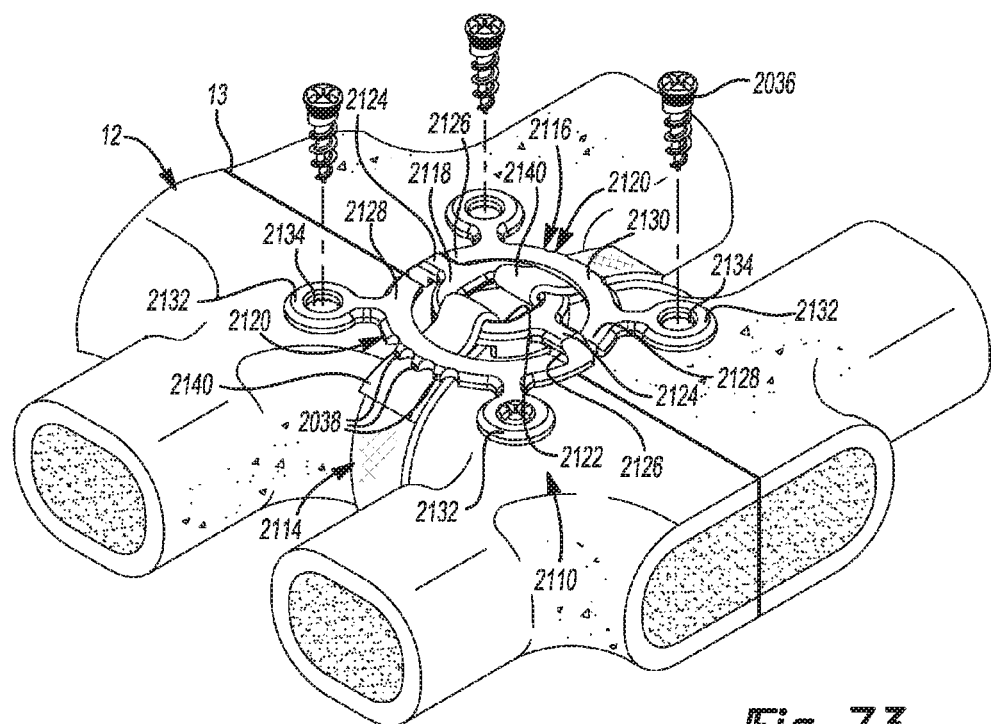
FIG. 73 is a partially exploded perspective view of yet another closure device according to the principles of the present disclosure.

With reference to FIG. 73, another closure system 2110 and method of closing the sternum 12 are provided. The closure system 2110 may include a band 2114 and a bracket 2116. The bracket 2116 may include a plate 2118 and a pair of curved legs 2120 extending partially around the periphery of the plate 2118 in opposite directions. The plate 2118 may include a central aperture 2022 extending therethrough and may have a thickness that is greater than thicknesses of the legs 2120.

The legs 2120 may each include a stem 2124 extending radially outward from the periphery of the plate 2118. Each leg 2120 may include first and second ends 2126, 2028 and a body 2130 extending between the first and second ends 2126, 2128. The stem 2124 may connect the first end 2126 with the plate 2118. The second end 2128 may be spaced apart from the plate 2118. The body 2130 of each leg 2120 may include a plurality of feet 2132 extending radially outward therefrom. Each foot 2132 may include an aperture 2134 through which a fastener 2036 may extend to secure the bracket 2116 to the sternum 12. An outer periphery of the body 2130 of each leg 2120 may include a plurality of teeth 2038.

To close the sternum 12 using the closure system 2110, the surgeon may first loop the band 2114 around the sternum 12. Then, the surgeon may pass ends 2140 of the band 2114 up through the aperture 2122 partially around the plate 2118 and then between the outer periphery of the plate 2118 and the body 2030 of a corresponding one of the legs 2120. Then, the surgeon may drive the fasteners 2036 through the apertures 2134 and into the sternum 12 to fix the bracket 2116 to the sternum 12 and clamp the ends 2140 of the band 2114 underneath the legs 2120.

Figure 74:
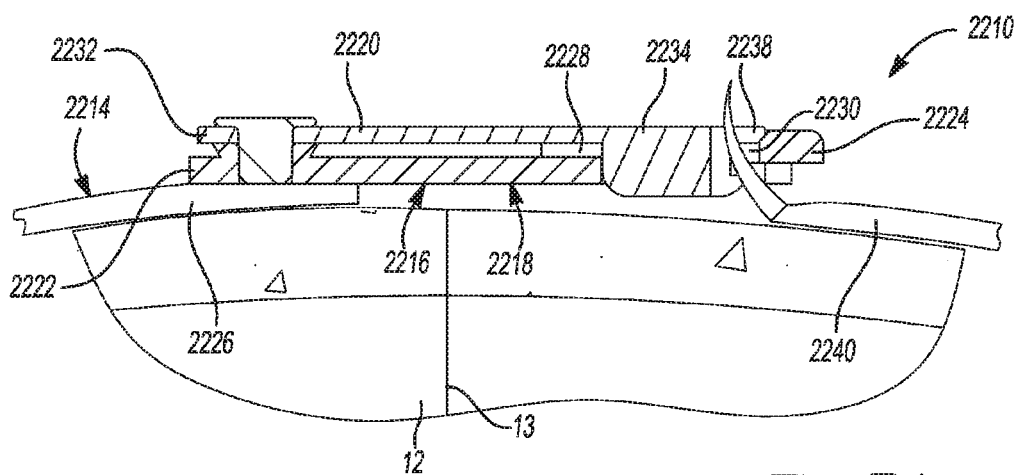
FIG. 74 is a cross-sectional view of yet another closure device according to the principles of the present disclosure.
Figure 75:
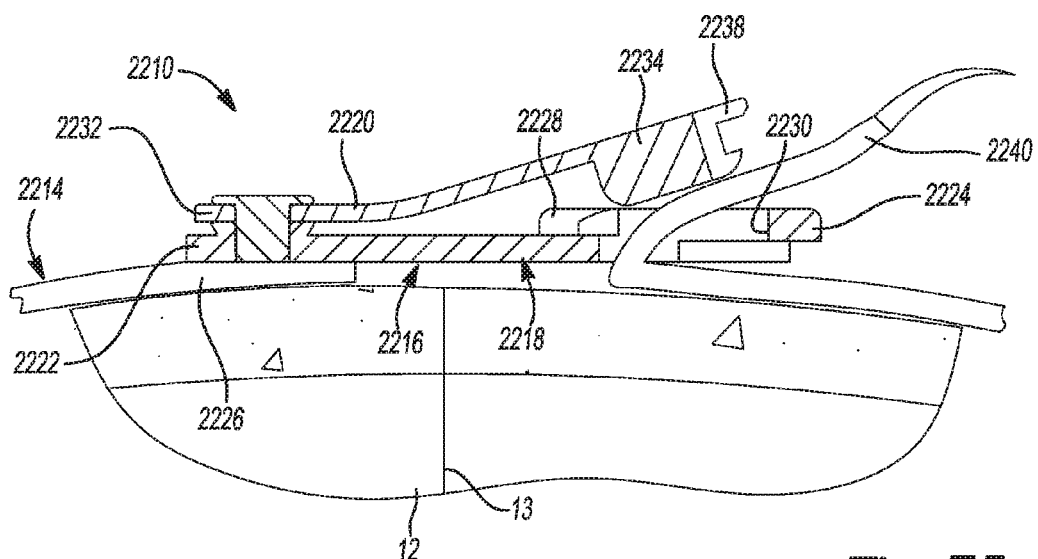
FIG. 75 is another cross-sectional view of the closure device of FIG. 74.
Figure 76:
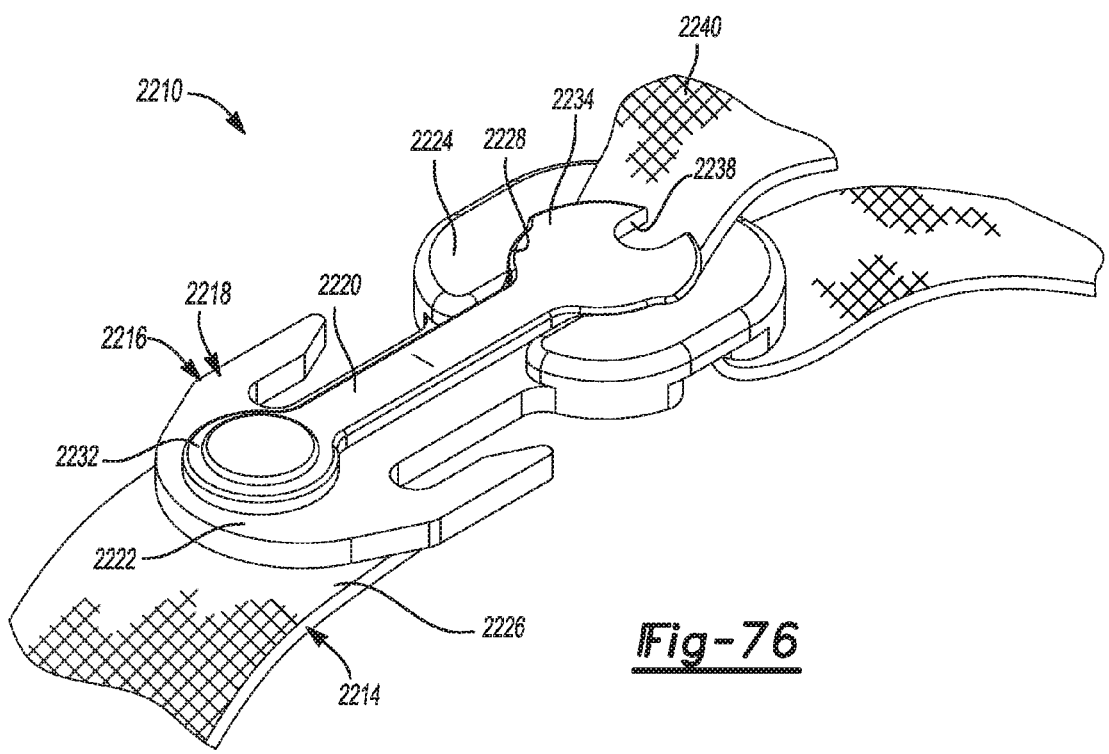
FIG. 76 is a perspective view of the closure device of FIG. 74.

With reference to FIGS. 74-76, another closure system 2210 and method of closing the sternum 12 are provided. The closure system 2210 may include a band 2214 and a bracket 2216. The bracket 2216 may include a base 2218 and a flexible locking arm 2220. The base 2218 may include first and second ends 2222, 2224. The first end 2222 may be fixed to one end 2226 of the 41 band 2214. The second end 2226 of the base 2218 may include a recess 2228 and an aperture 2230.

A first end 2232 of the locking arm 2220 may be fixed to the first end 2222 of the base 2218. The locking arm 2220 may flex about the first end 2232. A second end 2234 of the locking arm 2220 may be received in the recess 2228 of the base 2218. In some embodiments, the second end 2234 of the locking arm 2220 may snap into engagement with the recess 2228. In some embodiments, the second end 2234 of the locking arm 2220 may include a cutout 2238.

To close the sternum 12 using the closure system 2210, the surgeon may first loop the band 2214 around the sternum 12. Then, the surgeon may lift the second end 2234 of the locking arm 2220 out of the recess 2228 of the base 2218 and pass end 2240 of the band 2214 up through the aperture 2230 and recess 2228 of the base 2218. The surgeon may continue to pull the end 2240 of the band 2214 through the aperture 2230 and recess 2228 until the band 2214 is sufficiently taught around the sternum 12. Thereafter, the surgeon may push the second end 2234 of the locking arm 2220 back into the recess 2228 to lock the end 2240 of the band 2214 relative to the bracket 2216.

Figure 77:
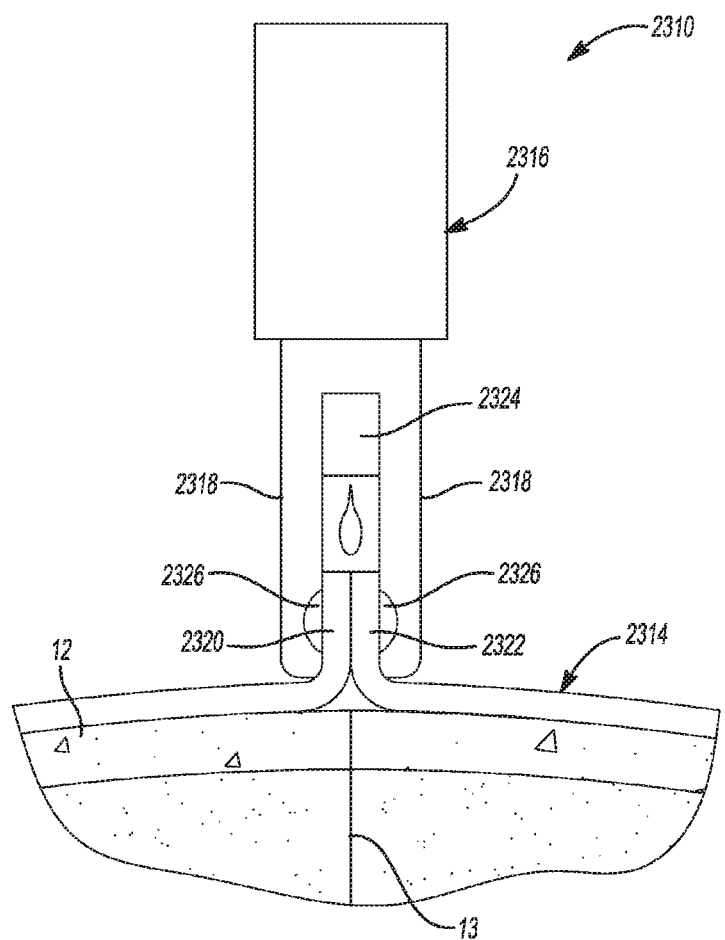
FIG. 77 is a partially cross-sectioned view of yet another closure device according to the principles of the present disclosure.

With reference to FIG. 77, another closure system 2310 and method of closing the sternum 12 are provided. The closure system 2310 may include a band 2314 and a bonding clamp 2316. The bonding clamp 2316 may include a pair of arms 2318 that are movable or resiliently flexible relative to each other and operable to clamp first and second ends 2320, 2322 of the band 2314 therebetween. The bonding clamp 2316 may include an adhesive dispenser 2324 and one or more ultraviolet light sources 2326.

To close the sternum 12 using the closure system 2310, the surgeon may first loop the band 2314 around the sternum 12. Then, the surgeon may clamp the ends 2320, 2322 of the band 2314 between the arms 2318. With the ends 2320, 2322 of the band 2314 clamped between the arms 2318, the surgeon may dispense adhesive from the adhesive dispenser 2324 onto the ends 2320, 2322 of the band 2314. The surgeon may maintain the ends 2320, 2322 clamped between the arms 2318 until the adhesive at least partially sets. The surgeon may activate the ultraviolet light sources 2326, which may accelerate the 42 setting and curing of the adhesive. While the bonding clamp 2316 is described above as including one or more ultraviolet light sources 2326, additionally or alternatively, the bonding clamp 2316 could include any other suitable radiation or heat source suitable for accelerating the setting or curing of an adhesive dispensed from the adhesive dispenser 2324.

Figures 78, 79:
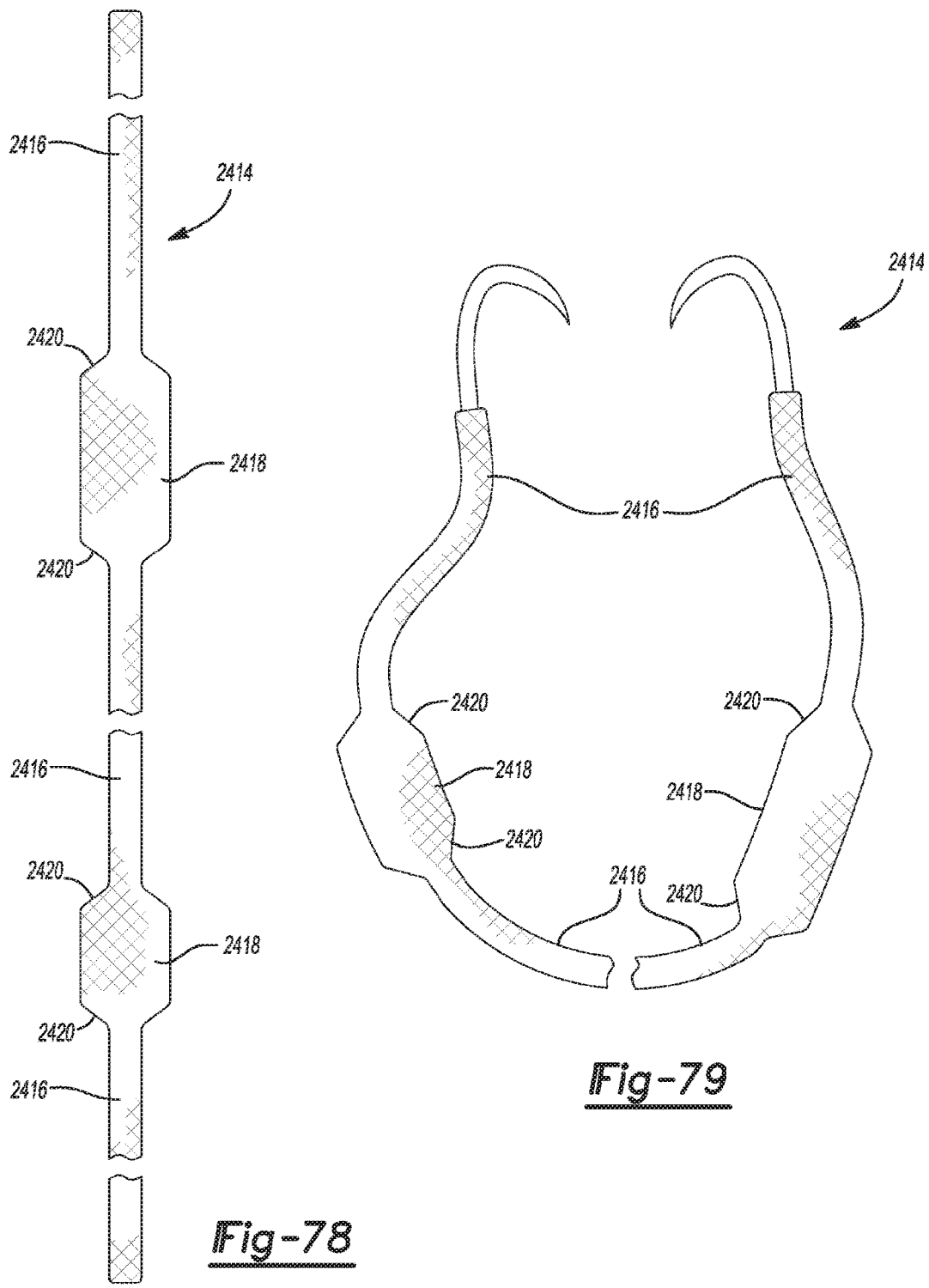
FIG. 78 is a partial plan view of a band according to the principles of the present disclosure.
FIG. 79 is a partial perspective view of the band of FIG. 78 with a needle attached thereto.

With reference to FIGS. 78 and 79, another band 2414 is provided that may be used in conjunction with any of the closure systems and/or methods described above and/or below. The band 2414 may include one or more relatively narrow sections 2416 and one or more relatively wide sections 2418. Ends 2420 of the wide sections 2418 may be tapered, as shown in FIGS. 478 and 79. Although, in some embodiments, the ends 2420 may be substantially square.

Lengths of the wide sections 2418 may be any suitable length. For example, in some embodiments, one or more of the wide sections 2418 may have a length of about one inch. In some embodiments, one or more of the wide sections 2418 may have a length of about one and three-quarters inches. In some embodiments, one or more of the wide sections 2418 may have a width of about 0.24 inches. In some embodiments, one or more of the narrow sections 2416 may have a width of about 0.12 inches. In some embodiments, one or more of the wide sections 2418 may be spaced apart from another of the wide sections 2418 by about ten inches. It will be appreciated that the narrow and wide sections 2416, 2418 could be formed with any suitable dimensions and any suitable spacing therebetween.

In use, the band 2414 may be wrapped around a sternum or any other bone or tissue. For example, the band 2414 aligned relative to the sternum so that the wide sections 2418 are wrapped around lateral sides and/or a posterior side of the sternum 12. The narrow sections 2416 may be tied in a knot or otherwise fixed relative to each other.

Figure 81:
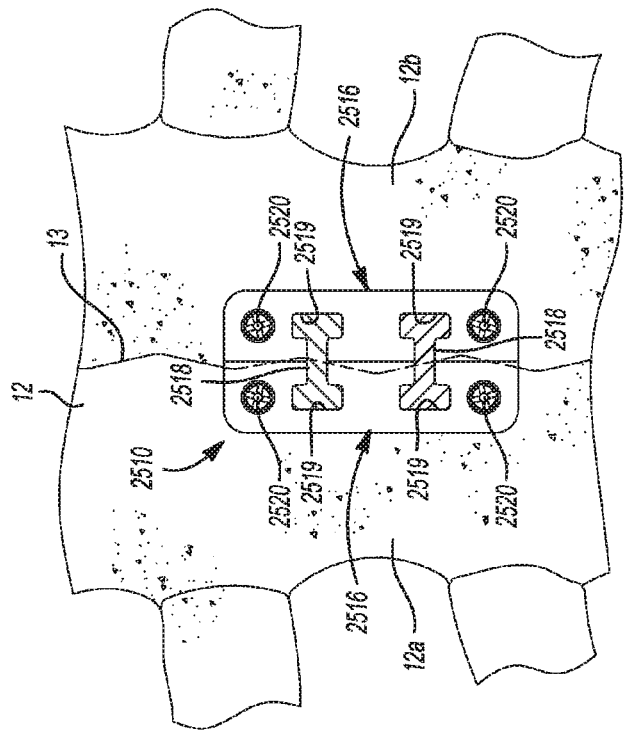
FIG. 81 is a plan view of inserts connecting the brackets according to the principles of the present disclosure.
Figure 80:
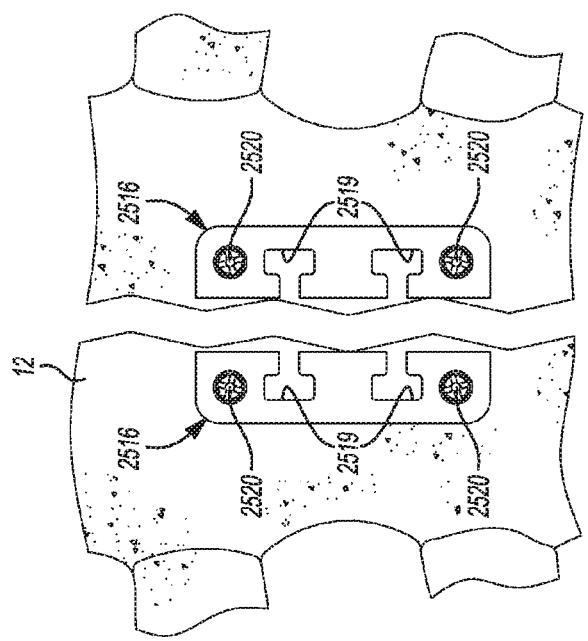
FIG. 80 is a plan view of a sternum having a pair of brackets of yet another closure device according to the principles of the present disclosure.

With reference to FIGS. 80 and 81, another closure system 2510 and method of closing the sternum 12 are provided. The closure system 2510 may include a pair of brackets 2516 and one or more inserts 2518. Each of the brackets 2516 may include one or more generally T-shaped slots 2519 formed therein and may be fixed to the sternum 12 by a plurality of fasteners 2520. The 43 inserts 2518 may be generally H-shaped bars or plates formed from a relatively rigid material and/or non-stretchable material. The inserts 2518 may engage the slots 2519 by a snap fit or press fit, for example.

In use, the brackets 2516 may be fastened to the sternum 12 prior to performing the sternotomy, as shown in FIG. 80. The brackets 2516 may be fixed to the sternum 12 in positions so that the brackets 2516 are spaced apart from each other and aligned relative to each other so that the T-shaped slots 2519 are aligned with each other, as shown in FIG. 80. After fixing the brackets 2516 to the sternum 12, the surgeon may perform the sternotomy and perform a surgical procedure (e.g., heart surgery). After the surgical procedure is complete, the surgeon may manually close the sternum 12 and hold the portions 12a, 12b of the sternum 12 in place while inserts 2518 are placed in the T-shaped slots 2519 of the brackets 2516. That is, each insert 2519 may engage the aligned slots 2519 of both of the brackets 2516, as shown in FIG. 81. Thereafter, the inserts 2518 may securely fix the brackets 2516 relative to each other, thereby maintaining the portions 12a, 12b of the sternum 12 together.

Figure 83:
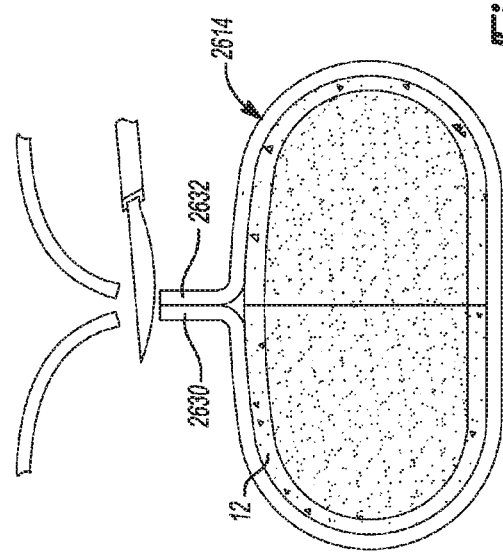
FIG. 83 is a cross-sectional view depicting another step of the method of closing the sternum.
Figure 84:
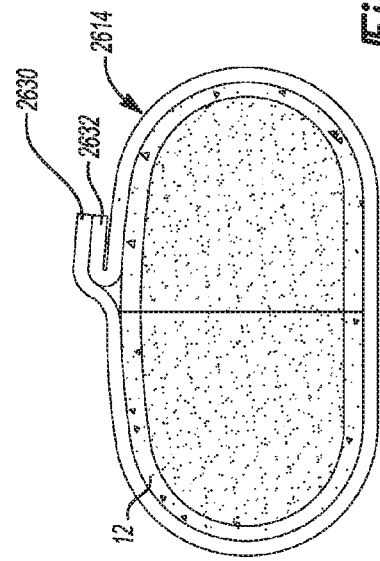
FIG. 84 is a cross-sectional view depicting yet another step of the method of closing the sternum.
Figure 82:
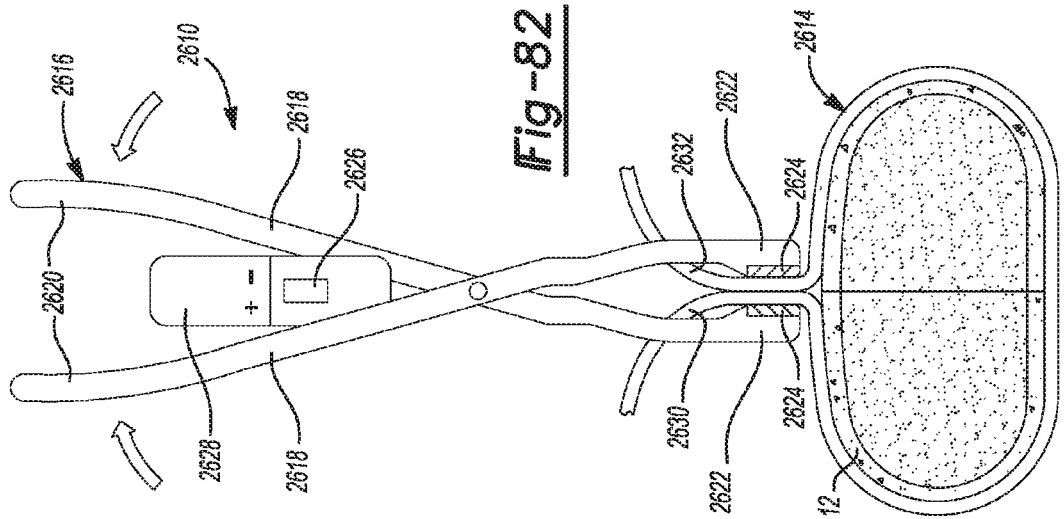
FIG. 82 is a cross-sectional view depicting a step of a method of closing a sternum using yet another closure device according to the principles of the present disclosure.

With reference to FIGS. 82-84, another closure system 2610 and method of closing the sternum 12 are provided. The closure system 2610 may include a band 2614 and forceps 2616. The forceps 2616 may include a pair of arms 2618 that are pivotably coupled relative to each other. Each arm 2618 may include a gripping end 2620 and a clamping end 2622. The clamping end 2622 of each arm 2618 may include a heating element 2624. The heating elements 2624 may be in electrical communication with a switch 2626 and a removable battery 2628 attached to one of the arms 2618 at or near the gripping end 2620. The heating elements 2624 may produce heat when provided with electrical current from the battery 2628. The switch 2626 may be actuated to selectively prevent and allow the flow of electrical current to the heating elements 2624.

To close the sternum 12 using the closure system 2610, the surgeon may first loop the band 2614 around the sternum 12. Then, the surgeon may clamp the ends 2630, 2632 of the band 2614 between the clamping ends 2622 of the forceps 2616. With the ends 2630, 2632 of the band 2614 clamped between the clamping ends 2622, the surgeon may actuate the switch 2626 to 44 allow electrical current to flow through the heating elements 2622. The surgeon may continue to clamp and apply heat to ends 2630, 2632 of the band 2614 until the ends 2630, 2632 are fused together. Thereafter, the surgeon may remove the forceps 2616 from the ends 2630, 2632 of the band 2614. As shown in FIG. 83, any access length of the ends 2630, 2632 of the band 2614 may be trimmed off using a scalpel, scissors, wire cutter or any other suitable cutting device. As shown in FIG. 84, the remaining fused ends 2630, 2632 may be bent or folded flat.

With reference to FIGS. 85 through 91, closure systems 2810a (FIGS. 85 and 86), 2810b (FIGS. 85 and 87), 2810c (FIGS. 85 and 88) are provided. Each system 2810a, 2810b, 2810c may include a cerclage or band 2814, a tensioning device 2818a, 2818b, 2818c, respectively, and a crimp element 2820. The band 2814 may be substantially identical to the band 14, though it is also contemplated that the band 2814 may be a flat, elongated and flexible member formed from a braided cloth or similar material. In one configuration, the system 2810 may only include the band 2814 and the tensioning device 2818, wherein the band 2814 and the tensioning device 2818 bind at least two parts of the sternum 12 together.

Figure 85:
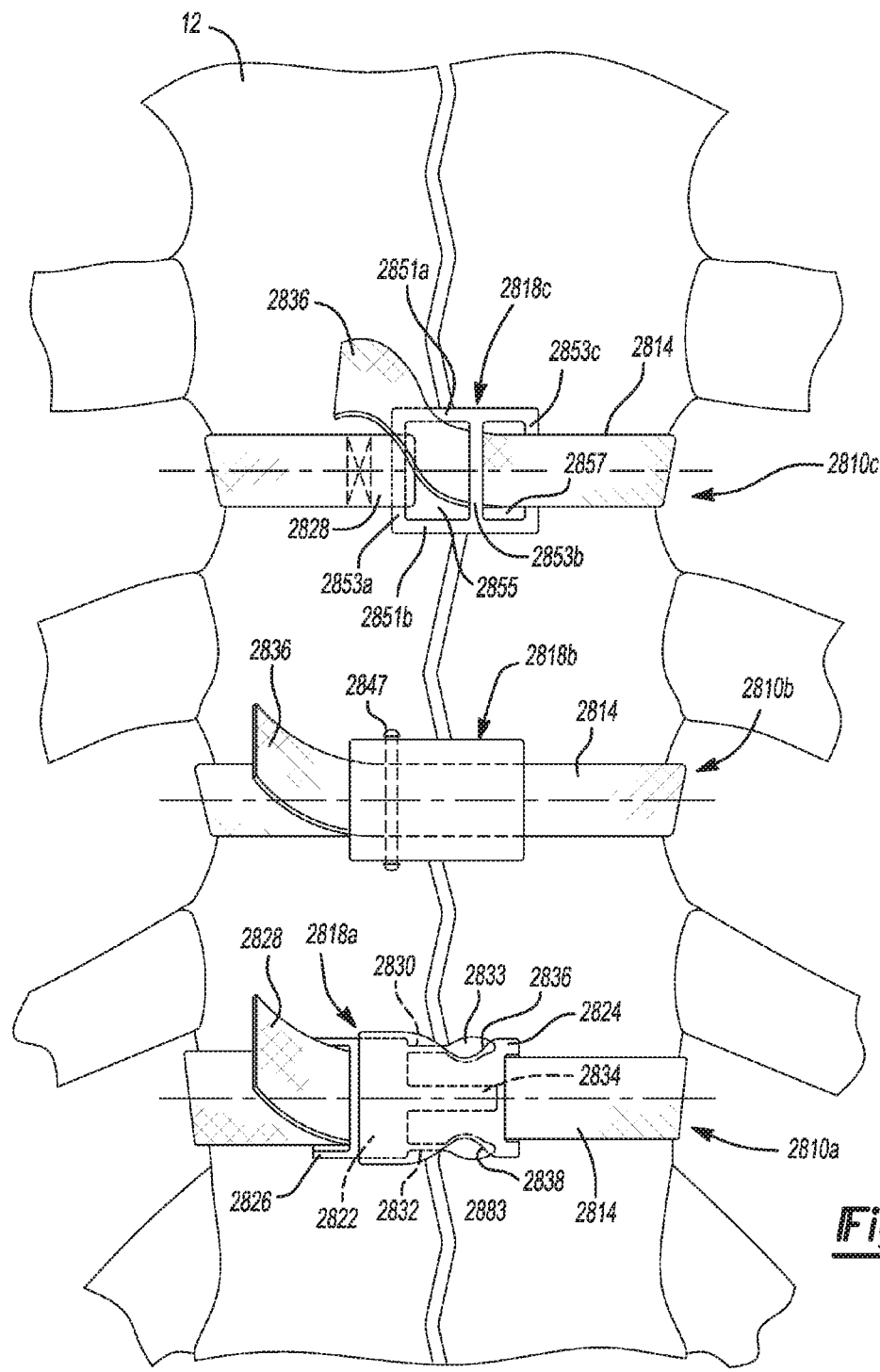
FIG. 85 is a perspective view of an anterior side of a sternum and ribs of a human body having other configurations of a closure device attached thereto according to the principles of the present disclosure.
Figure 88:
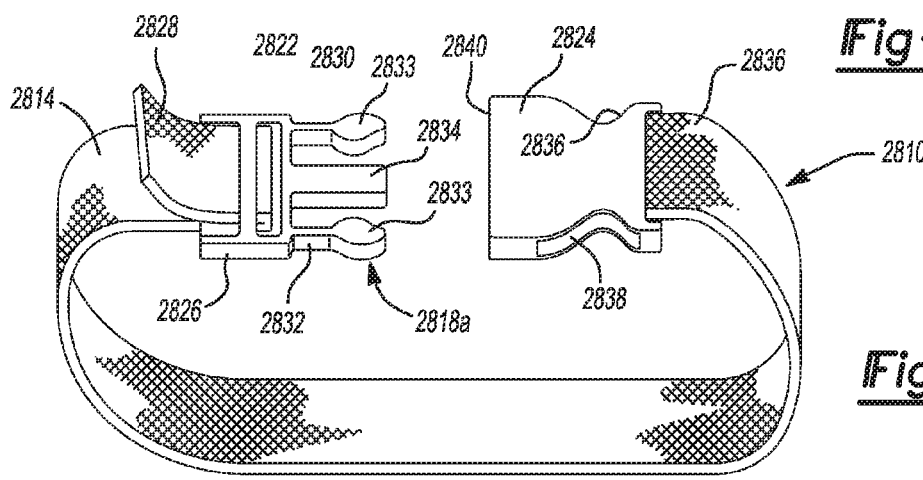
FIG. 88 is a perspective view of the closure device of FIG. 85.

With reference to FIGS. 85 and 88, in a first configuration, the tensioning device 2818a may include a male portion 2822, a female portion 2824, and an adjustment mechanism 2826. The male portion 2822 may be fixed to a first end 2828 of the band 2814 and may include a first arm 2830, a second arm 2832 and a guide element 2834. The guide element 2834 may be located between and substantially parallel to the first arm 2830 and the second arm 2832. The first arm 2830 may be substantially identical to the second arm 2832, and include a locking element or flanged portion 2833 at a distal end thereof.

The female portion 2824 of the tensioning device 2818a may be slidably coupled to a second end 2836 of the band 2814 and may include a first aperture 2836, a second aperture 2838, and an opening 2840. The male portion 2822 may be coupled to the female portion 2824 within the opening 2840, such that the flanged portions 2833 are disposed and secured within the first and second apertures 2836, 2838.

The adjustment mechanism 2826 of the tensioning device 2818a may be integrally formed with, or coupled to, the male portion 2822 or the female portion 2824 and slidably coupled to the band 2814. The adjustment mechanism 2826 may include a substantially rectangular frame 2842 and a substantially linear cross member 2844. The cross member 2844 may intersect the frame 2842, thereby forming a first aperture 2846 and a second aperture 2848. The band 2814 may be disposed within the first aperture 2846 and the second aperture 2848, and around the cross member 2844, such that the adjustment mechanism 2826 can be moved relative to the band 2814 to increase or decrease the distance between the male portion 2822 and the female portion 2824 of the tensioning device 2818a.

Figure 87:
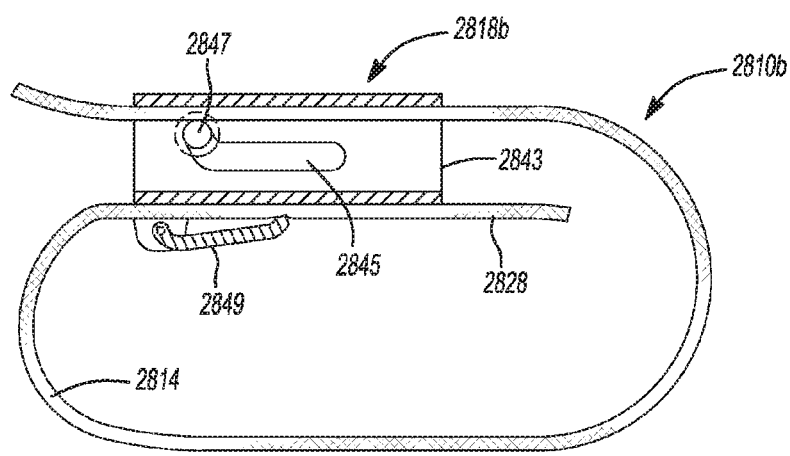
FIG. 87 is a cross-sectional view of the closure device taken along line 87-87 of FIG. 85.

With reference to FIGS. 85 and 87, in a second configuration, the tensioning device 2818b may include a longitudinally extending opening 2843, at least one slot 2845, a rod or pin element 2847, and a clasp member 2849. The slot 2845 may be substantially L-shaped. The pin element 2847 may be may be slidably or rotatably located within the opening 2845. The clasp member 2849 may be pivotably coupled to the tensioning device 2818b. The first end 2828 of the band 2814 may be secured between the clasp member 2849 and the tensioning device 2818b by rotating the clasp member 2849 relative to the tensioning device 2818b. The second end 2836 of the band 2814 may be secured between the pin element 2847 and the tensioning device 2818b by moving the pin element 2847 through the slot 2845. In this regard, pulling the second end 2836 of the band 2814 to the right (relative to the view shown in FIG. 87) may cause the pin element 2847 to move within the slot 2845 to secure the band 2814 between the pin element and the tensioning device 2818b, and thereby secure the closure system 2810b around the sternum.

Figure 86:
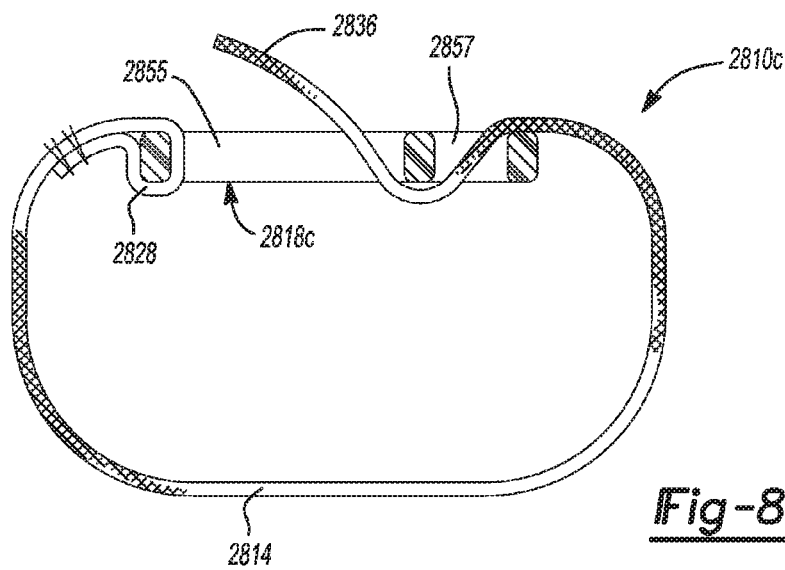
FIG. 86 is a cross-sectional view of the closure device taken along line 86-86 of FIG. 85.

With reference to FIGS. 85 and 86, in a third configuration, the tensioning device 2818c may include a side beam portions 2851a, 2851b and first, second and third cross beam portions 2853a, 2853b, 2853c. The side beam portions 2851a, 2851b and the first and second cross beam portions 2853a, 2853b may define a first opening 2855. The side beam portions 2851a, 2851b and the second and third cross beam portions 2853b, 2853c may define a second opening 2857. The first end 2828 of the band 2814 may be secured to the first 46 cross beam portion 2853a. The second end 2836 of the band 2814 may be extended through the opening 2857 in a first direction and through the opening 2855 in a second direction, opposite the first direction, to secure the second end 2836 of the band 2814 to the tensioning device 2818c.

Figure 89:
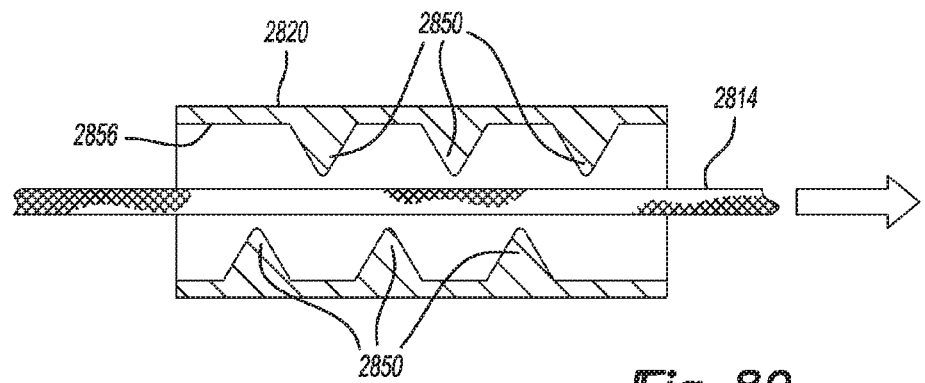
FIG. 89 is a cross-sectional view of a crimp element of the closure device of FIG. 85, depicting the crimp element in a first position.
Figure 90:
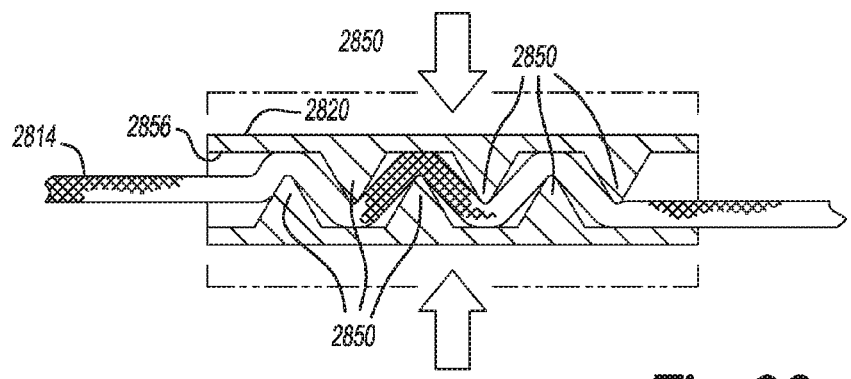
FIG. 90 is a cross-sectional view of the crimp element of FIG. 89, depicting the crimp element in a second position.
Figure 91:
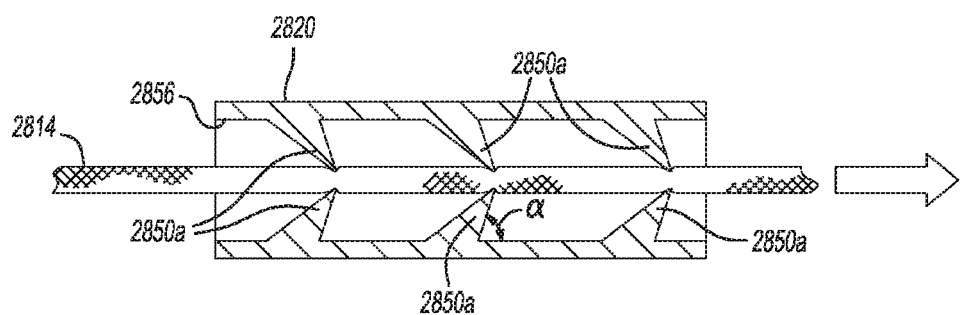
FIG. 91 is a cross-sectional view of another configuration of a crimp element of the closure device of FIG. 85.

With reference to FIGS. 89 through 91, the crimp element 2820 may be a cylindrical or tubular-shaped construct, and may include a plurality of teeth 2850. While the crimp element 2820 is shown as a tubular-shaped crimping device, it is also contemplated that the crimp element 2820 may include other shapes, including a U-shape. The teeth 2850 may be fixed to, or integrally formed with, an inner wall 2856 of the crimp element 2820. The tips 2854 may be offset such that the band 2814 can be slid through the crimp element 2820 (FIG. 89). Once the band 2814 has been positioned within the crimp element 2820, pliers (not shown) or another suitable crimping device may be used to compress the crimp element 2820 and force the teeth 2850 into engagement with the band 2814 (FIG. 90), thus preventing the band from moving relative to the crimp element 2820.

With reference to FIG. 91, in another configuration, teeth 2850a may extend from an inner wall 2856a of a crimp element 2820a at an angle a. The angle a may be between 15 degrees and 75 degrees. In one example configuration, the angle $\alpha$ is approximately 65 degrees. The angle $\alpha$ of teeth 2850a may allow the band 2814 to move relative to the crimp element 2820a in a first direction (e.g., to tighten the band 2814 around the sternum 12), and prevent the band 2814 from moving relative to the crimp element 2820a in a second direction (e.g., to loosen the band 2814 around the sternum 12).

Figure 92:
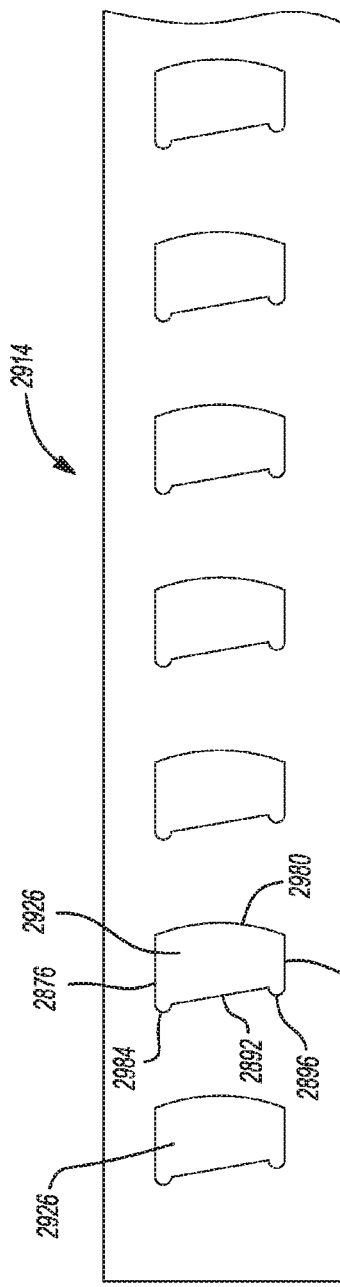
FIG. 92 is a plan view of a band of a closure device according to the principles of the present disclosure.

With reference to FIG. 92, another configuration of a band 2914 is shown. The band 2914 may include a plurality of slots 2926 extending along the length thereof. The slot 2926 may be defined by a first side wall 2976, a second side wall 2978, a first end wall 2980, a second end wall 2982, a first arcuate corner 2984, and a second arcuate corner 2986. The first side wall 2976 may extend between the first end wall 2980 and the first arcuate corner 2984. The second side wall 2978 may extend between the first end wall 2980 and the second arcuate corner 2986. The first side wall 2976 may be substantially parallel to the second side wall 2978. In one configuration, the first side wall 2976 is 47 approximately 0.014 inches longer than the second side wall 2978. The second end wall 2982 may extend between the first arcuate corner 2984 and the second arcuate corner 2986. The second end wall 2982 may form an angle 13 with the second side wall 2978. In one configuration, the angle 13 may be approximately 99 degrees. The first end wall 2980 may be substantially arcuate-shaped and have a radius of curvature of approximately 0.104 inches.

Figure 93:
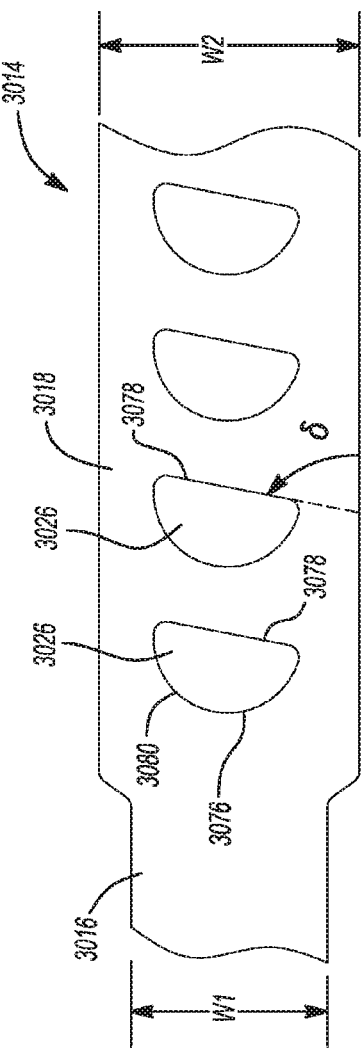
FIG. 93 is a plan view of another configuration of a band of a closure device according to the principles of the present disclosure.

With reference to FIG. 93, another configuration of a band 3014 is shown. The band 3014 may include a first portion 3016 and a second portion 3018. The first portion 3016 may have a substantially rectangular cross section, and have a width W1. The second portion 3018 may have a substantially rectangular cross section, and have a width W2. The ratio of the width W2 to the width W1 may be between one and two. In one configuration, the ratio of the width W2 to the width W1 may be substantially equal to one and fourteen hundredths. The second portion 3018 may include a plurality of slots 3026 extending along the length thereof. The slots 3026 may be substantially semi-circular shaped and defined by an arcuate wall 3076, a linear wall 3078, and a beveled edge 3080. The arcuate wall 3076 may have a radius of curvature of 0.04-0.06 inch. In one configuration, the radius of curvature of the arcuate wall 3076 may be approximately 0.045 inch. The length of the linear wall 3078 may be 0.05-0.07 inch. In one configuration, the length of the linear wall 3078 may be 0.063 inch. The linear wall 3078 may form an angle o with an edge 3082 of the band 3014. The angle o may be between 70 degrees and 88 degrees.

With reference to FIG. 94, another configuration of a band 3114 and a needle 3120 are shown. The band 3114 may be substantially similar to the band 14, or any of the other bands described herein. The needle 3120 may be used in conjunction with any of the closure systems and/or methods described herein. The needle 3120 may include a base portion 3122 and a tip portion 3124. The base portion 3122 may be integrally formed with the tip portion 3124. The base portion 3120 may be fastened to a band 3114 by welding, screwing, riveting, or other similar fastening methods. In this regard, the base portion 3120 may include at least one aperture 3125 for fastening the needle 3120 to the band 3114. The tip portion 3124 may include a proximal end 3126 and a distal end 3128. In one configuration, the needle 3120 may extend in an arcuate manner between the 48 proximal end 3126 and the distal end 3128. The arcuate shape of the needle 3120 allows the user to direct the needle in an appropriate direction, including around the sternum 12, without causing damage to any surrounding material or tissue. The width of the distal end 3128 may be substantially less than the width of the proximal end 3126, such that the needle 3120 forms a point at the distal end 3128.

With reference to FIG. 95, another configuration of a band 3214 and a needle 3220 are shown. The band 3214 may be substantially similar to the band 14, or any of the other bands described herein. The needle 3220 may extend in an arcuate manner from a proximal end 3222 to a distal end 3224. The width of the distal end 3224 may be substantially less than the width of the proximal end 3222, such that the needle 3220 forms a point at the distal end 3224 thereof. A longitudinal bore or slot 3226 may be formed in the proximal end 3222 of the needle 3220. A portion of the needle 3220 may form a longitudinally extending lip or flanged portion 3228 along a length of the slot 3226, such that the band 14 is visible within the slot 3226. The width of the slot 3226 may be substantially equal to, or slightly larger than, the width of the band 14, such that the band 14 slides within the slot 3226. In an assembled configuration, the flanged portion 3228 of the needle 3220 may be crimped or otherwise bent in the direction of the band 3214, such that the band is secured within the slot 3226.

With reference to FIGS. 96 through 99, another configuration of a needle 3320 is shown. The needle 3320 may be used in conjunction with any of the closure systems described herein. The needle 3320 may include a base portion 3322, an intermediate portion 3324, and a tip portion 3326. With reference to FIGS. 101 through 103, in one configuration, a needle 3320a only includes a tip portion 3326. The base portion 3322, the intermediate portion 3324, and the tip portion 3326 may be integrally formed. The base portion 3322 may include a proximal end 3328, a distal end 3330, and a slot 3332 extending from the proximal end 3328 to the distal end 3330. The dimensions of the slot 3332 and the dimensions of a band (not shown) may be such that the band slides within the slot 3332, and frictionally engages a peripheral surface 3333 of the slot 3332 to secure the band therein. The intermediate portion 3324 may include a proximal end 3334 and a distal end 3336. The proximal end 3334 of the intermediate portion 3324 may be wider than the distal end 3328 of the intermediate portion 3324. In this regard, the intermediate portion 3324 may be tapered between the proximal end 3334 and the distal end 3336.

The tip portion 3326 of the needle 3320 may extend in an arcuate manner from a proximal end 3340 to a distal end 3342. In one configuration, the tip portion 3326 may have a generally circular cross section (FIGS. 96 through 99). It will be appreciated, however, that the cross section of the tip portion 3326 may have other shapes within the scope of the present disclosure. With reference to FIGS. 104 through 107, a needle 3320b is shown. The needle 3320b may be substantially similar to the needle 3320, except as otherwise provided herein. The needle 3320b may include a tip portion 3326b having a substantially rectangular cross section. The tip portion 3326 or 3326b may have a radius of curvature of approximately 0.708-0.735 inch. The cross sectional area of the distal end 3342 or 3342b of the tip portion 3326 or 3326b may be substantially less than the diameter of the proximal end 3340, such that the tip portion 3326 or 3326b forms a point at the distal end 3342 or 3342b thereof. As illustrated in FIGS. 96 through 99, the tip portion 3326 may further include at least one beveled surface 3344 extending from the distal end 3342. The length L1 of the beveled surface 3344 may be approximately 0.37-0.39 inch. With reference to FIGS. 104 through 107, in one configuration the tip portion 3326b of the needle 3320b may include four beveled surfaces 3344b.

Figures 108, 109:
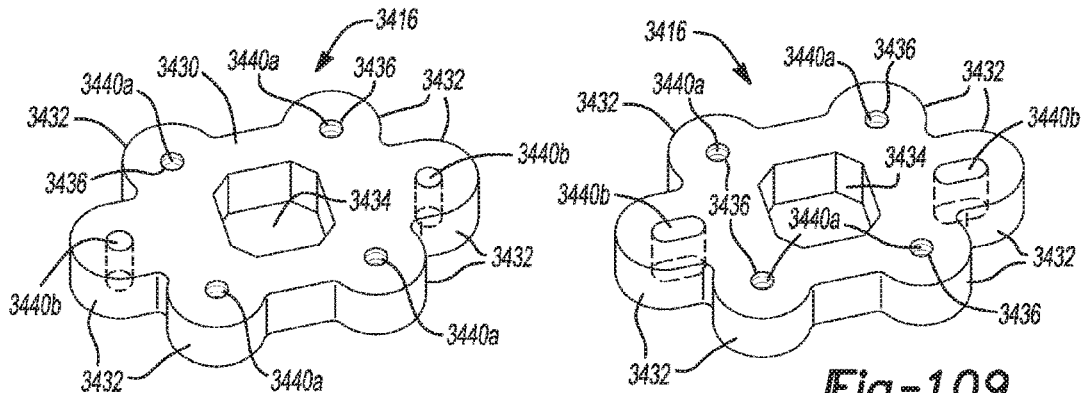
FIG. 108 is a perspective view of a bracket of a closure device according to the principles of the present disclosure.
FIG. 109 is a perspective view of another configuration of a bracket of a closure device according to the principles of the present disclosure.
Figure 110:
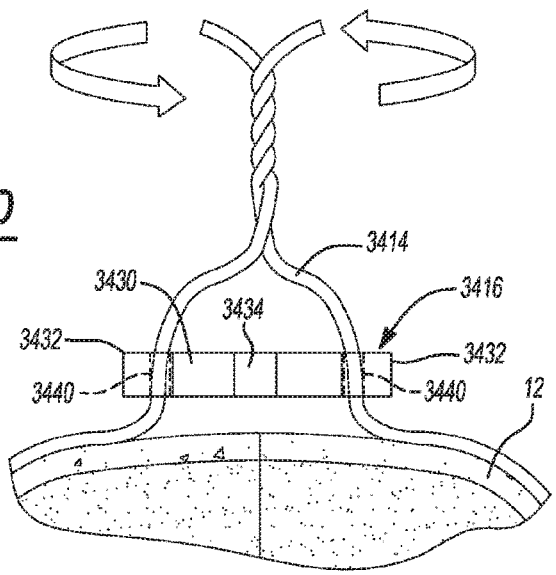
FIG. 110 is a cross-sectional view of a sternum and ribs of a human body depicting the bracket of FIG. 108 and a band attached thereto according to the principles of the present disclosure.

With reference to FIGS. 108 through 110, another configuration of a bracket 3416 is shown. Except as otherwise provided herein, the bracket 3416 may be substantially similar to the bracket 16, and may be used in conjunction with any of the closure systems described herein. The bracket 3416 may include a body portion 3430 and a plurality of lobes 3432 extending outward from the body portion 3430. The body portion 3430 may include a central aperture 3434 extending therethrough. The aperture 3434 may allow the bracket 3416 to be readily flexed or bent to allow for optimal positioning of the bracket 3416 relative to the sternum 12. The aperture 3434 may also allow the bracket 3416 to be cut using band cutters in case the sternum 12 needs to reopened after installation of the closure system. Each of the lobes 3432 may include one or more apertures 3440a, 3440b extending therethrough. At least one of the apertures 3440a may include threads 3436 for receiving a threaded fastener (not shown) that may threadably engage the sternum 12 and thereby fix the bracket 3416 to the sternum. At least two of the apertures 3440b, located on opposite sides of the bracket 3416, may slidably receive a band 3414 for securing the bracket 3416 to the sternum 12. The band 3414 may be a wire, a string, a polymeric band, or similar biocompatible flexible element that can be slidably received within the aperture 3440b. As illustrated, in one configuration, the bracket 3416 includes four apertures 3440a and two apertures 3440b. The apertures 3440b may be any suitable shape, including, but not limited to, a circle (FIG. 108), an oval/ellipse (FIG. 109), or a square.

Figures 111, 112:
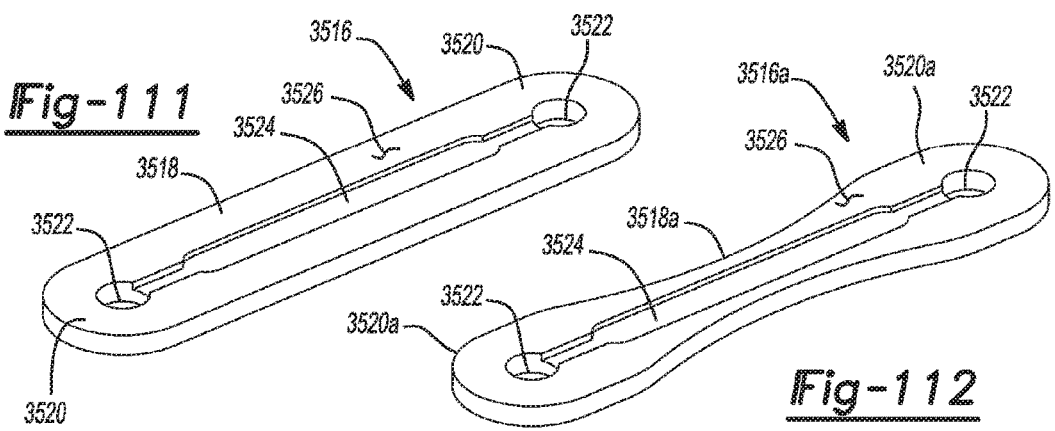
FIG. 111 is a perspective view of another configuration of a bracket of a closure device according to the principles of the present disclosure.
FIG. 112 is a perspective view of another configuration of a bracket of a closure device according to the principles of the present disclosure.

With reference to FIG. 111, another configuration of a bracket 3516 is shown. The bracket 3516 may be relatively flexible to enable the bracket 3516 to conform to the contours of the sternum (not shown) when the bracket 3516 is fastened thereto. The bracket 3516 may be any suitable shape, including, but not limited to, a circle, a square, an oval/ellipse (FIG. 111), and include a central portion 3518 extending between end portions 3520. With reference to FIG. 112, in one configuration, a bracket 3516a may include a central portion 3518a that is generally narrower than opposed end portions 3520a. The narrower central portion 3518a of the bracket 3516a shown in FIG. 112 may allow the bracket 3516a to be readily flexed or bent to allow for optimal positioning of the bracket 3516a relative to the sternum.

The brackets 3516, 3516a may include at least two apertures 3522 and a channel or groove 3524. The apertures 3522 may be located near or adjacent to the end portions 3520, 3520a to assist with properly securing the bracket 3516, 3516a to the sternum. The groove 3524 may extend between and connect the apertures 3522. A band (not shown), or other suitable flexible element such as a wire, a string, or a cable, may be threaded through the apertures 3522 and positioned within the groove 3524. The depth of the groove 3524 may be such that the band, when located within the groove 3524, does not extend above an outer surface 3526, 3526a of the bracket 3516, 3516a. In this regard, it is also understood that a portion of the groove 3524 may extend through the bracket 3516 to form an oblong aperture (not shown). In addition to ensuring proper positioning (for example, centering) of the band 3514 between the 51 apertures 3522, the groove 3524 and/or aperture (not shown) may help to ensure that the bracket 3516 is relatively flexible, thus enabling the bracket 3516 to conform to the contours of the sternum when the bracket 3516 is fastened thereto. The groove 3524 and/or aperture (not shown) may also help to ensure that the bracket 3516 is able to be readily cut in case the sternum needs to reopened after installation of the system 10.

Figure 113:
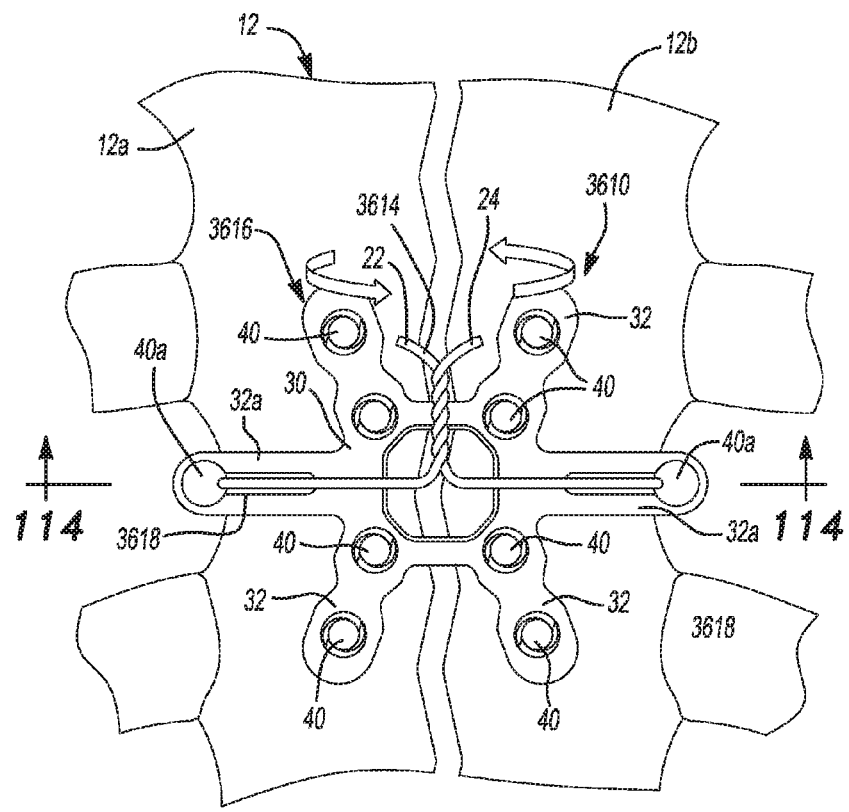
FIG. 113 is a perspective view of an anterior side of a sternum and ribs of a human body having another configuration of a closure device attached thereto according to the principles of the present disclosure.
Figure 114:
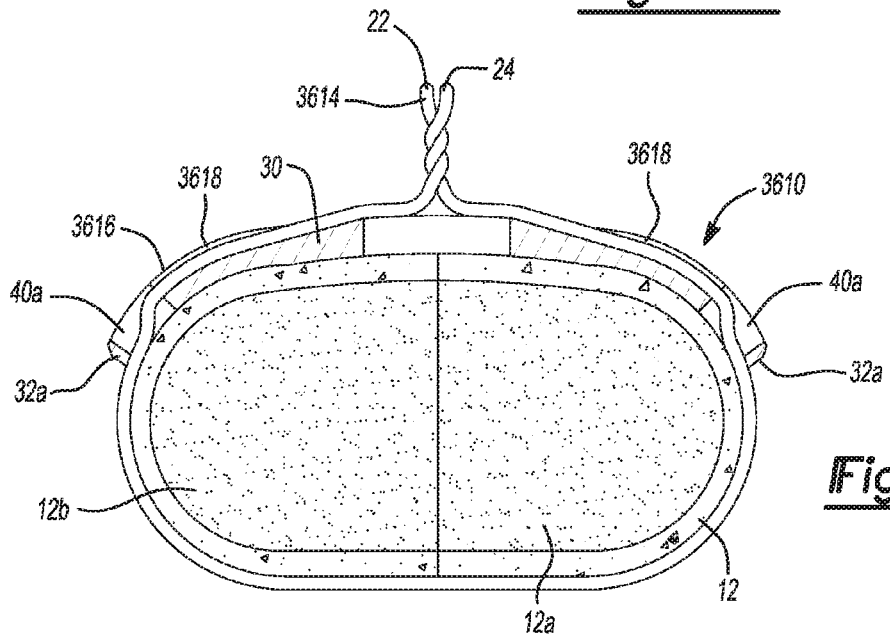
FIG. 114 is a cross-sectional view of the closure device taken along the line 114-114 of FIG. 113.

With reference to FIGS. 113 and 114, another closure system 3610 is shown. The closure system 3610 may include a band 3614 and a bracket 3616. The band 3614 may be a round or flat, elongated and flexible member formed from a metallic material and/or a polymeric material. In one configuration, the band 3614 is a wire having a circular cross section. The bracket 3616 may be substantially similar to the bracket 16, except as otherwise described herein.

The bracket 3616 may include a body portion 3630 and at least two arms 3632. The arms 3632 may extend outward from the body portion 3630, and may include one or more apertures 3640, a channel or groove 3618, and a central opening 3634. The channel or groove 3618 may extend between the aperture 3640 and the central opening 3634. The length of the arms 3632, and the location of the apertures 3640 with respect thereto, may be such that when the system 3610 is attached to the sternum 12, the location of a force that the band 3614 imparts on the sternum 12 is adjusted by the arms 3632 and the apertures 3640. By adjusting the location of the force that the band 3614 imparts on the sternum 12, the bracket 3616 is able to reduce the likelihood that the band 3614 will cut through, or otherwise damage, the sternum 12.

With continued reference to FIGS. 113 and 114, a method will be described for attaching the system 3610 to the sternum 12 and tensioning the band 3614 to reapproximate the sternum 12. The band 3614 may be inserted through the apertures 3640a and looped around the posterior side of the sternum 12 so that the band 3614 substantially circumscribes the sternum 12. Once the band 3614 is looped around the sternum 12, a portion of the band 3614 may be positioned or disposed within the groove 3618, and the band 3614 may be tensioned by twisting, crimping, or otherwise securing a first end 3622 of the band 3614 to a second end 3624 of the band 3614. Positioning the band 3614 within 52 the groove 3618 may help to contain the band 3614 and ensure that the band 3614 remains centered with respect to the arms 3632a. As shown in FIG. 113, the bracket 3616 may be positioned so that the fracture separating the two portions 12a, 12b of the sternum 12 is visible in the opening 3634 in the bracket 3616 (i.e., so that two of the legs 3632 of the bracket 3616 are aligned with one portion 12a or 12b of the sternum 12 and the other two legs 3632 are aligned with the other portion 12a or 12b of the sternum 12).

Figure 115A:
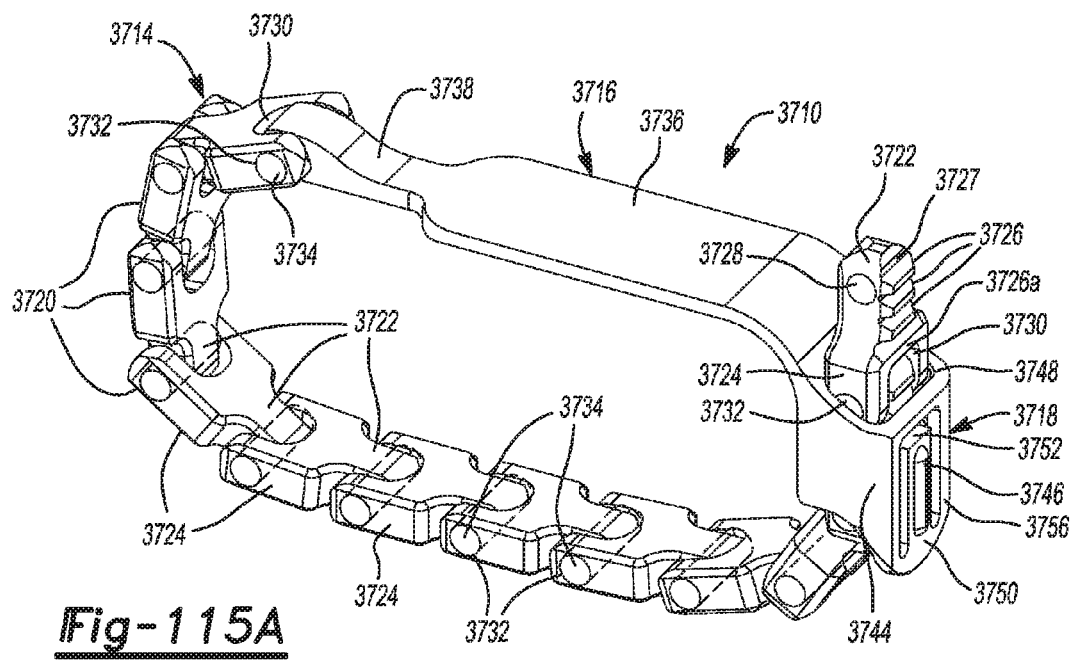
FIG. 115A is a perspective view of another configuration of a closure device according to the principles of the present disclosure.

With reference to FIG. 115A, another closure system 3710 is provided that may be used to reapproximate the sternum, or other bone, after a medical procedure. The closure system 3710 may include a chain or band 3714, a bracket 3716, and a tensioning device 3718.

The band 3714 may include a plurality of links 3720 that are pivotally mounted to each other or to the bracket 3716. Each link 3720 may include a tongue portion 3722 and a base portion 3724. The tongue portion 3722 may be substantially U-shaped and may include a plurality of ratcheting fins or teeth 3726 and an aperture 3728 extending therethrough. The teeth 3726 may extend from a first side 3727 of the link 3720. While the tongue portion 3722 is shown to include three teeth 3726, it is understood that the tongue 3726 may include more or fewer teeth 3726 within the scope of the present disclosure. It is also understood that the link 3720 may include more than one tongue portion 3722. For example, with reference to FIG. 1158, in one configuration, a link 3720a includes two tongue portions 3722a.

As illustrated in FIG. 115A, the base portion 3724 may include a channel 3730, an aperture 3732, and a tooth portion 3726a. With reference to FIG. 1158, it is also understood that the base portion 3724 may include more than one channel 3730a, corresponding to the number of tongue portions 3722a. The channel 3730 or 3730a may receive the U-shaped tongue portion 3722 or 3722a, respectively, such that the aperture 3728 is substantially aligned with the aperture 3732. A pin 3734 may be mounted within the aperture 3728 and the aperture 3732 such that the tongue portion 3722 of the link 3720 is pivotably supported by the base portion 3724 of an adjacent link 3720. The tooth portion 3726a may extend from the first side 3727 of the link 3720. The tooth portion 3726a may be of a similar size and shape as the teeth 3726, such that, when the 53 tongue portion 3722 is pivotably supported by the base portion 3724, the tooth portion 3726a is adjacent to, and substantially aligned with, the teeth 3726.

The bracket 3716 may be a plate formed from a metallic and/or polymeric material and may include a body portion 3736 and a tongue portion 3738. The bracket 3716 may be relatively flexible to enable the bracket 3716 to conform to the contours of the sternum 12 when the bracket 3716 is fastened thereto. The thickness of the body portion 3736 may be less than the thickness of the tongue portion 3738 to allow the bracket 3716 to be readily cut using band cutters, for example, or other standard operating room tools in case the sternum 12 needs to reopened after installation of the system 3710. The tongue portion 3738 may be of a similar size and shape as the tongue portion 3722 of the link 3720 and may include an aperture (not shown) extending therethrough. The channel 3730 of the base portion 3724 may receive the tongue portion 3738 of the bracket 3716, such that the aperture of the bracket 3716 is substantially aligned with the aperture 3732 of the base portion 3724. The pin 3734 may be mounted within the aperture of the bracket 3716 and the aperture 3732 of the base portion 3724 such that the tongue portion 3738 of the bracket 3716 is pivotably supported by the base portion 3724 of the link 3720.

Figure 116:
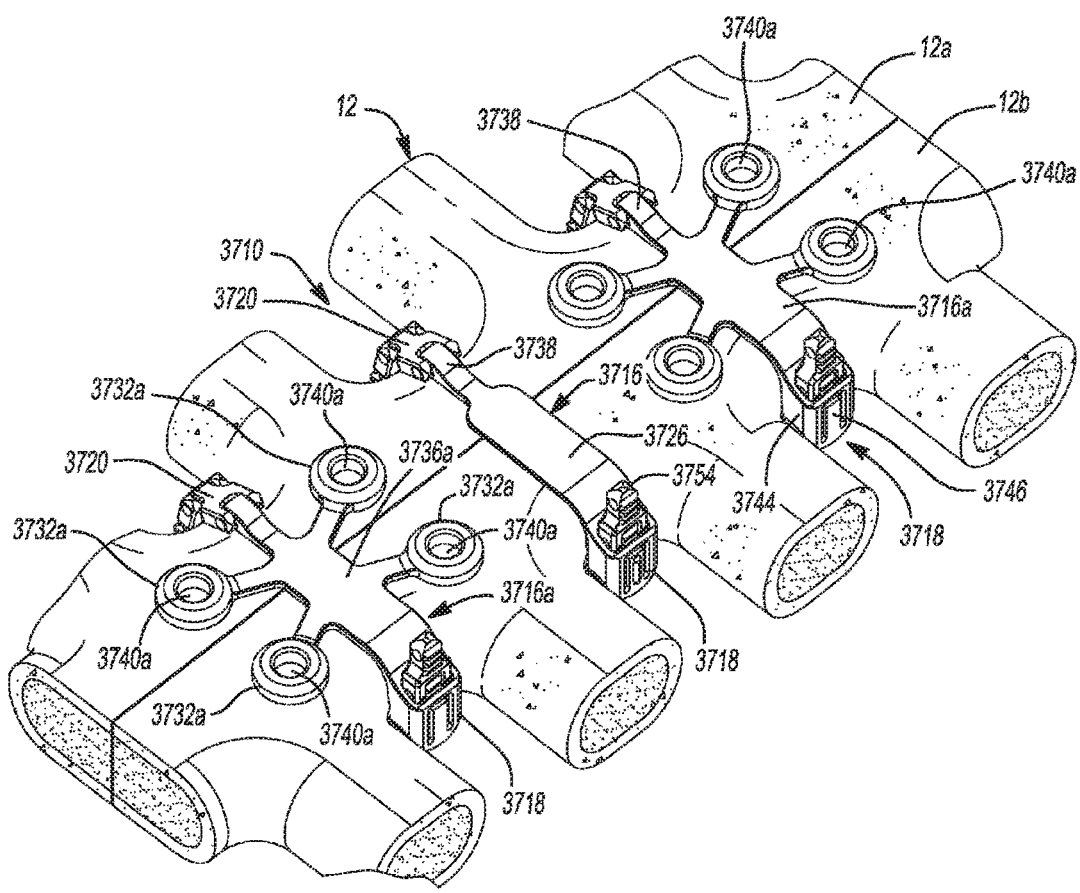
FIG. 116 is a perspective view of an anterior side of a sternum and ribs of a human body depicting the closure device of FIG. 115A attached thereto according to the principles of the present disclosure.

With reference to FIG. 116, another configuration of a bracket 3716a is shown. The bracket 3716a may be substantially similar to the bracket 3716, except as otherwise provided herein. The bracket 3716a may include a body portion 3736a. The body portion 3736a of the bracket 3716a may include a plurality of legs 3732a extending therefrom. Each leg 3732a may include an aperture 3740a therethrough. Mechanical fasteners (not shown) may extend through the apertures 3740a and may threadably engage the sternum 12 to fix the bracket 3716a to the sternum 12.

The tensioning device 3718 may include a receiver 3744 and at least one ratcheting arm 3746. The tensioning device 3718 may be integrally formed with the bracket 3716 and extend substantially perpendicularly therefrom in a substantially L-shaped configuration with the bracket 3716. The receiver 3744 may include an aperture 3748 extending therethrough. The aperture 3748 may be of a similar size and shape as the base portion 3724 of the link 3720, such that the links 3720 slide within the aperture 3748. In one configuration the 54 ratcheting arm 3746 may extend from a first side 3756 of the tensioning device 3718. A first end 3750 of the ratcheting arm 3746 may be integrally formed with the receiver 3744, while a second end 3752 of the ratcheting arm 3746 may extend at least partially into the aperture 3748. The second end 3752 of the ratcheting arm 3746 may engage the tooth portion 3726a and the teeth 3726 as the band 3714 slides within the aperture 3748, thereby allowing the band 3714 to slide in a first direction within the aperture 3748 and preventing the band 3714 from sliding in a second direction (opposite the first direction) within the aperture 3748.

Figure 117:
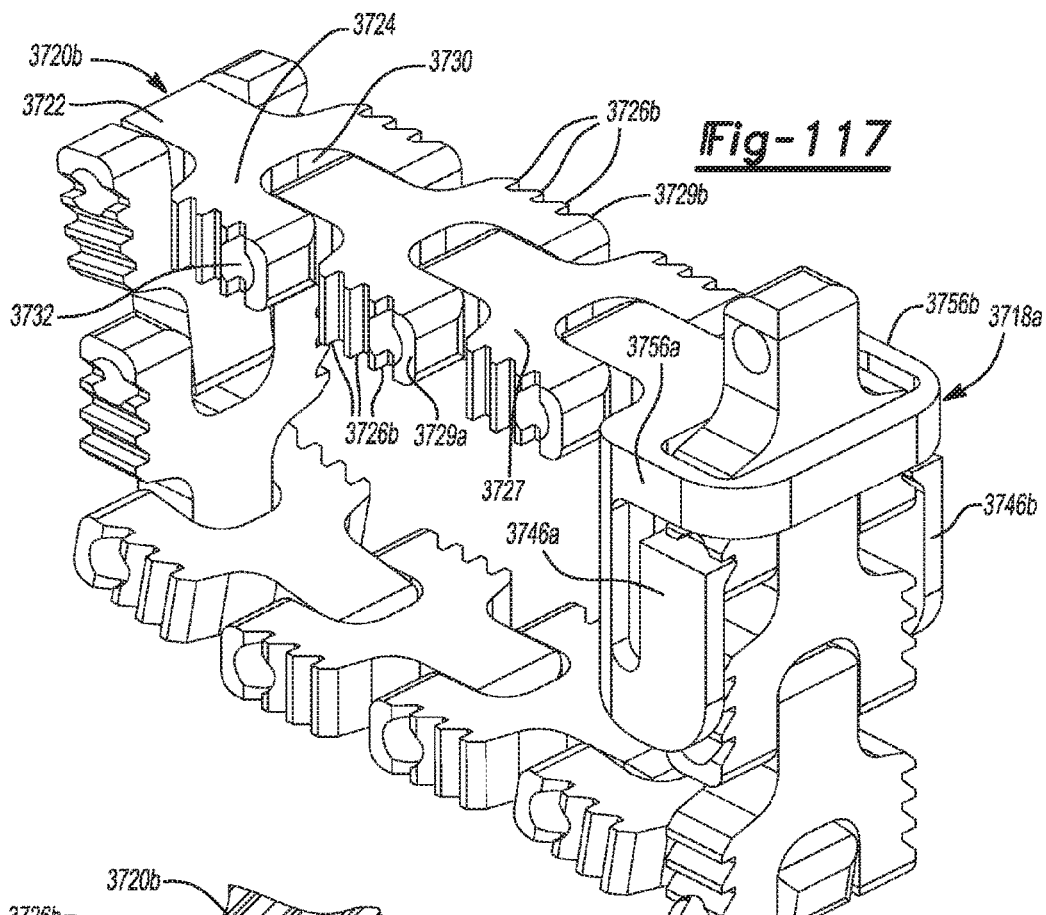
FIG. 117 is a perspective view of another configuration of a closure device according to the principles of the present disclosure.
Figure 118:
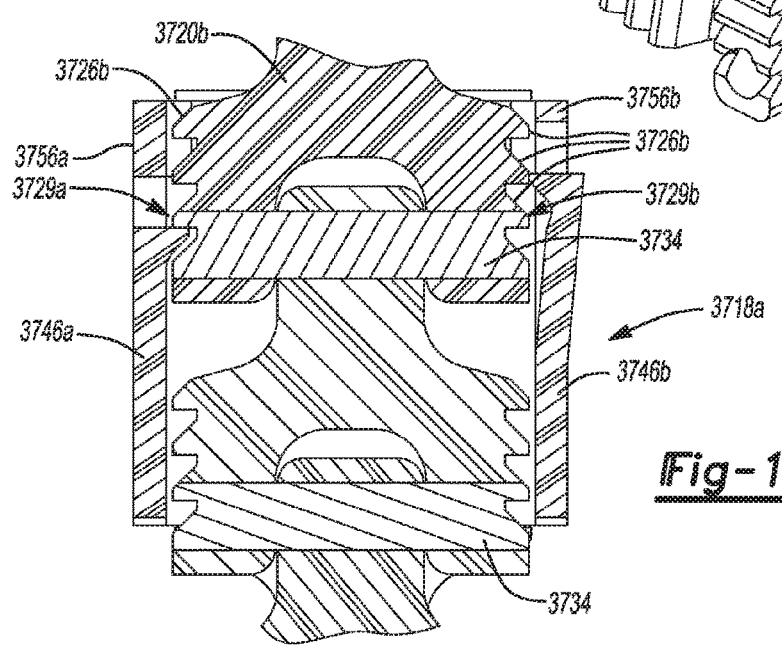

With reference to FIGS. 117 and 118, another configuration of a closure system 3710b is shown. The closure system 3710b may include a band 3714b and a tensioning device 3718b. The band 3714b and the tensioning device 3718b may be substantially similar to the band 3714 and the tensioning device 3718, except as otherwise provided herein. The band 3714b may include a plurality of links 3720b having teeth 3726b. Teeth 3726b may be formed on a second side 3729b and/or a third side 3729b of a link 3720b. The second side 3729b and the third side 3729b may each be substantially perpendicular to a first side 3727b. The teeth 3726b on the second side 3729b may be asymmetrically located, or offset, relative to the teeth 3726b on the third side 3729b to provide for a smaller or finer ratcheting increment, as described below. The second side 3729b may be generally parallel to the third side 3729b.

The tensioning device 3718b may include ratcheting arms 3746b extending from opposed sidewalls 3756b of the tensioning device 3718b. The sidewalls 3756b may be generally perpendicular to the sternum 12. The ratcheting arms 3746b may engage the teeth 3726b formed on sidewalls 3729b of a base portion 3724b of the link 3720b, thereby allowing the band 3714b to slide in a first direction within an aperture 3748b of the tensioning device 3718b and preventing the band from sliding in a second direction (opposite the first direction) within the aperture 3748b.

Figure 119:
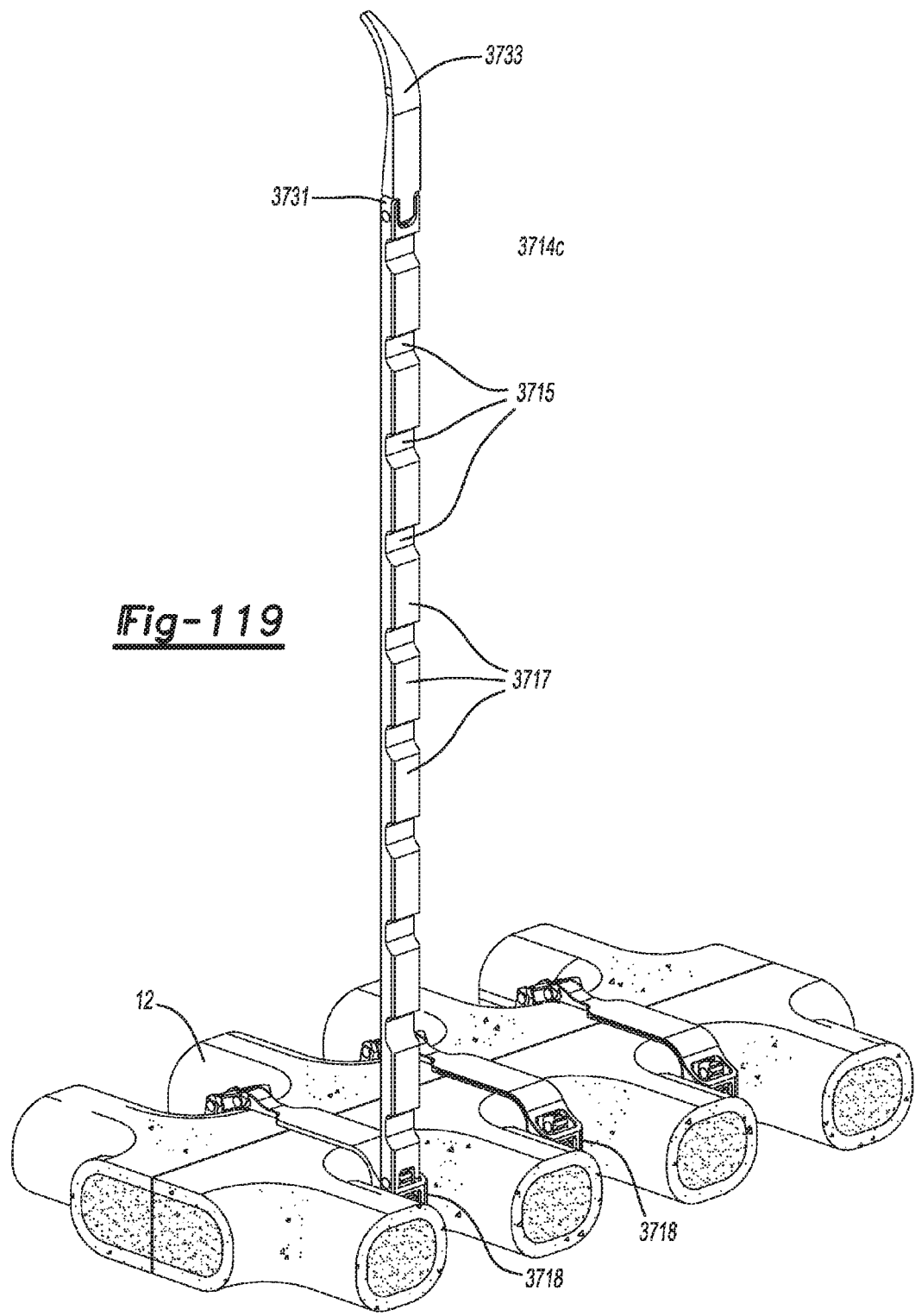

With reference to FIG. 119, another configuration of a closure system 3710c is shown. The closure system 3710c may include a band 3714c, a bracket 3716c and a tensioning device 3718c. The bracket 3716c and the tensioning device 3718c may be substantially similar to the bracket 3716 and the 55 tensioning device 3718, except as otherwise provided herein. The band 3714c may include alternating first portions 3715c and second portions 3717c. The first portions 3715c may be thinner than the second portions 3717c to allow for easier cutting of the band 3714c to an appropriate length after positioning the band 3714c around the sternum 12. The first portions 3715c may substantially define symmetrically displaced channels along the length of the band 3714c. A distal end 3731c of the band 3714c may include a needle portion 3733c. The needle portion 3733c may be arcuately-shaped and pivotably coupled to the band 3714c. In other configurations, the needle portion 3733c may be integrally-formed with the band 3714c. The needle portion 3733c may allow for easier insertion of the distal end 3731c of the band 3714c through the tensioning device 3718c.

Figure 120:
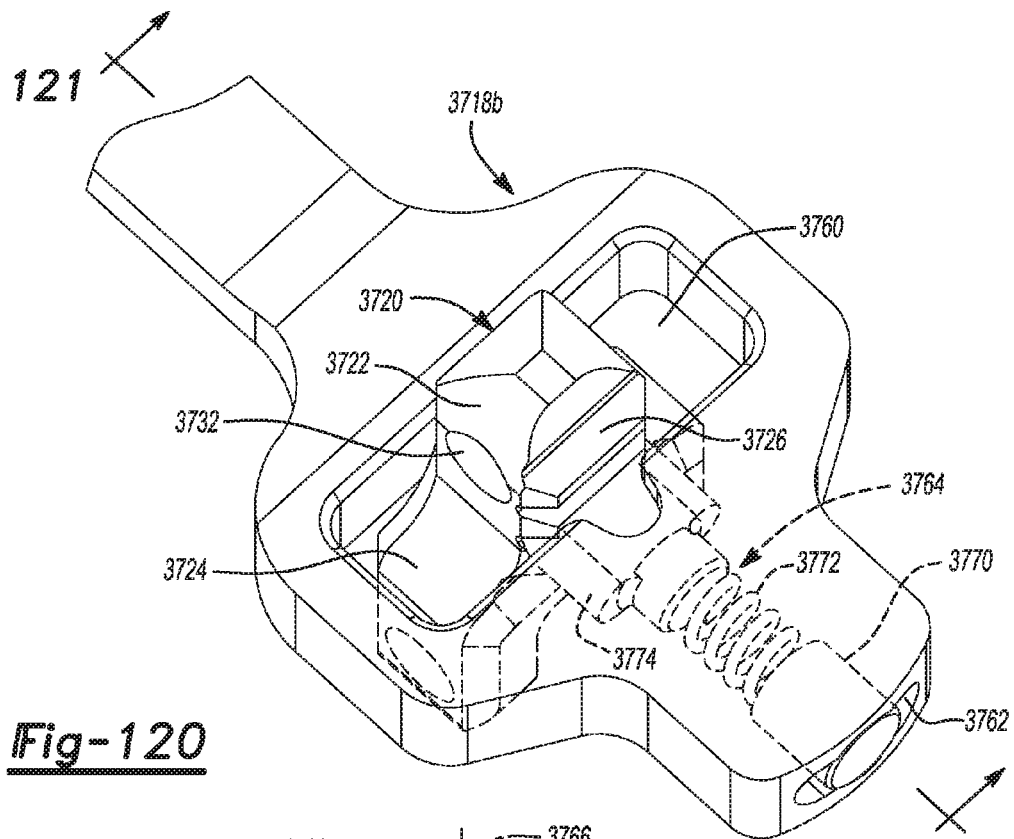
Figure 121:
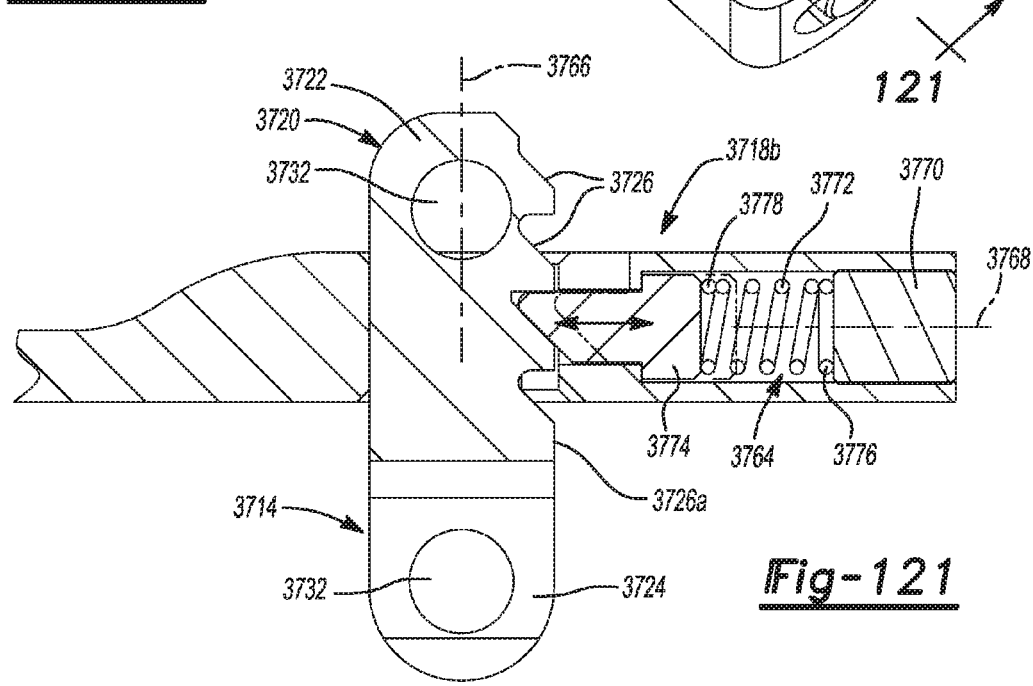

With reference to FIGS. 120 and 121, in another configuration a tensioning device 3718d may include a first aperture 3760d, a second aperture 3762d, and a catch assembly 3764d. The first aperture 3760d may be appropriately sized to receive the band 3714 therein. A longitudinal axis 3766d of the first aperture 3760d may be substantially perpendicular to a longitudinal axis 3768d of the second aperture 3762d. The catch assembly 3764d may include a base member 3770d, a biasing member 3772d, and a tooth member 3774d. The base member 3770d may be secured within the second aperture 3762d by friction, adhesive, or similar techniques. The biasing member 3772d may be a helical spring and may include a first end 3776d fixed to the base member 3770d and a second end 3778d fixed to the tooth member 3774d. The biasing member 3772d may be at least partially disposed within the second aperture 3762d and operable to bias the tooth member 3774d in a direction parallel to the longitudinal axis 3768d of the second aperture 3762d. As the band 3714 is inserted into the first aperture 3760d, the tooth member 3774d may engage the teeth 3726 and/or the tooth portion 3726a to secure the band 3714 therein. The catch assembly 3764d may allow the band 3714 to move in a first direction within the first aperture 3760d (parallel to the longitudinal axis 3766d) and prevent the band 3714 from moving in a second direction (opposite the first direction) within the first aperture 3760d.

With reference to FIG. 116, a method will be described for attaching the system 3710 to the sternum 12 and tensioning the band 3714 to 56 reapproximate the sternum 12. While the method is generally described with respect to the system 3710, it will also be appreciated that the method may be used with other closure systems described herein. A first end 3754 of the band 3714 may be looped around the posterior side of the sternum 12 so that the band 3714 substantially circumscribes the sternum 12. Once the band 3714 is looped around the sternum 12, the first end 3754 of the band 3714 may be inserted up through the receiver 3744. The bracket 3716 may be positioned so that the fracture separating the two portions 12a, 12b of the sternum 12 is substantially adjacent to the body portion 3736 of the bracket 3716.

The tensioning device 3718 may be used to tighten the band 3714 around the sternum 12 to bind the portions 12a, 12b of the sternum 12 together. Specifically, the first end 3754 of the band 3714 may be slid, or otherwise extended, through the receiver 3744 to tighten the band 3714 around the sternum 12 to a desired amount. As the band 3714 is slid through the receiver 3744 in the first direction, the second end 3752 of the ratcheting arm 3746 may engage the tooth portion 3726a or the teeth 3726 to hold the band 3714 at the desired tightness, and prevent the band 3714 from sliding in the second direction. After the band 3714 has been secured within the tensioning device 3718 at a desired tightness, excess links 3720 that extend beyond the tensioning device 3718 can be removed by removing the pin 3734 that extends through the apertures 3728, 3732 of the tongue portion 3722 and the base portion 3724, respectively.

Figure 122:
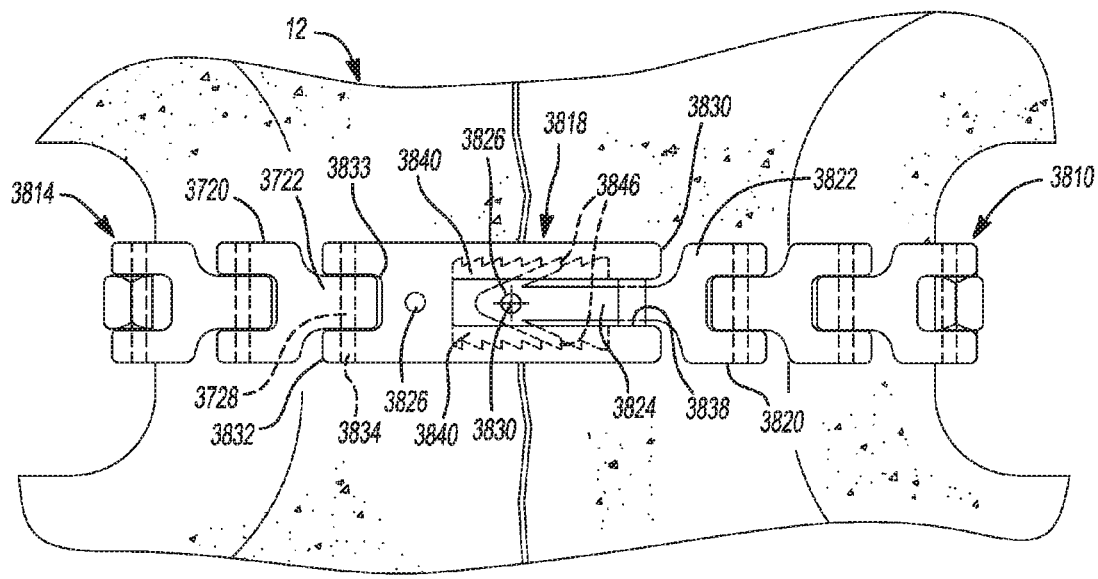

With reference to FIG. 122, another closure system 3810 is provided that may be used to reapproximate the sternum, or other bone, after a medical procedure. The closure system 3810 may include a band 3814 and a tensioning device 3818.

Figure 123:
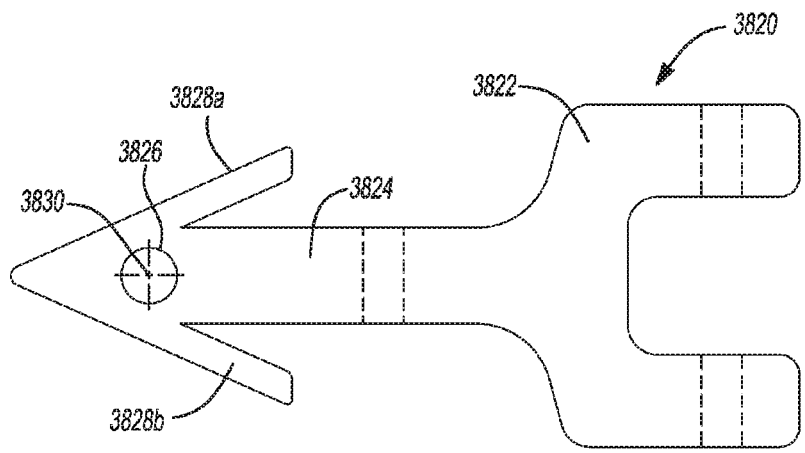

The band 3814 may be substantially similar to the band 3714, except as otherwise provided herein. Accordingly, like numerals will be used to describe like features and components. With reference to FIG. 123, the band 3814 may include a locking element 3820. The locking element 3820 may include a base portion 3822 and a tongue portion 3824. The base portion 3822 may be substantially similar to the base portion 3724 of the link 3720. The tongue portion 3824 may include a first aperture 3826, a first ratcheting arm 3828a and a second 57 ratcheting arm 3828b. The first aperture 3826 may include a first axis 3830 that perpendicularly intersects the sternum 12. The first ratcheting arm 3828a and the second ratcheting arm 3828b may be flexible and generally define a V-shaped tongue portion 3824.

The tensioning device 3818 may include a first end 3830 and a second end 3832. The first end 3830 may include a first Li-shaped channel 3833, a first aperture 3834, and a second aperture 3836. The first Li-shaped channel 3832 may receive the tongue portion 3722 of the link 3720, such that the aperture 3834 is substantially aligned with the aperture 3728. The pin 3734 may be mounted within the aperture 3728 and the aperture 3834 such that the tongue portion 3722 of the link 3722 is pivotably supported by the first end 3830 of the tensioning device 3818.

The second end 3832 of the tensioning device 3818 may include a second Li-shaped channel 3838 opposing the first Li-shaped channel 3832 and grooves 3840 on opposing lateral sides of the channel 3832. The grooves 3840 may extend the length of the second Li-shaped channel 3838. The channel 3838 and the grooves 3840 may be sized to receive the locking element 3820. The grooves 3840 may include a plurality of teeth 3846. When the locking element 3820 is inserted into the bore 3840, the first and second ratcheting arms 3828a, 3828b may engage at least one of the teeth 3846 to secure the locking element 3820 within the bore 3840. A second aperture 3846 may be formed between the first Li-shaped channel 3832 and the second Li-shaped channel 3838. The second aperture 3846 may be substantially parallel to the first aperture 3826, such that pliers or a similar device can be used to pull the first aperture 3826 in the direction of the second aperture 3846 and tighten the band 3818 around the sternum 12.

Figure 124:
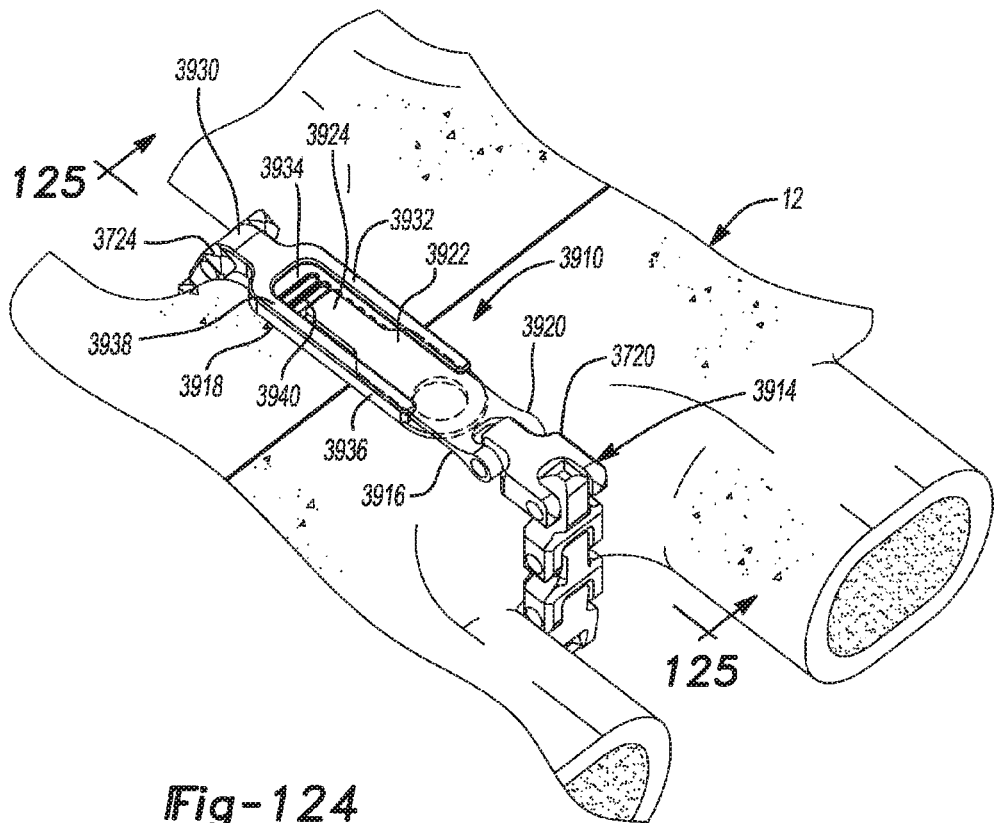

With reference to FIG. 124, another closure system 3910 is provided that may be used to reapproximate the sternum, or other bone, after a medical procedure. The closure system 3910 may include a band 3914, a bracket 3916 and a tensioning device 3918.

The band 3914 may be substantially similar to the band 3714, except as otherwise provided herein. Accordingly, like numerals will be used to describe like features and components.

The bracket 3916 may include a base portion 3920, a mid-portion 3922 and an end portion 3924. The base portion 3920 may be substantially similar to the base portion 3724 of the link 3720. The mid-portion 3922 may be wider than the end portion 3924. The end portion 3924 may include at least one tooth 3926 formed on a first side 3928 thereof.

Figure 125:
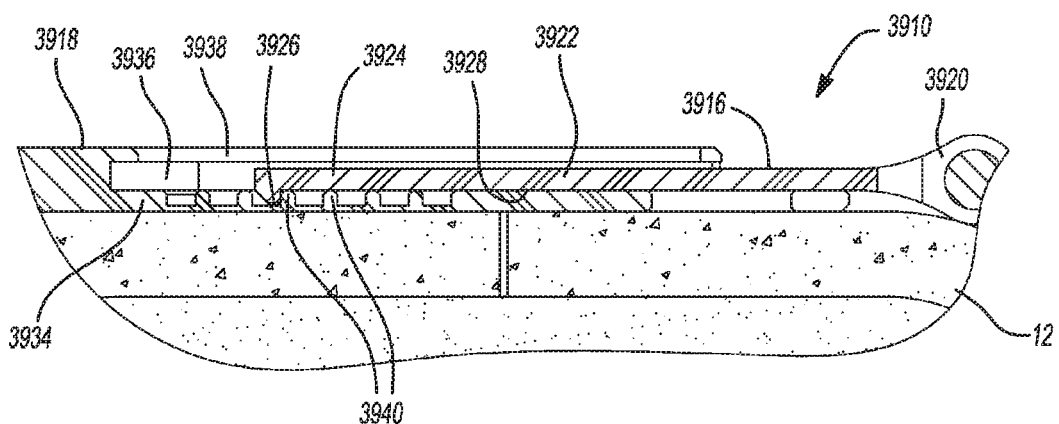

The tensioning device 3918 may include a tongue portion 3930 and a receiver 3932. The tongue portion 3930 may be substantially similar to the tongue portion 3722 of the link 3720, such that the tongue portion 3930 of the tensioning device 3918 can be rotatably mounted to the base portion 3724 of the link 3720. The receiver 3932 may include a first wall 3934, a second wall 3936, and a flange 3938. The flange 3938 may be substantially parallel to the first wall 3934 and extend around the periphery of the tensioning device 3918. The first wall 3934 may include a plurality of teeth 3940. As illustrated in FIGS. 124 and 125, as the bracket 3916 slides within the receiver 3932, the tooth 3926 may engage at least one of the plurality of teeth 3940 to prevent the bracket 3916 from moving in a first direction within the receiver 3932. The flange 3938 may engage the mid-portion 3922 of the bracket 3916 to prevent the bracket 3916 from moving in a second direction (perpendicular to the first direction) within the receiver.

Figure 126:
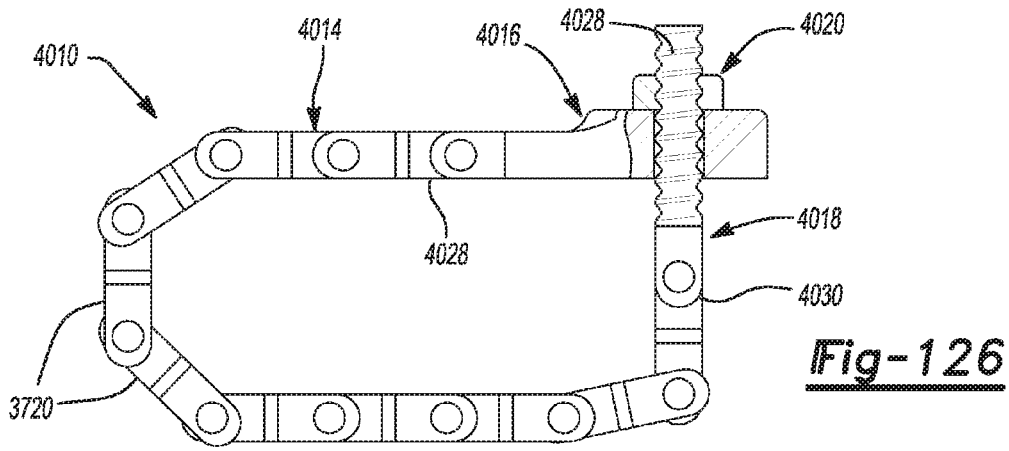

With reference to FIG. 126, another configuration of a closure system 4010 is provided that may be used to reapproximate the sternum, or other bone, after a medical procedure. The closure system 4010 may include a band 4014, a receiver 4016, a link member 4018, and a nut member 4020.

The band 4014 may be substantially similar to the band 3714, except as otherwise provided herein. Accordingly, like numerals will be used to describe like features and components.

Figure 127:
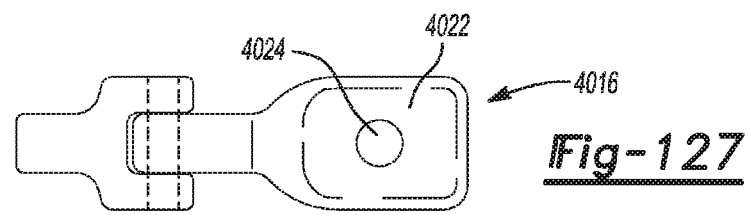
Figure 128:
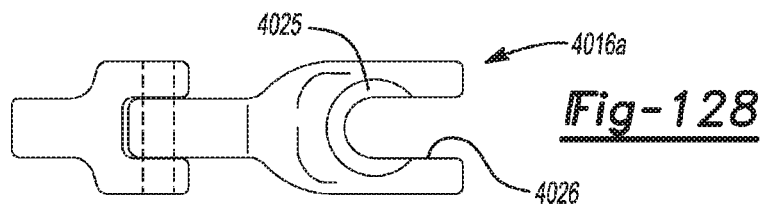

As illustrated in FIG. 127, the receiver 4016 may include a body portion 4022 having an aperture 4024 therethrough. As illustrated in FIG. 128, in another configuration, a receiver 4016a may include a countersink 4025 and a U-shaped recess 4026. The receiver 4016 may be rotatably mounted to a first end 4028 of the band 4014. The link member 4018 may be rotatably mounted to a second end 4030 of the band 4014 and may have a diameter substantially equal to a diameter of the aperture 4024 or a width of the U-shaped recess 4026. The link member 4018 may be an elongated rod-like member with a 59 male threaded portion 4028. After the link member 4018 has been slid into the aperture 4024, the nut member 4020 may be threaded onto the link member 4018 to secure the link member 4018 within the aperture 4024 and to tighten the band 4014 around the sternum 12. Alternatively, the nut member 4020 may be threaded onto the link member 4018 prior to inserting the link member 4018 into the U-shaped recess 4026. The link member 4018 may then be slid into the U-shaped recess 4026 prior to further tightening the nut member 4020 onto the link member 4018 to facilitate tightening of the band 4014 around the sternum 12. In a tightened configuration, the nut member 4020 may be secured within the countersink 4025 of the receiver 4016.

Figure 129:
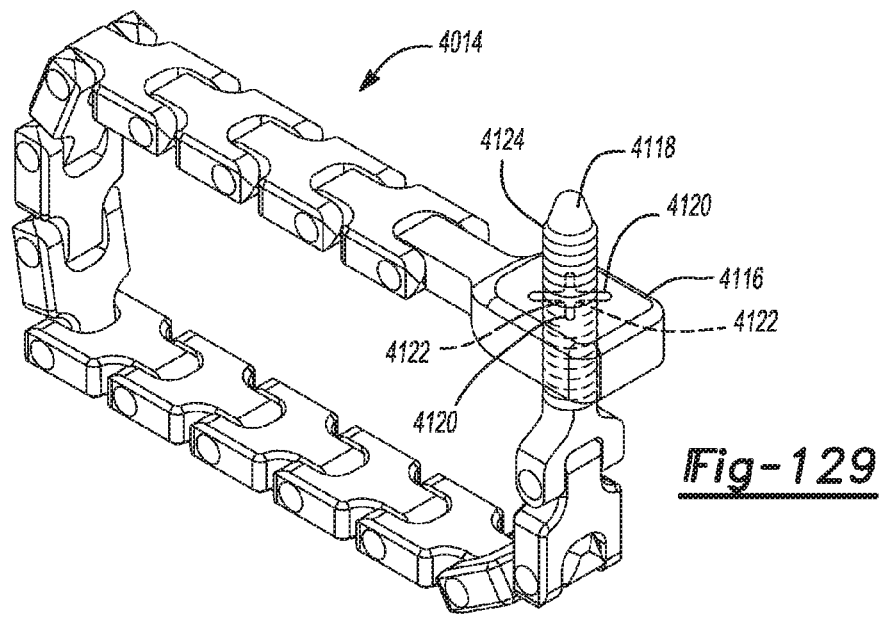

With reference to FIG. 129, another configuration of a receiver 4116 and a link member 4118 is shown. The receiver 4116 may include at least one slot 4120 therethrough. In one example, the receiver 4116 may include two slots 4120. The slots 4120 may intersect to define at least one catch portion 4122 of the receiver 4116, therebetween. While the slots 4120 are shown forming an X-shaped configuration, it will be appreciated that the receiver may include a plurality of intersecting slots 4120, forming variations of an asterisk or star-shaped aperture through the receiver 4116.

The link member 4118 may be an elongated rod-like member. The link member 4118 may include a plurality of bumps or dimples 4124. When the link member 4118 is inserted into the at least one slot 4120, at least one of the catch portions 4122 of the receiver 4116 may engage at least one of the plurality of dimples 4124 to secure the link member 4118 within the receiver 4116. Accordingly, once the band 4014 has been tightened around the sternum 12 and the link member 4118 has been inserted into the receiver 4116, the dimples 4124 and the catch portions 4122 may ensure that the band 4014 remains secured around the sternum 12.

With reference to FIG. 130, another configuration of a link member 4220 and a bracket member 4216 are shown. The link member 4220 and bracket member 4216 may be operatively associated with a band 4214. The band 4214 can be similar or identical to any of the bands described herein. The link member 4220 may be substantially similar to the link member 3720, except as otherwise provided herein. The link member 4220 may include at least one 60 aperture 4222. The at least one aperture 4222 may extend in a direction substantially perpendicular to the aperture 3728 and the aperture 3732. The bracket member 4216 may be a plate-like member having a first end 4224 and a second end 4226. The first end 4224 may be pivotably mounted to the band 4214. The second end 4226 may include at least one tooth element 4228. The at least one tooth element 4228 may be integrally formed with the bracket member 4216. At least one of the tooth elements 4228 may be received, and frictionally secured, within at least one of the apertures 4222. The tooth element 4228 and the aperture 4222 may cooperate to secure the band 4214 around the sternum 12. Alternatively, the at least one tooth element 4228 may be a separate piece, such as a mechanical fastener 4228a (FIGS. 130a and 130b), extending through first and second brackets 4216a, 4216b, and into the sternum 12.

With reference to FIG. 131, another configuration of a closure system 4310 is provided that may be used to reapproximate the sternum, or other bone, after a medical procedure. The closure system 4310 may include a band 4314, a receiver 4316, and a strap member 4318. The band 4314 can be similar or identical to any of the bands described herein. As illustrated, in one configuration, the band 4314 may be substantially similar to the band 3714, except as otherwise provided herein. Accordingly, like numerals may be used to describe similar features and components.

The receiver 4316 may include a base portion 4320, a tongue portion 4322, and a loop element 4324. The base portion 4320 may be substantially similar to the base portion 3724 of the link 3720. The tongue portion 4322 may extend from the base portion 4320. The loop element 4324 may be integrally formed with the tongue element 4322. The loop element 4324 may be formed from a flexible and crimpable metal.

The strap member 4318 may be a substantially elongated member having a first end 4326 and a second end 4328. The first end 4326 may be pivotably coupled to the band 4314. The second end 4328 may form a pointed tip to assist with inserting the strap member 4318 through the loop element 4324. The strap member 4318 may be formed from a bendable and flexible metal, or similar material.

Once the strap member 4318 has been inserted into the loop element 4324 and the band 4314 has been secured around the sternum 12 to a desired tightness, the strap member 4318 may be secured within the loop element 4324 by bending or folding the strap member 4318 at a substantially 180 degree angle. The strap member 4318 may also be secured within the loop element 4324 by crimping or otherwise bending the loop element 4324 on to the strap member 4318.

With reference to FIG. 132, another configuration of a closure system 4410 is provided that may be used to reapproximate the sternum, or other bone, after a medical procedure. The closure system 4410 may include a band 4414 and a receiver 4416.

The band 4414 can be similar or identical to any of the bands described herein. As illustrated, in one configuration, the band 4314 may be substantially similar to the band 3714, except as otherwise provided herein. Accordingly, like numerals may be used to describe similar features and components. The band 4414 may include a plurality of interconnected link members 4415. The link members 4415 may be substantially similar to the link member 4220 (FIG. 130), except as otherwise provided herein. Accordingly, like numerals will be used to describe like features and components.

The receiver 4416 may include a tongue portion 4418 and a loop portion 4420. The loop portion 4418 may be pivotably coupled to the band 4414. The loop portion 4420 may be integrally formed with the tongue portion 4418 and may include a tooth element 4422. The tooth element 4422 may extend in a radial direction relative to the loop portion 4420 and may be received and secured within the aperture 4222.

With reference to FIG. 133, another configuration of a closure system 4510 is provided that may be used to reapproximate the sternum 12, or other bone, after a medical procedure. The closure system 4510 may include a band 4514 and a securing means 4516. The securing means 4516 may be a wire, a string, a cable, or similar device extending through the aperture 3732 of one link 3724 and extending through the aperture 3728 of another link 3724.

The band 4514 can be similar or identical to any of the bands described herein. As illustrated, in one configuration, the band 4314 may be 62 substantially similar to the band 3714, except as otherwise provided herein. Accordingly, like numerals may be used to describe similar features and components.

The securing means 4516 may be a string, thread, wire, zip-tie, or other similar device. The closure system 4510 may be secured around the sternum 12 by inserting the securing means 4516 into the aperture 3728 of the tongue portion 3722 and into the aperture 3732 of the base portion 3724, and securing a first end 4518 of the securing means to a second end 4520 of the securing means 4520 by twisting, tying, crimping, or a similarly suitable technique.

With reference to FIGS. 134 and 135, another configuration of a closure system 4610 is provided that may be used to reapproximate the sternum 12, or other bone, after a medical procedure. The closure system 4610 may include a band 4614, a strap member 4616, and a tensioning device 4620.

The band 4614 can be similar or identical to any of the bands described herein. As illustrated, in one configuration, the band 4614 may be substantially similar to the band 3714, except as otherwise provided herein. Accordingly, like numerals may be used to describe similar features and components.

The strap member 4616 may be a substantially elongated member having a first end 4626 and a second end 4628. The first end 4626 may be pivotably coupled to the band 4614. The second end 4628 may form a pointed tip to assist with inserting the strap member 4616 through the receiver 4618.

The strap member 4616 may be a flat, elongated and flexible member formed from a metallic material and/or a polymeric material, for example. The strap member 4616 may include a plurality of elongated apertures or slots 4630 formed therein.

The tensioning device 4620 may include a receiver 4631 and a tensioning screw 4632. The receiver 4631 may be a loop member having a first end 4634 pivotably coupled to the band 4614. The tensioning screw 4632 may be may include a head portion 4636 and a stem 4638 and may be rotatably coupled to the receiver 4631. The stem portion 4638 may include male threaded portion and the head portion 4636 may include one or more slots that can receive the tip of a screwdriver. The threads of the tensioning screw 4632 may rotate the 63 receiver 4631 such that when the tensioning screw 4632 is rotated relative to the receiver 4631, the receiver 4631 engages the slots 4630 of the strap member 4616, and the strap member 4616 moves relative to, and within, the receiver 4630 based on the direction that the tensioning screw 4632 is rotated. In this way, the strap member 4616 and band 4614 of the closure system 4610 are operatively tightened or loosened around the sternum 12.

With reference to FIG. 136, another configuration of a closure system 4710 is provided that may be used to reapproximate the sternum, or other bone, after a medical procedure. The closure system 4710 may include a band 4714, a locking device 4716, and a receiver 4718.

The band 4714 can be similar or identical to any of the bands described herein. As illustrated, in one configuration, the band 4714 may be substantially similar to the band 3714, except as otherwise provided herein. Accordingly, like numerals may be used to describe similar features and components.

The locking device 4716 may extend from a first end 4720 to a second end 4722 and may include a housing 4724 and a locking element 4726. The first end 4720 may be pivotably coupled to the band 4714. The housing 4724 may be coupled to, or integrally formed with, the second end 4722. The locking element 4726 may include a stem portion 4728 and a head portion 4730. The stem portion 4728 may be rotatably secured within the housing 4724 for rotation about an axis 4727. The head portion 4730 may be integrally formed with the stem portion 4728 and may have a width extending perpendicular to the axis 4727 and a length extending perpendicular to the axis 4727. The width of the head portion 4730 may be greater than the length of the head portion.

The receiver 4718 may be pivotably coupled to the band 4714 and may define a cavity 4732 therein. The cavity 4732 may be sized to receive the head portion 4730 of the locking element 4726, such that when the locking element 4726 is rotated within the housing 4724, the head portion 4730 rotates within the receiver 4718 from an unlocked position in which the head can be moved within the receiver 4718 in a direction parallel to the axis 4727, to a locked position in which the head is prevented from moving within the receiver 4718 in a 64 direction parallel to the axis 4727. In this way, the closure system 4710 can be secured around the sternum 12.

FIGS. 137 through 157 generally illustrate alternative configurations of the bands and links previously described herein. It will be appreciated that the bands and links shown in FIGS. 137 through 157 may be used with any of the closure systems of the present disclosure.

With reference to FIG. 137, a band 4814 is shown. The band 4814 may include a plurality of pivotably interconnected links 4816. Each link 4816 may include a body portion 4818 and at least one tooth portion 4820. The tooth portion 4820 may angularly extend from the body portion 4818, including a first tooth portion 4820a extending from a first side 4822 of the body portion 4818 at an acute angle relative to the first side 4822, and a second tooth portion 4820b extending from a the second side 4824 (opposite the first side) of the body portion 4818 at an acute angle relative to the second side 4824. In one configuration, two tooth portions 4820a extend from the first side 4822 of the body portion 4818 and two tooth portions 4820b extend from the second side 4824 of the body portion 4818. It will be appreciated that the first and second sides 4826, 4828 may include varying numbers of tooth portions 4820. In an assembled configuration, the tooth portion 4820a on the first side 4822 will engage the tooth portion 4820b on the second side 4824 to secure the band 4814 around the sternum 12.

With reference to FIGS. 138 and 139, a band 4914 is shown. The band 4914 may include a plurality of pivotably interconnected links 4916. Each link 4816 may include a hub 4918 and an aperture 4920. The hub 4918 may be formed of a generally flexible material and integrally formed with, and extend from, the link 4916 in a first direction. The hub 4918 may include a cylindrical proximal end 4922 and a cylindrical distal end 4924. The distal end 4924 may include a bore 4925 extending in the first direction such that the distal end 4924 forms a generally hollow cylinder. The proximal end 4922 of the hub 4918 may have a diameter 01 and the distal end 4924 of the hub 4918 may have a diameter 02, greater than the diameter 01.

The aperture 4920 may extend through the link 4916 in the first direction and include a countersink portion 4926. The aperture 4920 may have a diameter 03 and the countersink portion 4926 may have a diameter 04, greater 65 than the diameter 03. The diameter 03 of the aperture 4920 may be less than the diameter 02 of the distal end 4924 of the hub 4918 and greater than the diameter 01 of the proximal end 4922 of the hub 4918. The diameter 04 of the countersink portion 4926 may be greater than the diameter 02 of the distal end 4924 of the hub 4918.

In an assembled configuration, the hub 4918 of a first link 4916a may be received within the aperture 4920 of a second link 4916b. The distal end 4924 of the hub 4918 may flex or deform to the diameter 03 within the aperture 4920 and return to the diameter 02 within the countersink portion 4926, such that the distal end 4924 of the hub 4918 is secured within the countersink portion 4926, and the second link 4916b can pivot about the hub 4918 of the first link 4916a.

With reference to FIG. 140, a band 5014 is shown. The band 5014 may include a plurality of pivotably interconnected links 5016. Each link 5016 may include a stem portion 5018 and a forked portion 5020. The stem portion 5018 may include a first segment 5022 and a second segment 5024. The first segment 5022 may be integrally formed with the forked portion 5020 and extend from the forked portion 5020 in a first direction. The second segment 5024 may be integrally formed with the first segment 5022 and extend from the first segment 5022 in a direction generally perpendicular to the first direction, such that the stem portion 5018 is generally T-shaped. The second segment 5024 may be generally cylindrical in shape having a diameter 01.

With particular reference to FIG. 141, the forked portion 5020 may be formed of a generally flexible or bendable material, and may include a first arm 5026a and a second arm 5026b. The first arm 5026a and second arm 5026b may define a void 5030 therebetween. The void 5030 may be created by machining, or otherwise removing, a portion of the forked portion 5020. The first and second arms 5026a, 5026b may each include an aperture 5032a, 5032b, respectively, each having a diameter 02. The diameter 02 of the apertures 5032a, 5032b may be greater than the diameter 01 of the second segment 5024 of the stem portion 5018.

To assemble the band 5014, the first arm 5026a may be bent or otherwise separated from the second arm 5026b, thereby increasing the general 66 dimensions of the void 5030. The second segment 5024 may be inserted into the apertures 5032a, 5032b. After the second segment 5024 has been inserted into the apertures 5032a, 5032b, the first and second arms 5026a, 5026b may be bent, or may otherwise resiliently return, to their prior configuration, thereby decreasing the general dimensions of the void 5030 and securing the second segment 5024 within the apertures 5032a, 5032b.

With reference to FIG. 142, a band 5114 is shown. The band 5114 may include a plurality of pivotably and rotatably interconnected links 5116. The links 5116 may be any suitable configuration, including herringbone, rope, anchor, bead, etc. As illustrated in FIG. 143, in one configuration, the links 5116 are formed from a spirally or helically-wrapped wire.

With reference to FIG. 144, a portion of a band 5214 is shown. The band 5214 may include a plurality of pivotably interconnected links 5216. Each link 5216 may include a stem portion 5218 and a hook portion 5220. The stem portion 5218 may include a first segment 5222 and a second segment 5224. The first segment 5222 and the second segment 5224 may each have a thickness T. The first segment 5222 may extend in a first direction from a proximal end 5226 to a distal end 5228 and include an aperture 5230 therethrough. The aperture 5230 may extend in a second direction (perpendicular to the first direction) through the first segment 5222.

The second segment 5224 may extend in a direction generally parallel to the first segment 5222 from a proximal end 5236 to a distal end 5238. The proximal end 5236 of the second segment 5224 may be integrally formed with, and offset in the second direction from, the distal end 5228 of the first segment 5222. In one configuration, the proximal end 5236 is offset in the second direction from the distal end 5228 a distance substantially equal to the thickness T of the first and second segments 5222, 5224. The second segment 5224 may include a plurality of ratcheting fins or teeth 5240 extending from the second segment 5224 in the second direction to a distal end 5225.

The hook portion 5220 may include an elbow 5242 and an arm 5244. The elbow 5242 may be arcuately shaped and integrally formed with the distal end 5238 of the second segment 5224. In one configuration, the elbow 5242 may have an angle of curvature substantially equal to 180 degrees. The 67 arm 5244 may extend in a direction generally parallel to the first and second segments 5222, 5224. The arm 5244 may be integrally formed with the elbow 5242.

To assemble the band 5214, the hook portion 5220 of a first link 5216a may be inserted into the aperture 5230 of a second link 5216b. It is also contemplated that a hook portion 5220a of the first link 5216a may be bent in the direction of the second segment 5224 in order to prevent the aperture 5230 of the second link 5216b from disassembling from the first link 5216a (FIGS. 144a through 144c).

Figure 115B:
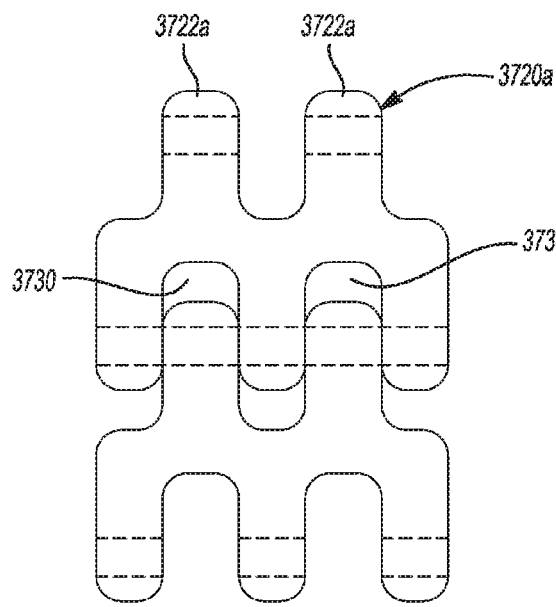
FIG. 115B is a top view of one configuration of a link member of the closure device of FIG. 115A.

The band 5214 and the links 5216 may be operatively associated with the closure system 3710 (FIG. 115), for example, such that the ratcheting arm 3746 ratchets with respect to the teeth 5240 when the band 5214 is inserted into the tensioning device 3718.

With reference to FIG. 145, a band 5314 is shown. The band 5314 may include at least one first link 5316a and at least one second link 5316b. Link 5316a may be identical, and pivotably interconnected, to link 5316b. Accordingly, like reference numerals will be used to describe similar features. The links 5316a, 5316b may include a first segment 5318 and a second segment 5320. The first and second segments 5318, 5320 may be integrally formed from a single piece of material by stamping, machining, or by another suitable manufacturing process. The first and second segments 5318, 5320 may generally extend arcuately from a first longitudinal end 5317 to a second longitudinal end 5319. The first segment 5318 may include an elongated aperture 5322 having a length L1 in the longitudinal direction. The elongated aperture 5322 may include a first longitudinal end portion 5324, a second longitudinal end portion 5326, and a central portion 5328 disposed between the first and second end portions 5324, 5326. The width of the first and second end portions 5324, 5326 may be less than the width of the central portion 5328.

The second segment 5320 may include a leg 5330 and an arm 5332. The leg 5330 and the arm 5332 may substantially define a T-shaped second segment 5320. The width of the leg 5330 may be substantially equal to the width of the first and second end portions 5324, 5326 of the aperture 5322. The length of the arm 5332 may be less than the length of the elongated aperture 68 5322 and greater than the width of the central portion 5328 of the aperture 5322. The arm 5332 may include a beveled or chamfered edge 5334 extending along the length of the arm 5332. A portion of the chamfered edge 5334 may form a planar surface 5336 with the leg 5330.

With reference to FIG. 146, in an alternative configuration, the arm 5332a of the second segment 5320a may include a first portion 5340 and a second portion 5342. The first portion 5340 may form a ninety degree angle with the leg 5330a. The second portion 5342 may be generally cylindrical in shape and form a T-shape with the first portion 5340 of the arm 5332a.

To assemble the band 5214, the second segment 5320 of a first link 5316a may be inserted into the aperture 5322 of the first segment 5318 of a second link 5316b. The leg 5330 of the first link 5316a may be rotatable within the central portion 5328 of the aperture 5322 of the second link 5316b, such that the first link 5316a can be rotated into alignment with the second link 5316b (FIG. 145). In the assembled configuration, the first longitudinal end portion 5324 of the aperture 5322 of the second link 5316b may prevent the leg 5330 of the first link 5316a from rotating out of alignment. Once the first link 5316a has been rotated into alignment with the second link 5316b, the arm 5332 of the first link 5316a may abut the first segment 5318 of the second link 5316b to prevent disassembly of the first and second links 5316a, 5316b. In addition, in the aligned and assembled configuration, the chamfered edge 5334 of the first link 5316a may abut the first segment 5318 of the second link 5316b to create a constant angle of curvature between the first longitudinal end 5317 of the first link 5316a and the second longitudinal end 5319 of the second link 5316b.

With reference to FIGS. 147 and 149, a band 5414 is shown. The band 5414 may include a plurality of pivotably interconnected first links 5416a and second links 5416b. The first link 5416a may be a substantially cylindrical member and may include a generally spherical bore or socket 5426 at each end thereof, defining annular rim portions 5424. The socket 5426 may have a diameter D1. The second link includes two head portions 5432a and a neck portion 5433. The head portions 5432a are generally spherical and have a diameter D2. The neck portion 5433 is generally cylindrical and extends between and connects the head portions 5432a. The diameter D3 of the neck portion 5433 is less than the diameter D2 of the head portions 5432a. The diameter D2 of the head portions 5432a may be less than the diameter D1 of the socket 5426.

As illustrated in FIG. 148, in another configuration, a third link 5416c may include a first segment 5418 and a second segment 5420. The third link 5416c may be substantially similar to the first link 5416a, except as otherwise provided herein. Accordingly, like reference numerals will be used to describe similar features. The first and second segments 5418, 5420 may be integrally formed from a single piece of material by stamping, machining, or by another suitable manufacturing process. The first segment 5418 may be substantially cylindrical and include a generally spherical bore or socket 5426, having a diameter 01 formed in a first end thereof. The second segment 5420 may extend from a first end 5428 to a second end 5430. The first end 5428 of the second segment 5420 may be adjacent to, and extend from, a second end of the first segment 5418. The second end 5430 of the second segment may include a generally spherical ball or head portion 5432b having a diameter 02. The diameter 02 of the head portion 5432b may be less than the diameter 01 of the socket 5426.

To assemble the band 5414, the head portion 5432a of the second link 5416b or the head portion 5432b of the third link 5416c can be inserted into the socket 5426 of a second link 5416b or the socket 5426 of the third link 5416c. The annular rim 5424 of the first link 5416a and/or the third link 5416c may be bent or otherwise crimped inward toward the neck portion 5433 of the second link 5416b or toward the second segment 5420 of the third link 5416c to prevent the head portion 5432a or 5432b, respectively, from being removed from the socket 5426.

With reference to FIGS. 150-152, a band 5514 is shown. The band 5514 may include a plurality of pivotably interconnected links 5516. The links 5516 may be formed from a loop of wire, or other suitable material. The wire may have a generally circular cross section to ensure that a first link 5516 smoothly pivots on a second link 5516.

To assembly the band 5414, the first link 5516 is folded such that a first portion 5518a of the first link 5516a overlaps a second portion 5520a of the first link 5516, substantially defining a U-shaped first link 5516. The second link 70 5516 is folded in the same manner as the first link 5516 around the first link 5516, such that the first portion 5518 of the second link 5516 overlaps the second portion 5520 of the second link 5516, substantially defining a U-shaped second link 5516. In this manner, multiple links 5516 can be interconnected until the band 5514 is a desirable length for reapproximating the sternum.

With reference to FIGS. 153 through 154, another configuration of a closure system 5810 is shown. The closure system 5810 may include a cerclage or band 5814 and a tensioning device 5818. The band 5814 can be similar or identical to any of the bands described herein. As illustrated, in one configuration, the band 5814 is a braided construct.

The tensioning device 5818 may include a first tubular portion 5820 and a second tubular portion 5822. The first tubular portion 5820 may be adjacent and substantially parallel to the second tubular portion 5822. As illustrated, in one configuration, the first tubular portion 5820 may be integral and/or monolithically formed with the second tubular portion 5822. The first tubular portion 5820 may include a first clamp portion 5824 and a first flanged portion 5826. The first clamp portion 5824 may be formed at a first end 5827 of the tensioning device 5818. The first clamp portion 5824 and the first flanged portion 5826 may extend radially and outwardly from the first tubular portion 5820 in a first direction. A slot 5828 may be formed between and separate the first clamp portion 5824 from the first flanged portion 5826. The first clamp portion 5824 may include opposed outer surfaces 5830 and opposed toothed portions 5832. The opposed outer surfaces 5830 may be substantially parallel to each other to allow for improved clamping of the first clamp portion 5824.

The second tubular portion 5822 may include a second clamp portion 5834 and a second flanged portion 5836. The second clamp portion 5834 may be formed at a second end 5837 of the tensioning device 5818. The second clamp portion 5834 and the second flanged portion 5836 may be substantially similar to the first clamp portion 5824 and the first flanged portion 5826, respectively, except as otherwise provided herein. Therefore, like reference numerals are used to describe similar features. The second clamp portion 5834 and the second flanged portion 5836 may extend radially and outwardly from the 71 second tubular portion 5822 in a second direction, opposite the first direction of the first clamp portion 5824 and first flanged portion 5826.

As illustrated, in an assembled configuration, an end 5838 of the band 5814 may be received through the first tubular portion 5822 and another end 5840 of the band 5814 may be received through the second tubular portion 5824. To secure the closure system 5810, the first end 5838 may be placed between the toothed portions 5832 of the first clamp portion 5824 and pliers 5842, or a similar clamping device, may be used to generally crimp or clamp the band 5814 between the toothed portions 5832 (FIGS. 154 and 155). The other end 5840 of the band 5814 may be placed between the toothed portions 5832 of the second clamp portion 5826 and the pliers 5842 may be used to generally crimp or clamp the band 5814 between the toothed portions 5832.

With reference to FIG. 156, another configuration of a closure system 5910 is shown. The closure system 5910 may include a first bracket member 5916a, a second bracket member 5916b, and a tensioning device 5917. The tensioning device 5917 may be a threaded fastener. The first bracket member 5916a may be a plate formed from a metallic and/or polymeric material and may include a body portion 5930a and a plurality of legs 5932 extending outward from the body portion 5930a. The bracket 5916 may be relatively flexible to enable the bracket 5916 to conform to the contours of the sternum when the bracket 5916 is fastened thereto. The body portion 5930a may include at least two parallel stems or beams 5931 extending from the body portion 5930a, and an aperture or bore 5933 extending through or into the body portion 5930a. The bore 5933 may extend in a direction substantially parallel to the beams 5931. Each of the legs 5932 may include one or more apertures 5940 extending therethrough. The apertures 5940 may extend in a direction substantially perpendicular to the bore 5933 and the beams 5931. Self-tapping threaded fasteners (not shown) may extend through the apertures 5940 and may threadably engage the sternum (not shown) to fix the bracket 5916 to the sternum.

The second bracket member 5916b may be substantially similar to the first bracket member 5916a, except as otherwise provided herein. Therefore, like reference numerals are used to describe similar features. The second bracket member 5916b may include a body portion 5930b. The body 72 portion 5930b may include at least two parallel apertures 5941 extending through the body portion 5930b. The body portion 5930b may further include another aperture 5943 extending through the body portion 5930b. The aperture 5943 may be substantially parallel to the apertures 5941.

In an assembled configuration, the beams 5931 may be received through the apertures 5941. The tensioning device 5917 may be a received through the aperture 5943. An end 5945 of the tensioning device 5917 may be received by the bore 5933 in order to generally secure the tensioning device 5917 relative to the first bracket member 5916a. As the tensioning device 5917 is rotated in a first direction within the aperture 5943, the second bracket member 5916b may move along the beams 5931 and away from the first bracket member 5916a. As the tensioning device 5917 is rotated in a second direction within the aperture 5943, the second bracket member 5916b may move along the beams 5931 and toward the first bracket member 5916a. To affect the closure of the sternum (not shown), fasteners (not shown) may extend through the apertures 5940 and into the sternum. In another configuration, a band (not shown) may be extended through the apertures 5940 and around the sternum. As the tensioning device 5917 is rotated in the second direction, and the second bracket member 5916b moves toward the first bracket member 5916a, the fasteners and/or band may draw and bind previously severed portions of the sternum together.

With reference to FIGS. 157 through 159, another configuration of a closure system 6010 is shown. The closure system 6010 may include a band 6014 and a fastener assembly 6015. The band 6014 can be similar or identical to any of the bands described herein. As illustrated, in one configuration, the band 6014 is a braided construct. The band 6014 may extend longitudinally from a first end 6022 to a second end 6024. The first end 6022 of the band 6014 may include a longitudinally extending slot or elongate aperture 6025.

The fastener assembly 6015 may include a first member 6027 and a second member 6029. The first member 6027 may be fixed to the second end 6024 of the band 6014 with a rivet, adhesive, mechanical fastener (e.g., a screw), or a similar fastening technique. The second member 6029 may receive the first member 6027. As illustrated, in one configuration the first member 6027 73 may be a male button or snap member and the second member 6029 may be a female button or snap member, or vice versa.

With reference to FIG. 158 the band 6014 may be looped around the posterior side of the sternum 12 so that the band 6014 substantially circumscribes and tightens around the sternum 12. With the band 6014 sufficiently tightened around the sternum 12, the first member 6027 may be positioned within the aperture 6025 and the second member 6029 may be secured to the first member 6027, thereby securing the first end 6022 of the band 6014 to the second end 6024. As illustrated in FIG. 159, in an assembled configuration, the band 6014 may be pinched, clamped, or otherwise secured between the first member 6027 and the second member 6029 to prevent the first end 6022 of the band 6014 from moving relative to the second end 6024 of the band.

With reference to FIGS. 160 and 161, another configuration of a closure system 6110 is shown. The closure system 6110 may include a strut or bracket 6116, fasteners 6118, and securing devices 6120. The bracket 6116 may include a first end portion 6145, a second end 6147, and a central portion 6149. The central portion 6149 may extend between and connect the first end portion 6145 to the second end portion 6147, and may be generally narrower than the first and second end portions 6145, 6147. The As illustrated in FIG. 160, first and second end portions 6145, 6147 may be substantially circular and each include an aperture 6151 therethrough.

As illustrated, the fasteners 6118 may be self-tapping threaded fasteners, including a head portion 6153 and a stem portion 6155. It will also be appreciated that the fasteners 6118 may be bolts, nails, or similar mechanical fastener devices, within the scope of the present disclosure. The securing devices 6120 may be washer or nut-like members, having an aperture 6157 therethrough. As illustrated in FIG. 160, in one configuration, the aperture 6157 may be a threaded aperture.

With reference to FIG. 161, in an assembled configuration, the fasteners 6118 may be extended through the sternum 12, such that the head portion 6153 is disposed on a first side 6159 of the sternum 12 and the stem portion 6155 extends through to a second side 6161 of the sternum 12. The first 74 side 6159 may be an anterior side of the sternum 12 and the second side 6161 may be a posterior side of the sternum 12. The bracket 6116 may be placed adjacent the second side 6161 of the sternum 12, such that the stem portions 6155 of the fasteners 6118 extend through the apertures 6151. The securing devices 6120 may be placed on the stem portions 6155 of the fasteners 6118 (e.g., by threading) to secure the bracket 6116 between the securing device 6120 and the second side 6161 of the sternum 12. An end 6163 of the stem portion 6155 may be broken off or otherwise removed such that the stem portion 6155 does not extend from a posterior side 6165 of the securing device 6120.

With reference to FIGS. 162 and 163, another configuration of a closure system 6210 is shown. The closure system 6210 may include at least one fastener 6212 and at least one securing device 6214. The at least one fastener 6212 and the at least one securing device 6214 may be may be similar or identical to the fastener 6118 and securing device 6120 described above, apart from any exceptions described below and/or shown in the figures. Therefore, similar features may not be described again in detail and will be referenced using like reference numerals.

In an assembled configuration, the fasteners 6212 may be extended through the sternum 12, such that a head portion 6153 is disposed on a first side 6259 of the sternum 12 and the stem portion 6155 extends through to a second side 6261 of the sternum 12. The first side 6259 may be a first lateral side of the sternum 12 and the second side 6261 may be a second lateral side of the sternum 12, generally opposite the first lateral side. The securing devices 6214 may be placed on the stem portions 6155 of the fasteners 6212 (e.g., by threading) to secure the head portion 6155 to the first side 6259 of the sternum 12 and secure the securing device 6214 to the second side 6261 of the sternum 12, and thereby draw and bind previously severed portions of the sternum 12 together. The end 6163 of the stem portion 6155 may be broken off or otherwise removed such that the stem portion 6155 does not extend from a posterior side 6165 of the securing device 6214.

With reference to FIGS. 164 through 166, another configuration of a closure system 6310 is shown. The closure system 6310 may include a band 6314 and a bracket 6316. The band 6314 can be similar or identical to any of the 75 bands described herein. As illustrated, in one configuration, the band 6314 is a braided construct extending from a first end 6322 to a second end 6324.

The bracket 6316 may include a base 6325 and a cover 6327. The cover 6327 may be pivotably coupled to the base 6325 by at least one hinge (not shown). The base 6325 may include one or more apertures 6340a extending therethrough. The cover 6327 may include one or more apertures 6340b extending therethrough. The apertures 6340a may be substantially aligned with the apertures 6340b. Self-tapping threaded fasteners 6342 may extend through the apertures 6340a and the apertures 6340b and may threadably engage the sternum 12 to fix the cover 6327 relative to the base 6325 and to fix the bracket 6316 to the sternum 12.

With continued reference to FIGS. 164 through 166, a method will be described for attaching the system 6310 to the sternum 12 and tensioning the band 6314 to reapproximate the sternum 12. The first end 6322 of the band 6314 may be looped around the posterior side of the sternum 12 so that the band 6314 substantially circumscribes the sternum 12. The first end 6322 of the band 6314 may be received in a first end 6329 of the bracket 6316 and the second end 6324 of the band 6314 may be received in a second end 6331 of the bracket 6316, such that the first and second ends 6322, 6324 extend through the bracket 6316, substantially between the base 6325 and the cover 6327. As shown in FIG. 164, the bracket 6316 may be positioned so that at least one of the one or more apertures 6340a is aligned with the portion 12a of the sternum 12, and at least one of the one or more apertures 6340a is aligned with the portion 12b of the sternum 12. A force may be applied to the first and second ends 6322, 6324 of the band 6314 to tighten the band 6314 around the sternum 12 to a desired amount. Once the band 6314 has been tightened to the desired amount, fasteners 6342 may be extended through the apertures 6340a, 6340b to draw the cover 6327 in the direction of the base 6325, and thereby clamp or otherwise secure the band 6314 between the cover 6327 and the base 6325. Extending the fasteners 6342 through the apertures 6340a, 6340b and into the sternum 12 may also fix the bracket 6316 to the sternum 12, as described above.

With reference to FIG. 167, in another configuration, a closure system 6310a may include a bracket 6316a. The closure system 6310a and the 76 bracket 6316a may be substantially similar to the closure system 6310 and the bracket 6316, except as otherwise provided herein. Accordingly, like reference numerals will be used to describe similar features. The bracket 6316a may include one or more apertures 6340a in the base 6325 may be threaded apertures. A fastener 6342a, including a head portion 6343, a stem portion 6345, and a tip portion 6347, may extend through the cover 6327 such that the head portion 6343 is located on a first side 6349 of the cover 6327 and the tip portion 6347 is located on a second side 6351 of the cover 6327. The stem portion 6345 may be rotatably disposed within the aperture 6340b. The tip portion 6327 may be threaded, such that it can threadingly engage the aperture 6340a in the base 6325. Once the band 6314 has been tightened to the desired amount around the sternum 12, the tip portion 6327 of the fastener 6342a may be extended into the aperture 6340a to draw the cover 6327 in the direction of the base 6325, and thereby clamp or otherwise secure the band 6314 between the cover 6327 and the base 6325.

With reference to FIGS. 168 and 169, another configuration of a closure system 6410 is shown. The closure system 6410 may include a cerclage or band 6414, a first link or implant 6415a, a second link or implant 6415b, a tie member 6417, a first needle member 6419a, and a second needle member 6419b. The band 6414 can be similar or identical to any of the bands described herein. As illustrated, in one configuration, the band 6414 is a braided construct extending from a first end 6422 to a second end 6424. The first and second ends 6422, 6424 may define looped portions 6425, 6427, respectively. The looped portions 6425, 6427 may be formed by folding and stitching the first and second ends 6422, 6424, respectively to the band 6414.

The first implant 6415a may include a hook portion 6429 and a loop portion 6431. As illustrated, in one configuration, the first implant 6415a may be formed in the shape of an "e." The second implant 6415a may be the same as the first implant 6415b. Therefore, like reference numerals will be used to describe similar features.

The tie member 6417 may be a flexible member construct extending from a first end 6433 to a second end 6435. One suitable flexible member construct-type is disclosed in commonly assigned U.S. Pat. Pub. No. 77 2012/0053630. The disclosure of U.S. Pat. Pub. No. 2012/0053630 is hereby incorporated by reference as if fully set forth herein.

The first needle member 6419a may be substantially rigid and extend from a first end 6437 to a second end 6439. The second end 6439 may be curved and generally form a hook. The second needle member 6419b may be the same as the first needle member 6419a. Therefore, like reference numerals are used to describe similar features.

Operation of the closure system 6410 will now be described in more detail. The closure system 6410 may be utilized with an implantation tool 6441. With reference to FIG. 169, in a first configuration, the first end 6437 of the first needle member 6419a may be fixed to the looped portion 6425 of the band 6414, and the first end 6437 of the second needle member 6419b may be fixed to the looped portion 6427 of the band 6414. The first and second needle members 6419a, 6419b may be used to direct the band 6414 around the sternum. The first and second needle members 6419a, 6419b may be removed from the band 6414, and the hook portion 6429 of the first and second implants 6415a, 6415b may be inserted through the looped portions 6425, 6427, respectively, of the band 6414. The tie member 6417 may be fixed to the loop portion 6431 of the first and second implants 6415a, 6415b.

The tool 6441 may include first arms 6443a, 6443b, second arms 6445a, 6445b, and a body 6447. A first end 6449 of the first arms 6443a, 6443b may be pivotably coupled to the body 6447. The second arms 6445a, 6445b may extend from a first end 6451 to a second end 6453. The second arms 6445a, 6445b may be pivotably coupled to the body 6447 at an elbow portion 6455. The elbow portion 6455 may be operably disposed between the first end 6451 and the second end 6453 of the second arms 6445a, 6445b.

In a first configuration of the closure system 6410, a second end 6457 of the first arms 6443a, 6443b may be coupled to the first and second implants 6415a, 6415b, respectively. The first end 6451 of the second arms 6445a, 6445b may be coupled to the first and second ends 6433, 6435, respectively, of the tie member 6417. The first arms 6443a, 6443b may pivot about the first end 6449 to generally move the first implant 6415a in the direction of the second implant 6415b, and vice versa, to tighten the band 6414 around the 78 sternum. The second arms 6445a, 6445b may pivot about the elbow portion 6455 to generally move the first implant 6415a in the direction of the second implant 6415b, and vice versa, to tighten and secure the band 6414 around the sternum.

With reference to FIGS. 170 through 172, another configuration of a closure system 6510 is shown. The closure system 6510 may include a band 6514, a first bracket 6516a, and a second bracket 6516b. The band 6514 may be a flexible member construct, such as a string, extending from a first end 6522 to a second end 6524.

The first bracket 6516a may be a plate formed from a biocompatible metallic and/or polymeric material. The first bracket 6516a may be relatively flexible to enable the first bracket 6516a to conform to the contours of the sternum 12 when the bracket 16 is fastened thereto (as shown in FIG. 170). The first bracket 6516a may include a plurality laterally extending nubs 6517 and a plurality of hook members 6519. The laterally extending nubs 6517 may be integrally formed with the first bracket 6516a. Each of the nubs 6517 may include one or more apertures 6540 extending therethrough. The apertures 6540 may include a chamfered or beveled edge 6541 adjacent a first or upper surface 6543 of the first bracket 6516a. Self-tapping threaded fasteners 6542 may extend through the apertures 6540 such that a head portion 6545 of the fasteners 6542 is adjacent the beveled edge 6541 of the apertures 6540. The fasteners 6542 may threadably engage the sternum 12 to fix the first bracket 6516a to the sternum 12 (as shown in FIG. 170). Each of the plurality of hook members 6519 may be interposed between two adjacent nubs 6517, defining an alternating pattern of nubs 6517 and hook members 6519. The second bracket 6516b may be the same as the first bracket 6516a. Therefore, like reference numerals will be used to describe similar features.

With continued reference to FIGS. 170 through 172, a method will be described for attaching the system 6510 to the sternum 12 to reapproximate the sternum 12. The first bracket 6516a may be fixed to the first portion 12a of the sternum 12 with the fasteners 6542. The second bracket 6516b may be fixed to the second portion 12b of the sternum 12 with the fasteners 6542. The band 6514 may be wrapped around or otherwise connected to and between the hook members 6519 on the first bracket 6516a and the hook members 6519 79 on the second bracket 6516b, such that the band 6514 forms at least one cross or "X" configuration between the first bracket 6516a and the second bracket 6516b. A force may be applied to the first and/or second end 6522, 6524 of the band 6514 to urge the first bracket 6516a in the direction of the second bracket 6516b, and thereby urge the first portion 12a of the sternum 12 in the direction of the second portion 12b.

With reference to FIGS. 173 through 177, another configuration of a closure system 6610 is shown. The closure system 6610 may include a band 6614 and a bracket 6616. The band 6614 may be identical to the tie member 6417, except as otherwise provided herein. Therefore like reference numerals will be used to describe similar features. The band 6614 may include a first toggle 6619a and a second toggle 6619b.

The bracket 6616 may be substantially similar to the bracket 16, except as otherwise provided herein. Therefore, like reference numerals will be used to describe similar features. The bracket 6616 may include one or more apertures 40a extending therethrough and one or more nubs 6621 formed on a first surface 6623 of the bracket 6616. As illustrated, in one configuration, the bracket 6616 includes two apertures 40a disposed on opposite lateral sides of the opening 34, and first and second annular nubs 6621a, 6621b (FIGS. 175 through 177) encircling each of the apertures 40a. The first annular nub 6621a may be concentric to the second annular nub 6621b. Threaded fasteners 42a may extend into the apertures 40a from the first side 6623 such that the fasteners 42a do not extend from a second side 6625 (opposite the first side 6621) of the bracket 6616. As illustrated in FIG. 177, in an assembled configuration, at least a portion of the band 6614 may be disposed and secured between a head 6627 of the fasteners 42a and the nubs 6621.

With continued reference to FIGS. 173 through 177, a method will be described for attaching the system 6610 to the sternum 12 to reapproximate the sternum 12. The band 6614 may be inserted into the apertures 40a and around the sternum 12, such that the first toggle 6619a is disposed adjacent one of the apertures 40a and the second toggle 6619b is disposed adjacent another of the apertures 40a. With particular reference to FIG. 174, a force may be applied to the first and second ends 6417a, 6417b of the band 6614 80 to secure the band 6614 around the sternum 12 and secure the first portion 12a of the sternum 12 relative to the second portion 12b of the sternum 12. With particular reference to FIGS. 176 and 177, the threaded fasteners 42a may extend into the apertures 40a such that the band 6614 is disposed between the head 6627 of the fasteners 42a and the nubs 6621 to secure the band 6614 around the sternum 12 and secure the first portion 12a of the sternum 12 relative to the second portion 12b of the sternum 12. With the band 6614 secured around the sternum 12 and the first portion 12a of the sternum 12 secured relative to the second portion 12b of the sternum 12, the bracket 6616 may be fixed to the sternum 12 with the fasteners 6642, such that the bracket 6616 additionally secures the first portion 12a of the sternum 12 secured relative to the second portion 12b of the sternum 12.

With reference to FIGS. 178 and 179, another configuration of a bracket 6716 is shown. The bracket 6716 may be substantially similar to the bracket 6616, except as otherwise provided herein. Accordingly, like reference numerals will be used to describe similar features. The bracket 6716 may include at least one hook portion 6718. As illustrated, in one exemplary configuration, the bracket includes two hook portions 6718 disposed on opposite lateral sides of the opening 34. The hook portions 6718 may extend from the first surface 6623 of the bracket 6616 such that an opening 6631 of one hook portion 6718 generally faces an opening 6631 of another hook portion 6718. The band (not shown) may be coupled to the hook portions 6718 and wrapped around the sternum 12 to secure the band around the sternum 12 and secure the first portion 12a of the sternum 12 relative to the second portion 12b of the sternum 12. The bracket 6616 may be fixed to the sternum 12 with the fasteners (not shown).

FIG. 180 is a perspective view of a bone punch tool 7000 in a retracted position, in accordance with at least one example of the present disclosure. The bone punch tool 7000 can include a support arm 7002 having a support arm distal portion 7004 and a support arm proximal portion 7006. The bone punch tool 7000 can include a pivot arm 7008 having a pivot arm distal portion 7010 and a pivot arm proximal portion 7012. In at least one example, the pivot arm distal portion 7010 can be pivotably coupled to the support arm distal portion 7004 such as at pivot point 7014. In some examples, one or both of the support arm 7002 and the pivot arm 7008 can include a grip 7044 so as to facilitate a user's use of the bone punch tool 7000.

The bone punch tool 7000 can include an arcuate punch 7016 having a bone piercing tip 7018 configured to punch through a bone portion so as to form an arcuate hole therethrough. The arcuate punch 7016 can be coupled to the pivot arm distal portion 7010. In at least one example, the arcuate punch 7016 can be formed integral with the pivot arm distal portion 7010, such that the pivot arm 7008 extends from the pivot arm proximal portion 7012 to the piercing tip 7018. In at least one example, the arcuate punch 7016 is curved (or arcuate) along its length.

In the illustrated example, the bone punch tool 7000 is depicted in the retracted position, with the arcuate punch 7016 retracted, and the pivot arm proximal portion 7012 a first distance 7050 from the support arm proximal portion 7006. The pivot arm proximal portion 7012 can be configured to be moved away from the support arm proximal portion 7006 (e.g., by a surgeon or other user) such as in a punch direction 7020. Movement of the pivot arm proximal portion 7012 in the punch direction 7020 can cause the pivot arm distal portion 7010 to pivot about the pivot point 7014 and the arcuate punch 7016 to extend into a punch position. In at least one example, the pivot point 7014 is positioned at the support arm distal portion 7004 at a center of curvature of the arcuate punch 7016.

In some examples, the bone punch tool 7000 can include a protrusion 7022 coupled to the support arm distal portion 7004. In at least one example, the protrusion 7022 can be configured to intercept an arc defined by the curvature of the arcuate punch 7016. In some examples, the protrusion 7022 comprises a plate. In some examples, the protrusion 7022 can be configured to receive the bone piercing tip 7018 of the arcuate punch 7016 when the bone punch tool 7000 is in the punch position. In at least one example, the protrusion 7022 can include a recess 7024 such as to receive the bone piercing tip 7018.

In some examples, the bone punch tool 7000 can include a housing 7026. In at least one example, the housing 7026 can be coupled to the support arm distal portion 7004. In at least one example, the housing 7026 can include a shoulder 7028 configured to engage a lip 7030 of the pivot arm distal portion 7010. In at least one example, when the shoulder 7028 engages the lip 7030, the pivot arm proximal portion 7012 is prevented from further movement in the punch direction 7020. In some examples, the housing 7026 can house a portion of the arcuate punch 7016. In some examples, the housing 7026 can house the pivot point 7014.

In some examples, the housing 7026 can be formed integral with the support arm distal portion 7004. In at least one example, the housing 7026 can be formed integral with the support arm distal portion 7004 and the protrusion 7022. In some examples, the housing 7026 and the protrusion 7022 together can define a receptacle 7032 configured to receive a bone portion. In some examples, the receptacle 7032 can be u-shaped or c-shaped. In at least one example, the receptacle 7032 can be dimensioned to receive a portion of a sternum. In at least one example, the receptacle 7032 can be dimensioned to receive a portion of a manubrium. In at least one example, the housing 7026 can include a wall 7036 configured to contact a cut surface of the portion of the sternum. In at least one example, the wall 7036 can align the bone punch tool 7000 relative to the cut surface of the portion of the sternum. In some examples, the wall 7036 has a height that corresponds to a thickness of a sternum. In at least one example, the height of the wall 7036 is greater than the thickest cross-section region of a sternum, the manubrium. In at least one example, the height of the wall 7036 can be greater than an average greatest thickness determined from computerized tomography (CT) scans of different patients. In at least one example, the height of the wall 7036 can accommodate any portion of a particular sternum (such that the bone punch tool 7000 can be used anywhere on the sternum). In some examples, the height of the wall 7036 can accommodate different size sternums across a patient population. In at least one example, the height of the portion of the wall 7036 within the receptacle 7032 can be adjustable, for example, by adjusting the protrusion 7022. In at least one example, the height of the wall 7036 can be approximately 20 millimeters (0.787 inches).

In some examples, the bone punch tool 7000 can include one or more alignment guides 7038, 7040. In some examples, the bone punch tool 7000 can include a support arm alignment guide 7038 positioned on the support arm 7002. In at least one example, the bone punch tool 7000 can include a pivot arm alignment guide 7040 positioned on the pivot arm 7008. The alignment guide 7038, 7040 can be configured to indicate the orientation of the bone punch tool 7000 relative to an existing bone hole, a patient's anatomy, or other markers. In at least one example, the alignment guide 7038, 7040 can include one or more windows. In at least one example, the width of the window can correspond to a width of the arcuate punch 7016.

In some examples, the bone punch tool 7000 can include a locking member 7042. In at least one example, the locking member 7042 is configured to urge the pivot arm 7008 toward the support arm 7002. In some examples, the locking member 7042 can be engaged to prevent movement of the pivot arm proximal portion 7012 in the punch direction 7020. In some examples, the locking member 7042 can help prevent exposure of the bone piercing tip 7018 of the arcuate punch 7016 when the bone punch tool 7000 is not being used to punch a hole. In some examples, the locking member 7042 can be disabled to allow the arcuate punch 7016 to move in the punch direction 7020. In at least one example, the locking member 7042 can include a biasing element that can be overcome by a user applying force to the pivot arm 7008. In at least one example, the locking member 7042 can include a pin. In some examples, the locking member 7042 can include a spring that urges one or more ball bearings outward to create sufficient friction for keeping the arcuate punch 7016 in the retracted position. In at least one example, the friction created by the locking member 7042 can be easily overcome by a user during operation, when the user applies the force to the pivot arm 7008 to adjust the bone punch tool 7000 from the retracted position to the punch position. In at least one example, the bone punch tool 7000 can include more than one locking member 7042, any number of which may be of different types.

The bone punch tool 7000 can comprise any of a variety of materials sufficient to withstand the forces of use. In some examples, one or more elements of the bone punch tool 7000 comprises surgical material, for example, metal. In at least one example, one or more elements of the bone punch tool 7000 can comprise heat-treated stainless steel. In some examples, one or more elements of the bone punch tool 7000 can comprise cobalt, Nitinol, ceramic, or the like.

FIG. 181 is a perspective view of the bone punch tool 7000 of FIG. 180 in a punch position, after the pivot arm proximal portion 7012 has moved in the punch direction 7020. The pivot arm distal portion 7010 has pivoted about the pivot point 7014, and the arcuate punch 7016 has extended into the recess 7024 of the protrusion 7022. In the illustrated example, the lip 7030 of the pivot arm distal portion 7010 is fully seated in the shoulder 7028 of the housing 7026, such that the pivot arm 7008 and the arcuate punch 7016 are prevented from further movement in the punch direction 7020. In the punch position, the pivot arm proximal portion 7012 is separated from the support arm proximal portion 7006 by a second distance 7060 that is greater than the first distance 7050.

In order to retract the arcuate punch 7016 to return the bone punch tool 7000 back to the retracted position, the pivot arm proximal portion 7012 can be moved toward the support arm proximal portion 7006 in a retraction direction 7054. As the pivot arm 7008 moves in the retraction direction 7054, the pivot arm distal portion 7010 pivots about the pivot point 7014 to retract the arcuate punch 7016. In at least one example, the locking member 7042 can include a biasing element that returns the bone punch tool 7000 from the punch position to the retracted position when a force in the punch direction 7020 is reduced.

FIGS. 182A and 182B are a perspective view and a top view, respectively, of the bone punch tool 7000 of FIGS. 180 and 181 engaging a first manubrium portion 7070 in a retracted position, in accordance with at least one example of the present disclosure. In the illustrated example, the u-shaped receptacle 7032 has received the first manubrium portion 7070, such that the wall 7036 of the housing 7026 is in contact with a cut surface 7072 of the first manubrium portion 7070 to align the bone punch tool 7000 relative to the cut surface 7072 of the manubrium portion 7070. A completed punch hole 7074 has been formed in a second manubrium portion 7076. In the illustrated example, alignment guides 7038, 7040, in the form of windows formed in the support arm 7002 and the pivot arm 7008, respectively, can allow a user to align the bone punch tool 7000 relative to the completed punch hole 7074 in the second manubrium portion 7076. For example, the user can place the window directly over the completed punch hole 7074 to align the bone punch tool 7000 to form a second punch hole substantially parallel to the completed punch hole 7074. In the illustrated example, the bone punch tool 7000 is aligned with both the cut surface 7072 of the first manubrium portion 7070 and the completed punch hole 7074 of the second manubrium portion 7076.

FIGS. 183A and 183B are a perspective view and a top view, respectively, of the bone punch tool 7000 of FIGS. 180-182B engaging the first manubrium portion 7070 in a punch position, in accordance with at least one example of the present disclosure. In the illustrated example, a user has applied a force to the pivot arm proximal portion 7012 in the punch direction 7020 to separate the pivot arm proximal portion 7012 from the support arm proximal portion 7006. The bone punch tool 7000 remains aligned with the cut surface 7072 of the first manubrium portion 7070 and the completed punch hole 7074 of the second manubrium portion 7076, such that an arcuate punch hole 7078 formed in the first manubrium portion 7070 is aligned with the completed punch hole 7074 formed in the second manubrium portion 7076. The bone piercing tip 7018 of the arcuate punch 7016 is driven through the first manubrium portion 7070 by the force applied to the pivot arm 7008.

In at least one example, the protrusion 7022 can be configured to shield other parts of a patient's anatomy from the bone piercing tip 7018. In at least one example, the protrusion 7022 receives the bone piercing tip 7018 and prevents further motion of the arcuate punch 7016 in the punch direction 7020. In some examples, the protrusion 7022 is dimensioned such that the piercing tip 7018 cannot penetrate the protrusion 7022. In some examples, the protrusion 7022 has a thickness of at least approximately 3 millimeters (0.118 inches). In at least one example, the protrusion 7022 has a thickness of at least approximately 3.81 millimeters (0.150 inches). In at least one example, the recess 7024 extends through most of the thickness of the protrusion 7022, but does not extend completely through the protrusion 7022.

The arcuate punch hole 7078 formed by the arcuate punch 7016 can allow a curved needle, a band, or both, to pass through bone. In some practices, a curved needle is attached to a band implant to help guide the band around the intercostal tissue of the sternum for a closing procedure, however it can be preferable to thread the band through the sternum itself. Further, it can be preferable to thread the band through the manubrium due to the significant width of the bone in that region of the sternum. These curved needles can be blunt to reduce the risk of injuring the patient during use and could not easily be threaded through bone on their own. The bone punch tool 7000 provides sufficient leverage for a user (e.g., a surgeon) to easily puncture through bone to create a punch hole configured to receive the curved needle, a band, or both.

The arcuate punch 7016 can have an arcuate geometry similar to the arcuate geometry of the curved needle. In some example, the radius of curvature varies throughout the length of the arcuate punch 7016. In at least one example, the arcuate punch 7016 has a radius of curvature of about 17.98-18.67 millimeters (0.708-0.735 inches). In at least one example, the arcuate punch 7016 has a radius of curvature of about 18.29-20.12 millimeters (0.720-0.729 inches). In some examples the arcuate punch 7016 can be wider and thicker than the maximum width and thickness of the curved needle, the band, or both, so as to provide an arcuate punch hole 7078 with a clearance fit. In at least one example, the arcuate punch 7016 can have the same width and thickness as the maximum width and thickness of the curved needle, the band, or both, so as to provide an arcuate punch hole 7078 with a transition fit. In at least one example, the arcuate punch 7016 can be narrower and thinner than the maximum width and thickness of the curved needle, the band, or both, so as to provide an arcuate punch hole 7078 with an interference fit. Further, in some examples, the width of the arcuate punch 7016 can correspond differently to the maximum width of the curved needle than the thickness of the arcuate punch 7016 corresponds to the maximum thickness.

FIG. 184 is a perspective view of a needle guide 8000, in accordance with at least one example of the present disclosure. The needle guide 8000 can include a handle 8002 at a proximal end 8004 and an arcuate portion 8006 at a distal end 8008. In some examples, the arcuate geometry of the arcuate portion 8006 of the needle guide 8000 corresponds to the arcuate geometry of the arcuate punch 7016 (described with reference to FIGS. 180-183B), a curved needle, or both. In some examples, the arcuate portion 8006 has a varying radius along its length. In at least one example, the arcuate portion 8006 has a radius of curvature of about 17.98-18.67 millimeters (0.708-0.735 inches). In at least one example, the arcuate portion 8006 has a radius of curvature of about 18.29-20.12 millimeters (0.720-0.729 inches). In at least one example, the arcuate portion 8006 can include a concave radius of curvature of about 18.6 millimeters (0.73 inches) and a convex radius of curvature of about 31.8 millimeters (1.25 inches) In some examples, the arcuate portion 8006 can be dimensioned so as to provide a clearance fit in an arcuate punch hole.

In some examples, the arcuate portion 8006 can include a grasping portion 8010 configured to grasp a tip of a curved needle. In at least one example, the grasping portion 8010 can include at least one slot 8012. In the illustrated example, the grasping portion 8010 includes an aperture 8014 and at least one slot 8012, such that the end of the arcuate portion 8006 is configured to expand with receipt of the needle within the aperture 8014, so as to grasp the needle with the grasping portion 8010. While the illustrated example depicts the grasping portion 8010 as having an aperture 8014 with two intersecting slots 8012, other examples may have different arrangements of apertures or slots that allow the grasping portion 8010 to grasp the tip of the curved needle.

In some examples, the handle 8002 of the needle guide 8000 can be curved or bent. In at least one example, the handle 8002 can be shaped and dimensioned to provide ease of use while inserting and removing the needle guide 8000 into an arcuate punch hole. Each of the handle 8002 and the arcuate portion 8010 can comprise any of a variety of materials, for example, plastic, metal, composite material, a combination of these or the like.

FIGS. 185A and 185B are perspective views of the needle guide 8000 of FIG. 184 inserted through an arcuate hole 7074 in a manubrium portion 7076, in accordance with at least one example of the present disclosure. In the illustrated example, arcuate hole punches 7074, 7078 have been formed in the manubrium portions 7070, 7076 (for example, using the bone punch tool 7000 and methods described above with reference to FIGS. 180-183B), and a band 8020 has been threaded through one of the arcuate holes 7078, the band being attached to a curved needle 8022 having a tip 8024. In order to facilitate threading the curved needle 8004 through the arcuate hole 7074 for the sternum closing procedure, in some examples, the arcuate portion 8006 of the needle guide 8000 can be inserted into the arcuate hole 7074. In at least one example, the grasping portion 8010 of the needle guide 8000 can pass entirely through the arcuate hole 7074.

FIGS. 186A and 186B are perspective views of the needle guide 8000 of FIGS. 184-185B engaging the curved needle 8022, in accordance with at least one example of the present disclosure. In the illustrated example, the curved needle 8022 has been inserted within the grasping portion 8010 of the needle guide 8000, such that the grasping portion 8010 grasps retains the tip 8024 of the curved needle 8022. In at least one example, the tip 8024 of the curved needle 8022 can be inserted into an aperture 8014 of the grasping portion 8010, and one or more slots 8012 intersecting the aperture 8014 allow the grasping portion 8010 to expand while maintaining an interference fit. In at least one example, each of the aperture 8014 and the one or more slots 8012 have a length parallel to a length of the arcuate portion 8006.

FIGS. 187A and 187B are perspective views of the needle guide 8000 of FIGS. 184-186B guiding the curved needle 8022 through the arcuate hole 7074, in accordance with at least one example of the present disclosure. While the grasping portion 8010 of the needle guide 8000 continues to grasp the tip 8024 of the curved needle 8022, the handle 8002 of the needle guide 8000 can be rotated, so as to remove the arcuate portion 8006 from the arcuate hole 7074, and guide the arcuate needle 8022 through the arcuate hole 7074. In at least one example, once the tip 8024 (or a greater portion) of the curved needle 8022 emerges from the arcuate hole 7074, the needle guide 8000 can be removed from the tip 8024 of the curved needle 8022, and the sternum closing procedure can proceed with the threaded arcuate holes 7074, 7078.

The bone punch tool 7000 and the needle guide 8000 described with reference to FIGS. 180-187B can allow for formation of an arcuate punch hole through a manubrium or other bone portion and efficient threading of the arcuate punch hole using a curved needle. Some other bone punches cannot accommodate a curved needle. Some other bone punches cannot form an arcuate punch hole. Some other bone punches require squeezing handles together to transition to a punched position. Some other bone punches do not provide sufficient leverage to punch through bone easily. Some other bone punches are inefficient or cumbersome.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. A bone punch apparatus comprising:
 a support arm having a support arm proximal portion and a support arm distal portion;
 a pivot arm having a pivot arm proximal portion and a pivot arm distal portion, the pivot arm distal portion pivotably coupled to the support arm distal portion;
 an arcuate punch configured to punch through bone, the arcuate punch coupled to the pivot arm distal portion;
 wherein the pivot arm proximal portion is configured to be moved away from the support arm proximal portion to cause the arcuate punch to extend into a punch position; and
 a protrusion extending from the support arm distal portion and configured to receive a bone piercing tip of the arcuate punch when in the punch position.

2. The bone punch apparatus of claim 1, wherein the pivot arm proximal portion is configured to be moved toward the support arm proximal portion to cause the arcuate punch to retract into a retracted position.

3. The bone punch apparatus of claim 1, wherein the pivot arm pivots about a pivot point positioned at the support arm distal portion at a center of curvature of the arcuate punch.

4. The bone punch apparatus of claim 1, further comprising:
 a housing coupled to the support arm distal portion, the housing and the protrusion together defining a receptacle configured to receive a bone portion.

5. The bone punch apparatus of claim 4, wherein the receptacle is a u-shaped receptacle configured to receive a portion of a sternum.

6. The bone punch apparatus of claim 1, wherein the arcuate punch is configured to form an arcuate hole through a bone portion.

7. The bone punch apparatus of claim 1, further comprising:
 a locking member configured to urge the pivot arm proximal portion toward the support arm proximal portion.

8. A bone punch apparatus comprising:
a support arm having a support arm proximal portion, a support arm distal portion, and a support arm alignment guide;
a pivot arm having a pivot arm proximal portion and a pivot arm distal portion, the pivot arm distal portion pivotally coupled to the support arm distal portion; and
an arcuate punch configured to punch through bone, the arcuate punch coupled to the pivot arm distal portion;
wherein the support arm alignment guide is configured to indicate an orientation of the arcuate punch;
the pivot arm proximal portion is configured to be moved away from the support arm proximal portion to cause the arcuate punch to extend into a punch position; and
the pivot arm proximal portion is configured to be moved toward the support arm proximal portion to cause the arcuate punch to retract into a retracted position.

9. The bone punch apparatus of claim 8, wherein the support arm alignment guide comprises a window.

10. The bone punch apparatus of claim 9, wherein a width of the window corresponds to a width of the arcuate punch.

11. The bone punch apparatus of claim 8, wherein the support arm alignment guide is configured to align with a completed punch hole.

12. The bone punch apparatus of claim 8, wherein the pivot arm comprises a pivot arm alignment guide configured to indicate an orientation of the arcuate punch.

13. A system comprising:
a bone punch tool configured to form an arcuate hole through a bone, the bone punch tool comprising:
a support arm having a support arm proximal portion and a support arm distal portion;
a pivot arm having a pivot arm proximal portion and a pivot arm distal portion, the pivot arm distal portion pivotably coupled to the support arm distal portion; and
an arcuate punch configured to punch through the bone, the arcuate punch coupled to the pivot arm distal portion;
wherein the pivot arm proximal portion is configured to be moved away from the support arm proximal portion to cause the arcuate punch to extend into a punch position; and
a needle guide configured to guide a needle through the arcuate hole;
wherein the arcuate punch is dimensioned to form the arcuate hole with geometry corresponding to an arcuate geometry of the needle; and
wherein the needle guide comprises:
a handle;
an arcuate portion coupled to the handle, the arcuate portion configured to be inserted into the arcuate hole; and
a grasping portion at an end of the arcuate portion, the grasping portion configured to grasp a tip of the needle.

14. The system of claim 13, wherein the grasping portion comprises a slot formed inure, arcuate portion.

15. The system of claim 13, wherein the grasping portion comprises an aperture and at least one slot intersecting the aperture, such that the end of the arcuate portion is configured to expand with receipt of the needle within the aperture.

16. The system of claim 13, wherein the arcuate portion is configured to be removed from the arcuate hole while grasping the needle, such that the needle guide is configured to guide the needle through the arcuate hole.

* * * * *

UNITED STATES PATENT AND TRADEMARK OFFICE
CERTIFICATE OF CORRECTION

PATENT NO. : 9,820,755 B2  
APPLICATION NO. : 15/204515  
DATED : November 21, 2017  
INVENTOR(S) : Garcia et al.

Page 1 of 1

It is certified that error appears in the above-identified patent and that said Letters Patent is hereby corrected as shown below:

In the Claims

In Column 58, Line 58, in Claim 5, delete "u-shaped" and insert --U-shaped-- therefor In Column 59, Line 7, in Claim 8, delete "pivotally" and insert --pivotably-- therefor In Column 60, Line 24, in Claim 14, delete "inure," and insert --in the-- therefor Signed and Sealed this  
Thirtieth Day of October, 2018

Andrei Iancu  
*Director of the United States Patent and Trademark Office*